(12) United States Patent
Silverman et al.

(10) Patent No.: US 10,337,043 B2
(45) Date of Patent: Jul. 2, 2019

(54) CARBOHYDRATE-ENRICHED RECOMBINANT MICROORGANISMS

(71) Applicant: CALYSTA, INC., Menlo Park, CA (US)

(72) Inventors: Joshua A. Silverman, Los Altos Hills, CA (US); Lorraine Joan Giver, Sunnyvale, CA (US); Jana Mueller, Sunnyvale, CA (US); Renee M. Saville, Mountain View, CA (US); Drew D. Regitsky, San Francisco, CA (US)

(73) Assignee: CALYSTA, INC., Menlo Park, CA (US)

( * ) Notice: Subject to any disclaimer, the term of this patent is extended or adjusted under 35 U.S.C. 154(b) by 0 days.

(21) Appl. No.: 15/111,733

(22) PCT Filed: Jan. 16, 2015

(86) PCT No.: PCT/US2015/011860
§ 371 (c)(1),
(2) Date: Jul. 14, 2016

(87) PCT Pub. No.: WO2015/109257
PCT Pub. Date: Jul. 23, 2015

(65) Prior Publication Data
US 2016/0333384 A1    Nov. 17, 2016

Related U.S. Application Data

(60) Provisional application No. 61/928,366, filed on Jan. 16, 2014.

(51) Int. Cl.
*C12P 19/18* (2006.01)
*A23K 10/12* (2016.01)
*A23K 50/00* (2016.01)
*C12N 9/00* (2006.01)
*A23K 20/163* (2016.01)
*C12N 9/10* (2006.01)
*C12P 19/04* (2006.01)

(52) U.S. Cl.
CPC .............. *C12P 19/18* (2013.01); *A23K 10/12* (2016.05); *A23K 20/163* (2016.05); *A23K 50/00* (2016.05); *C12N 9/00* (2013.01); *C12N 9/1051* (2013.01); *C12P 19/04* (2013.01); *C12Y 204/01034* (2013.01)

(58) Field of Classification Search
CPC .............. C12N 9/1051; C12N 15/8245; C12Y 204/01034
See application file for complete search history.

(56) References Cited

U.S. PATENT DOCUMENTS

| | | |
|---|---|---|
| 2,793,096 A | 5/1957 | Pomeroy |
| 3,846,289 A | 11/1974 | Jeris et al. |
| 4,009,098 A | 2/1977 | Jeris |
| 4,009,105 A | 2/1977 | Jeris |
| 4,032,407 A | 6/1977 | Scott et al. |
| 4,999,302 A | 3/1991 | Kahler et al. |
| 5,079,168 A | 1/1992 | Amiot |
| H1430 H | 4/1995 | Apel et al. |
| 5,585,266 A | 12/1996 | Plitt et al. |
| 6,143,556 A | 11/2000 | Trachtenberg |
| 6,818,424 B2 | 11/2004 | DiCosimo et al. |
| 7,022,481 B2 * | 4/2006 | Phillips ............... C12Q 1/6895 435/254.21 |
| 7,098,005 B2 | 8/2006 | DiCosimo et al. |
| 8,005,620 B2 | 8/2011 | Gustafsson et al. |
| 8,048,661 B2 | 11/2011 | Burgard et al. |
| 2002/0110885 A1 | 8/2002 | Koffas et al. |
| 2003/0003528 A1 | 1/2003 | Brzostowicz et al. |
| 2003/0032170 A1 | 2/2003 | Ito et al. |
| 2003/0138878 A1 | 7/2003 | Johannessen et al. |
| 2004/0147011 A1 | 7/2004 | Koffas et al. |
| 2007/0105202 A1 | 5/2007 | Ishida et al. |
| 2008/0026005 A1 | 1/2008 | Miguez et al. |
| 2008/0292918 A1 | 11/2008 | Finnerty et al. |
| 2010/0221813 A1 | 9/2010 | Miguez et al. |
| 2010/0304453 A1 | 12/2010 | Trawick et al. |
| 2011/0111413 A1 | 5/2011 | Padgett et al. |

FOREIGN PATENT DOCUMENTS

| | | |
|---|---|---|
| EP | 0 296 484 A2 | 12/1988 |
| JP | 2002-136263 A | 5/2002 |
| WO | 97/09433 A1 | 3/1997 |
| WO | 02/18617 A2 | 3/2002 |
| WO | 03/102201 A2 | 12/2003 |

OTHER PUBLICATIONS

Tomazett et al. 2010; 1,3-beta-D-glucan synthase of Paracoccidioides brasiliensis: recombinant protein, expression and cytolocalization in the yeast and mycelium. Fungal Biology. 114: 809-816.*

Akhverdyan et al., "Application of the bacteriophage Mu-driven system for the integration/amplification of target genes in the chromosomes of engineered Gram-negative bacteria—mini review," *Appl Microbiol Biotechnol* 91:857-871, 2011. (16 pages).

Ali et al., "Development and validation of promoter-probe vectors for the study of methane monooxygenase gene expression in *Methylococcus capsulatus* Bath," *Microbiology* 155:761-771, 2009.

Ali et al., "Duplication of the mmoX gene in *Methylosinus sporium*: cloning, sequencing and mutational analysis," *Microbiology* 152:2931-2942, 2006.

Altschul et al., "Basic Local Alignment Search Tool," *Journal of Molecular Biology* 215(3):403-410, 1990.

(Continued)

*Primary Examiner* — Karen Cochrane Carlson
(74) *Attorney, Agent, or Firm* — Seed IP Law Group LLP

(57) ABSTRACT

The present disclosure relates to recombinant microorganisms engineered for enhanced production of a desired carbohydrate, as well as related biomass, and compositions which are useful, inter alia, as animal feed ingredients. The present disclosure also provides related methods.

27 Claims, No Drawings
Specification includes a Sequence Listing.

(56) References Cited

OTHER PUBLICATIONS

Brosius, "Toxicity of an overproduced foreign gene product in *Escherichia coli* and its use in plasmid vectors for the selection of transcription terminators," *Gene* 27:161-172, 1984.
Deshpande, "Ethanol production from cellulose by coupled saccharification/fermentation using*Saccharomyces cerevisiae* and cellulase complex from*Sclerotiun rolfsii* UV-8 mutant," *Applied Biochemistry and Biotechnology* 36:227-234, 1992. (Abstract Only, 3 pages).
Drumright et al., "Polylactic Acid Technology," *Advanced Materials* 12(23):1841-1846, 2000.
Dusselier et al., "Top Chemical Opportunities from Carbohydrate Biomass: A Chemist's View of the Biorefinery," *Top Curr Chem* 353:1-40, 2014. (41 pages).
Eshinimaev et al., "Physiological, Biochemical, and Cytological Characteristics of a Haloalkalitolerant Methanotroph Grown on Methanol," *Microbiology* 71(5):512-518, 2002.
Fennell et al., "Methanotrophic Attached-Film Reactor Development and Biofilm Characteristics," *Biotechnology and Bioengineering* 40:1218-1232, 1992.
Föllner et al., "Expression of polyhydroxyalkanoic-acid-biosynthesis genes in methylotrophic bacteria relying on the ribulose monophosphate pathway," *Appl Microbiol Biotechnol* 40:284-291, 1993.
Gustafsson et al., "Codon bias and heterologous protein expression," *TRENDS in Biotechnology* 22(7):346-353, 2004.
Hanson et al., "Methanotrophic Bacteria," *Microbiological Reviews* 60(2):439-471, 1996.
Henikoff et al., "Amino acid substitution matrices from protein blocks," *Proc. Natl. Acad. Sci. USA* 89:10915-10919, 1992.
Ishida et al., "Metabolic Engineering of *Saccharomyces cerevisiae* for Efficient Production of Pure L-(+)-Lactic Acid," *Applied Biochemistry and Biotechnology* 131(1-3):795-807, 2006.
Kim et al., "Creating auxotrophic mutants in *Methylophilus methylotrophus* AS1 by combining electroporation and chemical mutagenesis," *Applied Microbiology and Biotechnology* 48(1):105-108, 1997.
Lloyd et al., "Heterologous expression of soluble methane monooxygenase genes in methanotrophs containing only particulate methane monooxygenase," *Arch Microbiol* 171:364-370, 1999.
Manivasakam et al., "Nonhomologous End Joining during Restriction Enzyme-Mediated DNA Integration in *Saccharomyces cerevisiae*," *Molecular and Cellular Biology* 18(3):1736-1745, 1998.
Martin et al., "Methane monooxygenase mutants of *Methylosinus trichosporium* constructed by marker-exchange mutagenesis," *FEMS Microbiology Letters* 127:243-248, 1995.
Motoyama et al., "Effects of the amplification of the genes coding for the L-threonine biosynthetic enzymes on the L-threonine production from methanol by a gram-negative obligate methylotroph, *Methylobacillus glycogenes*," *Appl Microbiol Biotechnol* 42:67-72, 1994.
Ojala et al., "Genetic Systems for Moderately Halo(alkali)philic Bacteria of the Genus *Methylomicrobium*," Chapter 7, *Methods in Enzymology* 495:99-118, 2011.
Pfluger et al., "Selection of Type I and Type II methanotrophic proteobacteria in a fluidized bed reactor under non-sterile conditions," *Bioresource Technology* 102:9919-9926, 2011.
Ruggeri et al., "Determination of Optimal Biofilm Activity in a Biological Fluidized Bed (BFB) Reactor," *Wat. Sci. Tech.* 29(10-11):347-351, 1994.
Södergård et al., "Properties of lactic acid based polymers and their correlation with composition," *Prog. Polym. Sci.* 27:1123-1163, 2002.
Springer et al., "Sequence and characterization of mxaB, a response regulator involved in regulation of methanol oxidation, and of mxaW, a methanol-regulated gene in *Methylobacterium extorquens* AM1," *FEMS Microbiology Letters* 160:119-124, 1998.
Stolyar et al., "Role of multiple gene copies in particulate methane monooxygenase activity in the methane-oxidizing bacterium *Methylococcus capsulatus* Bath,"*Microbiology* 145:1235-1244, 1999.
Stolyar et al., "Search for Systems of Genetic Exchange in Methane-Oxidizing Bacteria," *Microbiology* 64(5):584-588, 1995. (Translated from *Mikrobiologiya* 64(5):686-691, 1995).
Apel et al., "Bioprocessing of Environmentally Significant Gases and Vapors with Gas-Phase Bioreactors," Chapter 20, in Tedder et al., *Emerging Technologies in Hazardous Waste Management III*, American Chemical Society, Washington, D.C., 1993, pp. 411-428.
Templeton et al., "Variable carbon isotope fractionation expressed by aerobic $CH_4$-oxidizing bacteria," *Geochimica et Cosmochimica Acta* 70:1739-1752, 2006.
Toyama et al., "Construction of insertion and deletion mxa mutants of *Methylobacterium extorquens* AM1 by electroporation," *FEMS Microbiology Letters* 166:1-7, 1998.
Toyama et al., "pqqA is not required for biosynthesis of pyrroloquinoline quinone in *Methylobacterium extorquens* AM1," *Microbiology* 144:183-191, 1998.
Toyama et al., "Sequence analysis of pqq genes required for biosynthesis of pyrroloquinoline quinone in *Methylobacterium extorquens* AM1 and the purification of a biosynthetic intermediate," *Microbiology* 143:595-602, 1997.
Van Dien et al., "Reconstruction of $C_3$ and $C_4$ metabolism in *Methylobacterium extorquens* AM1 using transposon mutagenesis," *Microbiology* 149:601-609, 2003.
Varadarajan et al., "Catalytic Upgrading of Fermentation-Derived Organic Acids," *Biotechnology Progress* 15(5):845-854, 1999.
Villalobos et al., "Gene Designer: a synthetic biology tool for constructing artificial DNA segments," *BMC Bioinformatics* 7:285, 2006. (8 pages).
Vink et al., "Applications of life cycle assessment to NatureWorks™ polylactide (PLA) production," *Polymer Degradation and Stability* 80:403-419, 2003.
Welch et al., "Design Parameters to Control Synthetic Gene Expression in *Escherichia coli*," *PLoS One* 4(9):e7002, 2009. (10 pages).
Whiticar et al., "Methane oxidation in sediment and water column environments—Isotope evidence," *Org. Geochem.* 10:759-768, 1986.
Whiticar, "A geochemical perspective of natural gas and atmospheric methane," *Org. Geochem.* 16(1-3):531-547, 1990.
Wu et al., "SGDB: a database of synthetic genes re-designed for optimizing protein over-expression," *Nucleic Acids Research* 35:D76-D79, 2007.
Yoshida et al., "Improved conditions for the transformation by electroporation of the extracellular polysaccharide-producing methylotroph *Methylobacillus* sp.," *Biotechnology Letters* 23:787-791, 2001.
Eshinimaev et al., "Physiological, biochemical, and cytological characteristics of a halotolerant and alkalitolerant methanotroph grown on methanol," *Mikrobiologiia* 71(5):596-603, 2002. (English abstract only).
Ward et al., "Genomic Insights into Methanotrophy: The Complete Genome Sequence of *Methylococcus capsulatus* (Bath)," *PLoS Biology* 2(10):e303, 2004. (13 pages).

* cited by examiner

CARBOHYDRATE-ENRICHED RECOMBINANT MICROORGANISMS

REFERENCE TO SEQUENCE LISTING

The "Sequence Listing" submitted electronically concurrently herewith pursuant 37 C.F.R. § 1.821 in computer readable form (CRF) via EFS-Web as file name 200206_416WO_SEQUENCE_LISTING.txt is incorporated herein by reference. The electronic copy of the Sequence Listing was created on Jan. 16, 2015, and the size on disk is 277 kilobytes.

FIELD OF THE INVENTION

The present disclosure relates to novel recombinant $C_1$ metabolizing microorganisms comprising an engineered metabolic pathway for the enhanced production of carbohydrates, and related compositions and methods.

BACKGROUND

Advances in the efficiency in animal feed utilization have been achieved over the past several decades through the use of feed additives. These added substances augment the nutrient-content, energy-content, and/or disease fighting properties of animal feed compositions. A growing challenge for commercial animal producers is the rising cost of grain. The rising costs are due in part to competing demands for grains for biofuel and human food use. With the rising cost of grain and protein components, coupled with limited land available for feed production, alternative low cost animal feed products with beneficial nutritive and disease fighting properties would be highly desirable.

SUMMARY OF THE INVENTION

In one embodiment, the present disclosure provides a recombinant $C_1$ metabolizing microorganism comprising an exogenous nucleic acid selected from the group consisting of an exogenous nucleic acid that encodes a carbohydrate biosynthesis enzyme and an exogenous nucleic acid that encodes an expression control sequence that is operably linked to a nucleic acid encoding a native carbohydrate biosynthesis enzyme, wherein the recombinant $C_1$ metabolizing microorganism is capable of converting a natural gas-derived carbon feedstock into a desired carbohydrate. Typically, the natural gas-derived carbon feedstock is natural gas or methane.

In another embodiment, the present disclosure provides a biomass derived from the recombinant $C_1$ metabolizing microorganism of the present disclosure.

In a further embodiment, the present disclosure provides a carbohydrate composition comprising carbohydrates extracted from the biomass of the present disclosure, wherein the composition exhibits a $\delta^{13}C$ that is less than −30‰.

In a still further embodiment, the present disclosure provides an animal feed comprising the biomass of the present disclosure.

In another embodiment, the present disclosure provides a culture or fermentation medium comprising the biomass or composition of the present disclosure.

The present disclosure additionally provides related methods.

DETAILED DESCRIPTION

The instant disclosure provides novel recombinant $C_1$ metabolizing microorganisms that have the ability to utilize relatively low-cost carbon feedstock as an energy source, as well as related biomass, compositions, and methods. The recombinant microorganisms of the present disclosure are engineered for the enhanced production of certain carbohydrates that are commercially desirable. These recombinant microorganisms, as well as the biomass and carbohydrate compositions that are derived from them, are useful as a source of nutrition for animals (such as, for example, livestock, fish, poultry, and the like), as well as cultured or fermented microorganisms.

In one embodiment, the present disclosure provides a recombinant $C_1$ metabolizing microorganism, wherein the recombinant $C_1$ metabolizing microorganism comprises an exogenous nucleic acid selected from the group consisting of an exogenous nucleic acid that encodes a carbohydrate biosynthesis enzyme and an exogenous nucleic acid that encodes an expression control sequence that is operably linked to a nucleic acid encoding a native carbohydrate biosynthesis enzyme, wherein the recombinant $C_1$ metabolizing microorganism is capable of converting a natural gas carbon feedstock into the carbohydrate. When these recombinant microorganisms are cultured in the presence of a natural gas-derived $C_1$ substrate, they typically exhibit a $\delta^{13}C$ of less than −30‰, and often less than −40‰, as described in more detail herein. Typically, the recombinant microorganism is a non-photosynthetic $C_1$ metabolizing microorganism.

In these embodiments, the recombinant microorganisms of the present disclosure are engineered to convert a natural gas-derived feedstock, which is a relatively low cost and abundant resource (for example, natural gas, or a $C_1$ substrate such as methane from natural gas) as compared to more costly carbohydrates, to higher valued carbohydrates. As used herein, the term "natural gas-derived feedstock" refers to natural gas, or any of the components isolated from natural gas (including $C_1$ substrates) or converted from natural gas (i.e., syngas).

The term "natural gas" refers herein to naturally occurring gas mixtures that may be obtained by conventional processes (e.g., drilling and water flooding of porous reservoirs) or non-conventional processes (e.g., hydraulic fracturing, horizontal drilling or directional drilling of formations having low gas permeability). The gas mixtures are made up of methane and other compounds, including other $C_1$ compounds, as well as other light alkane gases (such as, for example, ethane, propane, butane, pentane, and the like), carbon dioxide, nitrogen, hydrogen sulfide, or the like, and combinations thereof. Unconventional natural gas may be obtained from sources such as, for example, tight gas sands formed in sandstone or carbonate, coal bed methane formed in coal deposits and adsorbed in coal particles, shale gas formed in fine-grained shale rock and adsorbed in clay particles or held within small pores or microfractures, methane hydrates that are a crystalline combination of natural gas and water formed at low temperature and high pressure in places such as under oceans and permafrost.

As used herein, "$C_1$ substrate" or "$C_1$ compound" refers to any carbon containing molecule or composition that lacks a carbon-carbon bond. Exemplary $C_1$ substrates include syngas, methane, methanol, formaldehyde, formic acid or a salt thereof, carbon monoxide, carbon dioxide, methylated amines (e.g., methylamine, dimethylamine, trimethylamine, etc.), methylated thiols, methyl halogens (e.g., bromomethane, chloromethane, iodomethane, dichloromethane, etc.), cyanide, or any combination thereof.

In certain embodiments of the present disclosure, a natural gas-derived feedstock may be natural gas, a $C_1$ substrate from natural gas, or syngas. Typically, a $C_1$ substrate is methane. Exemplary recombinant $C_1$ metabolizing microorganisms that have utilized a natural gas-derived carbon substrate as a feedstock exhibit a distinctive isotopic carbon signature, which is described in more detail herein. This distinctive isoptopic carbon signature is also exhibited by the compositions and products of such recombinant microorganisms (e.g., biomass, carbohydrate compositions, and the like).

In another embodiment, the present disclosure provides a recombinant $C_1$ metabolizing microorganism comprising an exogenous nucleic acid encoding a carbohydrate biosynthesis enzyme, wherein the $C_1$ metabolizing microorganism is capable of converting methane into a carbohydrate. Exemplary carbohydrates are glucans. In some embodiments, a carbohydrate is a β-(1,3)-glucan, and may be branched or unbranched or a mixture thereof. Usually, a $C_1$ metabolizing microorganism is a non-photosynthetic $C_1$ metabolizing microorganism.

As used herein, "$C_1$ metabolizing microorganism" or "$C_1$ metabolizing non-photosynthetic microorganism" refers to any microorganism having the ability to use a $C_1$ substrate as a source of energy or as its primary source of energy and biomass, and may or may not use other carbon substrates (such as sugars and complex carbohydrates) for energy and biomass. For example, a $C_1$ metabolizing microorganism may oxidize a $C_1$ substrate, such as methane or methanol. $C_1$ metabolizing microorganisms include bacteria (such as methanotrophs and methylotrophs) and yeast. In certain embodiments, a $C_1$ metabolizing microorganism does not include a photosynthetic microorganism, such as algae. In some embodiments, the $C_1$ metabolizing microorganism will be an "obligate $C_1$ metabolizing microorganism," meaning its sole source of energy are $C_1$ substrates. In further embodiments, a $C_1$ metabolizing microorganism (e.g., methanotroph) will be cultured in the presence of a $C_1$ substrate feedstock (i.e., using the $C_1$ substrate as a source of energy).

Recombinant $C_1$ metabolizing microorganisms of the present disclosure are engineered for enhanced production of a desired carbohydrate and in one embodiment, comprise an exogenous nucleic acid encoding a carbohydrate biosynthesis (CB) enzyme. The terms "carbohydrate biosynthesis enzyme" and "CB enzyme" are used interchangeably herein to refer to an enzyme that is involved in the production of a carbohydrate by the recombinant host $C_1$ metabolizing microorganism.

Exogenous nucleic acids encoding CB enzymes that are employed in the practice of the present disclosure are typically codon optimized for optimal expression from the recombinant host $C_1$ metabolizing microorganism and encode an enzyme that is either native to a species heterologous to the host $C_1$ microorganism or is a mutant (i.e., variant) of an enzyme that exists in nature.

As used herein, the term "carbohydrate" refers to a monosaccharide, a disaccharide, or a polysaccharide. Suitable exogenous nucleic acids employed in the practice of the present disclosure include those which encode enzymes that are involved in the production of a monosaccharide such as, for example, glucose, fructose, ribose, glyceraldehyde, galactose and the like; a disaccharide, such as, for example lactose, sucrose, maltose, cellobiose, and the like, and mixtures thereof; or a polysaccharide, including, for example, an unbranched or branched glucan, and the like, and mixtures thereof. Exemplary glucans include α-glucans, such as for example, dextran, glycogen, pullulan, starch, and the like, as well as β-glucans, such as, for example, β-1,4-glucan (i.e., cellulose), β-1,3-glucan, β-(1,3)(1,4)-glucan, β-(1,3)(1,6)-glucan, and the like, and mixtures thereof.

In a specific embodiments, the CB enzyme is an enzyme involved in the production of an unbranched or a branched glucan, or mixture thereof. β-glucans are known to have beneficial therapeutic properties, including as a powerful immune stimulant and a powerful antagonist to both benign and malignant tumors. β-glucans are also known to lower cholesterol and triglyceride levels. See D. Akramienė et al., *Medicina* (*kaunas*), 2007; 43(8):597. The β-glucans are a heterogeneous group of glucose polymers made up of β-D-glucopyranosyl units having β-(1,3) and/or β-(1,4), and/or β-(1,6) linkages. They have been isolated from a number of sources, including plants (oat, barley, bran, seaweed, corn, soy, and the like), bacteria (e.g., *Pneumocystis carinii, Cryptococcus neoformans, Aspergillus fumigatus, Histoplasma capsulatum, Candida albicans*, and the like), and fungi (i.e., *Saccharomyces cerevisiae* and mushrooms, such as, for example shiitake (*Lentinus edodes*), maitake (*Grifola frondosa*), schizophylan (*Schizophillum commune*), and SSG (*Sclerotinia sclerotiorum*). β-glucan extracts from *Lentinus edodes* and *Schizophillum commune* have been used for the treatment of cancer in Japan since 1980. Id.

Exogenous nucleic acids that are suitable for use in the practice of the present disclosure include those which encode enzymes involved in gluconeogenesis, glycogenesis, α- or β-glucan biosynthesis, and other metabolic pathways known to produce a carbohydrate.

Suitable exogenous nucleic acids include those which encode a gluconeogenesis enzyme selected from the group consisting of a pyruvate carboxylase, a phosphoenolpyruvate carboxykinase, an enolase, a phosphoglycerate mutase, a phosphoglycerate kinase, a glyceraldehyde-3-phosphate dehydrogenase, a Type A aldolase, a fructose 1,6-bisphosphatase, a phosphofructokinase, a phosphoglucose isomerase, a hexokinase, a glucose-6-phosphate, and the like.

Other suitable exogenous nucleic acids include those which encode a glycogenesis enzyme selected from the group consisting of a glucose-1-phosphate adenyltransferase, a glycogen synthase, and the like.

The above enzymes can be found in a number of heterologous species, including microorganisms, such as, for example, bacteria and yeast, including, for example, *E. coli, C. glutamicum, Saccharomyces cerevisiae*, and the like, as well as higher order fungi, such as mushrooms, and the like, as well as algae, and plants.

Suitable exogenous nucleic acids include those which encode a glucan biosynthesis enzyme, such as, for example, a glucan synthase. An exemplary glucan synthase is β-1,3-glucan synthase. The exogenous nucleic acid may encode a glucan biosynthesis enzyme (e.g., a glucan synthase (such as, for example a β-1,3-glucan synthase)) from a plant (oat, barley, bran, seaweed, corn, soy, and the like), a bacteria (e.g., *Pneumocystis carinii, Cryptococcus neoformans, Aspergillus fumigatus, Histoplasma capsulatum, Candida albicans*, and the like), or a fungi (i.e., *Saccharomyces cerevisiae* and mushrooms, such as, for example shiitake (*Lentinus edodes*), maitake (*Grifola frondosa*), schizophylan (*Schizophillum commune*), and SSG (*Sclerotinia sclerotiorum*). The amino acid and nucleic acid sequences of a number of β-(1,3)-glucan synthases are known. See, e.g., U.S. Pat. No. 5,194,600, WO99/49047, and EP 0 724 644 B1, all of which are incorporated herein by reference. In certain specific embodiments, the exogenous nucleic acid encodes a carbohydrate biosynthesis enzyme having the amino acid sequence of any of SEQ NOs: 2, 4, 6, 8, 10, 12, 14, 16, 18, 20, 22, 24, 26, 28, 30, 32, 34, 36, or 38, shown in Table A, hereinbelow. As described above, the exogenous nucleic acid is typically codon optimized for optimal expression from the recombinant $C_1$ microorganism. Exemplary nucleic acid sequences encoding these CB enzymes are also provided in Table A. These nucleic acid sequences have been codon optimized for expression in *Methylococcus capsulatus* Bath.

TABLE A

Exemplary Carbohydrate Biosynthesis Enzymes

| Source/Enzyme Name | Amino Acid Sequence (SEQ ID NO.) | Nucleic Acid Sequence (SEQ ID NO.) |
|---|---|---|
| *Saccharomyces cerevisiae*: mature KRE1 protein | 2 | 1 |
| *Saccharomyces cerevisiae*: mature KRE2 protein | 4 | 3 |
| *Saccharomyces cerevisiae* s288c: FKS1 | 6 | 5 |
| *Saccharomyces cerevisiae*: FKS2 | 8 | 7 |
| *Candida albicans*: FKS1 | 10 | 9 |
| *Zea mays* (corn): portion of 1,3-β-D-glucan synthase | 12 | 11 |
| *Zea mays* (corn): portion of 1,3-β-D-glucan synthase | 14 | 13 |
| *Oryza sativa* (rice): portion of 1,3-beta-D-glucan synthase | 16 | 15 |
| *Oryza sativa* (rice): portion of 1,3-beta-D-glucan synthase | 18 | 17 |
| *Gycine max* (soy): portion of 1,3-beta-D-glucan synthase. | 20 | 19 |
| *Veronia mespilifolia*: 1,3-beta-D-glucan synthase | 22 | 21 |
| *Triticum aestivum* (wheat): 1,3-beta-D-glucan synthase | 24 | 23 |
| *Horderum vulgars* (barley): 1,3-beta-D-glucan synthase | 26 | 25 |
| *E. coli*: Glucose-1-phosphate adenyltransfersase (Acc. No. YP 49003.1) | 28 | 27 |
| *Cornebacterium. Glutamicum* (ATCC 13032): Glucose-1-phosphate adenylyltransferase | 30 | 29 |
| *Escherichia coli* str. K-12 substr. W3110: Glycogen Synthase | 32 | 31 |
| *Cornebacterium glutamicum* (ATCC 13032): Glycosyltransferase | 34 | 33 |
| *E. coli*: 1,4-alpha-glucan branching enzyme (Acc. No. YP 492001.1) | 36 | 35 |
| *Corynebacterium glutamicum* (ATCC 13032): Glycogen branching enzyme | 38 | 37 |

Suitable exogenous nucleic acids employed in the practice of the present disclosure include those which encode a variant CB enzyme sequence that is at least 90%, at least 91%, at least 92%, at least 93%, at least 94%, at least 95%, at least 96%, at least 97%, at least 98%, or at least 99% identical to a reference or parental wild-type polypeptide sequence, such as, for example a reference sequence corresponding to any one of SEQ ID NOs:2, 4, 6, 8, 10, 12, 14, 16, 18, 20, 22, 24, 26, 28, 30, 32, 34, 36, or 38, provided that the variant retains the carbohydrate biosynthesis enzyme activity of interest. In certain embodiments, the CB enzyme variant polypeptides will include at least one amino acid substitution (e.g., 1, 2, 3, 5, 6, 7, 8, 9 or 10 or more or up to 20, 25, or 30 substitutions) at a pre-determined position relative to a reference or parental wild-type CB enzyme, provided that a variant retains the CB enzyme activity of interest. The CB enzyme variant polypeptides may further comprise one or more conservative substitutions. A "conservative substitution" is recognized in the art as a substitution of one amino acid for another amino acid that has similar properties. Exemplary conservative substitutions are well known in the art (see, e.g., WO 97/09433, p. 10; Lehninger, Biochemistry, $2^{nd}$ Edition; Worth Publishers, Inc. NY:N.Y. (1975), pp. 71-77; Lewin, Genes IV, Oxford University Press, NY and Cell Press, Cambridge, Mass. (1990), p. 8, which are incorporated herein by reference). Methods for generating suitable exogenous nucleic acids encoding such variant enzymes are described in more detail herein.

The "percent identity" between two or more nucleic acid or amino acid sequences is a function of the number of identical positions shared by the sequences (i.e., % identity=number of identical positions/total number of positions×100), taking into account the number of gaps, and the length of each gap that needs to be introduced to optimize alignment of two or more sequences. The comparison of sequences and determination of percent identity between two or more sequences can be accomplished using a mathematical algorithm, such as BLAST and Gapped BLAST programs at their default parameters (e.g., Altschul et al., *J. Mol. Biol.* 215:403, 1990; see also BLASTN at the world wide web at ncbi.nlm.nih.gov/BLAST, which are incorporated herein by reference).

As indicated above, the exogenous nucleic acids encoding CB enzymes employed in the practice of the present disclosure may be codon optimized for expression in the $C_1$ metabolizing microorganism. Expression of recombinant proteins may be difficult outside their original host. For example, variation in codon usage bias has been observed across different species of bacteria (Sharp et al., *Nucl. Acids. Res.* 33:1141, 2005, which is incorporated herein by reference). Overexpression of recombinant proteins even within their native host may also be difficult. In certain embodiments, the nucleic acid to be introduced into a host as described herein may be subjected to codon optimization prior to introduction into the host to ensure protein expression is effective or enhanced. Codon optimization refers to alteration of codons in genes or coding regions of nucleic acids before transformation to reflect the typical codon usage of the host without altering the polypeptide encoded by the non-natural DNA molecule. Codon optimization methods for optimum gene expression in heterologous hosts have been previously described (see, e.g., Welch et al., *PLoS One* 4:e7002, 2009; Gustafsson et al., *Trends Biotechnol.* 22:346, 2004; Wu et al., *Nucl. Acids Res.* 35:D76, 2007; Villalobos et al., *BMC Bioinformatics* 7:285, 2006; U.S. Patent Publication Nos. 2011/0111413 and 2008/0292918; disclosure of which methods are incorporated herein by reference, in their entirety). Exogenous nucleic acids encoding CB enzymes that are suitable for use in the practice of the present disclosure include those having a nucleic acid sequence that is at least about 85% identical to a nucleic acid reference sequence selected from the group consisting of SEQ ID NO.:1, 3, 5, 7, 9, 11, 13, 15, 17, 19, 21, 23, 25, 27, 29, 31, 33, 35, and 37. In some embodiments, the exogenous nucleic acid encoding the CB enzyme has a nucleic acid sequence that is at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% and at least about 99% sequence identity to a nucleic acid reference sequence selected from the group consisting of SEQ ID NO.:1, 3, 5, 7, 9, 11, 13, 15, 17, 19, 21, 23, 25, 27, 29, 31, 33, 35, and 37. Illustrative exogenous nucleic acids that encode a CB enzyme which are suitable for use in the practice of the invention include sequences which have been codon optimized for optimal expression in *Methylococcus capsulatus* Bath, such as, for example, any one of SEQ ID NO.:1, 3, 5, 7, 9, 11, 13, 15, 17, 19, 21, 23, 25, 27, 29, 31, 33, 35, and 37.

Similarly, exogenous nucleic acid molecules of this disclosure encoding polypeptide variants may be designed using the phylogenetic-based methods described in the references noted above (U.S. Pat. No. 8,005,620; Gustafsson et al.; Welch et al.; Villalobos et al.; Minshull et al., all of which are incorporated herein by reference.).

An exogenous nucleic acid encoding a carbohydrate biosynthesis enzyme includes polynucleotides that encode a polypeptide, a polypeptide fragment, a peptide, or a fusion polypeptide that has or retains the corresponding carbohydrate biosynthesis enzyme activity. Methods to determine whether a polypeptide has a particular activity by measuring the ability of the polypeptide to convert a substrate into a product are known in the art.

In some embodiments, the exogenous nucleic acid encodes an expression control sequence that is operably linked to a nucleic acid encoding a native carbohydrate biosynthesis enzyme. Typically, the expression control sequence is one that results in the overexpression of a native carbohydrate biosynthesis enzyme. As used herein, "overexpressed" and "overexpression" when referring to a gene or a protein means an increase in expression or activity of the gene or protein. Increased expression or activity includes expression or activity of a gene or protein being increased above the level of a wildtype (native or non-genetically engineered) control or reference microorganism. A gene or protein is overexpressed if the expression or activity is in a microorganism where it is not normally expressed or active. A gene or protein is overexpressed if the expression or activity is extended or present longer in the recombinant microorganism than in a wild-type control or reference microorganism.

In addition to the exogenous nucleic acids described hereinabove, recombinant $C_1$ metabolizing microorganisms of the present disclosure may comprise further genetic modifications which enhance the production of the desired carbohydrate. For example, when the exogenous nucleic acid encodes a carbohydrate biosynthesis enzyme, the recombinant $C_1$ metabolizing microorganism may further comprise an exogenous expression control sequence that is operatively linked to the exogenous nucleic acid encoding the carbohydrate biosynthesis enzyme to enhance production of the desired carbohydrate. Expression control sequences suitable for use in the practice of the present disclosure are described in more detail herein.

Alternatively, or in addition, the recombinant $C_1$ metabolizing microorganism of the present disclosure may further comprise an exogenous expression control sequence operatively linked to an endogenous nucleic acid encoding an endogenous enzyme that utilizes one or more of the same substrates utilized by carbohydrate biosynthesis enzymes, or utilizes the desired carbohydrate as a substrate (i.e., a "competing" endogenous enzyme). This may be done to downregulate the competing endogenous enzyme.

In some embodiments, it may be desirable to reduce or inhibit a competing endogenous enzyme activity by mutating the competing endogenous enzyme to delete or attenuate its activity. "Inhibit" or "inhibited," as used herein, refers to an alteration, reduction, down regulation, abrogation or deletion, directly or indirectly, in the expression of a target gene or in the activity of a target molecule relative to a control, endogenous or reference molecule, wherein the alteration, reduction, down regulation or abrogation is statistically, biologically, industrially, or clinically significant.

Various methods for downregulating, inactivating, knocking-out, or deleting endogenous gene function in $C_1$ metabolizing microorganisms are known in the art. For example, targeted gene disruption is an effective method for gene down-regulation where an exogenous polynucleotide is inserted into a structural gene to disrupt transcription. Genetic cassettes comprising the exogenous insertion DNA (e.g., a genetic marker) flanked by sequence having a high degree of homology to a portion of the target host gene to be disrupted are introduced into the host $C_1$ metabolizing microorganism. Exogenous DNA disrupts the target host gene via native DNA replication mechanisms. Allelic exchange to construct deletion/insertional mutants in $C_1$ metabolizing microorganisms, including methanotrophic bacteria, have been described in, for example, Toyama and Lidstrom, *Microbiol.* 144:183, 1998; Stoylar et al., *Microbiol.* 145:1235, 1999; Ali et al., *Microbiol.* 152:2931, 2006; Van Dien et al., *Microbiol.* 149:601, 2003; Martin and Murrell, *FEMS Microbiol. Lett.* 127:243, 2006, all of which are incorporated herein by reference.

For example, in some embodiments of the present disclosure, a recombinant $C_1$ metabolizing microorganisms may further comprise a deletion of endogenous glycogen synthase activity and/or endogenous phosphoglucomutase activity. Enzymes involved in other pathways, such as an amino acid synthesis pathway, may also be targeted for down regulation to focus metabolic activities of the host microorganism on carbohydrate biosynthesis.

The recombinant $C_1$ metabolizing microorganism may thus be engineered to have the ability to produce the desired carbohydrate at enhanced levels. In some of these embodiments, a recombinant $C_1$ metabolizing microorganism produces the desired carbohydrate at a level that is at least about 10% greater than that produced by the native $C_1$ metabolizing microorganism and up to about 2-fold, to about 3-, 4-, 5-, 10-, 20-, 30-, 40-, 50-, 60-, 70-, 80-, 90-, 100-, and up to about 500- or about 1000-fold the level produced by a native $C_1$ metabolizing microorganism, when cultured in the presence of a natural gas-derived feedstock (e.g., natural gas, methane, and the like) under at least one set of culture conditions. In other embodiments, a recombinant $C_1$ metabolizing microorganism produces the desired carbohydrate at a level that is from at least about 15%, at least about 20%, at least about 25%, at least about 30%, at least about 35%, at least about 40%, at least about 45%, at least about 50%, at least 55%, at least about 60%, at least about 65%, at least about 70%, at least about 75%, at least about 80%, at least about 85%, at least about 90%, or is at least about 95% greater than that produced by a native $C_1$ metabolizing microorganism, and up to about 2-fold, to about 3-, 4-, 5-, 10-, 20-, 30-, 40-, 50-, 60-, 70-, 80-, 90-, 100-, to about 500- or about 1000-fold the level produced by the native $C_1$ metabolizing microorganism, when cultured in the presence of a natural gas-derived feedstock under at least one set of culture conditions. Typically, the enhanced level of production of a desired carbohydrate by a recombinant $C_1$ metabolizing microorganism of the present invention is at least about 2-fold, 3-, 4-, 5-, 10-, 20-, 30-, 40-, 50-, 60-, 70-, 80-, 90-, or 100-fold that of the native $C_1$ metabolizing microorganism, when cultured in the presence of a natural gas-derived feedstock under at least one set of culture conditions.

Recombinant methods for expression of exogenous nucleic acids in microbial organisms are well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999), all of which are incorporated herein by reference. Genetic modifications to nucleic acid molecules encoding enzymes, or functional fragments thereof, can confer a biochemical or metabolic capability to a recombinant cell that is altered from its naturally occurring state.

As used herein, the terms "endogenous" and "native" when referring to a nucleic acid, polypeptide, such as an enzyme, compound or activity refers to a nucleic acid, polypeptide, compound or activity that is normally present in a host cell. The term "homologous" or "homolog" refers to a molecule or activity from an exogenous (non-native) source that is the same or similar molecule or activity as that found in or derived from a host cell, species or strain.

As used herein, the term "exogenous" when referring to a nucleic acid molecule, construct or sequence refers to a nucleic acid molecule or portion of a nucleic acid molecule sequence that is not native to a cell in which it is expressed, a nucleic acid molecule or portion of a nucleic acid molecule native to a host cell that has been altered or mutated, or a nucleic acid molecule with an altered expression as compared to the native expression levels under similar conditions. For example, an exogenous control sequence (e.g., promoter, enhancer) may be used to regulate expression of a gene or a nucleic acid molecule in a way that is different than the gene or a nucleic acid molecule that is normally expressed in nature or culture. In certain embodiments, an exogenous nucleic acid molecule may be homologous to a native host cell gene, but may have an altered expression level or have a different sequence or both. In other embodiments, exogenous nucleic acid molecules may not be endogenous to a host cell or host genome, but instead may have been added to a host cell by conjugation, transformation, transfection, electroporation, or the like, wherein the added molecule may integrate into the host genome or can exist as extra-chromosomal genetic material (e.g., plasmid or other self-replicating vector).

In certain embodiments, more than one exogenous nucleic acid molecule can be introduced into a host cell as separate nucleic acid molecules, as a polycistronic nucleic acid molecule, as a single nucleic acid molecule encoding a fusion protein, or any combination thereof, and still be considered as more than one exogenous nucleic acid. For example, a $C_1$ metabolizing microorganism can be modified to express two or more exogenous nucleic acid molecules, which may be the same or different, that encode one or more carbohydrate biosynthesis enzyme as disclosed herein. In certain embodiments, multiple copies of a carbohydrate biosynthesis enzyme-encoding polynucleotide molecule are introduced into a host cell, which may be two, three, four, five, six, seven, eight, nine, ten or more copies of the same carbohydrate biosynthesis enzyme or different carbohydrate biosynthesis enzyme encoding polynucleotides.

Host Cells and Transformation Methods

In carrying out the practice of the present invention, the exogenous nucleic acids described hereinabove are transformed into a host cell that is a $C_1$ metabolizing microorganism. The $C_1$ metabolizing microorganism employed may be natural, strain adapted (e.g., performing fermentation to select for strains with improved growth rates and increased total biomass yield compared to the parent strain), or recombinantly modified to produce or overexpress the carbohydrate biosynthesis enzyme of interest and/or to have increased growth rates. Typically, the $C_1$ metabolizing microorganism is a non-photosynthetic $C_1$ microorganism (e.g., is not an algae or a plant).

In certain embodiments, the present disclosure employs $C_1$ metabolizing microorganisms that are prokaryotes or bacteria, such as *Methylomonas*, *Methylobacter*, *Methylococcus*, *Methylosinus*, *Methylocystis*, *Methylomicrobium*, *Methanomonas*, *Methylophilus*, *Methylobacillus*, *Methylobacterium*, *Hyphomicrobium*, *Xanthobacter*, *Bacillus*, *Paracoccus*, *Nocardia*, *Arthrobacter*, *Rhodopseudomonas*, or *Pseudomonas*.

In further embodiments, the $C_1$ metabolizing bacteria employed is a methanotroph or a methylotroph. Exemplary methanotrophs include *Methylomonas*, *Methylobacter*, *Methylococcus*, *Methylosinus*, *Methylocystis*, *Methylomicrobium*, *Methanomonas*, *Methylocella*, or a combination thereof. Exemplary methylotrophs include *Methylobacterium extorquens*, *Methylobacterium radiotolerans*, *Methylobacterium populi*, *Methylobacterium chloromethanicum*, *Methylobacterium nodulans*, or a combination thereof. As used herein, the term "methylotrophic bacteria" refers to any bacteria capable of oxidizing any compound in any form (e.g., solid, liquid, gas) that contains at least one carbon and that do not contain carbon-carbon bonds. In certain embodiments, a methylotrophic bacterium may be a methanotroph. For example, "methanotrophic bacteria" refers to any methylotrophic bacteria that have the ability to oxidize methane as a source of carbon and energy, which may be the primary source of carbon and energy. Exemplary methanotrophic bacteria include *Methylomonas*, *Methylobacter*, *Methylococcus*, *Methylosinus*, *Methylocystis*, *Methylomicrobium*, or *Methanomonas*.

Methanotrophic bacteria are classified into three groups based on their carbon assimilation pathways and internal membrane structure: type I (gamma proteobacteria), type II (alpha proteobacteria, and type X (gamma proteobacteria). Type I methanotrophs use the ribulose monophosphate (RuMP) pathway for carbon assimilation whereas type II methanotrophs use the serine pathway. Type X methanotrophs use the RuMP pathway but also express low levels of enzymes of the serine pathway. Methanotrophic bacteria employed in the practice of the present invention include obligate methanotrophs, which can only utilize $C_1$ substrates for carbon and energy sources, and facultative methanotrophs, which naturally have the ability to utilize some multi-carbon substrates as a carbon and energy source.

Exemplary facultative methanotrophs employed in the practice of the present invention include some species of *Methylocella*, *Methylocystis*, and *Methylocapsa* (e.g., *Methylocella silvestris*, *Methylocella palustris*, *Methylocella tundrae*, *Methylocystis daltona* strain SB2, *Methylocystis bryophila*, and *Methylocapsa aurea* KYG), *Methylobacterium organophilum* (ATCC 27,886), *Methylibium petroleiphilum*, or high growth variants thereof. Exemplary obligate methanotrophic bacteria useful in the practice of the present invention include *Methylococcus capsulatus* Bath (NCIMB 11132), *Methylomonas* sp. 16a (ATCC PTA 2402), *Methylosinus trichosporium* OB3b (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* Y (NRRL B-11,201), *Methylomonas flagellata* sp. AJ-3670 (FERM P-2400), *Methylacidiphi-*

*lum infernorum*, *Methylacidiphilum fumariolicum*, *Methylomicrobium alcaliphilum*, *Methyloacida kamchatkensis*, or high growth variants thereof.

Suitable $C_1$ metabolizing microorganisms useful in the practice of the present invention include syngas metabolizing bacteria such as, for example, *Clostridium*, *Moorella*, *Pyrococcus*, *Eubacterium*, *Desulfobacterium*, *Carboxydothermus*, *Acetogenium*, *Acetobacterium*, *Acetoanaerobium*, *Butyribaceterium*, *Peptostreptococcus*, and the like. Exemplary syngas metabolizing bacteria include *Clostridium autoethanogenum*, *Clostridium ljungdahli*, *Clostridium ragsdalei*, *Clostridium carboxydivorans*, *Butyribacterium methylotrophicum*, *Clostridium woodii*, *Clostridium neopropanologen*, and the like.

Other suitable $C_1$ metabolizing microorganisms useful in the practice of the present invention include eukaryotes such as, for example, yeast, including *Candida*, *Yarrowia*, *Hansenula*, *Pichia*, *Torulopsis*, *Rhodotorula*, and the like.

Each of the microorganisms of this disclosure may be grown as an isolated culture, with a heterologous organism that may aid with growth, or one or more of these bacteria may be combined to generate a mixed culture. The term "heterologous" when referring to an organism refers to a species that is different from the host cell. In still further embodiments, $C_1$ metabolizing non-photosynthetic microorganisms of this disclosure are obligate $C_1$ metabolizing non-photosynthetic microorganisms, such as an obligate methanotroph or methylotroph.

Any one of the aforementioned $C_1$ metabolizing microorganisms can be used as a parent or reference host cell to make a recombinant $C_1$ metabolizing microorganisms of this disclosure. As used herein, "recombinant" refers to a non-naturally-occurring organism, microorganism, cell, nucleic acid molecule, or vector that has at least one genetic alteration or has been modified by the introduction of a exogenous nucleic acid molecule, or refers to a cell that has been altered such that the expression of an endogenous nucleic acid molecule or gene can be controlled. Recombinant also refers to a cell that is derived from a cell or is progeny of a cell having one or more such modifications. Genetic alterations include, for example, modifications introducing expressible nucleic acid molecules encoding proteins or enzymes, or other nucleic acid molecule additions, deletions, substitutions or other functional alteration of a cell's genetic material. For example, recombinant cells may express genes or other nucleic acid molecules that are not found in identical form within the native cell (i.e., unmodified or wild type cell), or may provide an altered expression pattern of endogenous genes, such genes that may otherwise be over-expressed, under-expressed, minimally expressed, or not expressed at all.

Any of the recombinant $C_1$ metabolizing microorganisms or methanotrophic bacteria described herein may be transformed to comprise at least one exogenous nucleic acid to provide the host with a new or enhanced activity (e.g., enzymatic activity) or may be genetically modified to remove or substantially reduce an endogenous gene function using any of a variety of methods known in the art.

Transformation refers to the introduction of a nucleic acid molecule (e.g., exogenous nucleic acid molecule) into a host cell. The transformed host cell may carry the exogenous nucleic acid molecule extra-chromosomally or integrated in the chromosome. Integration into a host cell genome and self-replicating vectors generally result in genetically stable inheritance of the transformed nucleic acid molecule. Host cells containing the transformed nucleic acid molecules are referred to as "non-naturally occurring" or "genetically engineered" or "recombinant" or "transformed" or "transgenic" cells (e.g., bacteria).

Expression systems and expression vectors useful for the expression of exogenous nucleic acids in $C_1$ metabolizing microorganisms (e.g., methanotrophic bacteria) are known.

Electroporation of $C_1$ metabolizing bacteria is described herein and has been previously described in, for example, Toyama et al., *FEMS Microbiol. Lett.* 166:1, 1998; Kim and Wood, *Appl. Microbiol. Biotechnol.* 48:105, 1997; Yoshida et al., *Biotechnol. Lett.* 23:787, 2001, and U.S. Patent Appl. Pub. No. 2008/0026005.

Bacterial conjugation, which refers to a particular type of transformation involving direct contact of donor and recipient cells, is more frequently used for the transfer of nucleic acid molecules into $C_1$ metabolizing bacteria. Bacterial conjugation involves mixing "donor" and "recipient" cells together in close contact with each other. Conjugation occurs by formation of cytoplasmic connections between donor and recipient bacteria, with unidirectional transfer of newly synthesized donor nucleic acid molecules into the recipient cells. A recipient in a conjugation reaction is any cell that can accept nucleic acids through horizontal transfer from a donor bacterium. A donor in a conjugation reaction is a bacterium that contains a conjugative plasmid, conjugative transposon, or mobilized plasmid. The physical transfer of the donor plasmid can occur through a self-transmissible plasmid or with the assistance of a "helper" plasmid. Conjugations involving $C_1$ metabolizing bacteria is described herein and have been previously described in Stolyar et al., *Mikrobiologiya* 64:686, 1995; Motoyama et al., *Appl. Micro. Biotech.* 42:67, 1994; Lloyd et al., *Arch. Microbiol.* 171:364, 1999; PCT Publication No. WO 02/18617; and Ali et al., *Microbiol.* 152:2931, 2006.

Expression control sequences suitable for use in the practice of the present invention include, for example, promoters, terminators, enhancers, repressors, inducers, and the like. Promoters suitable for use in the practice of the present invention may be constitutive, leaky, or inducible, and native or non-native to the host cell employed. Exemplary promoters include a pyruvate decarboxylase (PDC) a promoter, a deoxy-xylulose phosphate synthase promoter, a methanol dehydrogenase promoter (MDH) (such as, for example, the promoter in the upstream intergenic region of the mxaF gene from *Methylococcus capsulatus* Bath (Acc. No. MCA0779) or the MDH promoter from *M. extorquens* (See Springer et al., *FEMS Microbiol. Lett.* 160:119 (1998)), a hexulose 6-phosphate synthase promoter, a ribosomal protein S16 promoter, a serine hydroxymethyl transferase promoter, a serine-glyoxylate aminotransferase promoter, a phosphoenolpyruvate carboxylase promoter, a T5 promoter, Trc promoter, a promoter for PHA synthesis (Foellner et al., *Appl. Microbiol. Biotechnol.* 40:284, 1993), a pyruvate decarboxylase promoter (Tokuhiro et al., *Appl. Biochem. Biotechnol.* 131:795, 2006), the lac operon Plac promoter (Toyama et al., *Microbiol.* 143:595, 1997), a hybrid promoter such as Ptrc (Brosius et al., *Gene* 27:161, 1984), promoters identified from native plasmid in methylotrophs (EP 296484), methanotrophs, and the like.

Additionally, suitable homologous or heterologous promoters for high expression of exogenous nucleic acid molecules may be utilized. For example, U.S. Pat. No. 7,098,005 describes the use of promoters for high expression in the presence of methane or methanol of a heterologous coding nucleic acid in $C_1$ metabolizing bacteria.

In certain embodiments, regulated expression of exogenous nucleic acids encoding a carbohydrate biosynthesis enzyme may be desirable to optimize growth rate of the non-naturally occurring $C_1$ metabolizing microorganism and may improve bacterial growth in a variety of carbon source conditions. This may be achieved through the use of an inducible promoter system.

In certain embodiments, a nucleic acid encoding CB enzyme is operatively linked to an inducible promoter. Inducible promoter systems employed in the practice of the present invention include those known in the art and include tetracycline inducible promoter system; IPTG/lac operon inducible promoter system, heat shock inducible promoter system; metal-responsive promoter systems; nitrate inducible promoter system; light inducible promoter system; ecdysone inducible promoter system, the inducible/regulatable system described for use in methylotrophic and methanotrophic bacteria (see, e.g., U.S. Patent Appl. No. US 2010/0221813, which is incorporated herein by reference), and the like. For example, in one embodiment, the non-naturally occurring $C_1$ metabolizing microorganism (e.g., methanotroph, methylotroph) comprises: (1) an exogenous nucleic acid encoding CB enzyme, operatively linked to a promoter flanked by lacO operator sequences, and (2) an exogenous nucleic acid encoding a lad repressor protein operatively linked to a constitutive promoter (e.g., hexulose-6-phosphate synthase promoter). Induction is initiated when Lad repressor protein binds to lacO operator sequences flanking the LDH or other promoter, preventing transcription. IPTG binds lad repressor and releases it from lacO sequences, allowing transcription. By using an inducible promoter system, lactate synthesis may be controlled by the addition of an inducer.

The expression systems and expression vectors employed in the practice of the present invention optionally contain genetic elements, such as, for example, one or more ribosome binding sites for translation initiation and a transcription termination site, polyadenylation signals, restriction enzyme sites, multiple cloning sites, other coding segments, and the like. In certain embodiments, promoters and/or codon optimization (described in more detail hereinabove) are used for high constitutive expression of exogenous polynucleotides encoding one or more carbohydrate biosynthesis enzymes in host methanotrophic bacteria. Regulated expression of an exogenous nucleic acid in a host methanotrophic bacterium may also be utilized. For example, an inducible/regulatable system of recombinant protein expression in methylotrophic and methanotrophic bacteria as described in, for example, U.S. Patent Appl. No. US 2010/0221813 may be used.

Methods of Producing a Desired Carbohydrate

The present disclosure provides a method of producing a carbohydrate by culturing a recombinant $C_1$ metabolizing microorganism of the present disclosure in the presence of methane (from any source), or a natural gas-derived carbon feedstock under conditions sufficient to produce the carbohydrate. In a specific embodiment, the present disclosure provides a method of producing a carbohydrate by culturing a recombinant $C_1$ metabolizing microorganism in the presence of a natural gas-derived carbon feedstock under conditions sufficient to produce the carbohydrate, wherein the $C_1$ metabolizing microorganism comprises an exogenous nucleic acid encoding a carbohydrate biosynthesis enzyme. Typically, the natural gas-derived carbon feedstock is natural gas, methane, or syngas. Conditions for culturing exemplary $C_1$ metabolizing microorganisms are illustrated in Example 1.

In a further embodiment, the present disclosure provides a method of producing a carbohydrate, said method comprising culturing a recombinant $C_1$ metabolizing microorganism in the presence of methane under conditions sufficient to produce the carbohydrate, wherein the $C_1$ metabolizing microorganism comprises an exogenous nucleic acid encoding a carbohydrate biosynthesis enzyme. In this embodiment, methane from any source is suitable for use in the practice of the present invention, including natural gas, bio-methane, and the like. As used herein, the term "bio-methane" refers to methane generated by fermentation of organic matter such as, for example, manure, waste water sludge, municipal solid waste, and the like, under anaerobic conditions.

A variety of culture methodologies may be used for the microorganisms described herein. For example, $C_1$ metabolizing microorganisms (such as methanotroph or methylotroph bacteria) may be grown by batch culture or continuous culture methodologies. In certain embodiments, the cultures are grown in a controlled culture unit, such as a fermentor, bioreactor, hollow fiber cell, or the like. Generally cells in log phase are often responsible for the bulk production of a product or intermediate of interest in some systems, whereas stationary or post-exponential phase production can be obtained in other systems.

A classical batch culturing method is a closed system in which the media composition is set when the culture is started and is not altered during the culture process. That is, media is inoculated at the beginning of the culturing process with one or more microorganisms of choice and then are allowed to grow without adding anything to the system. As used herein, a "batch" culture is in reference to not changing the amount of a particular carbon source initially added, whereas control of factors such as pH and oxygen concentration can be monitored and altered during the culture. In batch systems, metabolite and biomass compositions of the system change constantly up to the time the culture is terminated. Within batch cultures, cells (e.g., bacteria such as methylotrophs) will generally move from a static lag phase to a high growth logarithmic phase to a stationary phase where growth rate is reduced or stopped (and will eventually lead to cell death if conditions do not change).

A fed-batch system is a variation on the standard batch system in which a carbon substrate of interest is added in increments as the culture progresses. Fed-batch systems are useful when cell metabolism is likely to be inhibited by catabolite repression and when it is desirable to have limited amounts of substrate in the media. Since it is difficult to measure actual substrate concentration in fed-batch systems, an estimate is made based on changes of measureable factors such as pH, dissolved oxygen, and the partial pressure of waste gases. Batch and fed-batch culturing methods are common and known in the art (see, e.g., Thomas D. Brock, Biotechnology: A Textbook of Industrial Microbiology, $2^{nd}$ Ed. (1989) Sinauer Associates, Inc., Sunderland, Mass.; Deshpande, *Appl. Biochem. Biotechnol.* 36:227, 1992).

Continuous cultures are "open" systems in the sense that defined culture media is continuously added to a bioreactor while an equal amount of used ("conditioned") media is removed simultaneously for processing. Continuous cultures generally maintain the cells at a constant high, liquid phase density where cells are primarily in logarithmic growth phase. Alternatively, continuous culture may be practiced with immobilized cells (e.g., biofilm) where carbon and nutrients are continuously added and valuable products, by-products, and waste products are continuously removed from the cell mass. Cell immobilization may be achieved with a wide range of solid supports composed of natural materials, synthetic materials, or a combination thereof.

Continuous or semi-continuous culture allows for the modulation of one or more factors that affect cell growth or end product concentration. For example, one method may maintain a limited nutrient at a fixed rate (e.g., carbon source, nitrogen) and allow all other parameters to change over time. In other embodiments, several factors affecting growth may be continuously altered while cell concentration, as measured by media turbidity, is kept constant. The goal of a continuous culture system is to maintain steady state growth conditions while balancing cell loss due to media being drawn off against the cell growth rate. Methods of modulating nutrients and growth factors for continuous culture processes and techniques for maximizing the rate of product formation are well known in the art (see Brock, 1992).

Liquid phase bioreactors (e.g., stirred tank, packed bed, one liquid phase, two liquid phase, hollow fiber membrane) are well known in the art and may be used for growth of non-naturally occurring microorganisms and biocatalysis.

By using gas phase bioreactors, substrates for bioproduction are absorbed from a gas by non-naturally occurring microorganisms, cell lysates or cell-free fractions thereof, rather than from a liquid. Use of gas phase bioreactors with microorganisms is known in the art (e.g., U.S. Pat. Nos. 2,793,096; 4,999,302; 5,585,266; 5,079,168; and 6,143,556; U.S. Statutory Invention Registration H1430; U.S. Patent Application Publication No. 2003/0032170; *Emerging Technologies in Hazardous Waste Management III*, 1993, eds. Tedder and Pohland, pp 411-428). Exemplary gas phase bioreactors include single pass system, closed loop pumping system, and fluidized bed reactor. By utilizing gas phase bioreactors, methane or other gaseous substrates are readily available for bioconversion by polypeptides with, for example, monooxygenase activity. In certain embodiments, methods for converting a gas into a carbohydrate are performed in gas phase bioreactors. In further embodiments, methods for converting a gas into a carbohydrate are performed in fluidized bed reactors. In a fluidized bed reactor, a fluid (i.e., gas or liquid) is passed upward through particle bed carriers, usually sand, granular-activated carbon, or diatomaceous earth, on which microorganisms can attach and grow. The fluid velocity is such that particle bed carriers and attached microorganisms are suspended (i.e., bed fluidization). The microorganisms attached to the particle bed carriers freely circulate in the fluid, allowing for effective mass transfer of substrates in the fluid to the microorganisms and increased microbial growth. Exemplary fluidized bed reactors include plug-flow reactors and completely mixed reactors. Uses of fluidized bed reactors with microbial biofilms are known in the art (e.g., Pfluger et al., *Bioresource Technol.* 102:9919, 2011; Fennell et al., *Biotechnol, Bioengin.* 40:1218, 1992; Ruggeri et al., *Water Sci. Technol.* 29:347, 1994; U.S. Pat. Nos. 4,032,407; 4,009,098; 4,009,105; and 3,846,289).

Recombinant $C_1$ metabolizing microorganisms described in the present disclosure may be grown as an isolated pure culture, with a heterologous non-$C_1$ metabolizing microorganism(s) that may aid with growth, or with one or more different strains or species of $C_1$ metabolizing microorganisms may be combined to generate a mixed culture.

In certain embodiments, carbohydrates of the present disclosure are produced during a specific phase of cell growth (e.g., lag phase, log phase, stationary phase, or death phase). It may be desirable for carbon from feedstock to be converted to the carbohydrate rather than to growth and maintenance of $C_1$ metabolizing microorganism. In some embodiments, non-naturally occurring $C_1$ metabolizing microorganism (e.g., methanotrophs, methylotrophs) as provided herein are cultured to a low to medium cell density ($OD_{600}$) and then production of carbohydrate is initiated. In some embodiments, a carbohydrate is produced while methanotrophic bacteria are no longer dividing or dividing very slowly. In some embodiments, the carbohydrate is produced only during stationary phase. In some embodiments, the carbohydrate is produced during log phase and stationary phase.

The fermenter composition comprising the carbohydrate produced by a recombinant $C_1$ metabolizing microorganism (e.g., methanotrophs, methylotrophs) provided herein may further comprise other organic compounds associated with biological fermentation processes. For example, biological by-products of fermentation may include one or more of alcohols, epoxides, aldehydes, ketones, esters, or a combination thereof. In certain embodiments, the fermenter composition may contain one or more of the following alcohols: methanol, ethanol, butanol, or propanol. Other compounds, such as $H_2O$, $CO$, $CO_2$, $CO$ $N_2$, $H_2$, $O_2$, and unutilized carbon feedstocks, such as methane, ethane, propane, and butane, may also be present in the fermenter off-gas.

In certain embodiments, the recombinant $C_1$ metabolizing microorganisms (e.g., methanotrophs, methylotrophs) provided herein produce a carbohydrate of the present invention at about 0.001 g/L of culture to about 500 g/L of culture. In some embodiments, the amount of carbohydrate produced is about 1 g/L of culture to about 100 g/L of culture. In some embodiments, the amount of carbohydrate produced is about 0.001 g/L, 0.01 g/L, 0.025 g/L, 0.05 g/L, 0.1 g/L, 0.15 g/L, 0.2 g/L, 0.25 g/L, 0.3 g/L, 0.4 g/L, 0.5 g/L, 0.6 g/L, 0.7 g/L, 0.8 g/L, 0.9 g/L, 1 g/L, 2.5 g/L, 5 g/L, 7.5 g/L, 10 g/L, 12.5 g/L, 15 g/L, 20 g/L, 25 g/L, 30 g/L, 35 g/L, 40 g/L, 45 g/L, 50 g/L, 60 g/L, 70 g/L, 80 g/L, 90 g/L, 100 g/L, 125 g/L, 150 g/L, 175 g/L, 200 g/L, 225 g/L, 250 g/L, 275 g/L, 300 g/L, 325 g/L, 350 g/L, 375 g/L, 400 g/L, 425 g/L, 450 g/L, 475 g/L, or 500 g/L.

Products

The present disclosure provides other useful products in addition to the recombinant $C_1$ metabolizing cells described herein. In one embodiment, the present disclosure provides a biomass comprising a recombinant $C_1$ metabolizing microorganism as described herein. In a specific embodiment, the present disclosure provides a biomass comprising a recombinant $C_1$ metabolizing microorganism, wherein the recombinant $C_1$ metabolizing microorganism comprises an exogenous nucleic acid encoding a carbohydrate biosynthesis enzyme and wherein the recombinant $C_1$ metabolizing microorganism is capable of converting a natural gas-derived feedstock into a desired carbohydrate. In a specific embodiment, the exogenous nucleic acid encodes a β-glucan biosynthesis enzyme, for example, a β-(1,3)-glucan synthase. In some embodiments, the biomass comprises a recombinant $C_1$ metabolizing microorganism and a desired carbohydrate, wherein the desired carbohydrate is a β-glucan and the recombinant $C_1$ metabolizing microorganism comprises an exogenous nucleic acid encoding a β-glucan biosynthesis enzyme, and wherein the $C_1$ metabolizing microorganism is capable of converting a natural gas-derived feedstock into a β-glucan. Exemplary β-glucans include a β-(1,3)-glucan, a β-(1,3)(1,6)-glucan, a β-(1,3) (1.4)-glucan, and a β-(1,4)-glucan. In certain embodiments, the desired carbohydrate is selected from a β-(1,3)-glucan, a β-(1,3)(1,6)-glucan, or a β-(1,3)(1.4)-glucan. In other embodiments, the desired carbohydrate is a β-(1,3)-glucan.

In a further embodiment, the present disclosure provides a biomass comprising a recombinant $C_1$ metabolizing microorganism, wherein the recombinant $C_1$ metabolizing microorganism comprises an exogenous nucleic acid encoding a carbohydrate biosynthesis enzyme and wherein the recombinant $C_1$ metabolizing microorganism is capable of converting methane into a desired carbohydrate. In a specific embodiment, the exogenous nucleic acid encodes a β-glucan biosynthesis enzyme, for example, a β-(1,3)-glucan synthase, and the $C_1$ metabolizing microorganism is capable of converting methane into a β-glucan. Typically the β-glucan is selected from the group consisting of a β-glucan, such as, for example, a β-(1,3)-glucan, a β-(1,3)(1,6)-glucan, a β-(1,3)(1,4)-glucan, and a β-(1,4)-glucan. In certain embodiments, the desired carbohydrate is selected from the group consisting of a β-(1,3)-glucan, a β-(1,3)(1,6)-glucan, a β-(1,3)(1,4)-glucan. In other embodiments, the desired carbohydrate is a β-(1,3)-glucan.

As used herein, "biomass" refers to organic material having a biological origin, which may include one or more of whole cells, lysed cells, extracellular material, or the like. For example, the material harvested from a cultured microorganism (e.g., bacterial or yeast culture) is considered the biomass, which can include cells, cell membranes, cell cytoplasm, inclusion bodies, products secreted or excreted into the culture medium, or any combination thereof. In certain embodiments, biomass comprises the $C_1$ metabolizing microorganisms of this disclosure together with the media of the culture in which the $C_1$ metabolizing microorganisms of this disclosure were grown. In other embodiments, biomass comprises a $C_1$ metabolizing microorganisms (whole or lysed or both) of this disclosure recovered from a culture grown on a $C_1$ substrate (e.g., natural gas, methane, and the like). In still other embodiments, biomass comprises the spent media supernatant from a culture of $C_1$ metabolizing microorganism cultured on a $C_1$ substrate. Such a culture may be considered a renewable resource. Biomass of the present invention is enriched with respect to levels of the desired carbohydrate.

Recombinant $C_1$ metabolizing microorganism of the present disclosure that are provided with a natural gas-derived substrate for cell growth are distinctive with respect to their carbon fingerprint as represented by their $\delta^{13}C$ values (as are the products derived from such recombinant $C_1$ metabolizing microorganisms). By way of background, stable isotopic measurements and mass balance approaches are widely used to evaluate global sources and sinks of methane (see Whiticar and Faber, *Org. Geochem.* 10:759, 1986; Whiticar, *Org. Geochem.* 16: 531, 1990). To use $\delta^{13}C$ values of residual methane to determine the amount oxidized, it is necessary to know the degree of isotopic fractionation caused by microbial oxidation of methane. For example, aerobic methanotrophs can metabolize methane through a specific enzyme, methane monooxygenase (MMO). Methanotrophs convert methane to methanol and subsequently formaldehyde. Formaldehyde can be further oxidized to $CO_2$ to provide energy to the cell in the form of reducing equivalents (NADH), or incorporated into biomass through either the RuMP or Serine cycles (Hanson and Hanson, *Microbiol. Rev.* 60:439, 1996), which are directly analogous to carbon assimilation pathways in photosynthetic organisms. More specifically, a Type I methanotroph uses the RuMP pathway for biomass synthesis and generates biomass entirely from $CH_4$, whereas a Type II methanotroph uses the serine pathway that assimilates 50-70% of the cell carbon from $CH_4$ and 30-50% from $CO_2$ (Hanson and Hanson, 1996). Methods for measuring carbon isotope compositions are provided in, for example, Templeton et al. (*Geochim. Cosmochim. Acta* 70:1739, 2006), which methods are hereby incorporated by reference in their entirety. Examples 2 describes the characterization of stable carbon isotope distribution in the cells of different $C_1$ metabolizing microorganisms. The highly negative $\delta^{13}C$ values for the cells was similarly reflected in the $\delta^{13}C$ of compounds extracted from these cells, i.e., lipid fractions. The $\delta^{13}C$ of the invention products described herein (i.e., a recombinant $C_1$ metabolizing microorganism of the present disclosure as described herein), related biomass and carbohydrate compositions derived therefrom) can vary depending on the source and purity of the $C_1$ substrate used as demonstrated in Example 2.

In certain embodiments, a recombinant $C_1$ metabolizing microorganism of the present disclosure, and related biomass and carbohydrate compositions derived therefrom, exhibit a $\delta^{13}C$ of less than −30‰, less than −31‰, less than −32‰, less than −33‰, less than −34‰, less than −35‰, less than −36‰, less than −37‰, less than −38‰, less than −39‰, less than −40‰, less than −41‰, less than −42‰, less than −43‰, less than −44‰, less than −45‰, less than −46‰, less than −47‰, less than −48‰, less than −49‰, less than −50‰, less than −51‰, less than −52‰, less than −53‰, less than −54‰, less than −55‰, less than −56‰, less than −57‰, less than −58‰, less than −59‰, less than −60‰, less than −61‰, less than −62‰, less than −63‰, less than −64‰, less than −65‰, less than −66‰, less than −67‰, less than −68‰, less than −69‰, or less than −70‰.

In certain embodiments, a recombinant $C_1$ metabolizing microorganism of the present disclosure, and related biomass and carbohydrate compositions derived therefrom, exhibit a $\delta^{13}C$ of about −35‰ to about −50‰, −45‰ to about −35‰, or about −50‰ to about −40‰, or about −45‰ to about −65‰, or about −60‰ to about −70‰, or about −30‰ to about −70‰.

In further embodiments, a $C_1$ metabolizing non-photosynthetic microorganism biomass has a $\delta^{13}C$ of less than about −30‰, or ranges from about −40‰ to about −60‰. In certain embodiments, the biomass comprises a recombinant $C_1$ metabolizing non-photosynthetic microorganism together with the spent media, or the biomass comprises a spent media supernatant composition from a culture of a recombinant $C_1$ metabolizing non-photosynthetic microorganism, wherein the $\delta^{13}C$ of the biomass is less than about −30‰. In certain other embodiments, the carbohydrate composition is extracted or concentrated from a biomass, which can comprise recombinant $C_1$ metabolizing non-photosynthetic microorganisms together with the spent media from a culture, or a spent media supernatant composition from a culture of a recombinant $C_1$ metabolizing non-photosynthetic microorganism.

In certain embodiments, a carbohydrate composition derived from a $C_1$ metabolizing microorganism (which may optionally be an extract or isolate from the $C_1$ metabolizing microorganism biomass) comprises hydrogen, oxygen, and carbon atoms of at least about 50% to about 80% of the weight of the composition, and wherein the $\delta^{13}C$ of the composition is less than about −35‰ or less than about −36‰ or less than about −37‰ or less than about −38‰ or less than about −39‰ or less than about −40‰. In certain embodiments, a carbohydrate composition derived therefrom comprises molecules having hydrogen, oxygen, and carbon atoms, wherein the hydrogen, oxygen, and carbon atoms are at least 50%, at least 55%, at least 60%, at least 65%, at least 70%, at least 75%, or at least 80%, or at least 90%, or at least 95% of the weight of the composition and wherein the $\delta^{13}C$ of the composition ranges from about −30‰ to about −70‰, or wherein the $\delta^{13}C$ in the biomass decreases as cell density increases by about −5‰ to about −20‰, or wherein the $\delta^{13}C$ of the biomass is higher than that of $CO_2$ produced at the same time by an average of 5‰ to 15‰ when cultured in the presence or absence of copper.

Typically, a carbohydrate composition comprises a polysaccharide, and in some instances, it comprises a monosaccharide. In other embodiments the carbohydrate composition comprises a disaccharide. In some embodiments, the carbohydrate comprises a β-glucan. Typically, the β-glucan is a β-(1,3)-glucan. In other embodiments, the β-glucan is aβ-(1,3)(1,6)-glucan, or aβ-(1,3)(1,4)-glucan, or aβ-(1,6)-glucan. Carbohydrate compositions derived from recombinant $C_1$ metabolizing microorganisms cultivated in the presence of a natural gas-derived substrate exhibit the $\delta^{13}C$ values described hereinabove.

Characterization of $\delta^{13}C$ of some $C_1$ metabolizing microorganisms cultivated in the presence of a natural gas-derived feedstock is illustrated in the examples, hereinbelow.

The present disclosure further provides an animal feed comprising the recombinant $C_1$ metabolizing microorganism, related biomass, and/or carbohydrate composition of the present disclosure. As contemplated in the practice of the present invention, the animal feed may be a livestock feed (such as, for example, pig feed, cattle feed, sheep feed, and the like), a poultry feed (such as, for example, chicken feed, turkey feed, and the like), or a fish feed (such as, for example, salmon feed, shell fish feed, and the like). The animal feed may further comprise an additive, such as, for example, a plant-derived material (including, for example, those derived from grains such as, for example, corn, barley, oats, rice, rye, wheat, sorghum, Brewer's spent grain, and the like; and those derived from legumes, such as, for example, alfalfa, clover, peas, beans, lentils, soybeans, and the like), an animal-derived material (such as, for example, fish meal), and/or a microorganism-derived material (including, for example, biomass from a heterologous microorganism that may be, for example, a bacteria, a yeast, or an algae). In some embodiments, the plant-derived material additive is soy meal or pea protein, In a further embodiment, the present disclosure provides a culture or fermentation medium comprising the recombinant $C_1$ metabolizing microorganism, related biomass, and/or carbohydrate composition of the present disclosure. Typically, the culture or fermentation medium further comprises an amino acid and/or water. In an additional embodiment, the present disclosure provides a cell culture composition comprising a culture or fermentation medium as described herein, and a second microorganism. Typically, a second microorganism is a bacteria, a yeast, or an algae.

Embodiments of the present invention include the following:

1. A biomass derived from a culture of a recombinant $C_1$ metabolizing microorganism, wherein the recombinant microorganism comprises an exogenous nucleic acid encoding a carbohydrate biosynthesis enzyme, wherein the recombinant $C_1$ metabolizing is capable of converting a natural gas-derived carbon feedstock into a desired carbohydrate.

2. A biomass derived from a culture of a recombinant $C_1$ metabolizing microorganism, wherein the recombinant $C_1$ metabolizing microorganism comprises an exogenous nucleic acid encoding a carbohydrate biosynthesis enzyme, wherein the recombinant $C_1$ metabolizing microorganism is capable of converting methane into a desired carbohydrate.

3. The biomass of any of embodiments 1-2, wherein the recombinant $C_1$ metabolizing microorganism is a non-photosynthetic $C_1$ metabolizing microorganism.

4. The biomass of any of embodiments 1-3, wherein the carbohydrate is selected from the group consisting of a polysaccharide, a disaccharide, and a monosaccharide.

5. The biomass of embodiment 4, wherein the carbohydrate is a monosaccharide.

6. The biomass of embodiment 4, wherein the carbohydrate is a disaccharide. 7. The biomass of embodiment 4, wherein the carbohydrate is a polysaccharide.

8. The biomass of embodiment 7, wherein the polysaccharide is a β-glucan.

9. The biomass of embodiment 8, wherein the β-glucan is β-(1,3)-glucan.

10. The biomass of embodiment 8, wherein the β-glucan is β-(1,3)(1,6)-glucan.

11. The biomass of embodiment 8, wherein the β-glucan is β-(1,3)(1,4)-glucan.

12. The biomass of embodiment 8, wherein the β-glucan is β-(1,4)-glucan.

13. The biomass of embodiment 8, wherein the β-glucan is β-(1,6)-glucan.

14. The biomass of any of embodiments 1-13, wherein the sequence of the exogenous nucleic acid is codon optimized for optimal expression from the recombinant $C_1$ metabolizing microorganism.

15. The biomass of any of embodiments 1-14, wherein the exogenous nucleic acid encodes a gluconeogenesis enzyme.

16. The biomass of embodiment 15, wherein the gluconeogenesis enzyme is selected from the group consisting of a pyruvate carboxylase, a phosphoenolpyruvate carboxykinase, an enolase, a phosphoglycerate mutase, a phosphoglycerate kinase, a glyceraldehyde-3-phosphate dehydrogenase, a Type A aldolase, a fructose 1,6-bisphosphatase, a phosphofructokinase, a phosphoglucose isomerase, a hexokinase, and a glucose-6-phosphate.

17. The biomass of any of embodiments 1-14, wherein the exogenous nucleic acid encodes a glycogenesis enzyme.

18. The biomass of embodiment 17, wherein the glycogenesis enzyme is selected from the group consisting of a glucose-1-phosphate adenyltransferase, a glycogen synthase, and a 1,4-alpha-glucan-branching protein.

19. The biomass of any of embodiments 8-14, wherein the exogenous nucleic acid is a β-glucan synthase.

20. The biomass of any of embodiments 1-19, wherein the exogenous nucleic acid encodes a carbohydrate biosynthesis enzyme that is endogenous to a bacteria.

21. The biomass of any of embodiments 1-19, wherein the exogenous nucleic acid encodes a carbohydrate biosynthesis enzyme that is endogenous to an organism selected from the group consisting of a yeast, a fungi, and a plant.

22. The biomass of any of embodiments 1-19, wherein the exogenous nucleic acid encodes a carbohydrate biosynthesis enzyme that is endogenous to a microorganism selected from the group consisting of *E. coli* and *C. glutamicum*.

23. The biomass of any of embodiments 1-14, wherein the exogenous nucleic acid encodes a carbohydrate biosynthesis enzyme selected from the group consisting of any of SEQ ID NOs:2, 4, 6, 8 10, 12, 14, 16, 18, 20, 22, 24, 26, 28, 30, 32, 34, 36, and 38.

24. The biomass of any of embodiments 1-23, wherein the exogenous nucleic acid encoding carbohydrate biosynthesis pathway enzyme is operatively linked to an expression control sequence.

25. The biomass of embodiment 24, wherein the expression control sequence is an exogenous expression control sequence.

26. The biomass of any of embodiments 1-25, wherein the $C_1$ metabolizing microorganism further comprises a deletion of an endogenous enzyme activity.

27. The biomass according to any of embodiments 1-26, wherein the $C_1$ metabolizing microorganism is a methanotroph.

28. The biomass according to embodiment 27, wherein the methanotroph is *Methylomonas, Methylobacter, Methylococcus, Methylosinus, Methylocystis, Methylomicrobium, Methanomonas, Methylocella,* or *Methylocapsa*.

29. The biomass of embodiment 27, wherein the methanotroph is selected from the group consisting of *Methylococcus capsulatus* Bath strain, *Methylomonas methanica* 16a (ATCC PTA 2402), *Methylosinus trichosporium* OB3b (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* (NRRL B-11,201), *Methylobacterium organophilum* (ATCC 27,886), *Methylomonas* sp AJ-3670 (FERM P-2400), *Methylocella silvestris, Methylocella palustris* (ATCC 700799), *Methylocella tundrae, Methylocystis* daltona strain SB2, *Methylocystis bryophila, Methylocapsa aurea* KYG, *Methylacidiphilum infernorum, Methylibium petroleiphilum,* and *Methylomicrobium alcaliphilum*.

30. The biomass according to any one of embodiments 1 and 3-29, wherein the natural gas-derived carbon feedstock is selected from the group consisting of natural gas, syngas, methane, methanol, formaldehyde, formic acid, carbon monoxide, carbon dioxide, cyanide, a methylamine, a methylthiol, a methylhalogen, and any combination or two or more thereof.

31. The biomass of embodiment 30, wherein the natural gas-derived carbon feedstock is natural gas.

32. The biomass of any of embodiments 1, and 3-30, wherein the natural gas-derived carbon feedstock is methane.

33. The biomass of embodiment 30, wherein the natural gas-derived carbon feedstock is syngas.

34. The biomass of embodiment 30, wherein the $C_1$ metabolizing microorganism is a syngas metabolizing bacteria.

35. The biomass according to embodiment 34, wherein the syngas metabolizing bacteria is selected from the group consisting of *Clostridiumautoethanogenum, Clostridium ljungdahli, Clostridium ragsdalei, Clostridium carboxydivorans, Butyridbacterium methylotrophicum, Clostridium woodii,* and *Clostridium neopropanologen*.

36. The biomass according to any one of embodiments 1 and 3-35, wherein the $\delta^{13}C$ of the biomass is less than −40‰.

37. The biomass of embodiment 2, wherein the methane is bio-methane.

38. A composition comprising a carbohydrate composition, wherein the carbohydrate composition exhibits a $\delta^{13}C$ of less than −40‰.

39. The composition of embodiment 38, wherein the carbohydrate comprises a β-glucan.

40. The composition of embodiment 39, wherein the β-glucan is β-(1,3)-glucan.

41. An animal feed comprising the biomass of any of embodiments 1-37 or the composition of any of embodiments 38-40.

42. The animal feed of embodiment 41, further comprising a plant-derived material.

43. The animal feed of embodiment 41, wherein the plant-derived material is selected from the group consisting of soybean meal and pea protein.

44. A culture or fermentation medium comprising the biomass of any of embodiments 1-37 or the composition of any of embodiments 38-40.

45. A recombinant $C_1$ metabolizing microorganism, wherein the recombinant microorganism comprises an exogenous nucleic acid encoding a carbohydrate biosynthesis enzyme, wherein the recombinant $C_1$ metabolizing microorganism is capable of converting a natural gas-derived carbon feedstock into a desired carbohydrate.

46. A recombinant $C_1$ metabolizing microorganism, wherein the recombinant $C_1$ metabolizing microorganism comprises an exogenous nucleic acid encoding a carbohydrate biosynthesis enzyme, wherein the recombinant $C_1$ metabolizing microorganism is capable of converting methane into a desired carbohydrate.

47. The recombinant $C_1$ metabolizing microorganism of any of embodiments 45-46, wherein the recombinant $C_1$ metabolizing microorganism is a non-photosynthetic $C_1$ metabolizing microorganism.

48. The recombinant $C_1$ metabolizing microorganism of any of embodiments 45-47, wherein the carbohydrate is selected from the group consisting of a polysaccharide, a disaccharide, and a monosaccharide.

49. The recombinant $C_1$ metabolizing microorganism of embodiment 48, wherein the carbohydrate is a monosaccharide.

50. The recombinant $C_1$ metabolizing microorganism of embodiment 48, wherein the carbohydrate is a disaccharide.

51. The recombinant $C_1$ metabolizing microorganism of embodiment 48, wherein the carbohydrate is a polysaccharide.

52. The recombinant $C_1$ metabolizing microorganism of embodiment 51, wherein the polysaccharide is a β-glucan.

53. The recombinant $C_1$ metabolizing microorganism of embodiment 52, wherein the β-glucan is β-(1,3)-glucan.

54. The recombinant $C_1$ metabolizing microorganism of embodiment 52, wherein the β-glucan is β-(1,3)(1,6)-glucan.

55. The recombinant $C_1$ metabolizing microorganism of embodiment 52, wherein the β-glucan is β-(1,3)(1,4)-glucan.

56. The recombinant $C_1$ metabolizing microorganism of embodiment 52, wherein the β-glucan is β-(1,4)-glucan.

57. The recombinant $C_1$ metabolizing microorganism of embodiment 52, wherein the β-glucan is β-(1,6)-glucan.

58. The recombinant $C_1$ metabolizing microorganism of any of embodiments 45-57, wherein the sequence of the exogenous nucleic acid is codon optimized for optimal expression from the recombinant $C_1$ metabolizing microorganism.

59. The recombinant $C_1$ metabolizing microorganism of any of embodiments 45-58, wherein the exogenous nucleic acid encodes a gluconeogenesis enzyme.

60. The recombinant $C_1$ metabolizing microorganism of embodiment 59, wherein the gluconeogenesis enzyme is selected from the group consisting of a pyruvate carboxylase, a phosphoenolpyruvate carboxykinase, an enolase, a phosphoglycerate mutase, a phosphoglycerate kinase, a glyceraldehyde-3-phosphate dehydrogenase, a Type A aldolase, a fructose 1,6-bisphosphatase, a phosphofructokinase, a phosphoglucose isomerase, a hexokinase, and a glucose-6-phosphate.

61. The recombinant $C_1$ metabolizing microorganism of any of embodiments 45-58, wherein the exogenous nucleic acid encodes a glycogenesis enzyme.

62. The recombinant $C_1$ metabolizing microorganism of embodiment 61, wherein the glycogenesis enzyme is selected from the group consisting of a glucose-1-phosphate adenyltransferase, a glycogen synthase, and a 1,4-alpha-glucan-branching protein.

63. The recombinant $C_1$ metabolizing microorganism of any of embodiments 52-57, wherein the exogenous nucleic acid is a β-glucan synthase.

64. The recombinant $C_1$ metabolizing microorganism of any of embodiments 45-63, wherein the exogenous nucleic acid encodes a carbohydrate biosynthesis enzyme that is endogenous to a bacteria.

65. The recombinant $C_1$ metabolizing microorganism of any of embodiments 45-63, wherein the exogenous nucleic acid encodes a carbohydrate biosynthesis enzyme that is endogenous to an organism selected from the group consisting of a yeast, a fungi, and a plant.

66. The recombinant $C_1$ metabolizing microorganism of any of embodiments 45-63, wherein the exogenous nucleic acid encodes a carbohydrate biosynthesis enzyme that is endogenous to a microorganism selected from the group consisting of *E. coli*, and *C. glutamicum*.

67. The recombinant $C_1$ metabolizing microorganism of any of embodiments 45-57, wherein the exogenous nucleic acid encodes a carbohydrate biosynthesis enzyme selected from the group consisting of any of SEQ ID NOs: 2, 4, 6, 8, 10, 12, 14, 16, 18, 20, 22, 24, 26, 28, 30, 32, 34, 36, and 38.

68. The recombinant $C_1$ metabolizing microorganism of any of embodiments 45-67, wherein the exogenous nucleic acid encoding carbohydrate biosynthesis pathway enzyme is operatively linked to an expression control sequence.

69. The recombinant $C_1$ metabolizing microorganism of embodiment 68, wherein the expression control sequence is an exogenous expression control sequence.

70. The recombinant $C_1$ metabolizing microorganism of any of embodiments 45-69, wherein the $C_1$ metabolizing microorganism further comprises a deletion of an endogenous enzyme activity.

71. The recombinant $C_1$ metabolizing microorganism according to any of embodiments 45-70, wherein the $C_1$ metabolizing microorganism is a methanotroph.

72. The recombinant $C_1$ metabolizing microorganism according to embodiment 71, wherein the methanotroph is *Methylomonas, Methylobacter, Methylococcus, Methylosinus, Methylocystis, Methylomicrobium, Methanomonas, Methylocella,* or *Methylocapsa*.

73. The recombinant $C_1$ metabolizing microorganism of embodiment 71, wherein the methanotroph is selected from the group consisting of *Methylococcus capsulatus* Bath strain, *Methylomonas methanica* 16a (ATCC PTA 2402), *Methylosinus trichosporium* OB3b (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* (NRRL B-11,201), *Methylobacterium organophilum* (ATCC 27,886), *Methylomonas* sp AJ-3670 (FERM P-2400), *Methylocella silvestris, Methylocella palustris* (ATCC 700799), *Methylocella tundrae, Methylocystis daltona* strain SB2, *Methylocystis bryophila, Methylocapsa aurea* KYG, *Methylacidiphilum infernorum, Methylibium petroleiphilum,* and *Methylomicrobium alcaliphilum*.

74. The recombinant $C_1$ metabolizing microorganism according to any one of embodiments 45 and 47-73 wherein the natural gas-derived carbon feedstock is selected from the group consisting of natural gas, syngas, methane, methanol, formaldehyde, formic acid, carbon monoxide, carbon dioxide, cyanide, a methylamine, a methylthiol, a methylhalogen, and any combination or two or more thereof.

75. The recombinant $C_1$ metabolizing microorganism of embodiment 74, wherein the natural gas-derived carbon feedstock is natural gas.

76. The recombinant $C_1$ metabolizing microorganism of embodiment 74, wherein the natural gas-derived carbon feedstock is methane.

77. The recombinant $C_1$ metabolizing microorganism of embodiment 74, wherein the natural gas-derived carbon feedstock is syngas.

78. The recombinant $C_1$ metabolizing microorganism of embodiment 77, wherein the $C_1$ metabolizing microorganism is a syngas metabolizing bacteria.

79. The biomass according to embodiment 78, wherein the syngas metabolizing bacteria is selected from the group consisting of *Clostridiumautoethanogenum, Clostridium ljungdahli, Clostridium ragsdalei, Clostridium carboxydivorans, Butyridbacterium methylotrophicum, Clostridium woodii,* and *Clostridium neopropanologen*.

80. The recombinant $C_1$ metabolizing microorganism according to any one of embodiments 45 and 47-79, wherein the $\delta^{13}C$ of the biomass is less than −40‰.

81. The recombinant $C_1$ metabolizing microorganism of embodiment 46, wherein the methane is bio-methane.

82. A method of producing a carbohydrate, said method comprising culturing the recombinant $C_1$ metabolizing microorganism of any of embodiments 45 and 47-68 in the presence of a natural gas-derived carbon feedstock under conditions sufficient to produce the carbohydrate.

83. A method of producing a carbohydrate, said method comprising culturing the recombinant $C_1$ metabolizing microorganism of embodiment 46 in the presence of a methane under conditions sufficient to produce the carbohydrate.

84. The method of embodiment 83, wherein the carbohydrate is a β-glucan.

85. A carbohydrate produced by the method of embodiment 82, wherein the carbohydrate exhibits a $\delta^{13}C$ in the range of from about −40‰ to about −60‰.

The foregoing and other aspects of the invention may be better understood in connection with the following, non-limiting examples.

EXAMPLES

Example 1

Culture and Bioreactor Conditions for $C_1$ Metabolizing Microorganisms

Exemplary $C_1$ metabolizing microorganisms of the instant disclosure (methanotrophs, methylotrophs, clostridia) were cultured in tubes, in vials, in bottles, on plates, or in a bioreactor (fermentation). Growth conditions, media, and carbon source for various microorganisms are described in this example.

*Methylosinus trichosporium* Strain OB3b (NCIMB 11131); *Methylomonas* sp. Strain 16a (ATCC PTA-2402); or *Methylomonas methanica*

For serum bottles, the bacteria were cultured at 30° C. in Higgins minimal nitrate salts medium (NSM; Cornish et al., *J. Gen. Microbiol.* 130:2565, 1984; Park et al., *Biotechnol. Bioeng.* 38:423, 1991) or MM-W1 medium. The headspace composition was adjusted to a 1:1 volume of methane:air. The bottles were shaken at a rate of 200-250 rpm. Alternatively, the culture was maintained on NSM-media plates containing 1.5% w/v agar grown in a gas-tight chamber containing a 1:1 (v/v) methane:air gas mixture, or in the presence of methanol vapor (via 0.5 mL methanol in the lid of parafilm-sealed plates) or on NSM-media plates supplemented with 0.5% methanol. Plates were incubated inverted in a humidified chamber at 30° C.

The composition of the NSM medium used was as follows: 1.0 g $MgSO_4*7H_2O$, 0.20 g $CaCl_2*6H_2O$, 2.0 ml chelated iron solution (0.1 g ferric (III) ammonium citrate or 0.5 g ferric (III) chloride; 0.2 g EDTA, sodium salt; 0.3 ml HCl, concentrated; 100.0 ml distilled deionized $H_2O$), 1.0 g $KNO_3$, 0.5 ml trace element solution (500.0 mg EDTA, 200.0 mg $FeSO_4 \cdot 7H_2O$, 10.0 mg $ZnSO_4*7H_2O$, 3.0 mg $MnCl_2*4H_2O$, 30.0 mg $H_3BO_3$, 20.0 mg $CoCl_2*6H_2O$, 1.0 mg $CaCl_2*2H_2O$, 2.0 mg $NiCl_2*6H_2O$, 3.0 mg $Na_2MoO_4*2H_2O$, 1.0 L distilled water), 0.272 g $KH_2PO_4$, 0.717 g $Na_2HPO_4*12H_2O$, optionally 12.5 g purified agar (e.g., Oxoid L28 or Bacto™ agar; used when making plates), 1.0 L distilled deionized water, pH adjusted to 6.8 and autoclaved at 121° C. for 15 minutes.

For fermentation, a 2-liter bioreactor containing 1 L of sterilized defined media MM-W1 was inoculated with cells from serum bottle batch cultures (10-20% v/v) grown in MM-W1 supplied with a 1:1 (v/v) mixture of methane and air. The composition of medium MM-W1 used was as follows: 0.8 mM $MgSO_4*7H_2O$, 10 mM $NaNO_3$, 0.14 mM $CaCl_2$, 1.2 mM $NaHCO_3$, 2.35 mM $KH_2PO_4$, 3.4 mM $K_2HPO_4$, 20.7 μM $Na_2MoO_4*2H_2O$, 1 μM $CuSO_4*5H_2O$, 10 μM $Fe^{III}$—Na-EDTA, and 1 mL per liter of trace metals solution (containing, per liter 500 mg $FeSO_4*7H_2O$, 400 mg $ZnSO_4*7H_2O$, 20 mg $MnCl_2*7H_2O$, 50 mg $CoCl_2*6H_2O$, 10 mg $NiCl_2*6H_2O$, 15 mg $H_3BO_3$, 250 mg EDTA). Phosphate, bicarbonate, and $Fe^{III}$—Na-EDTA were added after the media was autoclaved and cooled. Bicarbonate was added up to 0.1% (w/v) in certain fermentations. The reactor contents were stirred with an overhead impeller at a constant 750 rpm. The culture was fed with a constant methane sparging at about 60 mL/min to about 120 mL/min, while concentrated oxygen (at least 85%) was supplied at a variable rate of about 10-100 mL/min to maintain a dissolved oxygen level of about 40% to about 80% (relative to air saturation of the media).

Temperature in the bioreactor was maintained at 30° C. and pH was maintained at 7.1±0.1 using automated addition of 0.5M NaOH and 0.5M HCl, along with other additions, to the culture about every 4 hours to about 24 hours (corresponding to an $OD_{600}$ increase of approximately 5 OD units). The other additions alternated between a metal addition (10 μM CuSO4, 5 μM FeSO4, 5 μM $Fe^{III}$—Na-EDTA final concentrations) and a nutrient addition (5.75 mM KxHyPO4, 10 mM NaNO3). Under these conditions, essentially linear growth was observed, with an effective biomass generation rate of about 2.7 to about 3.3 grams dry cell weight per liter per day to an $OD_{600}$ of greater than 20. Culture biomass was harvested by centrifugation, washed once in MM-W1 media, and recovered biomass was either frozen at −80° C. or used immediately for fractionation of cellular components (e.g., lipid extraction).

A semi-continuous fermentation approach can also be applied to maintain biomass productivity and reduce time associated with fermentation shut-down and start-up (i.e., turn-around time or lead time).

Harvesting of the bacterial biomass was performed at approximately 12-24 hour intervals, as the culture density approached (but before entering) stationary phase. Approximately half of the bioreactor volume was removed by transferring to a separate container via centrifugal pump. An equal volume of sterilized or recycled media was then returned to the bioreactor such that the optical density of the reactor was approximately half of its initial value. The bioreactor fermentation was continued according to the above protocol so that multiple cycles of growth and biomass recovery could be carried out during a single fermentation run.

*Methylococcus capsulatus* Bath (NCIMB 11132)

The bacteria were cultured at 42° C. in serum bottles containing Higgins minimal nitrate salts medium (NSM) or MM-W1 medium. The headspace composition was adjusted to a 1:1 volume of methane:air. The bottles were shaken at a rate of 200-250 rpm. Alternatively, the culture was maintained on NSM-media plates solidified with 1.5% w/v agar grown in a gas-tight chamber containing a 1:1 (v/v) methane:air gas mixture. Plates were incubated inverted in the chamber at 42° C.

For fermentation, a 3-liter bioreactor containing 1.25 L sterilized media MMF1.1 was inoculated with cells from serum bottle batch cultures (10-20% v/v) grown in the same media supplied with a 1:1 (v/v) mixture of methane and air. The composition of medium MMF1.1 was as follows: 0.8 mM $MgSO_4*7H_2O$, 40 mM $NaNO_3$, 0.14 mM $CaCl_2$, 6 mM $NaHCO_3$, 4.7 mM $KH_2PO_4$, 6.8 mM $K_2HPO_4$, 20.7 μM $Na2MoO_4*2H_2O$, 6 μM $CuSO_4*5H_2O$, 10 μM $Fe^{III}$—Na-EDTA, and 1 mL per liter of trace metals solution (containing, per liter 500 mg $FeSO_4*7H_2O$, 400 mg $ZnSO_4*7H_2O$, 20 mg $MnCl_2*7H_2O$, 50 mg $CoCl_2*6H_2O$, 10 mg $NiCl_2*6H_2O$, 15 mg $H_3BO_3$, 250 mg EDTA). Phosphate, bicarbonate, and $Fe^{III}$—Na-EDTA were added after media was autoclaved and cooled. The reactor contents were stirred with an overhead impeller at a constant 750 rpm. The culture was fed with a constant methane sparging at about 60 to about 200 mL/min, while concentrated oxygen (>85%) was supplied at a variable rate of 15-90 mL/min and the dissolved oxygen level was maintained below 10% (relative to air saturation of the media).

Temperature in the bioreactor was maintained at 44° C. and pH was maintained at 7.0±0.1 using automated addition of 0.5M NaOH and 0.5M HCl, along with additions of copper and iron (5 μM CuSO4, 5 μM FeSO4, 10 μM $Fe^{III}$—Na-EDTA final concentration) to the culture every 3-6 hours (corresponding to an $OD_{600}$ increase of approximately 3-5 OD units after reaching OD 5). Under these conditions, essentially linear growth was observed, with effective biomass generation rate of more than 5 grams dry cell weight per liter per day to an $OD_{600}$ of greater than 10. Culture biomass was harvested by centrifugation, the cells washed once in MM-W1 media and cell pellets were either frozen at −80° C. or used immediately for fractionation of cellular components.

Nutrient depletion was recognized as an issue that could limit the growth yield during fermentation. To avoid limitation of nutrients, mainly nitrogen and phosphate, nutrient feeds composed of 2-fold concentrated MMF1.1 were initiated after culture $OD_{600}$ exceeded 5. The nutrient feed was initiated at dilution rates corresponding to approximately half of the cultures' growth rate to avoid wash-out and to maintain an increase in OD while expanding the culture volume. The bioreactor fermentation was continued according to the above protocol so that multiple cycles of growth and biomass recovery could be carried out during a single fermentation run.

*Methylobacterium extorquens* or *Methylosinus trichosporium* Strain OB3b (NCIMB 11131)

The bacteria is cultured at 30° C. in tubes containing Higgins minimal nitrate salts medium (NSM) supplemented with 0.5% methanol. The tubes are shaken at a rate of 200-250 rpm. Alternatively, the cultures are maintained on NSM-media plates containing 1.5% w/v agar grown in the presence of methanol vapor (via 0.5 mL methanol in the lid of parafilm-sealed plates) or supplemented with 0.5% methanol. Plates are incubated inverted in a humidified chamber under normal atmosphere at 30° C.

For fermentation, a 2-liter bioreactor containing 1 L defined media MM-W1 is inoculated with cells from culture tube batch culture (10-20% v/v). The composition of medium MM-W1 was as described above. The reactor contents are stirred with an overhead impeller at a constant 800 rpm. The culture is fed with an initial bolus of methanol to a final concentration of 0.5% and variable methanol feed, while pure oxygen was supplied at a variable rate of 30-100 mL/min to maintain a dissolved oxygen level of 60-90% (relative to air saturation of the media).

Temperature in the bioreactor was maintained at 30° C. and pH was maintained at 7.1±0.1 using automated addition of 0.5M NaOH and 1M HCl, along with the metal and nutrient additions as described above. Under these conditions, essentially linear growth is observed, with effective biomass generation rate 2.7 to 3.3 grams dry cell weight per liter per day to an $OD_{600}$ of greater than 20. Culture biomass was harvested by centrifugation, the cells washed once in MM-W1 media and cell pellets were either frozen at −80° C. or used immediately for fractionation of cellular components.

A semi-continuous fermentation approach can also be applied to maintain biomass productivity and reduce time associated with fermentation shut-down and start-up (i.e., turn-around time or lead time).

Harvesting of the accumulated bacterial biomass was performed at approximately 12-24 hour intervals, as the culture density approached (but before entering) stationary phase. Approximately half of the bioreactor volume was removed by transferring to a separate container via centrifugal pump. An equal volume of fresh or recycled media was then returned to the bioreactor such that the optical density of the reactor was approximately half of its initial value. The bioreactor fermentation was continued according to the above protocol so that multiple cycles of growth and biomass recovery was carried out during a single fermentation run.

*Clostridium autoethanogenum* and *Clostridium ljungdahlii*

The *Clostridium* bacteria are cultivated anaerobically in 100 mL modified PETC medium (ATCC medium 1754) at 37° C. in plastic-coated 500 ml-Schott Duran® GL45 bottles with butyl rubber stoppers and 200 kPa steel mill waste gas. Growth is monitored by measuring the optical density at 600 nm ($OD_{600}$).

The modified PETC medium contains (per liter) 1 g $NH_4Cl$, 0.4 g KCl, 0.2 g $MgSO_4*7\ H_2O$, 0.8 g NaCl, 0.1 g $KH_2PO_4$, 20 mg $CaCl_2*2\ H_2O$, 10 ml trace elements solution (see below), 10 ml Wolfe's vitamin solution (see below), 2 g $NaHCO_3$, and 1 mg resazurin. After the pH is adjusted to 5.6, the medium is boiled, dispensed anaerobically, and autoclaved at 121° C. for 15 min. Steel mill waste gas (composition: 44% CO, 32% $N_2$, 22% $CO_2$, 2% $H_2$) or equivalent synthetic mixtures are used as a carbon source. The media has a final pH of 5.9 and is reduced with cysteine-HCl and $Na_2S$ at a concentration of 0.008% (w/v).

The trace elements solution contains 2 g nitrilotriacetic acid (adjusted to pH 6 with KOH before addition of the remaining ingredients), 1 g $MnSO_4$, 0.8 g $Fe(SO_4)_2$ $(NH_4)_2*6\ H_2O$, 0.2 g $CoCl_2*6\ H_2O$, 0.2 mg $ZnSO_4*7\ H_2O$, 20 mg $CuCl_2*2\ H_2O$, 20 mg $NiCl_2*6\ H_2O$, 20 mg $Na_2MoO_4*2\ H_2O$, 20 mg $Na_2SeO_4$, and 20 mg $Na_2WO_4$ per liter.

Wolfe's vitamin solution (Wolin et al., *J. Biol. Chem.* 238:2882, 1963) contains (per liter) 2 mg biotin, 2 mg folic acid, 10 mg pyridoxine hydrochloride, 5 mg thiamine-HCl, 5 mg riboflavin, 5 mg nicotinic acid, 5 mg calcium D-(+)-pantothenate, 0.1 mg vitamin B12, 5 mg p-aminobenzoic acid, and 5 mg thioctic acid.

a. *Clostridium autoethanogenum* Fermentation

Fermentation of *Clostridium autoethanogenum* is conducted using methods similar to those described in, for example, U.S. Patent Appl. No. 2011/0300593. Briefly, a 2-liter bioreactor containing 1.3 L Solution A (3.083 g $NH_4Ac$; 0.61 g $MgCl_2*6H_2O$; 0.294 g $CaCl_2*2H_2O$; 0.15 g KCl; 0.12 g NaCl (optional); up to 1 L with distilled water) is sparged with $N_2$ gas. An 85% solution of $H_3PO_4$ (2.025 mL, 30 mM) is added and the pH adjusted to 5.3 using concentrated, aqueous $NH_4OH$. Then 13.5 mL Solution B (20.0 mg Biotin; 20.0 mg Folic acid; 10.0 mg pyridoxine HCl; 50.0 mg thiamine*HCl; 50.0 mg Riboflavin; 50.0 mg nicotinic acid; 50.0 mg calcium D-(*)-pantothenate; 50.0 mg vitamin B12; 50.0 mg p-aminobenzoic acid; 50.0 mg thioctic acid; up to 1 L with distilled water) is added and the solution sparged with $N_2$ gas. Chromium (II) chloride is added until the oxidation-reduction potential (ORP) of the solution decreases to approximately −200 mV, wherein resazurin (1.35 mL of a 2 g/L solution) is added. Sodium polysulfide (5.4 mL of a 3M solution, see below) is added and the solution sparged with $N_2$ and then CO containing gas (1% $H_2$; 13% $N_2$; 71% CO; 15% $CO_2$). A metal sulfide solution (150 mL, see below) is added and the solution sparged a further 30 minutes, before inoculation with an actively growing *C. autoethanogenum* culture at a level of approximately 5% (v/v).

The sodium polysulfide solution is prepared in a 500 ml flask that is charged with $Na_2S$ (93.7 g, 0.39 mol) and 200 ml $H_2O$. The solution is stirred until the salt dissolves and sulfur (25 g, 0.1 mol) is added under constant $N_2$ flow. After stirring at room temperature for 2 hours, the sodium polysulfide solution (about 4 M with respect to Na and about 5 M with respect to sulfur), now a clear reddish brown liquid, is transferred into $N_2$ purged serum bottles, and wrapped in aluminum foil.

The chromium (II) solution is prepared in a 1 L three necked flask that is fitted with a gas tight inlet and outlet to allow working under inert gas and subsequent transfer of the desired product into a suitable storage flask. The flask is charged with $CrCl_3*6\ H_2O$ (40 g, 0.15 mol), zinc granules [20 mesh] (18.3 g, 0.28 mol), mercury (13.55 g, 1 mL, 0.0676 mol) and 500 mL distilled water. Following flushing with $N_2$ for one hour, the mixture is warmed to about 80° C. to initiate the reaction. Following two hours of stirring under a constant $N_2$ flow, the mixture is cooled to room temperature and continuously stirred for another 48 hours by which time the reaction mixture turns into a deep blue solution. The solution is transferred into $N_2$ purged serum bottles and stored at 4° C. for future use.

The metal sulfide solution is prepared by adding about 950 mL Solution A into a 1 L fermenter and sparging with $N_2$ gas. An 85% solution of $H_3PO_4$ (1.5 mL, 30 mM) is added and the pH adjusted to 5.3 using concentrated aqueous $NH_4OH$. Solution B (10 mL) is added and the solution sparged with $N_2$. Chromium (II) chloride is added until the oxidation-reduction potential (ORP) of the solution decreases to approximately −200 mV, wherein resazurin (1 mL of a 2 g/L solution) is added. Solution C (⅒; 10 ml $FeCl_3$; 5 ml $CoCl_2$; 5 ml $NiCl_2$; 1 ml $H_3BO_3$; 1 ml $Na_2MoO_4$; 1 ml $MnCl_2$; 1 ml $Na_2WO_4$; 1 ml $ZnCl_2$; 1 ml $Na_2SeO_3$; into 1 L media) is added, then sodium polysulfide (2 mL of a 3M solution) is added, and then the solution is sparged with $N_2$ gas.

Fermentation of a substrate comprising CO by *C. autoethanogenum* under batch conditions in the presence of polysulfide results in a substantially increased rate of accumulation and a final biomass accumulation of approximately 4 g/L over a 2-3 day period. For example, following a short lag phase of approximately 1 day, the biomass can increase from about 0.5 g/L up to at least 3.5 g/L over approximately 36 hours of fermentation. Furthermore, acetate is not produced during the growth phase in the presence of polysulfide (as is typically found in batch fermentations) and in certain circumstances some of the acetate is consumed, such that there is a net decrease in the amount of acetate in the fermenter. Culture biomass was harvested by centrifugation, the cells washed once in media and cell pellets were either frozen at −80° C. or used immediately for fractionation of cellular components.

A semi-continuous fermentation approach can also be applied to maintain biomass productivity and reduce time associated with fermentation shut-down and start-up (i.e., turn-around time or lead time).

Harvesting of the accumulated bacterial biomass was performed at approximately 12-24 hour intervals, as the culture density approached (but before entering) stationary phase. Approximately half of the bioreactor volume was removed by transferring to a separate container via centrifugal pump. An equal volume of fresh or recycled media was then returned to the bioreactor such that the optical density of the reactor was approximately half of its initial value. The bioreactor fermentation was continued according to the above protocol so that multiple cycles of growth and biomass recovery was carried out during a single fermentation run.

b. *Clostridium ljungdahlii* Fermentation

Fermentation of *Clostridium ljungdahlii* is performed using similar methods to those described in, for example, U.S. Pat. Nos. 5,173,429 and 5,593,886. Briefly, batch fermentations are conducted using a biologically pure culture of *C. ljungdahlii*. Preparation of the medium ((1) 80.0 mL of a salt comprising $KH_2PO_4$ 3.00 g/L, $K_2HPO_4$ 3.00 g/L, $(NH_4)_2SO_4$ 6.00 g/L, NaCl 6.00 g/L, $MgSO_4*2H_2O$ 1.25 g/L; (2) 1.0 g of yeast extract; (3) 1.0 g of trypticase; (4) 3.0 ml of PFN (Pfenning) trace metal solution comprising $FeCl_2*4H_2O$ 1500 mg, $ZnSO_4*7H_2O$ 100 mg, $MnCl_2*4H_2O$ 30 mg, $H_3BO_3$ 300 mg, $CoCl_2*6H_2O$ 200 mg, $CuCl_2*H_2O$ 10 mg, $NiCl_2*6H_2O$ 20 mg, $NaMoO_4*2H_2O$ 30 mg, $Na_2SeO_3$ 10 mg, and distilled water up to 1 L; (5) 10.0 ml of B vitamins comprising Pyridoxal HCl 10 mg, Riboflavin 50 mg, Thiamine HCl 50 mg, Nictotinic acid 50 mg, Ca-D-Pantotheinate 50 mg, Lipoic acid 60 mg, p-aminobenzoic acid 50 mg, Folic acid 20 mg, Biotin 20 mg, cyanocobalamin 50 mg, and distilled water up to 1 L; (6) 0.5 g of cysteine HCl; (7) 0.06 g $CaCl_2*2H_2O$; (8) 2.0 g $NaHCO_3$; (9) 1.0 mL resazurin (0.01%); and (10) 920.0 mL distilled water) is carried out anaerobically in an atmosphere of 80% nitrogen and 20% $CO_2$. The pH of the medium is controlled during fermentation and maintained at 5.0 with HCl. If required, adjustments to the pH are made with sterile 10% NaOH or 1.0% acetic acid solution. The medium is transferred to 157.5 mL serum bottles and sealed with butyl rubber stoppers and aluminum seals. The bottles are then autoclaved at 121° C. for 20 minutes.

Approximately 48 hours before commencing the experiment, a seed culture is prepared from a stock culture of the *C. ljungdahlii* in a bottle similar to those as described above. The seed culture is grown in a shaker incubator at 37° C. and shaken at 100 rpm. Reducing solutions (2.0 ml $Na_2S$, 2.5% solution and 2.0 ml cysteine-HCl, 3.5% solution) are added to the culture, which is placed in the shaker incubator for approximately 15 minutes to allow for complete oxygen removal and temperature acclimation. Unlike the procedure used for isolating a biologically pure culture of the organism, addition of methane inhibitors is not required in batch fermentations.

Fermentation with *C. ljungdahlii* is performed in a New Brunswick Scientific Bioflow IIc 2.5-liter fermenter containing nutrient media at 37° C., and a constant fluid level of 1.5 liters is maintained while the fluid is agitated at variable rates of up to 1,000 revolutions per minute with gas introduced at a rate of approximately 500 cubic centimeters per minute. Optimal gas retention times are in the range of three minutes. The gas feed is varied with its uptake by the bacteria, which is in turn a function of the cell density.

Harvesting of the accumulated bacterial biomass was performed at approximately 12-24 hour intervals, as the culture density approached (but before entering) stationary phase. Approximately half of the bioreactor volume was removed by transferring to a separate container via centrifugal pump. An equal volume of fresh or recycled media was then returned to the bioreactor such that the optical density of the reactor was approximately half of its initial value. The bioreactor fermentation was continued according to the above protocol so that multiple cycles of growth and biomass recovery was carried out during a single fermentation run.

Example 2

Stable Carbon Isotope Distribution in Lipids from $C_1$ Metabolizing Microorganisms Dry samples of *M. trichosporium* biomass and lipid fractions were analyzed for carbon and nitrogen content (% dry weight), and carbon ($^{13}C$) and nitrogen ($^{15}N$) stable isotope ratios via elemental analyzer/continuous flow isotope ratio mass spectrometry using a CHNOS Elemental Analyzer (vario ISOTOPE cube, Elementar, Hanau, Germany) coupled with an IsoPrime100 IRMS (Isoprime, Cheadle, UK). Samples of methanotrophic biomass cultured in fermenters or serum bottles were centrifuged, resuspended in deionized water and volumes corresponding to 0.2-2 mg carbon (about 0.5-5 mg dry cell weight) were transferred to 5×9 mm tin capsules (Costech Analytical Technologies, Inc., Valencia, Calif.) and dried at 80° C. for 24 hours. Similarly, previously extracted lipid fractions were suspended in chloroform and volumes containing 0.1-1.5 mg carbon were transferred to tin capsules and evaporated to dryness at 80° C. for 24 hours. Standards containing 0.1 mg carbon provided reliable $\delta^{13}C$ values.

The isotope ratio is expressed in "delta" notation (‰), wherein the isotopic composition of a material relative to that of a standard on a per million deviation basis is given by $\delta^{13}C$ (or $\delta^{15}N$)=$(R_{sample}/R_{standard-1}) \times 1{,}000$, wherein R is the molecular ratio of heavy to light isotope forms. The standard for carbon is the Vienna Pee Dee Belemnite (V-PDB) and for nitrogen is air. The NIST (National Institute of Standards and Technology) proposed SRM (Standard Reference Material) No. 1547, peach leaves, was used as a calibration standard. All isotope analyses were conducted at the Center for Stable Isotope Biogeochemistry at the University of California, Berkeley. Long-term external precision for C and N isotope analyses is 0.10‰ and 0.15‰, respectively.

*M. trichosporium* strain OB3b was grown on methane in three different fermentation batches, *M. capsulatus* Bath was grown on methane in two different fermentation batches, and *Methylomonas* sp. 16a was grown on methane in a single fermentation batch. The biomass from each of these cultures was analyzed for stable carbon isotope distribution ($\delta^{13}C$ values; see Table 3).

TABLE 3

Stable Carbon Isotope Distribution in Different Methanotrophs

| Methanotroph | Batch No. | EFT (h)† | OD$_{600}$ | DCW* | $\delta^{13}C$ Cells |
|---|---|---|---|---|---|
| Mt OB3b | 68A | 48 | 1.80 | 1.00 | −57.9 |
| | | 64 | 1.97 | 1.10 | −57.8 |
| | | 71 | 2.10 | 1.17 | −58.0 |
| | | 88 | 3.10 | 1.73 | −58.1 |
| | | 97 | 4.30 | 2.40 | −57.8 |
| | | 113 | 6.00 | 3.35 | −57.0 |
| | | 127 | 8.40 | 4.69 | −56.3 |
| Mt OB3b | 68B | 32 | 2.90 | 1.62 | −58.3 |
| | | 41 | 4.60 | 2.57 | −58.4 |
| | | 47 | 5.89 | 3.29 | −58.0 |
| | | 56 | 7.90 | 4.41 | −57.5 |
| Mt OB3b | 68C | 72 | 5.32 | 2.97 | −57.9 |
| | | 79.5 | 5.90 | 3.29 | −58.0 |
| | | 88 | 5.60 | 3.12 | −57.8 |
| | | 94 | 5.62 | 3.14 | −57.7 |
| Mc Bath | 62B | 10 | 2.47 | 0.88 | −59.9 |
| | | 17.5 | 5.80 | 2.06 | −61.0 |
| | | 20 | 7.32 | 2.60 | −61.1 |
| | | 23 | 9.34 | 3.32 | −60.8 |
| | | 26 | 10.30 | 3.66 | −60.1 |
| Mc Bath | 62A | 10 | 2.95 | 1.05 | −55.9 |
| | | 13.5 | 3.59 | 1.27 | −56.8 |
| | | 17.5 | 5.40 | 1.92 | −55.2 |
| | | 23 | 6.08 | 2.16 | −57.2 |
| | | 26 | 6.26 | 2.22 | −57.6 |
| Mms 16a | 66B | 16 | 2.13 | 0.89 | −65.5 |
| | | 18 | 2.59 | 1.09 | −65.1 |
| | | 20.3 | 3.62 | 1.52 | −65.5 |
| | | 27 | 5.50 | 2.31 | −66.2 |
| | | 40.5 | 9.80 | 4.12 | −66.3 |

*DCW, Dry Cell Weight is reported in g/L calculated from the measured optical densities (OD$_{600}$) using specific correlation factors relating OD of 1.0 to 0.558 g/L for Mt OB3b, OD of 1.0 to 0.355 g/L for Mc Bath, and OD of 1.0 to 0.42 g/L for Mms 16a. For Mt OB3b, the initial concentration of bicarbonate used per fermentation was 1.2 mM or 0.01% (Batch No. 68C) and 0.1% or 12 mM (Batch Nos. 68A and 68B).
†EFT = effective fermentation time in hours In addition, stable carbon isotope analysis was performed for biomass and corresponding lipid fractions (see Table 4) from strains *Methylosinus trichosporium* OB3b (Mt OB3b), *Methylococcus capsulatus* Bath (Mc Bath), and *Methylomonas* sp. 16a (Mms 16a) grown on methane in bioreactors as described in Example 1.

TABLE 4

Stable Carbon Isotope Distribution in Cells and Lipids

| Batch No. | Strain | $\delta^{13}C$ Cells | $\delta^{13}C$ Lipids |
|---|---|---|---|
| 68C | Mt OB3b | −57.7 | −48.6 |
| 62A | Mc Bath | −57.6 | −52.8 |
| 66A | Mms 16a | −64.4 | −42.2 |

Biomass from strains Mt OB3b, Mc Bath and Mms 16a were harvested at 94 h (3.14 g DCW/L), 26 h (2.2 g DCW/L) and 39 h (1.14 g DCW/L), respectively. The $\delta^{13}C$ values for lipids in Table 4 represent an average of duplicate determinations.

Example 3

Effect of Methane Source and Purity on Stable Carbon Isotope Distribution in Lipids To examine methanotroph growth on methane containing natural gas components, a series of 0.5-liter serum bottles containing 100 mL defined media MMS 1.0 were inoculated with *Methylosinus trichosporium* OB3b or *Methylococcus capsulatus* Bath from a serum bottle batch culture (5% v/v) grown in the same media supplied with a 1:1 (v/v) mixture of methane and air. The composition of medium MMS 1.0 was as follows: 0.8 mM MgSO$_4$*7H$_2$O, 30 mM NaNO$_3$, 0.14 mM CaCl$_2$, 1.2 mM NaHCO$_3$, 2.35 mM KH$_2$PO$_4$, 3.4 mM K$_2$HPO$_4$, 20.7 µM Na$_2$MoO$_4$*2H$_2$O, 611M CuSO$_4$*5H$_2$O, 10 µM Fe$^{III}$—Na-EDTA, and 1 mL per liter of a trace metals solution (containing, per L: 500 mg FeSO$_4$*7H$_2$O, 400 mg ZnSO$_4$*7H$_2$O, 20 mg MnCl$_2$*7H2O, 50 mg CoCl$_2$*6H$_2$O, 10 mg NiCl$_2$*6H$_2$O, 15 mg H$_3$BO$_3$, 250 mg EDTA). Phosphate, bicarbonate, and Fe$^{III}$—Na-EDTA were added after media was autoclaved and cooled. The final pH of the media was 7.0±0.1.

The inoculated bottles were sealed with rubber sleeve stoppers and injected with 60 mL methane gas added via syringe through sterile 0.45 µm filter and sterile 27 G needles. Duplicate cultures were each injected with 60 mL volumes of (A) methane of 99% purity (grade 2.0, Praxair through Alliance Gas, San Carlos, Calif.), (B) methane of 70% purity representing a natural gas standard (Sigma-Aldrich; also containing 9% ethane, 6% propane, 3% methylpropane, 3% butane, and other minor hydrocarbon components), (C) methane of 85% purity delivered as a 1:1 mixture of methane sources A and B; and (D) >93% methane (grade 1.3, Specialty Chemical Products, South Houston, Tex.; in-house analysis showed composition >99% methane). The cultures were incubated at 30° C. (*M. trichosporium* strain OB3b) or 42° C. (*M. capsulatus* Bath) with rotary shaking at 250 rpm and growth was measured at approximately 12 hour intervals by withdrawing 1 mL samples to determine OD$_{600}$. At these times, the bottles were vented and headspace replaced with 60 mL of the respective methane source (A, B, C, or D) and 60 mL of concentrated oxygen (at least 85% purity). At about 24 hour intervals, 5 mL samples were removed, cells recovered by centrifugation (8,000 rpm, 10 minutes), and then stored at −80° C. before analysis.

Analysis of carbon and nitrogen content (% dry weight), and carbon ($^{13}C$) and nitrogen ($^{15}N$) stable isotope ratios, for methanotrophic biomass derived from *M. trichosporium* strain OB3b and *M. capsulatus* Bath were carried out. Table 5 shows the results of stable carbon isotope analysis for biomass samples from *M. capsulatus* Bath grown on methane having different levels of purity and in various batches of bottle cultures.

TABLE 5

Stable Carbon Isotope Distribution of *M. capsulatus* Bath Grown on Different Methane Sources having Different Purity

| Methane* | Batch No. | Time (h)† | OD$_{600}$ | DCW (g/L) | $\delta^{13}C$ Cells |
|---|---|---|---|---|---|
| A | 62C | 22 | 1.02 | 0.36 | −40.3 |
| | | 56 | 2.01 | 0.71 | −41.7 |
| | | 73 | 2.31 | 0.82 | −42.5 |

TABLE 5-continued

Stable Carbon Isotope Distribution of *M. capsulatus* Bath Grown on Different Methane Sources having Different Purity

| Methane* | Batch No. | Time (h)† | $OD_{600}$ | DCW (g/L) | $\delta^{13}C$ Cells |
|---|---|---|---|---|---|
|   | 62D | 22 | 1.14 | 0.40 | −39.3 |
|   |     | 56 | 2.07 | 0.73 | −41.6 |
|   |     | 73 | 2.39 | 0.85 | −42.0 |
| B | 62E | 22 | 0.47 | 0.17 | −44.7 |
|   |     | 56 | 0.49 | 0.17 | −45.4 |
|   |     | 73 | 0.29 | 0.10 | −45.4 |
|   | 62F | 22 | 0.62 | 0.22 | −42.3 |
|   |     | 56 | 0.63 | 0.22 | −43.6 |
|   |     | 73 | 0.30 | 0.11 | −43.7 |
| C | 62G | 22 | 0.70 | 0.25 | −40.7 |
|   |     | 56 | 1.14 | 0.40 | −44.8 |
|   |     | 73 | 1.36 | 0.48 | −45.8 |
|   | 62H | 22 | 0.62 | 0.22 | −40.9 |
|   |     | 56 | 1.03 | 0.37 | −44.7 |
|   |     | 73 | 1.23 | 0.44 | −45.9 |

*Methane purity: A: 99% methane, grade 2.0 (min. 99%); B: 70% methane, natural gas standard (contains 9% ethane, 6% propane, 3% methylpropane, 3% butane); C: 85% methane (1:1 mix of A and B methane)
†Time = bottle culture time in hours The average $\delta^{13}C$ for *M. capsulatus* Bath grown on one source of methane (A, 99%) was −41.2±1.2, while the average $\delta^{13}C$ for *M. capsulatus* Bath grown on a different source of methane (B, 70%) was −44.2±1.2. When methane sources A and B were mixed, an intermediate average $\delta^{13}C$ of −43.8±2.4 was observed. These data show that the $\delta^{13}C$ of cell material grown on methane sources A and B are significantly different from each other due to the differences in the $\delta^{13}C$ of the input methane. But, cells grown on a mixture of the two gasses preferentially utilize $^{12}C$ and, therefore, show a trend to more negative $\delta^{13}C$ values.

A similar experiment was performed to examine whether two different methanotrophs, *Methylococcus capsulatus* Bath and *Methylosinus trichosporium* OB3b, grown on different methane sources and in various batches of bottle cultures showed a difference in $\delta^{13}C$ distribution (see Table 6).

TABLE 6

Stable Carbon Isotope Distribution of Different Methanotrophs Grown on Different Methane Sources of Different Purity

| Strain | Methane* | Batch No. | Time (h)† | $OD_{600}$ | DCW (g/L) | $\delta^{13}C$ Cells |
|---|---|---|---|---|---|---|
| Mc Bath | A | 62I | 18 | 0.494 | 0.18 | −54.3 |
|         |   |     | 40 | 2.33  | 0.83 | −42.1 |
|         |   |     | 48 | 3.08  | 1.09 | −37.1 |
| Mc Bath | D | 62J | 18 | 0.592 | 0.21 | −38.3 |
|         |   |     | 40 | 1.93  | 0.69 | −37.8 |
|         |   |     | 48 | 2.5   | 0.89 | −37.8 |
| Mc Bath | D | 62K | 18 | 0.564 | 0.20 | −38.6 |
|         |   |     | 40 | 1.53  | 0.54 | −37.5 |
|         |   |     | 48 | 2.19  | 0.78 | −37.6 |
| Mt OB3b | A | 68D | 118 | 0.422 | 0.24 | −50.2 |
|         |   |     | 137 | 0.99  | 0.55 | −47.7 |
|         |   |     | 162 | 1.43  | 0.80 | −45.9 |
| Mt OB3b | A | 68E | 118 | 0.474 | 0.26 | −49.9 |
|         |   |     | 137 | 1.065 | 0.59 | −47.6 |
|         |   |     | 162 | 1.51  | 0.84 | −45.2 |
| Mt OB3b | D | 68F | 118 | 0.534 | 0.30 | −45.6 |
|         |   |     | 137 | 1.119 | 0.62 | −38.7 |
|         |   |     | 162 | 1.63  | 0.91 | −36.4 |
| Mt OB3b | D | 68G | 118 | 0.544 | 0.30 | −44.8 |
|         |   |     | 137 | 1.131 | 0.63 | −39.1 |
|         |   |     | 162 | 1.6   | 0.89 | −34.2 |

*Methane sources and purity: A: 99% methane (grade 2.0); D: >93% methane (grade 1.3)
†Time = bottle culture time in hours The average $\delta^{13}C$ for *M. capsulatus* grown on a first methane source (A) was −44.5±8.8, while the average $\delta^{13}C$ for *M. trichosporium* was −47.8±2.0 grown on the same methane source. The average $\delta^{13}C$ for *M. capsulatus* grown on the second methane source (B) was −37.9±0.4, while the average $\delta^{13}C$ for *M. trichosporium* was −39.8±4.5. These data show that the $\delta^{13}C$ of cell material grown on a methane source is highly similar to the $\delta^{13}C$ of cell material from a different strain grown on the same source of methane. Thus, the observed $\delta^{13}C$ of cell material appears to be primarily dependent on the composition of the input gas rather than a property of a particular bacterial strain being studied.

The various embodiments described above can be combined to provide further embodiments. All of the patent and non-patent publications referred to in this specification or listed in the Application Data Sheet, including the disclosure of U.S. provisional application No. 61/928,366, filed Jan. 16, 2014, are incorporated herein by reference in their entirety. Aspects of the embodiments can be modified, if necessary to employ concepts of the various patents, applications and publications to provide further embodiments.

These and other changes can be made to the embodiments in light of the above-detailed description. In general, in the following embodiments, the terms used should not be construed to limit the embodiments to the specific embodiments disclosed in the specification and the embodiments, but should be construed to include all possible embodiments along with the full scope of equivalents to which such embodiments are entitled. Accordingly, the embodiments are not limited by the disclosure.

What is claimed is:

1. A recombinant methanotrophic bacterium, comprising an exogenous nucleic acid that encodes a glucan synthase, wherein the recombinant methanotrophic bacterium is capable of producing glucan at a level that is greater than that produced by the parent methanotrophic bacterium; and
wherein the methanotrophic bacterium is selected from the group consisting of *Methylomonas, Methylobacter, Methylococcus, Methylosinus, Methylocystis, Methylomicrobium, Methanomonas,* and *Methylocella*.

2. The recombinant $C_1$ metabolizing microorganism of claim 1, wherein the $C_1$ substrate feedstock comprises natural gas or methane.

3. The recombinant methanotrophic bacterium of claim 1, wherein the methanotrophic bacterium is an obligate methanotrophic bacterium or a facultative methanotrophic bacterium.

4. The recombinant methanotrophic bacterium of claim 1, wherein the glucan produced is a β-glucan.

5. The recombinant methanotrophic bacterium of claim 4, wherein the β-glucan is selected from the group consisting of a β-(1,3)-glucan, a (β-(1,3)(1,6)-glucan, a β-(1,3)(1,4)-glucan, a β-(1,4)-glucan, and a β-(1,6)-glucan.

6. The recombinant methanotrophic bacterium of claim 1, wherein the encoded exogenous glucan synthase comprises a β-1,3-glucan synthase.

7. The recombinant methanotrophic bacterium of claim 1, wherein the exogenous nucleic acid encoding the glucan synthase is endogenous to an organism selected from the group consisting of a bacteria, a yeast, a fungi, and a plant.

8. The recombinant methanotrophic bacterium of claim 1, wherein the exogenous nucleic acid encoding the glucan synthase is endogenous to *Escherichia coli* or *Corynebacterium glutamicum*.

9. The recombinant methanotrophic bacterium of claim 1, wherein the exogenous nucleic acid encodes a glucan synthase that comprises a nucleic acid sequence having at least 85% sequence identity to a nucleic acid reference sequence selected from the group consisting of SEQ ID NOs:1, 3, 5, 7, 9, 11, 13, 15, 17, 19, 21, 23, and 25.

10. The recombinant methanotrophic bacterium of claim 1, wherein the exogenous nucleic acid encodes a glucan synthase having an amino acid sequence that has at least 90% sequence identity to a reference sequence selected from the group consisting of SEQ ID NOs:2, 4, 6, 8, 10, 12, 14, 16, 18, 20, 22, 24, and 26.

11. The recombinant methanotrophic bacterium of claim 1, wherein the exogenous nucleic acid comprises an expression control sequence that is operably linked to the nucleic acid encoding the glucan synthase.

12. The recombinant methanotrophic bacterium of claim 1, wherein the exogenous nucleic acid is codon optimized for the methanotrophic bacterium.

13. The recombinant methanotrophic bacterium of claim 1, wherein the methanotrophic bacterium further comprises an exogenous polynucleotide encoding one or more gluconeogenesis enzymes selected from the group consisting of a pyruvate carboxylase, a phosphoenolpyruvate carboxykinase, an enolase, a phosphoglycerate mutase, a phosphoglycerate kinase, a glyceraldehyde-3-phosphate dehydrogenase, a Type A aldolase, a fructose 1,6-bisphosphatase, a phosphofructokinase, a phosphoglucose isomerase, a hexokinase, and a glucose-6-phosphate.

14. The recombinant methanotrophic bacterium of claim 13, wherein the further exogenous polynucleotide encoding one or more gluconeogenesis enzymes comprises an expression control sequence that is operably linked to the polynucleotide encoding the one or more gluconeogenesis enzymes, wherein the one or more gluconeogenesis enzymes are heterologous gluconeogenesis enzymes, native gluconeogenesis enzymes, or a combination thereof.

15. The recombinant methanotrophic bacterium of claim 1, wherein the carbohydrates of the recombinant methanotrophic bacterium exhibits a $\delta^{13}C$ that is less than −30‰ or is less than −40‰.

16. The recombinant methanotrophic bacterium of claim 1, wherein the methanotrophic bacterium is selected from the group consisting of *Methylococcus capsulatus* Bath, *Methylomonas* sp. 16a, *Methylosinus trichosporium* OB3b, *Methylosinus sporium, Methylocystis parvus, Methylomonas methanica, Methylomonas albus, Methylobacter capsulatus* Y, *Methylomonas flagellata* AJ-3670, *Methylacidiphilum infernorum, Methylacidiphdum fumariolicum, Methylomicrobium alcaliphilum,* and *Methyloacida kamchatkensis*.

17. A biomass derived from whole and/or lysed cells of the recombinant methanotrophic bacterium of claim 1.

18. The biomass of claim 17, wherein the biomass exhibits a $\delta^{13}C$ that is less than −30‰ or is less than −40‰.

19. A carbohydrate composition, comprising carbohydrates extracted from a biomass derived from the methanotrophic bacterium of claim 1, wherein the composition exhibits a $\delta^{13}C$ that is less than −30‰ or is less than −40‰.

20. An animal feed, comprising the recombinant methanotrophic bacterium of claim 1, a biomass derived from whole and/or lysed cells of the recombinant methanotrophic bacterium of claim 1, or a carbohydrate composition comprising carbohydrates extracted from a biomass derived from the recombinant methanotrophic bacterium of claim 1.

21. The animal feed of claim 20, further comprising an additive selected from the group consisting of a plant-derived material, an animal-derived material, and a microorganism-derived material.

22. The animal feed of claim 21, wherein the additive is microorganism-derived material that is derived from a microorganism heterologous to the methanotrophic bacterium.

23. The animal feed of claim 21, wherein the additive is a plant-derived material that is derived from corn, soybean meal or pea protein.

24. The animal feed of claim 21, wherein the additive is an animal-derived material that is fish meal.

25. A method of producing a desired carbohydrate, the method comprising culturing the recombinant methanotrophic bacterium of claim 1 in the presence of a $C_1$ substrate feedstock comprising methane under conditions sufficient to produce the glucan.

26. The method of claim 25, wherein the $C_1$ substrate feedstock comprises natural gas.

27. The method of claim 25, wherein the methanotrophic bacterium is selected from the group consisting of *Methylococcus capsulatus* Bath, *Methylomonas* sp. 16a, *Methylosinus trichosporium* OB3b, *Methylosinus sporium, Methylocystis parvus, Methylomonas methanica, Methylomonas albus, Methylobacter capsulatus* Y, *Methylomonas flagellata* AJ-3670, *Methylacidiphilum infernorum, Methylacidiphilum fumariolicum, Methylomicrobium alcaliphilum*, and *Methyloacida kamchatkensis*.

\* \* \* \* \*

SEQUENCE LISTING

```
<160> NUMBER OF SEQ ID NOS: 38

<210> SEQ ID NO 1
<211> LENGTH: 852
<212> TYPE: DNA
<213> ORGANISM: Artificial sequence
<220> FEATURE:
<223> OTHER INFORMATION: Synthetic construct
```

<220> FEATURE:
<221> NAME/KEY: CDS
<222> LOCATION: (1)..(852)
<223> OTHER INFORMATION: Saccharomyces cerevisiae mature KRE1 protein
      (codon optimized)

<400> SEQUENCE: 1

| | | | | | | | | | | | | | | | | |
|---|---|---|---|---|---|---|---|---|---|---|---|---|---|---|---|---|
| gtc | atg | gcc | gct | gtt | acc | acc | caa | gtc | acc | gtc | gtc | acc | aat | gtt | gct | 48 |
| Val | Met | Ala | Ala | Val | Thr | Thr | Gln | Val | Thr | Val | Val | Thr | Asn | Val | Ala | |
| 1 | | | | 5 | | | | | 10 | | | | | 15 | | |

| gga | gcc | ctt | gtc | acc | gaa | acc | acc | atc | tgg | gac | ccc | gcg | acc | gcc | gca | 96 |
| Gly | Ala | Leu | Val | Thr | Glu | Thr | Thr | Ile | Trp | Asp | Pro | Ala | Thr | Ala | Ala | |
| | | | 20 | | | | | 25 | | | | | 30 | | | |

| gcc | gca | gcg | acg | acc | acc | gcc | cag | acg | ggc | ttc | ttc | acc | acc | gtg | ttc | 144 |
| Ala | Ala | Ala | Thr | Thr | Thr | Ala | Gln | Thr | Gly | Phe | Phe | Thr | Thr | Val | Phe | |
| | | 35 | | | | | 40 | | | | | 45 | | | | |

| acg | acc | acc | aac | gac | gtg | ggt | acc | act | gtc | acg | ctg | acg | cag | acc | gtg | 192 |
| Thr | Thr | Thr | Asn | Asp | Val | Gly | Thr | Thr | Val | Thr | Leu | Thr | Gln | Thr | Val | |
| | 50 | | | | | 55 | | | | | 60 | | | | | |

| aat | cgc | gcc | acg | atg | ctg | ccc | act | acc | acg | acg | agc | acc | agc | agc | acc | 240 |
| Asn | Arg | Ala | Thr | Met | Leu | Pro | Thr | Thr | Thr | Thr | Ser | Thr | Ser | Ser | Thr | |
| 65 | | | | 70 | | | | | 75 | | | | | 80 | | |

| ggc | aag | acc | acc | acg | acg | gtg | ccg | act | gcg | acg | tcc | tcg | ctc | agt | tcg | 288 |
| Gly | Lys | Thr | Thr | Thr | Thr | Val | Pro | Thr | Ala | Thr | Ser | Ser | Leu | Ser | Ser | |
| | | | | 85 | | | | | 90 | | | | | 95 | | |

| ggc | ctg | tcg | acc | gtc | acc | acc | acg | aac | gac | ctg | ggc | acg | acc | gtg | acg | 336 |
| Gly | Leu | Ser | Thr | Val | Thr | Thr | Thr | Asn | Asp | Leu | Gly | Thr | Thr | Val | Thr | |
| | | | 100 | | | | | 105 | | | | | 110 | | | |

| ctc | acc | cag | acc | ttc | acg | cac | tcc | tcc | acg | tcc | gcg | acc | tcc | tcg | gcc | 384 |
| Leu | Thr | Gln | Thr | Phe | Thr | His | Ser | Ser | Thr | Ser | Ala | Thr | Ser | Ser | Ala | |
| | | 115 | | | | | 120 | | | | | 125 | | | | |

| tcc | tcg | tcg | gtg | agc | tcg | tcc | gtc | agt | agc | agt | ggc | tcc | tcc | agc | agc | 432 |
| Ser | Ser | Ser | Val | Ser | Ser | Val | Ser | Ser | Ser | Gly | Ser | Ser | Ser | Ser | Ser | |
| | 130 | | | | | 135 | | | | | 140 | | | | | |

| gtc | aag | acc | acg | acc | tcg | acc | ggc | tcc | gcg | gtg | gcg | gaa | acc | ggg | tgg | 480 |
| Val | Lys | Thr | Thr | Thr | Ser | Thr | Gly | Ser | Ala | Val | Ala | Glu | Thr | Gly | Trp | |
| 145 | | | | 150 | | | | | 155 | | | | | 160 | | |

| gac | ccg | agc | acg | gat | ttt | acc | gag | ccg | cca | gtg | agc | gcg | gtc | acc | agc | 528 |
| Asp | Pro | Ser | Thr | Asp | Phe | Thr | Glu | Pro | Pro | Val | Ser | Ala | Val | Thr | Ser | |
| | | | | 165 | | | | | 170 | | | | | 175 | | |

| ctc | tcg | atc | gac | tcg | tat | ata | acg | atc | acc | gag | ggc | acc | acc | tcg | acc | 576 |
| Leu | Ser | Ile | Asp | Ser | Tyr | Ile | Thr | Ile | Thr | Glu | Gly | Thr | Thr | Ser | Thr | |
| | | | 180 | | | | | 185 | | | | | 190 | | | |

| tac | act | acc | acc | cgg | gcg | ccg | acc | tcg | atg | tgg | gtg | acc | gtc | gtc | cgc | 624 |
| Tyr | Thr | Thr | Thr | Arg | Ala | Pro | Thr | Ser | Met | Trp | Val | Thr | Val | Val | Arg | |
| | | 195 | | | | | 200 | | | | | 205 | | | | |

| cag | ggg | aac | acg | atc | acc | gtg | caa | acc | acc | ttc | gtc | cag | cgc | ttc | agc | 672 |
| Gln | Gly | Asn | Thr | Ile | Thr | Val | Gln | Thr | Thr | Phe | Val | Gln | Arg | Phe | Ser | |
| | 210 | | | | | 215 | | | | | 220 | | | | | |

| tcc | caa | tac | gtg | acc | gtg | gat | tcc | gtc | ggc | agc | atc | ggc | atg | ggt | acg | 720 |
| Ser | Gln | Tyr | Val | Thr | Val | Asp | Ser | Val | Gly | Ser | Ile | Gly | Met | Gly | Thr | |
| 225 | | | | 230 | | | | | 235 | | | | | 240 | | |

| ctg | acc | ggt | acc | gtc | ggc | gtg | atc | aag | tcc | gcc | atc | aag | aaa | acc | gtg | 768 |
| Leu | Thr | Gly | Thr | Val | Gly | Val | Ile | Lys | Ser | Ala | Ile | Lys | Lys | Thr | Val | |
| | | | | 245 | | | | | 250 | | | | | 255 | | |

| tcc | cat | aac | gag | gcc | cag | cat | ctc | ggc | atg | tcg | tcg | ttc | acg | tcg | att | 816 |
| Ser | His | Asn | Glu | Ala | Gln | His | Leu | Gly | Met | Ser | Ser | Phe | Thr | Ser | Ile | |
| | | | 260 | | | | | 265 | | | | | 270 | | | |

| ctg | ggt | ggc | ctc | ctc | acg | gtc | ttg | atc | tgg | ttc | ctg | | | | | 852 |
| Leu | Gly | Gly | Leu | Leu | Thr | Val | Leu | Ile | Trp | Phe | Leu | | | | | |
| | | 275 | | | | | 280 | | | | | | | | | |

<210> SEQ ID NO 2
<211> LENGTH: 284
<212> TYPE: PRT
<213> ORGANISM: Artificial sequence
<220> FEATURE:
<223> OTHER INFORMATION: Synthetic Construct

<400> SEQUENCE: 2

```
Val Met Ala Ala Val Thr Thr Gln Val Thr Val Thr Asn Val Ala
1               5                   10                  15

Gly Ala Leu Val Thr Glu Thr Thr Ile Trp Asp Pro Ala Thr Ala Ala
            20                  25                  30

Ala Ala Ala Thr Thr Thr Ala Gln Thr Gly Phe Phe Thr Thr Val Phe
        35                  40                  45

Thr Thr Thr Asn Asp Val Gly Thr Thr Val Thr Leu Thr Gln Thr Val
    50                  55                  60

Asn Arg Ala Thr Met Leu Pro Thr Thr Thr Thr Ser Thr Ser Ser Thr
65                  70                  75                  80

Gly Lys Thr Thr Thr Thr Val Pro Thr Ala Thr Ser Ser Leu Ser Ser
                85                  90                  95

Gly Leu Ser Thr Val Thr Thr Thr Asn Asp Leu Gly Thr Thr Val Thr
            100                 105                 110

Leu Thr Gln Thr Phe Thr His Ser Ser Thr Ser Ala Thr Ser Ser Ala
        115                 120                 125

Ser Ser Ser Val Ser Ser Ser Val Ser Ser Ser Gly Ser Ser Ser Ser
    130                 135                 140

Val Lys Thr Thr Thr Ser Thr Gly Ser Ala Val Ala Glu Thr Gly Trp
145                 150                 155                 160

Asp Pro Ser Thr Asp Phe Thr Glu Pro Pro Val Ser Ala Val Thr Ser
                165                 170                 175

Leu Ser Ile Asp Ser Tyr Ile Thr Ile Thr Glu Gly Thr Thr Ser Thr
            180                 185                 190

Tyr Thr Thr Thr Arg Ala Pro Thr Ser Met Trp Val Thr Val Val Arg
        195                 200                 205

Gln Gly Asn Thr Ile Thr Val Gln Thr Thr Phe Val Gln Arg Phe Ser
    210                 215                 220

Ser Gln Tyr Val Thr Val Asp Ser Val Gly Ser Ile Gly Met Gly Thr
225                 230                 235                 240

Leu Thr Gly Thr Val Gly Val Ile Lys Ser Ala Ile Lys Lys Thr Val
                245                 250                 255

Ser His Asn Glu Ala Gln His Leu Gly Met Ser Ser Phe Thr Ser Ile
            260                 265                 270

Leu Gly Gly Leu Leu Thr Val Leu Ile Trp Phe Leu
        275                 280
```

<210> SEQ ID NO 3
<211> LENGTH: 4065
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(4065)
<223> OTHER INFORMATION: Saccharomyces cerevisiae mature KRE2 protein (codon optimized)

<400> SEQUENCE: 3

```
atg cgc ctt ctt gcc ctt gtc ttg ttg ctt ctc tgt gca ccg ctt cgc        48
Met Arg Leu Leu Ala Leu Val Leu Leu Leu Leu Cys Ala Pro Leu Arg
1               5                   10                  15 gcc tgg acc tat tcg ctc cgc tat ggt atc ccc gag tcc gcc cag gtg        96
Ala Trp Thr Tyr Ser Leu Arg Tyr Gly Ile Pro Glu Ser Ala Gln Val
                20                  25                  30 tgg tcg atc ctc gtt cat ctg ctc ggc gac gtg gac aac caa ctc ctt       144
Trp Ser Ile Leu Val His Leu Leu Gly Asp Val Asp Asn Gln Leu Leu
            35                  40                  45 act aac ctg tat ccc ctg gtc acc ggg ctc gac gat gag atc gac atc       192
Thr Asn Leu Tyr Pro Leu Val Thr Gly Leu Asp Asp Glu Ile Asp Ile
        50                  55                  60 cag gag aac ctc gtt acg tcc aac gtg ctg cgc gag cgc tac gat aaa       240
Gln Glu Asn Leu Val Thr Ser Asn Val Leu Arg Glu Arg Tyr Asp Lys
65                  70                  75                  80 gag gac gtc gcg gat ctg ctg gaa ctc tac gca tcg ctc tac ccc atg       288
Glu Asp Val Ala Asp Leu Leu Glu Leu Tyr Ala Ser Leu Tyr Pro Met
                85                  90                  95 ggg atg atc caa cac gac atc tcg tcg aat gcc gag caa gac gac gcg       336
Gly Met Ile Gln His Asp Ile Ser Ser Asn Ala Glu Gln Asp Asp Ala
            100                 105                 110 aat tcc tcc tat ttc gtc ctg aac ggc aat cgg tat gag aaa ccc gac       384
Asn Ser Ser Tyr Phe Val Leu Asn Gly Asn Arg Tyr Glu Lys Pro Asp
        115                 120                 125 gac gtc ttt tac ctg aag tcg aag gac ctg acc atc cag cag aaa gtg       432
Asp Val Phe Tyr Leu Lys Ser Lys Asp Leu Thr Ile Gln Gln Lys Val
130                 135                 140 ccc gat gtc gac gtc atc caa ccg tac gac gtc gtg att gga acc aac       480
Pro Asp Val Asp Val Ile Gln Pro Tyr Asp Val Val Ile Gly Thr Asn
145                 150                 155                 160 tcc gag gcg ccc ata ctg atc ctc tac ggc tgc ccg acc gtc atc gac       528
Ser Glu Ala Pro Ile Leu Ile Leu Tyr Gly Cys Pro Thr Val Ile Asp
                165                 170                 175 agc gac ttc gag gag ttc aat cgg aat ctc ttc atg gag gct atg aac       576
Ser Asp Phe Glu Glu Phe Asn Arg Asn Leu Phe Met Glu Ala Met Asn
            180                 185                 190 ggc gag ggc aag ttc cgc ttc att tgg cgg agc acg tgt agc ctg gac       624
Gly Glu Gly Lys Phe Arg Phe Ile Trp Arg Ser Thr Cys Ser Leu Asp
        195                 200                 205 ggc aag tcc gtg gag tac ccg ctg acc cac ccc ctg gag atc acc ctg       672
Gly Lys Ser Val Glu Tyr Pro Leu Thr His Pro Leu Glu Ile Thr Leu
    210                 215                 220 cag aac ggc agc cgc atg tcc tcc atc cct cag ctc aag aag atc ctg       720
Gln Asn Gly Ser Arg Met Ser Ser Ile Pro Gln Leu Lys Lys Ile Leu
225                 230                 235                 240 tac acc gtt ccg aaa gaa atc ctc gtg ggc gca gat aac gac gac cag       768
Tyr Thr Val Pro Lys Glu Ile Leu Val Gly Ala Asp Asn Asp Asp Gln
                245                 250                 255 ctg cac gac ctg gag ccc gag gag ctg cgc gag ctg gac ctc cgc gtg       816
Leu His Asp Leu Glu Pro Glu Glu Leu Arg Glu Leu Asp Leu Arg Val
            260                 265                 270 acc tcg ctc att tcc gag ttc tat cag tat aag aaa gac att acg gcc       864
Thr Ser Leu Ile Ser Glu Phe Tyr Gln Tyr Lys Lys Asp Ile Thr Ala
        275                 280                 285 acc ctg aat ttc acc aaa agt atc gtc aac aat ttc ccg ctg att tcg       912
Thr Leu Asn Phe Thr Lys Ser Ile Val Asn Asn Phe Pro Leu Ile Ser
    290                 295                 300 aag cag ctg atc aag gtt tcg tcg gtc aat aaa gac atc atc acc tcc       960
Lys Gln Leu Ile Lys Val Ser Ser Val Asn Lys Asp Ile Ile Thr Ser
```

-continued

| | |
|---|---|
| aac gag gag ttg aat tcc aag ggc ttc gac tac aac atg ctg ggc atc<br>Asn Glu Glu Leu Asn Ser Lys Gly Phe Asp Tyr Asn Met Leu Gly Ile<br>325 330 335 | 1008 |
| aac ggc cag aac tgg aag atc acc tcc ctg acg ccc tac aat ctt ctc<br>Asn Gly Gln Asn Trp Lys Ile Thr Ser Leu Thr Pro Tyr Asn Leu Leu<br>340 345 350 | 1056 |
| acg gcc ctg aaa acg gag tac cag agt ctg ctg aag atc acc aac ctc<br>Thr Ala Leu Lys Thr Glu Tyr Gln Ser Leu Leu Lys Ile Thr Asn Leu<br>355 360 365 | 1104 |
| ctc cag gag ctg gag ccc tcc aag tgc atc ctc gac tcc aag ttc ctg<br>Leu Gln Glu Leu Glu Pro Ser Lys Cys Ile Leu Asp Ser Lys Phe Leu<br>370 375 380 | 1152 |
| ctc aat aag ttc tcg cag ttc agc ctg ggt aaa ctg cag aat ctg caa<br>Leu Asn Lys Phe Ser Gln Phe Ser Leu Gly Lys Leu Gln Asn Leu Gln<br>385 390 395 400 | 1200 |
| ccg atc aaa atg gac ctc cat acc atc ccg ggt ttt agc gag tcc gtc<br>Pro Ile Lys Met Asp Leu His Thr Ile Pro Gly Phe Ser Glu Ser Val<br>405 410 415 | 1248 |
| atc tac ttc aat gat att gag agt gac ccg cag tac gac gag ctc gtc<br>Ile Tyr Phe Asn Asp Ile Glu Ser Asp Pro Gln Tyr Asp Glu Leu Val<br>420 425 430 | 1296 |
| aac tcg gtg caa gca ttc ttc gac aag tcg aag ttc ggc gag ctg ccc<br>Asn Ser Val Gln Ala Phe Phe Asp Lys Ser Lys Phe Gly Glu Leu Pro<br>435 440 445 | 1344 |
| gag atc aag cag aac tgg tcc gag att atc ttc gtc ata gat ttt gcc<br>Glu Ile Lys Gln Asn Trp Ser Glu Ile Ile Phe Val Ile Asp Phe Ala<br>450 455 460 | 1392 |
| cgg ctg gag gac tcg gaa gtc aaa gag gcc ctc ggc gga ctg gtg agg<br>Arg Leu Glu Asp Ser Glu Val Lys Glu Ala Leu Gly Gly Leu Val Arg<br>465 470 475 480 | 1440 |
| gct gtg aac gtc gtg agc cag ggg tac ccc cag cgc gtg gga ctc ctc<br>Ala Val Asn Val Val Ser Gln Gly Tyr Pro Gln Arg Val Gly Leu Leu<br>485 490 495 | 1488 |
| ccg ttc agc agt gat agc gac aag agc gtc gtc aat aag atc tac gag<br>Pro Phe Ser Ser Asp Ser Asp Lys Ser Val Val Asn Lys Ile Tyr Glu<br>500 505 510 | 1536 |
| ctg aag aac tcg acc gac aat ctc acc gag ctg aag tcg ttc ctg gaa<br>Leu Lys Asn Ser Thr Asp Asn Leu Thr Glu Leu Lys Ser Phe Leu Glu<br>515 520 525 | 1584 |
| acc atg ttg ctg gcc gac ggc ctg tcc gcc aac gcg aag cat agt aag<br>Thr Met Leu Leu Ala Asp Gly Leu Ser Ala Asn Ala Lys His Ser Lys<br>530 535 540 | 1632 |
| cat atc ccc gtg ccg gac gtg ttc cac ctc ctc gac gag ctg cag atc<br>His Ile Pro Val Pro Asp Val Phe His Leu Leu Asp Glu Leu Gln Ile<br>545 550 555 560 | 1680 |
| gac gaa acg tcc atc atc atc aac ggc gag ata tac ccg ttc cgc aag<br>Asp Glu Thr Ser Ile Ile Ile Asn Gly Glu Ile Tyr Pro Phe Arg Lys<br>565 570 575 | 1728 |
| aat tgg aac tac ctc atc gcc aag gtc atc aag aaa gac acc gaa ttc<br>Asn Trp Asn Tyr Leu Ile Ala Lys Val Ile Lys Lys Asp Thr Glu Phe<br>580 585 590 | 1776 |
| atc cgc aag gag ctg tcg aac tcg tcg ccg aag aac aag cag att agt<br>Ile Arg Lys Glu Leu Ser Asn Ser Ser Pro Lys Asn Lys Gln Ile Ser<br>595 600 605 | 1824 |
| gtg cgc gac ctg ttg cac tat aag agc gcg aac ctc cgc cat aac aag<br>Val Arg Asp Leu Leu His Tyr Lys Ser Ala Asn Leu Arg His Asn Lys<br>610 615 620 | 1872 |
| tat acg ccg aac tat ttc gcg gat agt gtg tat tcc tcg gtc aac aat<br> | 1920 |

```
Tyr Thr Pro Asn Tyr Phe Ala Asp Ser Val Tyr Ser Ser Val Asn Asn
625                 630                 635                 640 acc gct ctg gaa agc gtc tgc tcg atc ggt tac tac acc aaa aac gag     1968
Thr Ala Leu Glu Ser Val Cys Ser Ile Gly Tyr Tyr Thr Lys Asn Glu
                    645                 650                 655 gaa tat aac ctc ctg cat acc att acg ctc gtg gat gac ttc ggc tcg     2016
Glu Tyr Asn Leu Leu His Thr Ile Thr Leu Val Asp Asp Phe Gly Ser
                660                 665                 670 atc cat gcg ctg aag cgg ctg cgg aac ctg ttg cat acg tcc ttc gtg     2064
Ile His Ala Leu Lys Arg Leu Arg Asn Leu Leu His Thr Ser Phe Val
            675                 680                 685 ggc gtg cgg atc cgc att atc cat gtc ggc gat atc agc gac atc tgg     2112
Gly Val Arg Ile Arg Ile Ile His Val Gly Asp Ile Ser Asp Ile Trp
        690                 695                 700 tat cag ctc cgc gga tcc ctg agt cag aaa gac ccg atc ggc agc atc     2160
Tyr Gln Leu Arg Gly Ser Leu Ser Gln Lys Asp Pro Ile Gly Ser Ile
705                 710                 715                 720 aac acc ttc atc gac gcc ctg aaa ctc aaa aag gtc aag tcc cat acg     2208
Asn Thr Phe Ile Asp Ala Leu Lys Leu Lys Lys Val Lys Ser His Thr
                725                 730                 735 tat aag aag tcg cag cag ctc ggc ttg cat aag tgg ctc ccc gac atc     2256
Tyr Lys Lys Ser Gln Gln Leu Gly Leu His Lys Trp Leu Pro Asp Ile
                740                 745                 750 ccg ctg ttc gag ctc caa aag ggt tcg ttc atc gcg ctc aac ggc cgg     2304
Pro Leu Phe Glu Leu Gln Lys Gly Ser Phe Ile Ala Leu Asn Gly Arg
            755                 760                 765 ttc atc atc ctg atc aag atg aaa tgc cag aag caa aac atc tcc aaa     2352
Phe Ile Ile Leu Ile Lys Met Lys Cys Gln Lys Gln Asn Ile Ser Lys
        770                 775                 780 gcc aag atc atc aag cgc gag gcc ctt cgg acc ata gat tcg gtg ttc     2400
Ala Lys Ile Ile Lys Arg Glu Ala Leu Arg Thr Ile Asp Ser Val Phe
785                 790                 795                 800 gcg ctg gac ctc ctc ttt cct ggc ttc agc caa gag atc ata aat ccc     2448
Ala Leu Asp Leu Leu Phe Pro Gly Phe Ser Gln Glu Ile Ile Asn Pro
                805                 810                 815 gat ctc atc gag atg atc tcc tcg atc ctt acc cgc ctc ttc tat cag     2496
Asp Leu Ile Glu Met Ile Ser Ser Ile Leu Thr Arg Leu Phe Tyr Gln
                820                 825                 830 ggg acc cac ata tac aac aac ggc att gac tat act acc gag tcg tcg     2544
Gly Thr His Ile Tyr Asn Asn Gly Ile Asp Tyr Thr Thr Glu Ser Ser
            835                 840                 845 ctg ccg cgc atg gac ttg tcc gag ttc ttc cgc ccg aat aac ctg acc     2592
Leu Pro Arg Met Asp Leu Ser Glu Phe Phe Arg Pro Asn Asn Leu Thr
        850                 855                 860 atg ttc gag gat ggc aaa tcg gcg tcc atc gat ctc ctc atc ctt         2640
Met Phe Glu Asp Gly Lys Ser Ala Ser Ile Asp Leu Leu Ile Leu
865                 870                 875                 880 gac ccg ctg gaa gaa cgg act cag atg att ctt tcc ctc gtg gag caa     2688
Asp Pro Leu Glu Glu Arg Thr Gln Met Ile Leu Ser Leu Val Glu Gln
                885                 890                 895 ttc cgg cca ctg aag ttc gtg aat atc cag gtc atc ctg atg ccg acc     2736
Phe Arg Pro Leu Lys Phe Val Asn Ile Gln Val Ile Leu Met Pro Thr
                900                 905                 910 ctg gag ctg aat att gtc ccg atc cgg cgc atc tac gtg gac gac gcg     2784
Leu Glu Leu Asn Ile Val Pro Ile Arg Arg Ile Tyr Val Asp Asp Ala
            915                 920                 925 gat atc gtc aag tcc atc acg tcc gag gac tcc cgg tcg gac cct gag     2832
Asp Ile Val Lys Ser Ile Thr Ser Glu Asp Ser Arg Ser Asp Pro Glu
        930                 935                 940
```

-continued

| | | |
|---|---|---|
| gtt gac atc gag atg gat gtg ccg aac tcg ttc atc gtc gac aat aac<br>Val Asp Ile Glu Met Asp Val Pro Asn Ser Phe Ile Val Asp Asn Asn<br>945                    950                    955                    960 | 2880 |
| tac agg att aag aaa ctg ttg att gag ctg cat tcg ttc tcc agt aaa<br>Tyr Arg Ile Lys Lys Leu Leu Ile Glu Leu His Ser Phe Ser Ser Lys<br>                965                    970                    975 | 2928 |
| acc gtg ctg tcc acg ggc aat atc gac ggc atg ggt ggc gtg tgc ctt<br>Thr Val Leu Ser Thr Gly Asn Ile Asp Gly Met Gly Gly Val Cys Leu<br>                    980                    985                    990 | 2976 |
| gcg ctc gtc gat tcg gct ggc aac att atc gac aaa acc acg acc atg<br>Ala Leu Val Asp Ser Ala Gly Asn Ile Ile Asp Lys Thr Thr Thr Met<br>        995                    1000                    1005 | 3024 |
| aaa acg ttc ggg tac ggc cag ttc cac acc gac aag ttc ttg aag<br>Lys Thr Phe Gly Tyr Gly Gln Phe His Thr Asp Lys Phe Leu Lys<br>     1010                   1015                   1020 | 3069 |
| ggt tgc tac atc aaa agc tgc gac agc cgc tat acc gtc cag tcc<br>Gly Cys Tyr Ile Lys Ser Cys Asp Ser Arg Tyr Thr Val Gln Ser<br>1025                    1030                    1035 | 3114 |
| ttc agc act gat ggc cac ccc gat ttc atc ccg tcc gac tcc ctc<br>Phe Ser Thr Asp Gly His Pro Asp Phe Ile Pro Ser Asp Ser Leu<br>     1040                   1045                   1050 | 3159 |
| gac atc ctg agc tat aac ccg cag aag att gcg gtt aag atc tcc<br>Asp Ile Leu Ser Tyr Asn Pro Gln Lys Ile Ala Val Lys Ile Ser<br>1055                    1060                    1065 | 3204 |
| gag gag ccg acg cac gaa gaa gag tat gaa gag ggt cgc aat aac<br>Glu Glu Pro Thr His Glu Glu Glu Tyr Glu Glu Gly Arg Asn Asn<br>     1070                   1075                   1080 | 3249 |
| gac acg atc atc aat atc ttt acc att tcg ggt ccc gat gaa gaa<br>Asp Thr Ile Ile Asn Ile Phe Thr Ile Ser Gly Pro Asp Glu Glu<br>1085                    1090                    1095 | 3294 |
| gag agg tac atg caa atg atc ctg tcg atc ctc agc aaa tgc cca<br>Glu Arg Tyr Met Gln Met Ile Leu Ser Ile Leu Ser Lys Cys Pro<br>     1100                   1105                   1110 | 3339 |
| gaa acc caa aaa gtg aat ttc ttt ata ctg gac cag ccg ttc att<br>Glu Thr Gln Lys Val Asn Phe Phe Ile Leu Asp Gln Pro Phe Ile<br>1115                    1120                    1125 | 3384 |
| tcg gac acc ctg cgc aag tcc tgc gaa tac atc aat tcc agt gat<br>Ser Asp Thr Leu Arg Lys Ser Cys Glu Tyr Ile Asn Ser Ser Asp<br>     1130                   1135                   1140 | 3429 |
| gag atg cgc ggc aat gtc ata ttc ctc aac tat gag tgg ccc cag<br>Glu Met Arg Gly Asn Val Ile Phe Leu Asn Tyr Glu Trp Pro Gln<br>1145                    1150                    1155 | 3474 |
| tgg ctg cgc cct cag cgg ttc agc agc cgc agg cgc gac gtc agc<br>Trp Leu Arg Pro Gln Arg Phe Ser Ser Arg Arg Arg Asp Val Ser<br>     1160                   1165                   1170 | 3519 |
| cgg ttc ctc ttc ctg gac gtg ctc ctc ccg cag aac atc agc aag<br>Arg Phe Leu Phe Leu Asp Val Leu Leu Pro Gln Asn Ile Ser Lys<br>1175                    1180                    1185 | 3564 |
| gtc ctc tat atg tcg ccg acc gag gtc ccg ctt gat ccg ttc gac<br>Val Leu Tyr Met Ser Pro Thr Glu Val Pro Leu Asp Pro Phe Asp<br>     1190                   1195                   1200 | 3609 |
| atc ttc caa ttc cag ggc ctc aag cgc gca ccg ctg ggc ctg ttt<br>Ile Phe Gln Phe Gln Gly Leu Lys Arg Ala Pro Leu Gly Leu Phe<br>1205                    1210                    1215 | 3654 |
| cgc atg agc ggt gac ggc tat tgg aaa gag ggc tac tgg gag aag<br>Arg Met Ser Gly Asp Gly Tyr Trp Lys Glu Gly Tyr Trp Glu Lys<br>     1220                   1225                   1230 | 3699 |
| atg ctg cgc gag aac aac ttg gaa ttc tat agc acc gag ccg gcg<br>Met Leu Arg Glu Asn Asn Leu Glu Phe Tyr Ser Thr Glu Pro Ala<br>1235                    1240                    1245 | 3744 |

```
ttc ttg gtc aat ctg gaa cgc ttc cgc gag ctg gac gcc ggc gac          3789
Phe Leu Val Asn Leu Glu Arg Phe Arg Glu Leu Asp Ala Gly Asp
    1250                1255                1260 aag tac agg atc cat tac caa cgc att agc acc gac gcg atg agc          3834
Lys Tyr Arg Ile His Tyr Gln Arg Ile Ser Thr Asp Ala Met Ser
1265                1270                1275 ctg gtg aac atc ggg caa gac ctc gtc aat aat ctg caa ctt gag          3879
Leu Val Asn Ile Gly Gln Asp Leu Val Asn Asn Leu Gln Leu Glu
    1280                1285                1290 gtc ccg atc cgg ttc ctg aag ggt agt tat aag aaa aag ctc gtg          3924
Val Pro Ile Arg Phe Leu Lys Gly Ser Tyr Lys Lys Lys Leu Val
    1295                1300                1305 atc aat gat gag tgc gtc agc gag tgg aag aaa aag atc aac aag          3969
Ile Asn Asp Glu Cys Val Ser Glu Trp Lys Lys Lys Ile Asn Lys
1310                1315                1320 ttt gcc tcg tcc cca ggg gac gag gac gtt ccc ggc gag agt gtg          4014
Phe Ala Ser Ser Pro Gly Asp Glu Asp Val Pro Gly Glu Ser Val
    1325                1330                1335 agc tcg aag tat cag gat tcg gat aac gcc gcg cca ctc cat gac          4059
Ser Ser Lys Tyr Gln Asp Ser Asp Asn Ala Ala Pro Leu His Asp
    1340                1345                1350 gaa ctc                                                               4065
Glu Leu
    1355

<210> SEQ ID NO 4
<211> LENGTH: 1355
<212> TYPE: PRT
<213> ORGANISM: Artificial sequence
<220> FEATURE:
<223> OTHER INFORMATION: Synthetic Construct

<400> SEQUENCE: 4

Met Arg Leu Leu Ala Leu Val Leu Leu Leu Cys Ala Pro Leu Arg
1               5                   10                  15

Ala Trp Thr Tyr Ser Leu Arg Tyr Gly Ile Pro Glu Ser Ala Gln Val
            20                  25                  30

Trp Ser Ile Leu Val His Leu Leu Gly Asp Val Asp Asn Gln Leu Leu
        35                  40                  45

Thr Asn Leu Tyr Pro Leu Val Thr Gly Leu Asp Asp Glu Ile Asp Ile
    50                  55                  60

Gln Glu Asn Leu Val Thr Ser Asn Val Leu Arg Glu Arg Tyr Asp Lys
65                  70                  75                  80

Glu Asp Val Ala Asp Leu Leu Glu Leu Tyr Ala Ser Leu Tyr Pro Met
                85                  90                  95

Gly Met Ile Gln His Asp Ile Ser Ser Asn Ala Glu Gln Asp Asp Ala
            100                 105                 110

Asn Ser Ser Tyr Phe Val Leu Asn Gly Asn Arg Tyr Glu Lys Pro Asp
        115                 120                 125

Asp Val Phe Tyr Leu Lys Ser Lys Asp Leu Thr Ile Gln Gln Lys Val
    130                 135                 140

Pro Asp Val Asp Val Ile Gln Pro Tyr Asp Val Val Ile Gly Thr Asn
145                 150                 155                 160

Ser Glu Ala Pro Ile Leu Ile Leu Tyr Gly Cys Pro Thr Val Ile Asp
                165                 170                 175

Ser Asp Phe Glu Glu Phe Asn Arg Asn Leu Phe Met Glu Ala Met Asn
            180                 185                 190
```

-continued

Gly Glu Gly Lys Phe Arg Phe Ile Trp Arg Ser Thr Cys Ser Leu Asp
            195                 200                 205

Gly Lys Ser Val Glu Tyr Pro Leu Thr His Pro Leu Glu Ile Thr Leu
        210                 215                 220

Gln Asn Gly Ser Arg Met Ser Ser Ile Pro Gln Leu Lys Lys Ile Leu
225                 230                 235                 240

Tyr Thr Val Pro Lys Glu Ile Leu Val Gly Ala Asp Asn Asp Asp Gln
                245                 250                 255

Leu His Asp Leu Glu Pro Glu Glu Leu Arg Glu Leu Asp Leu Arg Val
            260                 265                 270

Thr Ser Leu Ile Ser Glu Phe Tyr Gln Tyr Lys Lys Asp Ile Thr Ala
        275                 280                 285

Thr Leu Asn Phe Thr Lys Ser Ile Val Asn Asn Phe Pro Leu Ile Ser
    290                 295                 300

Lys Gln Leu Ile Lys Val Ser Ser Val Asn Lys Asp Ile Ile Thr Ser
305                 310                 315                 320

Asn Glu Glu Leu Asn Ser Lys Gly Phe Asp Tyr Asn Met Leu Gly Ile
                325                 330                 335

Asn Gly Gln Asn Trp Lys Ile Thr Ser Leu Thr Pro Tyr Asn Leu Leu
            340                 345                 350

Thr Ala Leu Lys Thr Glu Tyr Gln Ser Leu Leu Lys Ile Thr Asn Leu
        355                 360                 365

Leu Gln Glu Leu Glu Pro Ser Lys Cys Ile Leu Asp Ser Lys Phe Leu
    370                 375                 380

Leu Asn Lys Phe Ser Gln Phe Ser Leu Gly Lys Leu Gln Asn Leu Gln
385                 390                 395                 400

Pro Ile Lys Met Asp Leu His Thr Ile Pro Gly Phe Ser Glu Ser Val
                405                 410                 415

Ile Tyr Phe Asn Asp Ile Glu Ser Asp Pro Gln Tyr Asp Glu Leu Val
            420                 425                 430

Asn Ser Val Gln Ala Phe Phe Asp Lys Ser Lys Phe Gly Glu Leu Pro
        435                 440                 445

Glu Ile Lys Gln Asn Trp Ser Glu Ile Ile Phe Val Ile Asp Phe Ala
    450                 455                 460

Arg Leu Glu Asp Ser Glu Val Lys Glu Ala Leu Gly Gly Leu Val Arg
465                 470                 475                 480

Ala Val Asn Val Val Ser Gln Gly Tyr Pro Gln Arg Val Gly Leu Leu
                485                 490                 495

Pro Phe Ser Ser Asp Ser Asp Lys Ser Val Val Asn Lys Ile Tyr Glu
            500                 505                 510

Leu Lys Asn Ser Thr Asp Asn Leu Thr Glu Leu Lys Ser Phe Leu Glu
        515                 520                 525

Thr Met Leu Leu Ala Asp Gly Leu Ser Ala Asn Ala Lys His Ser Lys
    530                 535                 540

His Ile Pro Val Pro Asp Val Phe His Leu Leu Asp Glu Leu Gln Ile
545                 550                 555                 560

Asp Glu Thr Ser Ile Ile Ile Asn Gly Glu Ile Tyr Pro Phe Arg Lys
                565                 570                 575

Asn Trp Asn Tyr Leu Ile Ala Lys Val Ile Lys Lys Asp Thr Glu Phe
            580                 585                 590

Ile Arg Lys Glu Leu Ser Asn Ser Ser Pro Lys Asn Lys Gln Ile Ser
        595                 600                 605

Val Arg Asp Leu Leu His Tyr Lys Ser Ala Asn Leu Arg His Asn Lys

-continued

```
            610                 615                 620
Tyr Thr Pro Asn Tyr Phe Ala Asp Ser Val Tyr Ser Val Asn Asn
625                 630                 635                 640

Thr Ala Leu Glu Ser Val Cys Ser Ile Gly Tyr Tyr Thr Lys Asn Glu
                    645                 650                 655

Glu Tyr Asn Leu Leu His Thr Ile Thr Leu Val Asp Asp Phe Gly Ser
                660                 665                 670

Ile His Ala Leu Lys Arg Leu Arg Asn Leu Leu His Thr Ser Phe Val
            675                 680                 685

Gly Val Arg Ile Arg Ile Ile His Val Gly Asp Ile Ser Asp Ile Trp
        690                 695                 700

Tyr Gln Leu Arg Gly Ser Leu Ser Gln Lys Asp Pro Ile Gly Ser Ile
705                 710                 715                 720

Asn Thr Phe Ile Asp Ala Leu Lys Leu Lys Val Lys Ser His Thr
                    725                 730                 735

Tyr Lys Lys Ser Gln Gln Leu Gly Leu His Lys Trp Leu Pro Asp Ile
                740                 745                 750

Pro Leu Phe Glu Leu Gln Lys Gly Ser Phe Ile Ala Leu Asn Gly Arg
            755                 760                 765

Phe Ile Ile Leu Ile Lys Met Lys Cys Gln Lys Gln Asn Ile Ser Lys
770                 775                 780

Ala Lys Ile Ile Lys Arg Glu Ala Leu Arg Thr Ile Asp Ser Val Phe
785                 790                 795                 800

Ala Leu Asp Leu Leu Phe Pro Gly Phe Ser Gln Glu Ile Ile Asn Pro
                805                 810                 815

Asp Leu Ile Glu Met Ile Ser Ser Ile Leu Thr Arg Leu Phe Tyr Gln
                820                 825                 830

Gly Thr His Ile Tyr Asn Asn Gly Ile Asp Tyr Thr Thr Glu Ser Ser
                835                 840                 845

Leu Pro Arg Met Asp Leu Ser Glu Phe Phe Arg Pro Asn Asn Leu Thr
850                 855                 860

Met Phe Glu Asp Gly Lys Ser Ala Ser Ile Asp Leu Leu Ile Leu
865                 870                 875                 880

Asp Pro Leu Glu Glu Arg Thr Gln Met Ile Leu Ser Leu Val Glu Gln
                885                 890                 895

Phe Arg Pro Leu Lys Phe Val Asn Ile Gln Val Ile Leu Met Pro Thr
                900                 905                 910

Leu Glu Leu Asn Ile Val Pro Ile Arg Arg Ile Tyr Val Asp Asp Ala
            915                 920                 925

Asp Ile Val Lys Ser Ile Thr Ser Glu Asp Ser Arg Ser Asp Pro Glu
930                 935                 940

Val Asp Ile Glu Met Asp Val Pro Asn Ser Phe Ile Val Asp Asn Asn
945                 950                 955                 960

Tyr Arg Ile Lys Lys Leu Leu Ile Glu Leu His Ser Phe Ser Ser Lys
                965                 970                 975

Thr Val Leu Ser Thr Gly Asn Ile Asp Gly Met Gly Gly Val Cys Leu
                980                 985                 990

Ala Leu Val Asp Ser Ala Gly Asn Ile Ile Asp Lys Thr Thr Thr Met
            995                 1000                1005

Lys Thr Phe Gly Tyr Gly Gln Phe His Thr Asp Lys Phe Leu Lys
    1010                1015                1020

Gly Cys Tyr Ile Lys Ser Cys Asp Ser Arg Tyr Thr Val Gln Ser
    1025                1030                1035
```

Phe Ser Thr Asp Gly His Pro Asp Phe Ile Pro Ser Asp Ser Leu
        1040                1045                1050

Asp Ile Leu Ser Tyr Asn Pro Gln Lys Ile Ala Val Lys Ile Ser
    1055                1060                1065

Glu Glu Pro Thr His Glu Glu Gly Tyr Glu Glu Gly Arg Asn Asn
    1070                1075                1080

Asp Thr Ile Ile Asn Ile Phe Thr Ile Ser Gly Pro Asp Glu Glu
    1085                1090                1095

Glu Arg Tyr Met Gln Met Ile Leu Ser Ile Leu Ser Lys Cys Pro
    1100                1105                1110

Glu Thr Gln Lys Val Asn Phe Phe Ile Leu Asp Gln Pro Phe Ile
    1115                1120                1125

Ser Asp Thr Leu Arg Lys Ser Cys Glu Tyr Ile Asn Ser Ser Asp
    1130                1135                1140

Glu Met Arg Gly Asn Val Ile Phe Leu Asn Tyr Glu Trp Pro Gln
    1145                1150                1155

Trp Leu Arg Pro Gln Arg Phe Ser Ser Arg Arg Arg Asp Val Ser
    1160                1165                1170

Arg Phe Leu Phe Leu Asp Val Leu Leu Pro Gln Asn Ile Ser Lys
    1175                1180                1185

Val Leu Tyr Met Ser Pro Thr Glu Val Pro Leu Asp Pro Phe Asp
    1190                1195                1200

Ile Phe Gln Phe Gln Gly Leu Lys Arg Ala Pro Leu Gly Leu Phe
    1205                1210                1215

Arg Met Ser Gly Asp Gly Tyr Trp Lys Glu Gly Tyr Trp Glu Lys
    1220                1225                1230

Met Leu Arg Glu Asn Asn Leu Glu Phe Tyr Ser Thr Glu Pro Ala
    1235                1240                1245

Phe Leu Val Asn Leu Glu Arg Phe Arg Glu Leu Asp Ala Gly Asp
    1250                1255                1260

Lys Tyr Arg Ile His Tyr Gln Arg Ile Ser Thr Asp Ala Met Ser
    1265                1270                1275

Leu Val Asn Ile Gly Gln Asp Leu Val Asn Asn Leu Gln Leu Glu
    1280                1285                1290

Val Pro Ile Arg Phe Leu Lys Gly Ser Tyr Lys Lys Lys Leu Val
    1295                1300                1305

Ile Asn Asp Glu Cys Val Ser Glu Trp Lys Lys Ile Asn Lys
    1310                1315                1320

Phe Ala Ser Ser Pro Gly Asp Glu Asp Val Pro Gly Glu Ser Val
    1325                1330                1335

Ser Ser Lys Tyr Gln Asp Ser Asp Asn Ala Ala Pro Leu His Asp
    1340                1345                1350

Glu Leu
    1355

<210> SEQ ID NO 5
<211> LENGTH: 5616
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(5616)
<223> OTHER INFORMATION: Saccharomyces cerevisiae s288c FKS1 (codon
      optimized)

<400> SEQUENCE: 5

| | |
|---|---:|
| atg aat acc gac cag caa ccg tac caa gga cag acc gac tat acc caa<br>Met Asn Thr Asp Gln Gln Pro Tyr Gln Gly Gln Thr Asp Tyr Thr Gln<br>1                           5                           10                       15 | 48 |
| ggc cca gga aac gga cag agc caa gag caa gac tac gat caa tac ggg<br>Gly Pro Gly Asn Gly Gln Ser Gln Glu Gln Asp Tyr Asp Gln Tyr Gly<br>                    20                           25                           30 | 96 |
| cag ccg ctg tat ccg agt caa gcg gat ggc tac tac gac ccg aac gtt<br>Gln Pro Leu Tyr Pro Ser Gln Ala Asp Gly Tyr Tyr Asp Pro Asn Val<br>          35                         40                         45 | 144 |
| gcc gca ggc acg gaa gcc gac atg tat ggc cag cag ccc ccg aac gag<br>Ala Ala Gly Thr Glu Ala Asp Met Tyr Gly Gln Gln Pro Pro Asn Glu<br> 50                           55                         60 | 192 |
| tcg tat gac cag gat tat acc aac ggc gag tat tat ggc cag ccg ccc<br>Ser Tyr Asp Gln Asp Tyr Thr Asn Gly Glu Tyr Tyr Gly Gln Pro Pro<br>65                          70                         75                       80 | 240 |
| aac atg gcc gct caa gac ggc gag aat ttc agc gac ttc tcc tcg tat<br>Asn Met Ala Ala Gln Asp Gly Glu Asn Phe Ser Asp Phe Ser Ser Tyr<br>                    85                         90                       95 | 288 |
| ggt ccg cct ggt acc ccg ggg tac gat tcc tat ggc ggg cag tac acg<br>Gly Pro Pro Gly Thr Pro Gly Tyr Asp Ser Tyr Gly Gly Gln Tyr Thr<br>                  100                      105                      110 | 336 |
| gca tcg caa atg tcc tat ggc gag ccg aat agc tcg ggc acc agt acg<br>Ala Ser Gln Met Ser Tyr Gly Glu Pro Asn Ser Ser Gly Thr Ser Thr<br>           115                      120                      125 | 384 |
| ccg ata tac ggc aac tac gat ccg aac gcc atc gca atg gca ctg ccc<br>Pro Ile Tyr Gly Asn Tyr Asp Pro Asn Ala Ile Ala Met Ala Leu Pro<br>130                           135                        140 | 432 |
| aac gag ccg tac ccc gcg tgg acg gcc gac tcg cag agc ccg gtc agc<br>Asn Glu Pro Tyr Pro Ala Trp Thr Ala Asp Ser Gln Ser Pro Val Ser<br>145                         150                         155                       160 | 480 |
| atc gaa cag atc gag gac ata ttc atc gac ctc acc aat cgc ctc ggc<br>Ile Glu Gln Ile Glu Asp Ile Phe Ile Asp Leu Thr Asn Arg Leu Gly<br>                    165                      170                      175 | 528 |
| ttc cag cgc gac tcc atg cgc aac atg ttc gac cat ttc atg gtc ctc<br>Phe Gln Arg Asp Ser Met Arg Asn Met Phe Asp His Phe Met Val Leu<br>           180                      185                      190 | 576 |
| ctc gac tcc cgc tcc tcg cgc atg agc ccg gac caa gcg ctc ctg tcc<br>Leu Asp Ser Arg Ser Ser Arg Met Ser Pro Asp Gln Ala Leu Leu Ser<br>               195                      200                      205 | 624 |
| ttg cat gct gac tat att ggc ggc gac acc gcc aac tat aag aaa tgg<br>Leu His Ala Asp Tyr Ile Gly Gly Asp Thr Ala Asn Tyr Lys Lys Trp<br>210                         215                         220 | 672 |
| tat ttc gcc gcc cag ctc gac atg gac gac gag att ggc ttc cgg aat<br>Tyr Phe Ala Ala Gln Leu Asp Met Asp Asp Glu Ile Gly Phe Arg Asn<br>225                         230                      235                    240 | 720 |
| atg tcc ctc ggg aag ctc tcg cgc aag gcc cgc aag gca aag aaa aag<br>Met Ser Leu Gly Lys Leu Ser Arg Lys Ala Arg Lys Ala Lys Lys Lys<br>                    245                      250                      255 | 768 |
| aac aag aag gca atg gaa gag gcg aat ccc gag gat acc gag gaa acc<br>Asn Lys Lys Ala Met Glu Glu Ala Asn Pro Glu Asp Thr Glu Glu Thr<br>           260                      265                      270 | 816 |
| ctc aat aag att gag ggc gac aac agc ctt gag gct gcg gac ttc cgc<br>Leu Asn Lys Ile Glu Gly Asp Asn Ser Leu Glu Ala Ala Asp Phe Arg<br>           275                      280                      285 | 864 |
| tgg aaa gcg aag atg aat cag ctg tcg ccc ctt gag cgc gtc cgc cac<br>Trp Lys Ala Lys Met Asn Gln Leu Ser Pro Leu Glu Arg Val Arg His<br>290                         295                         300 | 912 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| atc | gcg | ctc | tat | ctc | ctg | tgt | tgg | ggg | gaa | gcc | aat | cag | gtc | cgc | ttc | 960  |
| Ile | Ala | Leu | Tyr | Leu | Leu | Cys | Trp | Gly | Glu | Ala | Asn | Gln | Val | Arg | Phe |      |
| 305 |     |     |     |     | 310 |     |     |     |     | 315 |     |     |     |     | 320 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| acc | gcc | gaa | tgc | ctc | tgc | ttc | atc | tac | aag | tgc | gcg | ctc | gat | tac | ctg | 1008 |
| Thr | Ala | Glu | Cys | Leu | Cys | Phe | Ile | Tyr | Lys | Cys | Ala | Leu | Asp | Tyr | Leu |      |
|     |     |     |     | 325 |     |     |     |     | 330 |     |     |     |     | 335 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| gac | agc | ccg | ctc | tgc | cag | cag | cgg | caa | gaa | ccc | atg | ccc | gag | ggt | gac | 1056 |
| Asp | Ser | Pro | Leu | Cys | Gln | Gln | Arg | Gln | Glu | Pro | Met | Pro | Glu | Gly | Asp |      |
|     |     |     | 340 |     |     |     |     | 345 |     |     |     |     | 350 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| ttc | ctg | aat | cgc | gtg | atc | acc | ccg | atc | tat | cac | ttc | ata | cgc | aac | cag | 1104 |
| Phe | Leu | Asn | Arg | Val | Ile | Thr | Pro | Ile | Tyr | His | Phe | Ile | Arg | Asn | Gln |      |
|     |     | 355 |     |     |     |     | 360 |     |     |     |     | 365 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| gtg | tac | gag | att | gtg | gat | ggc | cgg | ttc | gtc | aag | cgc | gag | cgc | gat | cac | 1152 |
| Val | Tyr | Glu | Ile | Val | Asp | Gly | Arg | Phe | Val | Lys | Arg | Glu | Arg | Asp | His |      |
|     | 370 |     |     |     |     | 375 |     |     |     |     | 380 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| aat | aag | atc | gtg | ggc | tat | gat | gac | ctg | aac | cag | ctc | ttt | tgg | tac | ccg | 1200 |
| Asn | Lys | Ile | Val | Gly | Tyr | Asp | Asp | Leu | Asn | Gln | Leu | Phe | Trp | Tyr | Pro |      |
| 385 |     |     |     |     | 390 |     |     |     |     | 395 |     |     |     |     | 400 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| gaa | gga | atc | gcg | aag | ata | gtt | ctg | gaa | gat | ggc | acc | aag | ctt | atc | gag | 1248 |
| Glu | Gly | Ile | Ala | Lys | Ile | Val | Leu | Glu | Asp | Gly | Thr | Lys | Leu | Ile | Glu |      |
|     |     |     |     | 405 |     |     |     |     | 410 |     |     |     |     | 415 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| ctc | ccg | ctt | gag | gag | cgc | tat | ctg | cgg | ctg | ggt | gac | gtc | gtg | tgg | gac | 1296 |
| Leu | Pro | Leu | Glu | Glu | Arg | Tyr | Leu | Arg | Leu | Gly | Asp | Val | Val | Trp | Asp |      |
|     |     |     | 420 |     |     |     |     | 425 |     |     |     |     | 430 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| gac | gtg | ttc | ttc | aaa | acg | tac | aag | gaa | acg | cgc | acc | tgg | ctg | cac | ctt | 1344 |
| Asp | Val | Phe | Phe | Lys | Thr | Tyr | Lys | Glu | Thr | Arg | Thr | Trp | Leu | His | Leu |      |
|     |     |     | 435 |     |     |     |     | 440 |     |     |     |     | 445 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| gtc | acg | aac | ttc | aat | cgc | atc | tgg | gtg | atg | cat | atc | tcg | att | ttc | tgg | 1392 |
| Val | Thr | Asn | Phe | Asn | Arg | Ile | Trp | Val | Met | His | Ile | Ser | Ile | Phe | Trp |      |
|     | 450 |     |     |     |     | 455 |     |     |     |     | 460 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| atg | tac | ttc | gca | tac | aac | tcg | ccg | acg | ttc | tat | acc | cac | aat | tat | cag | 1440 |
| Met | Tyr | Phe | Ala | Tyr | Asn | Ser | Pro | Thr | Phe | Tyr | Thr | His | Asn | Tyr | Gln |      |
| 465 |     |     |     |     | 470 |     |     |     |     | 475 |     |     |     |     | 480 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| caa | ctc | gtc | gac | aat | caa | ccg | ctg | gcc | gcg | tac | aag | tgg | gcg | tcg | tgc | 1488 |
| Gln | Leu | Val | Asp | Asn | Gln | Pro | Leu | Ala | Ala | Tyr | Lys | Trp | Ala | Ser | Cys |      |
|     |     |     |     | 485 |     |     |     |     | 490 |     |     |     |     | 495 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| gct | ctg | ggc | ggc | acc | gtg | gcg | tcc | ctc | atc | cag | att | gtc | gcc | acg | ctc | 1536 |
| Ala | Leu | Gly | Gly | Thr | Val | Ala | Ser | Leu | Ile | Gln | Ile | Val | Ala | Thr | Leu |      |
|     |     |     | 500 |     |     |     |     | 505 |     |     |     |     | 510 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| tgt | gag | tgg | tcc | ttc | gtc | ccg | cgg | aaa | tgg | gcg | gga | gcc | cag | cat | ctg | 1584 |
| Cys | Glu | Trp | Ser | Phe | Val | Pro | Arg | Lys | Trp | Ala | Gly | Ala | Gln | His | Leu |      |
|     |     | 515 |     |     |     |     | 520 |     |     |     |     | 525 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| tcg | cgc | cgg | ttc | tgg | ttc | ctg | tgc | atc | atc | ttc | ggg | atc | aac | ctg | ggc | 1632 |
| Ser | Arg | Arg | Phe | Trp | Phe | Leu | Cys | Ile | Ile | Phe | Gly | Ile | Asn | Leu | Gly |      |
|     | 530 |     |     |     |     | 535 |     |     |     |     | 540 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| ccg | atc | atc | ttc | gtg | ttc | gcc | tac | gac | aag | gac | acg | gtc | tat | tcc | acc | 1680 |
| Pro | Ile | Ile | Phe | Val | Phe | Ala | Tyr | Asp | Lys | Asp | Thr | Val | Tyr | Ser | Thr |      |
| 545 |     |     |     |     | 550 |     |     |     |     | 555 |     |     |     |     | 560 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| gca | gcg | cat | gtc | gtc | gca | gcg | gtc | atg | ttc | ttc | gtt | gcg | gtc | gcg | acc | 1728 |
| Ala | Ala | His | Val | Val | Ala | Ala | Val | Met | Phe | Phe | Val | Ala | Val | Ala | Thr |      |
|     |     |     |     | 565 |     |     |     |     | 570 |     |     |     |     | 575 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| atc | atc | ttt | ttc | tcc | atc | atg | cca | ctg | ggt | ggc | ctc | ttc | acc | agc | tat | 1776 |
| Ile | Ile | Phe | Phe | Ser | Ile | Met | Pro | Leu | Gly | Gly | Leu | Phe | Thr | Ser | Tyr |      |
|     |     |     | 580 |     |     |     |     | 585 |     |     |     |     | 590 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| atg | aag | aaa | tcg | act | cgc | cgg | tac | gtc | gct | agc | cag | acc | ttc | acg | gca | 1824 |
| Met | Lys | Lys | Ser | Thr | Arg | Arg | Tyr | Val | Ala | Ser | Gln | Thr | Phe | Thr | Ala |      |
|     |     | 595 |     |     |     |     | 600 |     |     |     |     | 605 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| gcg | ttc | gca | ccc | ctg | cat | ggc | ctc | gac | cgc | tgg | atg | agc | tac | ttg | gtg | 1872 |
| Ala | Phe | Ala | Pro | Leu | His | Gly | Leu | Asp | Arg | Trp | Met | Ser | Tyr | Leu | Val |      |
|     | 610 |     |     |     |     | 615 |     |     |     |     | 620 |     |     |     |     |      |

```
tgg gtc acg gtg ttc gcg gcc aag tat tcc gag tcc tac tat ttc ctc    1920
Trp Val Thr Val Phe Ala Ala Lys Tyr Ser Glu Ser Tyr Tyr Phe Leu
625                 630                 635                 640 gtg ctg tcc ctc cgc gac ccg atc cgc atc ctg agc acc acc gcc atg    1968
Val Leu Ser Leu Arg Asp Pro Ile Arg Ile Leu Ser Thr Thr Ala Met
            645                 650                 655 cgc tgc acc ggg gag tac tgg tgg ggt gcg gtg ctc tgc aaa gtc cag    2016
Arg Cys Thr Gly Glu Tyr Trp Trp Gly Ala Val Leu Cys Lys Val Gln
        660                 665                 670 ccc aag atc gtt ctt ggc ctg gtg atc gcg acg gac ttc atc ctc ttt    2064
Pro Lys Ile Val Leu Gly Leu Val Ile Ala Thr Asp Phe Ile Leu Phe
    675                 680                 685 ttc ctt gac acc tat ctg tgg tac att atc gtc aac acc att ttc agc    2112
Phe Leu Asp Thr Tyr Leu Trp Tyr Ile Ile Val Asn Thr Ile Phe Ser
690                 695                 700 gtg ggc aag tcg ttc tac ctc ggc atc agt atc ctg acc ccg tgg cgc    2160
Val Gly Lys Ser Phe Tyr Leu Gly Ile Ser Ile Leu Thr Pro Trp Arg
705                 710                 715                 720 aac atc ttc acc cgg ctc ccc aag cgc ata tac tcg aag att ctg gcc    2208
Asn Ile Phe Thr Arg Leu Pro Lys Arg Ile Tyr Ser Lys Ile Leu Ala
            725                 730                 735 acc act gac atg gag atc aag tat aag ccg aag gtc ctc att agc cag    2256
Thr Thr Asp Met Glu Ile Lys Tyr Lys Pro Lys Val Leu Ile Ser Gln
        740                 745                 750 gtg tgg aac gcg atc ata atc tcg atg tat cgg gag cac ttg ctg gct    2304
Val Trp Asn Ala Ile Ile Ile Ser Met Tyr Arg Glu His Leu Leu Ala
    755                 760                 765 atc gac cac gtg cag aaa ctg ctg tat cat caa gtg ccc agt gag atc    2352
Ile Asp His Val Gln Lys Leu Leu Tyr His Gln Val Pro Ser Glu Ile
770                 775                 780 gag ggt aaa cgg acg ctg agg gca ccc acc ttc ttt gtg agc cag gat    2400
Glu Gly Lys Arg Thr Leu Arg Ala Pro Thr Phe Phe Val Ser Gln Asp
785                 790                 795                 800 gac aat aat ttt gaa acc gaa ttc ttc cct cgc gat tcc gag gcc gag    2448
Asp Asn Asn Phe Glu Thr Glu Phe Phe Pro Arg Asp Ser Glu Ala Glu
            805                 810                 815 cgg cgc atc agc ttc ttt gcc caa tcc ctg tcg acg ccc atc ccg gag    2496
Arg Arg Ile Ser Phe Phe Ala Gln Ser Leu Ser Thr Pro Ile Pro Glu
        820                 825                 830 ccc ctg ccg gtg gac aac atg ccg acc ttt acc gtg ctc acg ccc cat    2544
Pro Leu Pro Val Asp Asn Met Pro Thr Phe Thr Val Leu Thr Pro His
    835                 840                 845 tat gcc gag cgc atc ctc ctg agc ttg cgc gag atc atc cgc gag gac    2592
Tyr Ala Glu Arg Ile Leu Leu Ser Leu Arg Glu Ile Ile Arg Glu Asp
850                 855                 860 gac cag ttc tcg cgg gtt acg ctc ctg gag tac ctc aag caa ctg cat    2640
Asp Gln Phe Ser Arg Val Thr Leu Leu Glu Tyr Leu Lys Gln Leu His
865                 870                 875                 880 ccg gtg gag tgg gag tgc ttc gtc aaa gac acc aaa atc ctg gcc gag    2688
Pro Val Glu Trp Glu Cys Phe Val Lys Asp Thr Lys Ile Leu Ala Glu
            885                 890                 895 gaa act gct gcg tac gag ggc aat gag aac gag gcc gag aag gaa gat    2736
Glu Thr Ala Ala Tyr Glu Gly Asn Glu Asn Glu Ala Glu Lys Glu Asp
        900                 905                 910 gca ctg aaa tcc cag atc gac gat ttg cct ttc tat tgt atc ggc ttc    2784
Ala Leu Lys Ser Gln Ile Asp Asp Leu Pro Phe Tyr Cys Ile Gly Phe
    915                 920                 925 aag agt gcg gcc ccg gag tac acg ctc cgc acc cgg atc tgg gcg agt    2832
Lys Ser Ala Ala Pro Glu Tyr Thr Leu Arg Thr Arg Ile Trp Ala Ser
```

-continued

```
              930             935             940
ctg cgc tcc cag acc ctc tac cgc acc atc tcg ggc ttc atg aac tat      2880
Leu Arg Ser Gln Thr Leu Tyr Arg Thr Ile Ser Gly Phe Met Asn Tyr
945                 950             955                 960 tcg cgc gct atc aag ctg ctt tat cgg gtc gag aac ccc gag atc gtg      2928
Ser Arg Ala Ile Lys Leu Leu Tyr Arg Val Glu Asn Pro Glu Ile Val
            965             970                 975 caa atg ttc ggt ggc aat gcc gag ggc ctt gag cgc gag ctg gag aaa      2976
Gln Met Phe Gly Gly Asn Ala Glu Gly Leu Glu Arg Glu Leu Glu Lys
                980             985                 990 atg gcg agg cgc aag ttc aag ttc ctg gtg tcc atg cag cgg ctg gcg      3024
Met Ala Arg Arg Lys Phe Lys Phe Leu Val Ser Met Gln Arg Leu Ala
            995                 1000            1005 aag ttt aag ttc ctc gaa aat gcc gag ttc ctc ctc cgg gcg tac          3069
Lys Phe Lys Phe Leu Glu Asn Ala Glu Phe Leu Leu Arg Ala Tyr
1010            1015            1020 ccg gac ctc cag atc gcc tat ctt gac gag gaa ccc ccg ctg acg          3114
Pro Asp Leu Gln Ile Ala Tyr Leu Asp Glu Glu Pro Pro Leu Thr
1025            1030            1035 gag ggc gag gag ccg cgg atc tat tcg gcg ctc att gac ggc cac          3159
Glu Gly Glu Glu Pro Arg Ile Tyr Ser Ala Leu Ile Asp Gly His
1040            1045            1050 tgc gag atc ctc gac aac ggt cgg cgg agg cca aag ttc cgc gtg          3204
Cys Glu Ile Leu Asp Asn Gly Arg Arg Arg Pro Lys Phe Arg Val
1055            1060            1065 caa ctc agc ggc aat ccc att ctg ggc gac ggc aaa tcc gac aac          3249
Gln Leu Ser Gly Asn Pro Ile Leu Gly Asp Gly Lys Ser Asp Asn
1070            1075            1080 caa aac cat gcc ctg atc ttc tat agg ggt gag tat att cag ctg          3294
Gln Asn His Ala Leu Ile Phe Tyr Arg Gly Glu Tyr Ile Gln Leu
1085            1090            1095 atc gac gcg aac cag gac aat tat ctt gag gaa tgc ctc aag atc          3339
Ile Asp Ala Asn Gln Asp Asn Tyr Leu Glu Glu Cys Leu Lys Ile
1100            1105            1110 cgc tcg gtc ctg gcc gag ttc gag gag ctc aac gtc gaa cag gtc          3384
Arg Ser Val Leu Ala Glu Phe Glu Glu Leu Asn Val Glu Gln Val
1115            1120            1125 aac cct tat gct ccg ggc ctg cgg tac gaa gaa cag acc acg aac          3429
Asn Pro Tyr Ala Pro Gly Leu Arg Tyr Glu Glu Gln Thr Thr Asn
1130            1135            1140 cat ccg gtc gcc atc gtc gga gcg cgc gag tac att ttc tcg gag          3474
His Pro Val Ala Ile Val Gly Ala Arg Glu Tyr Ile Phe Ser Glu
1145            1150            1155 aat tcc ggc gtc ctc ggc gat gtg gcg gca ggc aag gag cag acc          3519
Asn Ser Gly Val Leu Gly Asp Val Ala Ala Gly Lys Glu Gln Thr
1160            1165            1170 ttc ggc acc ctg ttc gcc cgc acc ctc tcc cag att ggt ggc aaa          3564
Phe Gly Thr Leu Phe Ala Arg Thr Leu Ser Gln Ile Gly Gly Lys
1175            1180            1185 ctg cat tac ggc cat ccg gac ttc ata aac gcg acc ttc atg acc          3609
Leu His Tyr Gly His Pro Asp Phe Ile Asn Ala Thr Phe Met Thr
1190            1195            1200 acc cgg ggt ggc gtc agc aag gcc caa aag ggc ctc cat ctt aac          3654
Thr Arg Gly Gly Val Ser Lys Ala Gln Lys Gly Leu His Leu Asn
1205            1210            1215 gaa gat atc tac gcg ggt atg aat gcc atg ctc agg ggc ggt cgg          3699
Glu Asp Ile Tyr Ala Gly Met Asn Ala Met Leu Arg Gly Gly Arg
1220            1225            1230 atc aag cat tgt gag tat tac cag tgc gga aag ggc agg gat ctg          3744
```

-continued

```
                Ile Lys His Cys Glu Tyr Tyr Gln Cys Gly Lys Gly Arg Asp Leu
                    1235                1240                1245 ggc ttc ggc acc atc ctc aat ttc acc acc aag atc ggg gca ggc           3789
Gly Phe Gly Thr Ile Leu Asn Phe Thr Thr Lys Ile Gly Ala Gly
1250                1255                1260 atg gga gaa cag atg ttg agc cgg gag tac tat tac ctc ggg acg           3834
Met Gly Glu Gln Met Leu Ser Arg Glu Tyr Tyr Tyr Leu Gly Thr
1265                1270                1275 cag ctc ccg gtc gat cgg ttc ctg acc ttc tac tat gcc cat ccg           3879
Gln Leu Pro Val Asp Arg Phe Leu Thr Phe Tyr Tyr Ala His Pro
1280                1285                1290 ggt ttc cat ctg aat aac ctc ttc atc caa ctg tcc ctt cag atg           3924
Gly Phe His Leu Asn Asn Leu Phe Ile Gln Leu Ser Leu Gln Met
1295                1300                1305 ttc atg ttg acg ctc gtg aac ctg agt agc ctc gca cat gag tcg           3969
Phe Met Leu Thr Leu Val Asn Leu Ser Ser Leu Ala His Glu Ser
1310                1315                1320 atc atg tgc atc tac gat cgg aat aag ccg aaa acc gac gtc ctg           4014
Ile Met Cys Ile Tyr Asp Arg Asn Lys Pro Lys Thr Asp Val Leu
1325                1330                1335 gtg ccg att ggc tgc tac aac ttc cag ccc gcg gtc gac tgg gtc           4059
Val Pro Ile Gly Cys Tyr Asn Phe Gln Pro Ala Val Asp Trp Val
1340                1345                1350 cgc cgc tat acg ctt agc atc ttt atc gtg ttc tgg atc gcg ttc           4104
Arg Arg Tyr Thr Leu Ser Ile Phe Ile Val Phe Trp Ile Ala Phe
1355                1360                1365 gtg ccg atc gtt gtg cag gag ctg atc gag cgc ggt ctg tgg aag           4149
Val Pro Ile Val Val Gln Glu Leu Ile Glu Arg Gly Leu Trp Lys
1370                1375                1380 gcc acg cag cgc ttc ttc tgc cat ctg ctg tcg ctg agt ccg atg           4194
Ala Thr Gln Arg Phe Phe Cys His Leu Leu Ser Leu Ser Pro Met
1385                1390                1395 ttc gag gtc ttt gcg ggc caa atc tat tcg agc gcg ctc ctg agc           4239
Phe Glu Val Phe Ala Gly Gln Ile Tyr Ser Ser Ala Leu Leu Ser
1400                1405                1410 gat ttg gcg atc ggg gga gcg cgc tac atc tcg acg ggt cgg ggc           4284
Asp Leu Ala Ile Gly Gly Ala Arg Tyr Ile Ser Thr Gly Arg Gly
1415                1420                1425 ttc gcc acc tcc cgc att cca ttc agc atc aag cgc ttc gcg ggc           4329
Phe Ala Thr Ser Arg Ile Pro Phe Ser Ile Lys Arg Phe Ala Gly
1430                1435                1440 tcg gcg atc tac atg ggc gca cgc tcg atg ttg atg ctg ctg ttc           4374
Ser Ala Ile Tyr Met Gly Ala Arg Ser Met Leu Met Leu Leu Phe
1445                1450                1455 ggc acc gtg gct cat tgg cag gcg ccg ctc ctg tgg ttc tgg gcg           4419
Gly Thr Val Ala His Trp Gln Ala Pro Leu Leu Trp Phe Trp Ala
1460                1465                1470 tcc ctg agc agc ctc atc ttc gcc ccc ttc gtg ttc aac ccg cat           4464
Ser Leu Ser Ser Leu Ile Phe Ala Pro Phe Val Phe Asn Pro His
1475                1480                1485 cag ttt gcg tgg gag gac ttt ttc ctg gac tac cgc gac tac atc           4509
Gln Phe Ala Trp Glu Asp Phe Phe Leu Asp Tyr Arg Asp Tyr Ile
1490                1495                1500 cgg tgg ctc tcc cgg gga aat aac cag tac cac cgc aat tcc tgg           4554
Arg Trp Leu Ser Arg Gly Asn Asn Gln Tyr His Arg Asn Ser Trp
1505                1510                1515 att ggc tat gtg cgg atg agc cgc gct cgc atc acc ggc ttc aag           4599
Ile Gly Tyr Val Arg Met Ser Arg Ala Arg Ile Thr Gly Phe Lys
1520                1525                1530
```

| | | | | | | | | | | |
|---|---|---|---|---|---|---|---|---|---|---|
| cgg | aaa | ctg | gtc | ggt | gac | gaa | agc | gag | aaa | gcc | gcg | ggc | gac | gcc | 4644 |
| Arg | Lys | Leu | Val | Gly | Asp | Glu | Ser | Glu | Lys | Ala | Ala | Gly | Asp | Ala | |
| 1535 | | | | | 1540 | | | | | 1545 | | | | | |

| tcg | cgg | gcc | cac | cgc | acc | aac | ctg | atc | atg | gcc | gag | atc | atc | ccc | 4689 |
| Ser | Arg | Ala | His | Arg | Thr | Asn | Leu | Ile | Met | Ala | Glu | Ile | Ile | Pro | |
| 1550 | | | | | 1555 | | | | | 1560 | | | | | |

| tgc | gcc | atc | tat | gcg | gca | ggg | tgc | ttc | ata | gcg | ttc | acc | ttc | atc | 4734 |
| Cys | Ala | Ile | Tyr | Ala | Ala | Gly | Cys | Phe | Ile | Ala | Phe | Thr | Phe | Ile | |
| 1565 | | | | | 1570 | | | | | 1575 | | | | | |

| aac | gcc | cag | act | ggc | gtc | aag | acc | acc | gac | gac | gac | cgg | gtc | aac | 4779 |
| Asn | Ala | Gln | Thr | Gly | Val | Lys | Thr | Thr | Asp | Asp | Asp | Arg | Val | Asn | |
| 1580 | | | | | 1585 | | | | | 1590 | | | | | |

| tcg | gtg | ctc | cgc | atc | atc | atc | tgc | acg | ctg | gcg | ccg | att | gcg | gtc | 4824 |
| Ser | Val | Leu | Arg | Ile | Ile | Ile | Cys | Thr | Leu | Ala | Pro | Ile | Ala | Val | |
| 1595 | | | | | 1600 | | | | | 1605 | | | | | |

| aat | ctc | ggg | gtc | ctc | ttc | ttc | tgc | atg | ggc | atg | tcg | tgc | tgc | tcc | 4869 |
| Asn | Leu | Gly | Val | Leu | Phe | Phe | Cys | Met | Gly | Met | Ser | Cys | Cys | Ser | |
| 1610 | | | | | 1615 | | | | | 1620 | | | | | |

| ggc | cca | ctg | ttc | ggc | atg | tgc | tgc | aag | aaa | acg | ggc | tcg | gtc | atg | 4914 |
| Gly | Pro | Leu | Phe | Gly | Met | Cys | Cys | Lys | Lys | Thr | Gly | Ser | Val | Met | |
| 1625 | | | | | 1630 | | | | | 1635 | | | | | |

| gcc | ggc | atc | gcc | cac | ggc | gtc | gcg | gtc | att | gtg | cat | atc | gct | ttc | 4959 |
| Ala | Gly | Ile | Ala | His | Gly | Val | Ala | Val | Ile | Val | His | Ile | Ala | Phe | |
| 1640 | | | | | 1645 | | | | | 1650 | | | | | |

| ttc | atc | gtg | atg | tgg | gtt | ctg | gag | tcc | ttc | aat | ttc | gtc | cgg | atg | 5004 |
| Phe | Ile | Val | Met | Trp | Val | Leu | Glu | Ser | Phe | Asn | Phe | Val | Arg | Met | |
| 1655 | | | | | 1660 | | | | | 1665 | | | | | |

| ctg | atc | ggc | gtg | gtg | acg | tgc | atc | cag | tgc | cag | cgc | ctc | atc | ttc | 5049 |
| Leu | Ile | Gly | Val | Val | Thr | Cys | Ile | Gln | Cys | Gln | Arg | Leu | Ile | Phe | |
| 1670 | | | | | 1675 | | | | | 1680 | | | | | |

| cac | tgc | atg | acc | gcc | ctc | atg | ctc | acg | cgg | gag | ttc | aaa | aat | gat | 5094 |
| His | Cys | Met | Thr | Ala | Leu | Met | Leu | Thr | Arg | Glu | Phe | Lys | Asn | Asp | |
| 1685 | | | | | 1690 | | | | | 1695 | | | | | |

| cat | gcg | aat | acg | gcc | ttc | tgg | acc | ggc | aaa | tgg | tac | ggc | aag | ggc | 5139 |
| His | Ala | Asn | Thr | Ala | Phe | Trp | Thr | Gly | Lys | Trp | Tyr | Gly | Lys | Gly | |
| 1700 | | | | | 1705 | | | | | 1710 | | | | | |

| atg | ggc | tat | atg | gcc | tgg | acg | caa | ccc | tcg | cgc | gag | ctg | acg | gcc | 5184 |
| Met | Gly | Tyr | Met | Ala | Trp | Thr | Gln | Pro | Ser | Arg | Glu | Leu | Thr | Ala | |
| 1715 | | | | | 1720 | | | | | 1725 | | | | | |

| aag | gtc | atc | gag | ttg | tcc | gag | ttt | gcc | gct | gac | ttc | gtc | ctc | ggc | 5229 |
| Lys | Val | Ile | Glu | Leu | Ser | Glu | Phe | Ala | Ala | Asp | Phe | Val | Leu | Gly | |
| 1730 | | | | | 1735 | | | | | 1740 | | | | | |

| cat | gtt | atc | ttg | atc | tgc | cag | ctg | ccg | ctg | ata | atc | ata | ccg | aag | 5274 |
| His | Val | Ile | Leu | Ile | Cys | Gln | Leu | Pro | Leu | Ile | Ile | Ile | Pro | Lys | |
| 1745 | | | | | 1750 | | | | | 1755 | | | | | |

| atc | gac | aag | ttt | cat | tcc | atc | atg | ctg | ttc | tgg | ctg | aaa | ccg | tcg | 5319 |
| Ile | Asp | Lys | Phe | His | Ser | Ile | Met | Leu | Phe | Trp | Leu | Lys | Pro | Ser | |
| 1760 | | | | | 1765 | | | | | 1770 | | | | | |

| cgc | cag | att | agg | ccc | cct | atc | tac | tcg | ctc | aaa | cag | act | agg | ctc | 5364 |
| Arg | Gln | Ile | Arg | Pro | Pro | Ile | Tyr | Ser | Leu | Lys | Gln | Thr | Arg | Leu | |
| 1775 | | | | | 1780 | | | | | 1785 | | | | | |

| cgg | aaa | cgc | atg | gtc | aag | aaa | tac | tgc | tcg | ctg | tat | ttc | ctc | gtg | 5409 |
| Arg | Lys | Arg | Met | Val | Lys | Lys | Tyr | Cys | Ser | Leu | Tyr | Phe | Leu | Val | |
| 1790 | | | | | 1795 | | | | | 1800 | | | | | |

| ctg | gcc | ata | ttc | gcg | ggc | tgc | atc | atc | gga | ccg | gcc | gtg | gcg | agc | 5454 |
| Leu | Ala | Ile | Phe | Ala | Gly | Cys | Ile | Ile | Gly | Pro | Ala | Val | Ala | Ser | |
| 1805 | | | | | 1810 | | | | | 1815 | | | | | |

| gcc | aag | atc | cat | aag | cat | atc | ggg | gat | tcc | ctg | gac | ggt | gtc | gtc | 5499 |
| Ala | Lys | Ile | His | Lys | His | Ile | Gly | Asp | Ser | Leu | Asp | Gly | Val | Val | |
| 1820 | | | | | 1825 | | | | | 1830 | | | | | |

```
cac  aac  ctg  ttc  cag  ccg  atc  aac  act  acc  aac  aac  gac  acc  ggc           5544
His  Asn  Leu  Phe  Gln  Pro  Ile  Asn  Thr  Thr  Asn  Asn  Asp  Thr  Gly
     1835                1840                     1845 tcc  cag  atg  tcg  acc  tac  cag  tcg  cac  tac  tac  acc  cac  acc  ccg           5589
Ser  Gln  Met  Ser  Thr  Tyr  Gln  Ser  His  Tyr  Tyr  Thr  His  Thr  Pro
1850                1855                     1860 tcc  ctt  aag  acc  tgg  agc  acc  ata  aag                                          5616
Ser  Leu  Lys  Thr  Trp  Ser  Thr  Ile  Lys
     1865                1870

<210> SEQ ID NO 6
<211> LENGTH: 1872
<212> TYPE: PRT
<213> ORGANISM: Artificial sequence
<220> FEATURE:
<223> OTHER INFORMATION: Synthetic Construct

<400> SEQUENCE: 6
```

Met Asn Thr Asp Gln Gln Pro Tyr Gln Gly Gln Thr Asp Tyr Thr Gln
1               5                   10                  15

Gly Pro Gly Asn Gly Gln Ser Gln Glu Gln Asp Tyr Asp Gln Tyr Gly
            20                  25                  30

Gln Pro Leu Tyr Pro Ser Gln Ala Asp Gly Tyr Tyr Asp Pro Asn Val
        35                  40                  45

Ala Ala Gly Thr Glu Ala Asp Met Tyr Gly Gln Gln Pro Pro Asn Glu
    50                  55                  60

Ser Tyr Asp Gln Asp Tyr Thr Asn Gly Glu Tyr Tyr Gly Gln Pro Pro
65                  70                  75                  80

Asn Met Ala Ala Gln Asp Gly Glu Asn Phe Ser Asp Phe Ser Ser Tyr
                85                  90                  95

Gly Pro Pro Gly Thr Pro Gly Tyr Asp Ser Tyr Gly Gln Tyr Thr
            100                 105                 110

Ala Ser Gln Met Ser Tyr Gly Glu Pro Asn Ser Ser Gly Thr Ser Thr
        115                 120                 125

Pro Ile Tyr Gly Asn Tyr Asp Pro Asn Ala Ile Ala Met Ala Leu Pro
    130                 135                 140

Asn Glu Pro Tyr Pro Ala Trp Thr Ala Asp Ser Gln Ser Pro Val Ser
145                 150                 155                 160

Ile Glu Gln Ile Glu Asp Ile Phe Ile Asp Leu Thr Asn Arg Leu Gly
                165                 170                 175

Phe Gln Arg Asp Ser Met Arg Asn Met Phe Asp His Phe Met Val Leu
            180                 185                 190

Leu Asp Ser Arg Ser Ser Arg Met Ser Pro Asp Gln Ala Leu Leu Ser
        195                 200                 205

Leu His Ala Asp Tyr Ile Gly Gly Asp Thr Ala Asn Tyr Lys Lys Trp
    210                 215                 220

Tyr Phe Ala Ala Gln Leu Asp Met Asp Asp Glu Ile Gly Phe Arg Asn
225                 230                 235                 240

Met Ser Leu Gly Lys Leu Ser Arg Lys Ala Arg Lys Ala Lys Lys
                245                 250                 255

Asn Lys Lys Ala Met Glu Glu Ala Asn Pro Glu Asp Thr Glu Glu Thr
            260                 265                 270

Leu Asn Lys Ile Glu Gly Asp Asn Ser Leu Glu Ala Ala Asp Phe Arg
        275                 280                 285

Trp Lys Ala Lys Met Asn Gln Leu Ser Pro Leu Glu Arg Val Arg His
    290                 295                 300

```
Ile Ala Leu Tyr Leu Leu Cys Trp Gly Glu Ala Asn Gln Val Arg Phe
305                 310                 315                 320

Thr Ala Glu Cys Leu Cys Phe Ile Tyr Lys Cys Ala Leu Asp Tyr Leu
            325                 330                 335

Asp Ser Pro Leu Cys Gln Gln Arg Gln Glu Pro Met Pro Glu Gly Asp
        340                 345                 350

Phe Leu Asn Arg Val Ile Thr Pro Ile Tyr His Phe Ile Arg Asn Gln
            355                 360                 365

Val Tyr Glu Ile Val Asp Gly Arg Phe Val Lys Arg Glu Arg Asp His
        370                 375                 380

Asn Lys Ile Val Gly Tyr Asp Asp Leu Asn Gln Leu Phe Trp Tyr Pro
385                 390                 395                 400

Glu Gly Ile Ala Lys Ile Val Leu Glu Asp Gly Thr Lys Leu Ile Glu
                405                 410                 415

Leu Pro Leu Glu Glu Arg Tyr Leu Arg Leu Gly Asp Val Val Trp Asp
            420                 425                 430

Asp Val Phe Phe Lys Thr Tyr Lys Glu Thr Arg Thr Trp Leu His Leu
        435                 440                 445

Val Thr Asn Phe Asn Arg Ile Trp Val Met His Ile Ser Ile Phe Trp
450                 455                 460

Met Tyr Phe Ala Tyr Asn Ser Pro Thr Phe Tyr Thr His Asn Tyr Gln
465                 470                 475                 480

Gln Leu Val Asp Asn Gln Pro Leu Ala Ala Tyr Lys Trp Ala Ser Cys
                485                 490                 495

Ala Leu Gly Gly Thr Val Ala Ser Leu Ile Gln Ile Val Ala Thr Leu
            500                 505                 510

Cys Glu Trp Ser Phe Val Pro Arg Lys Trp Ala Gly Ala Gln His Leu
        515                 520                 525

Ser Arg Arg Phe Trp Phe Leu Cys Ile Ile Phe Gly Ile Asn Leu Gly
530                 535                 540

Pro Ile Ile Phe Val Phe Ala Tyr Asp Lys Asp Thr Val Tyr Ser Thr
545                 550                 555                 560

Ala Ala His Val Val Ala Ala Val Met Phe Phe Val Ala Val Ala Thr
                565                 570                 575

Ile Ile Phe Phe Ser Ile Met Pro Leu Gly Gly Leu Phe Thr Ser Tyr
            580                 585                 590

Met Lys Lys Ser Thr Arg Arg Tyr Val Ala Ser Gln Thr Phe Thr Ala
        595                 600                 605

Ala Phe Ala Pro Leu His Gly Leu Asp Arg Trp Met Ser Tyr Leu Val
            610                 615                 620

Trp Val Thr Val Phe Ala Ala Lys Tyr Ser Glu Ser Tyr Tyr Phe Leu
625                 630                 635                 640

Val Leu Ser Leu Arg Asp Pro Ile Arg Ile Leu Ser Thr Thr Ala Met
            645                 650                 655

Arg Cys Thr Gly Glu Tyr Trp Trp Gly Ala Val Leu Cys Lys Val Gln
            660                 665                 670

Pro Lys Ile Val Leu Gly Leu Val Ile Ala Thr Asp Phe Ile Leu Phe
        675                 680                 685

Phe Leu Asp Thr Tyr Leu Trp Tyr Ile Ile Val Asn Thr Ile Phe Ser
        690                 695                 700

Val Gly Lys Ser Phe Tyr Leu Gly Ile Ser Ile Leu Thr Pro Trp Arg
705                 710                 715                 720
```

-continued

```
Asn Ile Phe Thr Arg Leu Pro Lys Arg Ile Tyr Ser Lys Ile Leu Ala
            725                 730                 735

Thr Thr Asp Met Glu Ile Lys Tyr Lys Pro Lys Val Leu Ile Ser Gln
            740                 745                 750

Val Trp Asn Ala Ile Ile Ile Ser Met Tyr Arg Glu His Leu Leu Ala
            755                 760                 765

Ile Asp His Val Gln Lys Leu Leu Tyr His Gln Val Pro Ser Glu Ile
            770                 775                 780

Glu Gly Lys Arg Thr Leu Arg Ala Pro Thr Phe Val Ser Gln Asp
785                 790                 795                 800

Asp Asn Asn Phe Glu Thr Glu Phe Phe Pro Arg Asp Ser Glu Ala Glu
            805                 810                 815

Arg Arg Ile Ser Phe Phe Ala Gln Ser Leu Ser Thr Pro Ile Pro Glu
            820                 825                 830

Pro Leu Pro Val Asp Asn Met Pro Thr Phe Thr Val Leu Thr Pro His
            835                 840                 845

Tyr Ala Glu Arg Ile Leu Leu Ser Leu Arg Glu Ile Ile Arg Glu Asp
            850                 855                 860

Asp Gln Phe Ser Arg Val Thr Leu Leu Glu Tyr Leu Lys Gln Leu His
865                 870                 875                 880

Pro Val Glu Trp Glu Cys Phe Val Lys Asp Thr Lys Ile Leu Ala Glu
            885                 890                 895

Glu Thr Ala Ala Tyr Glu Gly Asn Glu Asn Glu Ala Glu Lys Glu Asp
            900                 905                 910

Ala Leu Lys Ser Gln Ile Asp Asp Leu Pro Phe Tyr Cys Ile Gly Phe
            915                 920                 925

Lys Ser Ala Ala Pro Glu Tyr Thr Leu Arg Thr Arg Ile Trp Ala Ser
            930                 935                 940

Leu Arg Ser Gln Thr Leu Tyr Arg Thr Ile Ser Gly Phe Met Asn Tyr
945                 950                 955                 960

Ser Arg Ala Ile Lys Leu Leu Tyr Arg Val Glu Asn Pro Glu Ile Val
                    965                 970                 975

Gln Met Phe Gly Gly Asn Ala Glu Gly Leu Glu Arg Glu Leu Glu Lys
            980                 985                 990

Met Ala Arg Arg Lys Phe Lys Phe Leu Val Ser Met Gln Arg Leu Ala
            995                 1000                1005

Lys Phe  Lys Phe Leu Glu Asn  Ala Glu Phe Leu Leu  Arg Ala Tyr
    1010                 1015                 1020

Pro Asp  Leu Gln Ile Ala Tyr  Leu Asp Glu Glu Pro  Pro Leu Thr
    1025                 1030                 1035

Glu Gly  Glu Glu Pro Arg Ile  Tyr Ser Ala Leu Ile  Asp Gly His
    1040                 1045                 1050

Cys Glu  Ile Leu Asp Asn Gly  Arg Arg Arg Pro Lys  Phe Arg Val
    1055                 1060                 1065

Gln Leu  Ser Gly Asn Pro Ile  Leu Gly Asp Gly Lys  Ser Asp Asn
    1070                 1075                 1080

Gln Asn  His Ala Leu Ile Phe  Tyr Arg Gly Glu Tyr  Ile Gln Leu
    1085                 1090                 1095

Ile Asp  Ala Asn Gln Asp Asn  Tyr Leu Glu Glu Cys  Leu Lys Ile
    1100                 1105                 1110

Arg Ser  Val Leu Ala Glu Phe  Glu Glu Leu Asn Val  Glu Gln Val
    1115                 1120                 1125

Asn Pro  Tyr Ala Pro Gly Leu  Arg Tyr Glu Glu Gln  Thr Thr Asn
```

-continued

```
            1130                1135                1140

His Pro Val Ala Ile Val Gly Ala Arg Glu Tyr Ile Phe Ser Glu
    1145                1150                1155

Asn Ser Gly Val Leu Gly Asp Val Ala Ala Gly Lys Glu Gln Thr
    1160                1165                1170

Phe Gly Thr Leu Phe Ala Arg Thr Leu Ser Gln Ile Gly Gly Lys
    1175                1180                1185

Leu His Tyr Gly His Pro Asp Phe Ile Asn Ala Thr Phe Met Thr
    1190                1195                1200

Thr Arg Gly Gly Val Ser Lys Ala Gln Lys Gly Leu His Leu Asn
    1205                1210                1215

Glu Asp Ile Tyr Ala Gly Met Asn Ala Met Leu Arg Gly Gly Arg
    1220                1225                1230

Ile Lys His Cys Glu Tyr Tyr Gln Cys Gly Lys Gly Arg Asp Leu
    1235                1240                1245

Gly Phe Gly Thr Ile Leu Asn Phe Thr Thr Lys Ile Gly Ala Gly
    1250                1255                1260

Met Gly Glu Gln Met Leu Ser Arg Glu Tyr Tyr Leu Gly Thr
    1265                1270                1275

Gln Leu Pro Val Asp Arg Phe Leu Thr Phe Tyr Ala His Pro
    1280                1285                1290

Gly Phe His Leu Asn Asn Leu Phe Ile Gln Leu Ser Leu Gln Met
    1295                1300                1305

Phe Met Leu Thr Leu Val Asn Leu Ser Ser Leu Ala His Glu Ser
    1310                1315                1320

Ile Met Cys Ile Tyr Asp Arg Asn Lys Pro Lys Thr Asp Val Leu
    1325                1330                1335

Val Pro Ile Gly Cys Tyr Asn Phe Gln Pro Ala Val Asp Trp Val
    1340                1345                1350

Arg Arg Tyr Thr Leu Ser Ile Phe Ile Val Phe Trp Ile Ala Phe
    1355                1360                1365

Val Pro Ile Val Val Gln Glu Leu Ile Glu Arg Gly Leu Trp Lys
    1370                1375                1380

Ala Thr Gln Arg Phe Phe Cys His Leu Leu Ser Leu Ser Pro Met
    1385                1390                1395

Phe Glu Val Phe Ala Gly Gln Ile Tyr Ser Ser Ala Leu Leu Ser
    1400                1405                1410

Asp Leu Ala Ile Gly Gly Ala Arg Tyr Ile Ser Thr Gly Arg Gly
    1415                1420                1425

Phe Ala Thr Ser Arg Ile Pro Phe Ser Ile Lys Arg Phe Ala Gly
    1430                1435                1440

Ser Ala Ile Tyr Met Gly Ala Arg Ser Met Leu Met Leu Leu Phe
    1445                1450                1455

Gly Thr Val Ala His Trp Gln Ala Pro Leu Leu Trp Phe Trp Ala
    1460                1465                1470

Ser Leu Ser Ser Leu Ile Phe Ala Pro Phe Val Phe Asn Pro His
    1475                1480                1485

Gln Phe Ala Trp Glu Asp Phe Leu Asp Tyr Arg Asp Tyr Ile
    1490                1495                1500

Arg Trp Leu Ser Arg Gly Asn Asn Gln Tyr His Arg Asn Ser Trp
    1505                1510                1515

Ile Gly Tyr Val Arg Met Ser Arg Ala Arg Ile Thr Gly Phe Lys
    1520                1525                1530
```

Arg Lys Leu Val Gly Asp Glu Ser Glu Lys Ala Ala Gly Asp Ala
1535                1540                1545

Ser Arg Ala His Arg Thr Asn Leu Ile Met Ala Glu Ile Ile Pro
1550                1555                1560

Cys Ala Ile Tyr Ala Ala Gly Cys Phe Ile Ala Phe Thr Phe Ile
1565                1570                1575

Asn Ala Gln Thr Gly Val Lys Thr Thr Asp Asp Arg Val Asn
1580                1585                1590

Ser Val Leu Arg Ile Ile Ile Cys Thr Leu Ala Pro Ile Ala Val
1595                1600                1605

Asn Leu Gly Val Leu Phe Phe Cys Met Gly Met Ser Cys Cys Ser
1610                1615                1620

Gly Pro Leu Phe Gly Met Cys Cys Lys Lys Thr Gly Ser Val Met
1625                1630                1635

Ala Gly Ile Ala His Gly Val Ala Val Ile Val His Ile Ala Phe
1640                1645                1650

Phe Ile Val Met Trp Val Leu Glu Ser Phe Asn Phe Val Arg Met
1655                1660                1665

Leu Ile Gly Val Val Thr Cys Ile Gln Cys Gln Arg Leu Ile Phe
1670                1675                1680

His Cys Met Thr Ala Leu Met Leu Thr Arg Glu Phe Lys Asn Asp
1685                1690                1695

His Ala Asn Thr Ala Phe Trp Thr Gly Lys Trp Tyr Gly Lys Gly
1700                1705                1710

Met Gly Tyr Met Ala Trp Thr Gln Pro Ser Arg Glu Leu Thr Ala
1715                1720                1725

Lys Val Ile Glu Leu Ser Glu Phe Ala Ala Asp Phe Val Leu Gly
1730                1735                1740

His Val Ile Leu Ile Cys Gln Leu Pro Leu Ile Ile Ile Pro Lys
1745                1750                1755

Ile Asp Lys Phe His Ser Ile Met Leu Phe Trp Leu Lys Pro Ser
1760                1765                1770

Arg Gln Ile Arg Pro Pro Ile Tyr Ser Leu Lys Gln Thr Arg Leu
1775                1780                1785

Arg Lys Arg Met Val Lys Lys Tyr Cys Ser Leu Tyr Phe Leu Val
1790                1795                1800

Leu Ala Ile Phe Ala Gly Cys Ile Ile Gly Pro Ala Val Ala Ser
1805                1810                1815

Ala Lys Ile His Lys His Ile Gly Asp Ser Leu Asp Gly Val Val
1820                1825                1830

His Asn Leu Phe Gln Pro Ile Asn Thr Thr Asn Asn Asp Thr Gly
1835                1840                1845

Ser Gln Met Ser Thr Tyr Gln Ser His Tyr Tyr Thr His Thr Pro
1850                1855                1860

Ser Leu Lys Thr Trp Ser Thr Ile Lys
1865                1870

<210> SEQ ID NO 7
<211> LENGTH: 5661
<212> TYPE: DNA
<213> ORGANISM: Artificial sequence
<220> FEATURE:
<223> OTHER INFORMATION: Synthetic construct
<220> FEATURE:
<221> NAME/KEY: CDS -continued
<222> LOCATION: (1)..(5661)
<223> OTHER INFORMATION: Saccharomyces cerevisiae FKS2 (codon optimized)

<400> SEQUENCE: 7

| | | | | | | | | | | | | | | | | |
|---|---|---|---|---|---|---|---|---|---|---|---|---|---|---|---|---|
| atg | tcc | tac | aac | gat | ccc | aat | ctc | aat | ggc | cag | tat | tac | tcc | aac | ggc | 48 |
| Met | Ser | Tyr | Asn | Asp | Pro | Asn | Leu | Asn | Gly | Gln | Tyr | Tyr | Ser | Asn | Gly | |
| 1 | | | | 5 | | | | | 10 | | | | | 15 | | |

| gac | ggc | acc | ggc | gat | ggc | aat | tat | ccg | acc | tac | cag | gtg | acc | cag | gat | 96 |
|---|---|---|---|---|---|---|---|---|---|---|---|---|---|---|---|---|
| Asp | Gly | Thr | Gly | Asp | Gly | Asn | Tyr | Pro | Thr | Tyr | Gln | Val | Thr | Gln | Asp | |
| | | | 20 | | | | | 25 | | | | | 30 | | | |

| caa | agc | gcg | tac | gac | gag | tac | ggc | cag | ccc | atc | tat | acc | caa | aat | caa | 144 |
|---|---|---|---|---|---|---|---|---|---|---|---|---|---|---|---|---|
| Gln | Ser | Ala | Tyr | Asp | Glu | Tyr | Gly | Gln | Pro | Ile | Tyr | Thr | Gln | Asn | Gln | |
| | | 35 | | | | | 40 | | | | | 45 | | | | |

| ctg | gac | gat | ggc | tac | tat | gac | ccg | aat | gaa | caa | tac | gtg | gat | ggc | acc | 192 |
|---|---|---|---|---|---|---|---|---|---|---|---|---|---|---|---|---|
| Leu | Asp | Asp | Gly | Tyr | Tyr | Asp | Pro | Asn | Glu | Gln | Tyr | Val | Asp | Gly | Thr | |
| | 50 | | | | | 55 | | | | | 60 | | | | | |

| cag | ttc | ccg | cag | ggc | cag | gac | ccg | tcg | cag | gac | caa | ggc | ccg | tat | aac | 240 |
|---|---|---|---|---|---|---|---|---|---|---|---|---|---|---|---|---|
| Gln | Phe | Pro | Gln | Gly | Gln | Asp | Pro | Ser | Gln | Asp | Gln | Gly | Pro | Tyr | Asn | |
| 65 | | | | | 70 | | | | | 75 | | | | | 80 | |

| aat | gac | gcc | agc | tat | tac | aac | cag | ccg | ccg | aac | atg | atg | aac | ccg | tcg | 288 |
|---|---|---|---|---|---|---|---|---|---|---|---|---|---|---|---|---|
| Asn | Asp | Ala | Ser | Tyr | Tyr | Asn | Gln | Pro | Pro | Asn | Met | Met | Asn | Pro | Ser | |
| | | | | 85 | | | | | 90 | | | | | 95 | | |

| tcc | cag | gac | ggt | gag | aat | ttc | tcg | gac | ttc | agc | tcg | tat | gga | ccg | ccc | 336 |
|---|---|---|---|---|---|---|---|---|---|---|---|---|---|---|---|---|
| Ser | Gln | Asp | Gly | Glu | Asn | Phe | Ser | Asp | Phe | Ser | Ser | Tyr | Gly | Pro | Pro | |
| | | | 100 | | | | | 105 | | | | | 110 | | | |

| tcg | gga | acg | tac | cct | aat | gac | cag | tat | acg | ccc | agt | cag | atg | tcc | tac | 384 |
|---|---|---|---|---|---|---|---|---|---|---|---|---|---|---|---|---|
| Ser | Gly | Thr | Tyr | Pro | Asn | Asp | Gln | Tyr | Thr | Pro | Ser | Gln | Met | Ser | Tyr | |
| | | 115 | | | | | 120 | | | | | 125 | | | | |

| ccg | gat | cag | gac | ggc | tcg | tcg | ggt | gcg | tcg | acg | ccg | tat | ggc | aac | ggc | 432 |
|---|---|---|---|---|---|---|---|---|---|---|---|---|---|---|---|---|
| Pro | Asp | Gln | Asp | Gly | Ser | Ser | Gly | Ala | Ser | Thr | Pro | Tyr | Gly | Asn | Gly | |
| | 130 | | | | | 135 | | | | | 140 | | | | | |

| gtc | gtc | aat | ggg | aac | ggc | cag | tat | tat | gat | ccg | aat | gcg | atc | gag | atg | 480 |
|---|---|---|---|---|---|---|---|---|---|---|---|---|---|---|---|---|
| Val | Val | Asn | Gly | Asn | Gly | Gln | Tyr | Tyr | Asp | Pro | Asn | Ala | Ile | Glu | Met | |
| 145 | | | | | 150 | | | | | 155 | | | | | 160 | |

| gcg | ctg | ccc | aat | gac | ccg | tat | ccg | gcg | tgg | acc | gcc | gat | ccc | cag | tcc | 528 |
|---|---|---|---|---|---|---|---|---|---|---|---|---|---|---|---|---|
| Ala | Leu | Pro | Asn | Asp | Pro | Tyr | Pro | Ala | Trp | Thr | Ala | Asp | Pro | Gln | Ser | |
| | | | | 165 | | | | | 170 | | | | | 175 | | |

| cct | ctc | ccc | atc | gag | caa | att | gag | gac | atc | ttc | ata | gat | ctc | acc | aat | 576 |
|---|---|---|---|---|---|---|---|---|---|---|---|---|---|---|---|---|
| Pro | Leu | Pro | Ile | Glu | Gln | Ile | Glu | Asp | Ile | Phe | Ile | Asp | Leu | Thr | Asn | |
| | | | 180 | | | | | 185 | | | | | 190 | | | |

| aag | ttc | ggc | ttc | cag | cgc | gac | tcg | atg | cgg | aac | atg | ttc | gac | cac | ttc | 624 |
|---|---|---|---|---|---|---|---|---|---|---|---|---|---|---|---|---|
| Lys | Phe | Gly | Phe | Gln | Arg | Asp | Ser | Met | Arg | Asn | Met | Phe | Asp | His | Phe | |
| | | 195 | | | | | 200 | | | | | 205 | | | | |

| atg | acc | ctg | ctg | gat | tcg | cgc | agc | tcg | cgc | atg | tcg | ccg | gaa | cag | gcc | 672 |
|---|---|---|---|---|---|---|---|---|---|---|---|---|---|---|---|---|
| Met | Thr | Leu | Leu | Asp | Ser | Arg | Ser | Ser | Arg | Met | Ser | Pro | Glu | Gln | Ala | |
| | 210 | | | | | 215 | | | | | 220 | | | | | |

| ttg | ctc | tcc | ctc | cat | gcc | gac | tac | att | ggc | ggc | gac | acc | gcc | aac | tac | 720 |
|---|---|---|---|---|---|---|---|---|---|---|---|---|---|---|---|---|
| Leu | Leu | Ser | Leu | His | Ala | Asp | Tyr | Ile | Gly | Gly | Asp | Thr | Ala | Asn | Tyr | |
| 225 | | | | | 230 | | | | | 235 | | | | | 240 | |

| aag | aaa | tgg | tat | ttt | gcg | gcc | caa | ctg | gat | atg | gac | gat | gag | atc | ggc | 768 |
|---|---|---|---|---|---|---|---|---|---|---|---|---|---|---|---|---|
| Lys | Lys | Trp | Tyr | Phe | Ala | Ala | Gln | Leu | Asp | Met | Asp | Asp | Glu | Ile | Gly | |
| | | | | 245 | | | | | 250 | | | | | 255 | | |

| ttc | cgg | aac | atg | aaa | ctc | ggc | aag | ctg | tcc | cgc | aaa | gcg | cgc | aaa | gcg | 816 |
|---|---|---|---|---|---|---|---|---|---|---|---|---|---|---|---|---|
| Phe | Arg | Asn | Met | Lys | Leu | Gly | Lys | Leu | Ser | Arg | Lys | Ala | Arg | Lys | Ala | |
| | | | 260 | | | | | 265 | | | | | 270 | | | |

| aag | aag | aaa | aac | aaa | aag | gcc | atg | caa | gag | gat | gag | gac | act | gaa | gag | 864 |
|---|---|---|---|---|---|---|---|---|---|---|---|---|---|---|---|---|
| Lys | Lys | Lys | Asn | Lys | Lys | Ala | Met | Gln | Glu | Asp | Glu | Asp | Thr | Glu | Glu | |
| | | 275 | | | | | 280 | | | | | 285 | | | | |

| act | ctg | aac | cag | atc | gag | ggc | gat | aac | tcc | ctc | gaa | gcc | gct | gac | ttc | 912 |
|---|---|---|---|---|---|---|---|---|---|---|---|---|---|---|---|---|
| Thr | Leu | Asn | Gln | Ile | Glu | Gly | Asp | Asn | Ser | Leu | Glu | Ala | Ala | Asp | Phe | |

-continued

```
              290                 295                 300
cgg tgg aag agt aaa atg aat caa ctc agc ccc ttc gag atg gtg cgg     960
Arg Trp Lys Ser Lys Met Asn Gln Leu Ser Pro Phe Glu Met Val Arg
305                 310                 315                 320 caa atc gcc ctc ttc ctc ctg tgc tgg ggc gag gcc aat caa gtg cgg    1008
Gln Ile Ala Leu Phe Leu Leu Cys Trp Gly Glu Ala Asn Gln Val Arg
                325                 330                 335 ttc acc ccg gag tgc ctg tgc ttt atc tac aag tgc gcg agc gac tac    1056
Phe Thr Pro Glu Cys Leu Cys Phe Ile Tyr Lys Cys Ala Ser Asp Tyr
            340                 345                 350 ctg gac tcc gcc caa tgc cag cag cgg ccc gac ccc ctg ccc gag ggc    1104
Leu Asp Ser Ala Gln Cys Gln Gln Arg Pro Asp Pro Leu Pro Glu Gly
                355                 360                 365 gac ttt ctc aat cgg gtg atc acg ccc ttg tac cgc ttc att cgc agc    1152
Asp Phe Leu Asn Arg Val Ile Thr Pro Leu Tyr Arg Phe Ile Arg Ser
370                 375                 380 cag gtg tac gag atc gtc gac ggc cgc tac gtg aag tcc gag aag gac    1200
Gln Val Tyr Glu Ile Val Asp Gly Arg Tyr Val Lys Ser Glu Lys Asp
385                 390                 395                 400 cat aac aag gtc att ggt tat gac gac gtc aac caa ctt ttc tgg tat    1248
His Asn Lys Val Ile Gly Tyr Asp Asp Val Asn Gln Leu Phe Trp Tyr
                405                 410                 415 ccg gaa ggc atc gcc aag atc gtg atg gag gac ggc acg cgc ctt atc    1296
Pro Glu Gly Ile Ala Lys Ile Val Met Glu Asp Gly Thr Arg Leu Ile
            420                 425                 430 gac ctc ccc gct gag gaa cgg tac ctc aag ctc ggc gag atc ccc tgg    1344
Asp Leu Pro Ala Glu Glu Arg Tyr Leu Lys Leu Gly Glu Ile Pro Trp
                435                 440                 445 gac gat gtg ttc ttc aag acc tat aag gaa acc cgc tcc tgg ctc cat    1392
Asp Asp Val Phe Phe Lys Thr Tyr Lys Glu Thr Arg Ser Trp Leu His
450                 455                 460 ctg gtg acc aac ttc aat cgg att tgg att atg cac gtg tat tgg atg    1440
Leu Val Thr Asn Phe Asn Arg Ile Trp Ile Met His Val Tyr Trp Met
465                 470                 475                 480 tat tgt gca tac aat gcc ccc acc ttc tat acg cac aat tac caa cag    1488
Tyr Cys Ala Tyr Asn Ala Pro Thr Phe Tyr Thr His Asn Tyr Gln Gln
                485                 490                 495 ctt gtc gac aac cag ccg ctc gcc gca tac aag tgg gcc acc gct gcc    1536
Leu Val Asp Asn Gln Pro Leu Ala Ala Tyr Lys Trp Ala Thr Ala Ala
            500                 505                 510 ctc ggg ggg acg gtc gcg tcg ttg atc cag gtc gcg gcg acg ctg tgc    1584
Leu Gly Gly Thr Val Ala Ser Leu Ile Gln Val Ala Ala Thr Leu Cys
                515                 520                 525 gag tgg tcc ttc gtg ccg cgg aaa tgg gca ggc gcg cag cac ctg tcc    1632
Glu Trp Ser Phe Val Pro Arg Lys Trp Ala Gly Ala Gln His Leu Ser
530                 535                 540 cgg cgc ttc tgg ttc ctg tgc gtc atc atg ggc atc aat ctt ggc ccc    1680
Arg Arg Phe Trp Phe Leu Cys Val Ile Met Gly Ile Asn Leu Gly Pro
545                 550                 555                 560 gtc atc ttc gtg ttc gcc tat gac aaa gat acg gtc tac tcg acg gcc    1728
Val Ile Phe Val Phe Ala Tyr Asp Lys Asp Thr Val Tyr Ser Thr Ala
                565                 570                 575 gca cac gtc gtg ggc gca gtt atg ttc ttt gtc gcc gtg gcg act ctg    1776
Ala His Val Val Gly Ala Val Met Phe Phe Val Ala Val Ala Thr Leu
            580                 585                 590 gtc ttt ttc agc gtc atg ccg ctg ggt ggc ctg ttc acc agt tat atg    1824
Val Phe Phe Ser Val Met Pro Leu Gly Gly Leu Phe Thr Ser Tyr Met
                595                 600                 605 aag aaa agt acc cgg tcg tac gtc gcg agt cag acc ttc acc gcc agc    1872
```

```
                Lys Lys Ser Thr Arg Ser Tyr Val Ala Ser Gln Thr Phe Thr Ala Ser
                    610             615                 620 ttc gcg cca ctg cat ggg ctg gac cgg tgg atg agt tac ctc gtg tgg             1920
Phe Ala Pro Leu His Gly Leu Asp Arg Trp Met Ser Tyr Leu Val Trp
625                 630                 635                 640 gtg acc gtt ttc gcc gcc aaa tat gcg gag tcg tac ttc ttc ctg atc             1968
Val Thr Val Phe Ala Ala Lys Tyr Ala Glu Ser Tyr Phe Phe Leu Ile
                    645                 650                 655 ctt tcg ctc cgc gat ccg att cgc atc ctg tcg acg acc tcg atg cgc             2016
Leu Ser Leu Arg Asp Pro Ile Arg Ile Leu Ser Thr Thr Ser Met Arg
                660                 665                 670 tgc acg ggc gag tac tgg tgg gga aac aag atc tgc aag gtc caa ccg             2064
Cys Thr Gly Glu Tyr Trp Trp Gly Asn Lys Ile Cys Lys Val Gln Pro
            675                 680                 685 aag atc gtc ttg ggc ctc atg atc gcc acg gac ttc atc ctg ttc ttc             2112
Lys Ile Val Leu Gly Leu Met Ile Ala Thr Asp Phe Ile Leu Phe Phe
        690                 695                 700 ctg gac acc tac ctc tgg tac atc gtc gtg aac acg gtt ttc agc gtc             2160
Leu Asp Thr Tyr Leu Trp Tyr Ile Val Val Asn Thr Val Phe Ser Val
705                 710                 715                 720 gga aaa tcg ttc tac ctg ggc atc tcc att ctc acc ccg tgg cgc aac             2208
Gly Lys Ser Phe Tyr Leu Gly Ile Ser Ile Leu Thr Pro Trp Arg Asn
                    725                 730                 735 atc ttt acc cgg ctg ccc aag cgc ata tac agc aag atc ctg gcc acc             2256
Ile Phe Thr Arg Leu Pro Lys Arg Ile Tyr Ser Lys Ile Leu Ala Thr
                740                 745                 750 acc gac atg gag atc aag tac aaa ccc aag gtc ctc atc agc cag atc             2304
Thr Asp Met Glu Ile Lys Tyr Lys Pro Lys Val Leu Ile Ser Gln Ile
            755                 760                 765 tgg aat gcg ata atc ata tcc atg tat cgc gag cat ctt ctg gcg atc             2352
Trp Asn Ala Ile Ile Ile Ser Met Tyr Arg Glu His Leu Leu Ala Ile
        770                 775                 780 gac cat gtc caa aag ctg ctg tat cat cag gtg ccg agc gag atc gag             2400
Asp His Val Gln Lys Leu Leu Tyr His Gln Val Pro Ser Glu Ile Glu
785                 790                 795                 800 ggt aag cgc acc ttg cgc gct ccg acc ttc ttc gtt tcg caa gac gat             2448
Gly Lys Arg Thr Leu Arg Ala Pro Thr Phe Phe Val Ser Gln Asp Asp
                    805                 810                 815 aac aac ttc gag act gag ttc ttc cca agg gat tcc gag gcc gag cgc             2496
Asn Asn Phe Glu Thr Glu Phe Phe Pro Arg Asp Ser Glu Ala Glu Arg
                820                 825                 830 cgg atc agc ttt ttc gcg cag agc ctt tcc acc ccc atc ccc gag ccg             2544
Arg Ile Ser Phe Phe Ala Gln Ser Leu Ser Thr Pro Ile Pro Glu Pro
            835                 840                 845 ctg ccg gtg gac aac atg ccc acg ttc acg gtt ctg acc ccg cat tac             2592
Leu Pro Val Asp Asn Met Pro Thr Phe Thr Val Leu Thr Pro His Tyr
        850                 855                 860 gcc gag cgc atc ttg ctg agc ctg cgg gaa atc atc cgc gag gac gac             2640
Ala Glu Arg Ile Leu Leu Ser Leu Arg Glu Ile Ile Arg Glu Asp Asp
865                 870                 875                 880 cag ttc agc cgc gtg acc ctc ctg gag tat ctg aag caa ctc cat ccc             2688
Gln Phe Ser Arg Val Thr Leu Leu Glu Tyr Leu Lys Gln Leu His Pro
                    885                 890                 895 gtg gag tgg gat tgc ttc gtc aaa gac acc aag atc ctg gcc gag gaa             2736
Val Glu Trp Asp Cys Phe Val Lys Asp Thr Lys Ile Leu Ala Glu Glu
                900                 905                 910 acc gcc gct tac gaa aac aac gag gac gag cct gag aag gag gac gcg             2784
Thr Ala Ala Tyr Glu Asn Asn Glu Asp Glu Pro Glu Lys Glu Asp Ala
            915                 920                 925
```

-continued

| | |
|---|---|
| ctc aaa agt cag atc gac gac ttg ccg ttc tac tgc att gga ttc aaa<br>Leu Lys Ser Gln Ile Asp Asp Leu Pro Phe Tyr Cys Ile Gly Phe Lys<br>930                935                  940 | 2832 |
| tcg gcg gca ccg gag tac acg ctt cgg acc cgg atc tgg gcg agc ctc<br>Ser Ala Ala Pro Glu Tyr Thr Leu Arg Thr Arg Ile Trp Ala Ser Leu<br>945                950                955                960 | 2880 |
| cgc tcg cag acc ctc tat cgg acc atc tcg gga ttc atg aat tac tcc<br>Arg Ser Gln Thr Leu Tyr Arg Thr Ile Ser Gly Phe Met Asn Tyr Ser<br>965                970                  975 | 2928 |
| cgg gca atc aag ctg ctg tat cgc gtg gag aac ccg gag atc gtg caa<br>Arg Ala Ile Lys Leu Leu Tyr Arg Val Glu Asn Pro Glu Ile Val Gln<br>980                985                  990 | 2976 |
| atg ttc ggc ggc aat gcc gac ggc ctg gag cgc gag ctt gag aag atg<br>Met Phe Gly Gly Asn Ala Asp Gly Leu Glu Arg Glu Leu Glu Lys Met<br>            995                  1000                1005 | 3024 |
| gcg agg cgc aag ttc aag ttc ctc gtg agt atg cag cgc ctg gca<br>Ala Arg Arg Lys Phe Lys Phe Leu Val Ser Met Gln Arg Leu Ala<br>1010                  1015                  1020 | 3069 |
| aag ttc aag ttc ctg gag aac gcc gag ttc ctg ctt cgg gcg tat<br>Lys Phe Lys Phe Leu Glu Asn Ala Glu Phe Leu Leu Arg Ala Tyr<br>1025                  1030                  1035 | 3114 |
| ccg gac ctc cag atc gcc tac ctg gac gaa gaa ccg ccc ctg aat<br>Pro Asp Leu Gln Ile Ala Tyr Leu Asp Glu Glu Pro Pro Leu Asn<br>1040                  1045                  1050 | 3159 |
| gag ggc gag gag cca cgc atc tat tcc gcg ctc atc gac ggc cac<br>Glu Gly Glu Glu Pro Arg Ile Tyr Ser Ala Leu Ile Asp Gly His<br>1055                  1060                  1065 | 3204 |
| tgc gag att aat ggc cgc cgg cgc ccg aag ttc agg gtc cag ctc<br>Cys Glu Ile Asn Gly Arg Arg Arg Pro Lys Phe Arg Val Gln Leu<br>1070                  1075                  1080 | 3249 |
| tcc ggc aac ccg att ttg ggc gat ggg aaa tcg gac aac cag aat<br>Ser Gly Asn Pro Ile Leu Gly Asp Gly Lys Ser Asp Asn Gln Asn<br>1085                  1090                  1095 | 3294 |
| cat gcg ctc atc ttc tat cgc ggc gag tac att cag ctg atc gac<br>His Ala Leu Ile Phe Tyr Arg Gly Glu Tyr Ile Gln Leu Ile Asp<br>1100                  1105                  1110 | 3339 |
| gcc aac caa gat aac tat ctt gag gag tgc ctg aag atc cgc tcg<br>Ala Asn Gln Asp Asn Tyr Leu Glu Glu Cys Leu Lys Ile Arg Ser<br>1115                  1120                  1125 | 3384 |
| gtg ctg gcg gag ttt gag gaa ctc ggt att gaa cag ata cac ccg<br>Val Leu Ala Glu Phe Glu Glu Leu Gly Ile Glu Gln Ile His Pro<br>1130                  1135                  1140 | 3429 |
| tat acc ccc gga ctc aag tac gag gac cag tcg acg aat cat cca<br>Tyr Thr Pro Gly Leu Lys Tyr Glu Asp Gln Ser Thr Asn His Pro<br>1145                  1150                  1155 | 3474 |
| gtg gct atc gtc ggt gcc cgc gag tat atc ttc agc gag aac tcc<br>Val Ala Ile Val Gly Ala Arg Glu Tyr Ile Phe Ser Glu Asn Ser<br>1160                  1165                  1170 | 3519 |
| ggt gtc ctc ggc gac gtg gcg gct ggc aag gaa cag acc ttc ggc<br>Gly Val Leu Gly Asp Val Ala Ala Gly Lys Glu Gln Thr Phe Gly<br>1175                  1180                  1185 | 3564 |
| acc ctc ttc gcc cgg acc ctc gcg cag atc ggc ggc aag ctg cac<br>Thr Leu Phe Ala Arg Thr Leu Ala Gln Ile Gly Gly Lys Leu His<br>1190                  1195                  1200 | 3609 |
| tac ggc cat ccg gac ttc atc aac gcg acc ttc atg acg acc cgg<br>Tyr Gly His Pro Asp Phe Ile Asn Ala Thr Phe Met Thr Thr Arg<br>1205                  1210                  1215 | 3654 |
| ggt ggg gtc agc aag gcc cag aaa ggg ctg cat ctc aat gaa gat<br>Gly Gly Val Ser Lys Ala Gln Lys Gly Leu His Leu Asn Glu Asp<br>1220                  1225                  1230 | 3699 |

-continued

| | | |
|---|---|---|
| atc tac gcg ggg atg aac gct gtc ctc cgc ggt ggc cgc att aag<br>Ile Tyr Ala Gly Met Asn Ala Val Leu Arg Gly Gly Arg Ile Lys<br>1235                  1240                 1245 | | 3744 |
| cac tgc gag tat tac cag tgc ggc aag ggt cgc gac ttg ggc ttt<br>His Cys Glu Tyr Tyr Gln Cys Gly Lys Gly Arg Asp Leu Gly Phe<br>1250                  1255                 1260 | | 3789 |
| ggc acc atc ctc aac ttc acg acg aaa atc ggc gct ggc atg ggc<br>Gly Thr Ile Leu Asn Phe Thr Thr Lys Ile Gly Ala Gly Met Gly<br>1265                  1270                 1275 | | 3834 |
| gag caa atg ctg agt cgg gag tac tat tac ctg ggc acc cag ctg<br>Glu Gln Met Leu Ser Arg Glu Tyr Tyr Tyr Leu Gly Thr Gln Leu<br>1280                  1285                 1290 | | 3879 |
| cca atc gac cgc ttc ctc acc ttc tac tat gcg cat ccc ggc ttc<br>Pro Ile Asp Arg Phe Leu Thr Phe Tyr Tyr Ala His Pro Gly Phe<br>1295                  1300                 1305 | | 3924 |
| cat ctg aat aac ctg ttc ata cag ctg tcg ctg cag atg ttc atg<br>His Leu Asn Asn Leu Phe Ile Gln Leu Ser Leu Gln Met Phe Met<br>1310                  1315                 1320 | | 3969 |
| ctg act ctg gtc aac ctc cac gca ctc gcg cat gag agc att ttg<br>Leu Thr Leu Val Asn Leu His Ala Leu Ala His Glu Ser Ile Leu<br>1325                  1330                 1335 | | 4014 |
| tgc gtg tat gac agg gat aaa ccg atc acc gac gtc ctc tat cct<br>Cys Val Tyr Asp Arg Asp Lys Pro Ile Thr Asp Val Leu Tyr Pro<br>1340                  1345                 1350 | | 4059 |
| atc ggt tgc tat aac ttc cat ccg gcg atc gac tgg gtt cgc cgc<br>Ile Gly Cys Tyr Asn Phe His Pro Ala Ile Asp Trp Val Arg Arg<br>1355                  1360                 1365 | | 4104 |
| tac acc ctg agc atc ttt atc gtg ttc tgg ata gcg ttc gtc ccg<br>Tyr Thr Leu Ser Ile Phe Ile Val Phe Trp Ile Ala Phe Val Pro<br>1370                  1375                 1380 | | 4149 |
| atc gtc gtc cag gag ctg atc gag agg ggc ctg tgg aag gcc acg<br>Ile Val Val Gln Glu Leu Ile Glu Arg Gly Leu Trp Lys Ala Thr<br>1385                  1390                 1395 | | 4194 |
| cag cgg ttc ttc agg cac atc ttg tcg ctc agc ccg atg ttc gaa<br>Gln Arg Phe Phe Arg His Ile Leu Ser Leu Ser Pro Met Phe Glu<br>1400                  1405                 1410 | | 4239 |
| gtg ttc gcg ggt cag atc tat tcc agc gcg ctc ctg agc gac att<br>Val Phe Ala Gly Gln Ile Tyr Ser Ser Ala Leu Leu Ser Asp Ile<br>1415                  1420                 1425 | | 4284 |
| gcc gtg ggc ggc gcc cgg tac atc tcc acg ggc cgc ggt ttc gcg<br>Ala Val Gly Gly Ala Arg Tyr Ile Ser Thr Gly Arg Gly Phe Ala<br>1430                  1435                 1440 | | 4329 |
| acc tcc cgc atc ccg ttc tcg atc ctc tat tcg cgc ttc gcg ggc<br>Thr Ser Arg Ile Pro Phe Ser Ile Leu Tyr Ser Arg Phe Ala Gly<br>1445                  1450                 1455 | | 4374 |
| agc gcg atc tac atg ggt tcc cgg agc atg ctc atg ctc ctg ttc<br>Ser Ala Ile Tyr Met Gly Ser Arg Ser Met Leu Met Leu Leu Phe<br>1460                  1465                 1470 | | 4419 |
| ggc acc gtc gcc cac tgg cag gct ccc ctg ctt tgg ttc tgg gcg<br>Gly Thr Val Ala His Trp Gln Ala Pro Leu Leu Trp Phe Trp Ala<br>1475                  1480                 1485 | | 4464 |
| agc ctt agc gcg ctg atc ttc gcc ccg ttc atc ttc aat ccg cat<br>Ser Leu Ser Ala Leu Ile Phe Ala Pro Phe Ile Phe Asn Pro His<br>1490                  1495                 1500 | | 4509 |
| cag ttc gcc tgg gag gac ttc ctc gac tat agg gac tac atc<br>Gln Phe Ala Trp Glu Asp Phe Leu Asp Tyr Arg Asp Tyr Ile<br>1505                  1510                 1515 | | 4554 |
| cgc tgg ctg tcc cgc gga aac aac aag tat cac cgc aac tcg tgg<br>Arg Trp Leu Ser Arg Gly Asn Asn Lys Tyr His Arg Asn Ser Trp | | 4599 |

```
                    1520                1525                1530
atc  ggt  tac  gtg  cgc  atg  tcg  cgg  tcc  cgg  gtg  acg  ggt  ttc  aag        4644
Ile  Gly  Tyr  Val  Arg  Met  Ser  Arg  Ser  Arg  Val  Thr  Gly  Phe  Lys
     1535                1540                1545 cgc  aag  ctc  gtc  ggc  gat  gag  tcg  gag  aag  agt  gcc  ggg  gac  gcc        4689
Arg  Lys  Leu  Val  Gly  Asp  Glu  Ser  Glu  Lys  Ser  Ala  Gly  Asp  Ala
     1550                1555                1560 tcc  cgc  gcc  cat  cgc  acc  aac  ctc  atc  atg  gcc  gag  atc  atc  ccg        4734
Ser  Arg  Ala  His  Arg  Thr  Asn  Leu  Ile  Met  Ala  Glu  Ile  Ile  Pro
     1565                1570                1575 tgc  gcc  atc  tac  gcg  gca  ggc  tgc  ttc  atc  gcc  ttc  acc  ttt  atc        4779
Cys  Ala  Ile  Tyr  Ala  Ala  Gly  Cys  Phe  Ile  Ala  Phe  Thr  Phe  Ile
     1580                1585                1590 aac  gcg  cag  acc  ggc  gtc  aag  acc  acc  gat  gag  gac  cgc  gtg  aac        4824
Asn  Ala  Gln  Thr  Gly  Val  Lys  Thr  Thr  Asp  Glu  Asp  Arg  Val  Asn
     1595                1600                1605 tcc  acg  ctg  cgc  atc  atc  atc  tgt  acc  ctg  gca  ccg  atc  gtc  ata        4869
Ser  Thr  Leu  Arg  Ile  Ile  Ile  Cys  Thr  Leu  Ala  Pro  Ile  Val  Ile
     1610                1615                1620 gac  atc  ggg  gtg  ctg  ttc  ttc  tgc  atg  ggc  ttg  agc  tgt  tgc  tcg        4914
Asp  Ile  Gly  Val  Leu  Phe  Phe  Cys  Met  Gly  Leu  Ser  Cys  Cys  Ser
     1625                1630                1635 gga  ccg  ctc  ctc  ggc  atg  tgc  tgc  aag  aaa  act  ggc  agc  gtc  atg        4959
Gly  Pro  Leu  Leu  Gly  Met  Cys  Cys  Lys  Lys  Thr  Gly  Ser  Val  Met
     1640                1645                1650 gcc  ggc  att  gcc  cat  ggc  atc  gcc  gtc  gtc  cat  att  gtc  ttt             5004
Ala  Gly  Ile  Ala  His  Gly  Ile  Ala  Val  Val  His  Ile  Val  Phe
     1655                1660                1665 ttc  atc  gtc  atg  tgg  gtg  ctc  gaa  ggc  ttc  tcc  ttc  gtc  cgc  atg        5049
Phe  Ile  Val  Met  Trp  Val  Leu  Glu  Gly  Phe  Ser  Phe  Val  Arg  Met
     1670                1675                1680 ctg  atc  ggt  gtc  gtg  acg  tgc  atc  cag  tgt  cag  cgg  ctt  atc  ttt        5094
Leu  Ile  Gly  Val  Val  Thr  Cys  Ile  Gln  Cys  Gln  Arg  Leu  Ile  Phe
     1685                1690                1695 cat  tgc  atg  acc  gtg  ctc  ctc  acg  cgg  gaa  ttc  aag  aat  gac             5139
His  Cys  Met  Thr  Val  Leu  Leu  Thr  Arg  Glu  Phe  Lys  Asn  Asp
     1700                1705                1710 cac  gcc  aac  acc  gcg  ttc  tgg  acc  ggc  aag  tgg  tat  tcg  acg  gga        5184
His  Ala  Asn  Thr  Ala  Phe  Trp  Thr  Gly  Lys  Trp  Tyr  Ser  Thr  Gly
     1715                1720                1725 ctc  ggt  tat  atg  gcc  tgg  acg  cag  cca  acg  cgc  gag  ctg  acg  gca        5229
Leu  Gly  Tyr  Met  Ala  Trp  Thr  Gln  Pro  Thr  Arg  Glu  Leu  Thr  Ala
     1730                1735                1740 aag  gtt  atc  gag  ctg  agc  gaa  ttc  gcg  gct  gac  ttc  gtg  ctg  ggc        5274
Lys  Val  Ile  Glu  Leu  Ser  Glu  Phe  Ala  Ala  Asp  Phe  Val  Leu  Gly
     1745                1750                1755 cat  gtc  atc  ctc  atc  ttc  cag  ctc  ccg  gtt  atc  tgc  atc  ccg  aag        5319
His  Val  Ile  Leu  Ile  Phe  Gln  Leu  Pro  Val  Ile  Cys  Ile  Pro  Lys
     1760                1765                1770 atc  gac  aaa  ttc  cac  tcg  att  atg  ctc  ttt  tgg  ctg  aag  ccg  tcg        5364
Ile  Asp  Lys  Phe  His  Ser  Ile  Met  Leu  Phe  Trp  Leu  Lys  Pro  Ser
     1775                1780                1785 cgc  caa  atc  cgc  cct  ccg  atc  tac  tcc  ctg  aaa  cag  gcg  cgc  ctg        5409
Arg  Gln  Ile  Arg  Pro  Pro  Ile  Tyr  Ser  Leu  Lys  Gln  Ala  Arg  Leu
     1790                1795                1800 cgc  aag  cgc  atg  gtc  cgg  cgc  tac  tgc  tcc  ctc  tac  ttc  ctg  gtg        5454
Arg  Lys  Arg  Met  Val  Arg  Arg  Tyr  Cys  Ser  Leu  Tyr  Phe  Leu  Val
     1805                1810                1815 ctg  atc  atc  ttc  gcg  ggt  tgc  atc  gtg  ggt  ccc  gcc  gtg  gcg  tcg        5499
```

```
Leu Ile Ile Phe Ala Gly Cys Ile Val Gly Pro Ala Val Ala Ser
    1820                1825                1830 gct cac gtg ccg aaa gac ctg ggc tcc ggg ctg acc ggc acc ttt    5544
Ala His Val Pro Lys Asp Leu Gly Ser Gly Leu Thr Gly Thr Phe
    1835                1840                1845 cat aac ctg gtg cag ccg cgc aac gtc agc aat aat gac acg ggc    5589
His Asn Leu Val Gln Pro Arg Asn Val Ser Asn Asn Asp Thr Gly
    1850                1855                1860 tcg caa atg tcc acc tat aag tcg cat tac tac acc cat acc ccg    5634
Ser Gln Met Ser Thr Tyr Lys Ser His Tyr Tyr Thr His Thr Pro
    1865                1870                1875 tcg ctc aaa acc tgg tcg acc att aaa                            5661
Ser Leu Lys Thr Trp Ser Thr Ile Lys
    1880                1885
```

<210> SEQ ID NO 8
<211> LENGTH: 1887
<212> TYPE: PRT
<213> ORGANISM: Artificial sequence
<220> FEATURE:
<223> OTHER INFORMATION: Synthetic Construct

<400> SEQUENCE: 8

```
Met Ser Tyr Asn Asp Pro Asn Leu Asn Gly Gln Tyr Tyr Ser Asn Gly
1               5                   10                  15

Asp Gly Thr Gly Asp Gly Asn Tyr Pro Thr Tyr Gln Val Thr Gln Asp
            20                  25                  30

Gln Ser Ala Tyr Asp Glu Tyr Gly Gln Pro Ile Tyr Thr Gln Asn Gln
        35                  40                  45

Leu Asp Asp Gly Tyr Tyr Asp Pro Asn Glu Gln Tyr Val Asp Gly Thr
    50                  55                  60

Gln Phe Pro Gln Gly Gln Asp Pro Ser Gln Asp Gln Gly Pro Tyr Asn
65                  70                  75                  80

Asn Asp Ala Ser Tyr Tyr Asn Gln Pro Pro Asn Met Met Asn Pro Ser
                85                  90                  95

Ser Gln Asp Gly Glu Asn Phe Ser Asp Phe Ser Ser Tyr Gly Pro Pro
            100                 105                 110

Ser Gly Thr Tyr Pro Asn Asp Gln Tyr Thr Pro Ser Gln Met Ser Tyr
        115                 120                 125

Pro Asp Gln Asp Gly Ser Ser Gly Ala Ser Thr Pro Tyr Gly Asn Gly
    130                 135                 140

Val Val Asn Gly Asn Gly Gln Tyr Tyr Asp Pro Asn Ala Ile Glu Met
145                 150                 155                 160

Ala Leu Pro Asn Asp Pro Tyr Pro Ala Trp Thr Ala Asp Pro Gln Ser
                165                 170                 175

Pro Leu Pro Ile Glu Gln Ile Glu Asp Ile Phe Ile Asp Leu Thr Asn
            180                 185                 190

Lys Phe Gly Phe Gln Arg Asp Ser Met Arg Asn Met Phe Asp His Phe
        195                 200                 205

Met Thr Leu Leu Asp Ser Arg Ser Ser Arg Met Ser Pro Glu Gln Ala
    210                 215                 220

Leu Leu Ser Leu His Ala Asp Tyr Ile Gly Gly Asp Thr Ala Asn Tyr
225                 230                 235                 240

Lys Lys Trp Tyr Phe Ala Ala Gln Leu Asp Met Asp Asp Glu Ile Gly
                245                 250                 255

Phe Arg Asn Met Lys Leu Gly Lys Leu Ser Arg Lys Ala Arg Lys Ala
            260                 265                 270
```

```
Lys Lys Lys Asn Lys Lys Ala Met Gln Glu Asp Glu Asp Thr Glu Glu
            275                 280                 285

Thr Leu Asn Gln Ile Glu Gly Asp Asn Ser Leu Glu Ala Ala Asp Phe
        290                 295                 300

Arg Trp Lys Ser Lys Met Asn Gln Leu Ser Pro Phe Glu Met Val Arg
305                 310                 315                 320

Gln Ile Ala Leu Phe Leu Leu Cys Trp Gly Glu Ala Asn Gln Val Arg
                325                 330                 335

Phe Thr Pro Glu Cys Leu Cys Phe Ile Tyr Lys Cys Ala Ser Asp Tyr
            340                 345                 350

Leu Asp Ser Ala Gln Cys Gln Arg Pro Asp Pro Leu Pro Glu Gly
        355                 360                 365

Asp Phe Leu Asn Arg Val Ile Thr Pro Leu Tyr Arg Phe Ile Arg Ser
        370                 375                 380

Gln Val Tyr Glu Ile Val Asp Gly Arg Tyr Val Lys Ser Glu Lys Asp
385                 390                 395                 400

His Asn Lys Val Ile Gly Tyr Asp Asp Val Asn Gln Leu Phe Trp Tyr
                405                 410                 415

Pro Glu Gly Ile Ala Lys Ile Val Met Glu Asp Gly Thr Arg Leu Ile
            420                 425                 430

Asp Leu Pro Ala Glu Arg Tyr Leu Lys Leu Gly Glu Ile Pro Trp
        435                 440                 445

Asp Asp Val Phe Phe Lys Thr Tyr Lys Glu Thr Arg Ser Trp Leu His
        450                 455                 460

Leu Val Thr Asn Phe Asn Arg Ile Trp Ile Met His Val Tyr Trp Met
465                 470                 475                 480

Tyr Cys Ala Tyr Asn Ala Pro Thr Phe Tyr Thr His Asn Tyr Gln Gln
                485                 490                 495

Leu Val Asp Asn Gln Pro Leu Ala Ala Tyr Lys Trp Ala Thr Ala Ala
            500                 505                 510

Leu Gly Gly Thr Val Ala Ser Leu Ile Gln Val Ala Ala Thr Leu Cys
        515                 520                 525

Glu Trp Ser Phe Val Pro Arg Lys Trp Ala Gly Ala Gln His Leu Ser
        530                 535                 540

Arg Arg Phe Trp Phe Leu Cys Val Ile Met Gly Ile Asn Leu Gly Pro
545                 550                 555                 560

Val Ile Phe Val Phe Ala Tyr Asp Lys Asp Thr Val Tyr Ser Thr Ala
                565                 570                 575

Ala His Val Val Gly Ala Val Met Phe Phe Val Ala Val Ala Thr Leu
            580                 585                 590

Val Phe Phe Ser Val Met Pro Leu Gly Gly Leu Phe Thr Ser Tyr Met
        595                 600                 605

Lys Lys Ser Thr Arg Ser Tyr Val Ala Ser Gln Thr Phe Thr Ala Ser
        610                 615                 620

Phe Ala Pro Leu His Gly Leu Asp Arg Trp Met Ser Tyr Leu Val Trp
625                 630                 635                 640

Val Thr Val Phe Ala Ala Lys Tyr Ala Glu Ser Tyr Phe Phe Leu Ile
                645                 650                 655

Leu Ser Leu Arg Asp Pro Ile Arg Ile Leu Ser Thr Thr Ser Met Arg
            660                 665                 670

Cys Thr Gly Glu Tyr Trp Trp Gly Asn Lys Ile Cys Lys Val Gln Pro
        675                 680                 685
```

-continued

```
Lys Ile Val Leu Gly Leu Met Ile Ala Thr Asp Phe Ile Leu Phe Phe
    690                 695                 700
Leu Asp Thr Tyr Leu Trp Tyr Ile Val Asn Thr Val Phe Ser Val
705                 710                 715                 720
Gly Lys Ser Phe Tyr Leu Gly Ile Ser Ile Leu Thr Pro Trp Arg Asn
                725                 730                 735
Ile Phe Thr Arg Leu Pro Lys Arg Ile Tyr Ser Lys Ile Leu Ala Thr
                740                 745                 750
Thr Asp Met Glu Ile Lys Tyr Lys Pro Lys Val Leu Ile Ser Gln Ile
                755                 760                 765
Trp Asn Ala Ile Ile Ile Ser Met Tyr Arg Glu His Leu Leu Ala Ile
770                 775                 780
Asp His Val Gln Lys Leu Leu Tyr His Gln Val Pro Ser Glu Ile Glu
785                 790                 795                 800
Gly Lys Arg Thr Leu Arg Ala Pro Thr Phe Phe Val Ser Gln Asp Asp
                805                 810                 815
Asn Asn Phe Glu Thr Glu Phe Phe Pro Arg Asp Ser Glu Ala Glu Arg
                820                 825                 830
Arg Ile Ser Phe Phe Ala Gln Ser Leu Ser Thr Pro Ile Pro Glu Pro
                835                 840                 845
Leu Pro Val Asp Asn Met Pro Thr Phe Thr Val Leu Thr Pro His Tyr
850                 855                 860
Ala Glu Arg Ile Leu Leu Ser Leu Arg Glu Ile Ile Arg Glu Asp Asp
865                 870                 875                 880
Gln Phe Ser Arg Val Thr Leu Leu Glu Tyr Leu Lys Gln Leu His Pro
                885                 890                 895
Val Glu Trp Asp Cys Phe Val Lys Asp Thr Lys Ile Leu Ala Glu Glu
                900                 905                 910
Thr Ala Ala Tyr Glu Asn Asn Glu Asp Glu Pro Glu Lys Glu Asp Ala
                915                 920                 925
Leu Lys Ser Gln Ile Asp Asp Leu Pro Phe Tyr Cys Ile Gly Phe Lys
                930                 935                 940
Ser Ala Ala Pro Glu Tyr Thr Leu Arg Thr Arg Ile Trp Ala Ser Leu
945                 950                 955                 960
Arg Ser Gln Thr Leu Tyr Arg Thr Ile Ser Gly Phe Met Asn Tyr Ser
                965                 970                 975
Arg Ala Ile Lys Leu Leu Tyr Arg Val Glu Asn Pro Glu Ile Val Gln
                980                 985                 990
Met Phe Gly Gly Asn Ala Asp Gly Leu Glu Arg Glu Leu Glu Lys Met
                995                 1000                1005
Ala Arg Arg Lys Phe Lys Phe Leu Val Ser Met Gln Arg Leu Ala
    1010                1015                1020
Lys Phe Lys Phe Leu Glu Asn Ala Glu Phe Leu Leu Arg Ala Tyr
    1025                1030                1035
Pro Asp Leu Gln Ile Ala Tyr Leu Asp Glu Glu Pro Pro Leu Asn
    1040                1045                1050
Glu Gly Glu Glu Pro Arg Ile Tyr Ser Ala Leu Ile Asp Gly His
    1055                1060                1065
Cys Glu Ile Asn Gly Arg Arg Arg Pro Lys Phe Arg Val Gln Leu
    1070                1075                1080
Ser Gly Asn Pro Ile Leu Gly Asp Gly Lys Ser Asp Asn Gln Asn
    1085                1090                1095
His Ala Leu Ile Phe Tyr Arg Gly Glu Tyr Ile Gln Leu Ile Asp
```

```
                    1100                1105                1110

Ala Asn Gln Asp Asn Tyr Leu Glu Glu Cys Leu Lys Ile Arg Ser
    1115                1120                1125

Val Leu Ala Glu Phe Glu Glu Leu Gly Ile Glu Gln Ile His Pro
    1130                1135                1140

Tyr Thr Pro Gly Leu Lys Tyr Glu Asp Gln Ser Thr Asn His Pro
    1145                1150                1155

Val Ala Ile Val Gly Ala Arg Glu Tyr Ile Phe Ser Glu Asn Ser
    1160                1165                1170

Gly Val Leu Gly Asp Val Ala Ala Gly Lys Glu Gln Thr Phe Gly
    1175                1180                1185

Thr Leu Phe Ala Arg Thr Leu Ala Gln Ile Gly Gly Lys Leu His
    1190                1195                1200

Tyr Gly His Pro Asp Phe Ile Asn Ala Thr Phe Met Thr Thr Arg
    1205                1210                1215

Gly Gly Val Ser Lys Ala Gln Lys Gly Leu His Leu Asn Glu Asp
    1220                1225                1230

Ile Tyr Ala Gly Met Asn Ala Val Leu Arg Gly Gly Arg Ile Lys
    1235                1240                1245

His Cys Glu Tyr Tyr Gln Cys Gly Lys Gly Arg Asp Leu Gly Phe
    1250                1255                1260

Gly Thr Ile Leu Asn Phe Thr Thr Lys Ile Gly Ala Gly Met Gly
    1265                1270                1275

Glu Gln Met Leu Ser Arg Glu Tyr Tyr Tyr Leu Gly Thr Gln Leu
    1280                1285                1290

Pro Ile Asp Arg Phe Leu Thr Phe Tyr Tyr Ala His Pro Gly Phe
    1295                1300                1305

His Leu Asn Asn Leu Phe Ile Gln Leu Ser Leu Gln Met Phe Met
    1310                1315                1320

Leu Thr Leu Val Asn Leu His Ala Leu Ala His Glu Ser Ile Leu
    1325                1330                1335

Cys Val Tyr Asp Arg Asp Lys Pro Ile Thr Asp Val Leu Tyr Pro
    1340                1345                1350

Ile Gly Cys Tyr Asn Phe His Pro Ala Ile Asp Trp Val Arg Arg
    1355                1360                1365

Tyr Thr Leu Ser Ile Phe Ile Val Phe Trp Ile Ala Phe Val Pro
    1370                1375                1380

Ile Val Val Gln Glu Leu Ile Glu Arg Gly Leu Trp Lys Ala Thr
    1385                1390                1395

Gln Arg Phe Phe Arg His Ile Leu Ser Leu Ser Pro Met Phe Glu
    1400                1405                1410

Val Phe Ala Gly Gln Ile Tyr Ser Ser Ala Leu Leu Ser Asp Ile
    1415                1420                1425

Ala Val Gly Gly Ala Arg Tyr Ile Ser Thr Gly Arg Gly Phe Ala
    1430                1435                1440

Thr Ser Arg Ile Pro Phe Ser Ile Leu Tyr Ser Arg Phe Ala Gly
    1445                1450                1455

Ser Ala Ile Tyr Met Gly Ser Arg Ser Met Leu Met Leu Leu Phe
    1460                1465                1470

Gly Thr Val Ala His Trp Gln Ala Pro Leu Leu Trp Phe Trp Ala
    1475                1480                1485

Ser Leu Ser Ala Leu Ile Phe Ala Pro Phe Ile Phe Asn Pro His
    1490                1495                1500
```

```
Gln Phe Ala Trp Glu Asp Phe Phe Leu Asp Tyr Arg Asp Tyr Ile
1505                1510                1515

Arg Trp Leu Ser Arg Gly Asn Asn Lys Tyr His Arg Asn Ser Trp
1520                1525                1530

Ile Gly Tyr Val Arg Met Ser Arg Ser Arg Val Thr Gly Phe Lys
1535                1540                1545

Arg Lys Leu Val Gly Asp Glu Ser Glu Lys Ser Ala Gly Asp Ala
1550                1555                1560

Ser Arg Ala His Arg Thr Asn Leu Ile Met Ala Glu Ile Ile Pro
1565                1570                1575

Cys Ala Ile Tyr Ala Ala Gly Cys Phe Ile Ala Phe Thr Phe Ile
1580                1585                1590

Asn Ala Gln Thr Gly Val Lys Thr Thr Asp Glu Asp Arg Val Asn
1595                1600                1605

Ser Thr Leu Arg Ile Ile Ile Cys Thr Leu Ala Pro Ile Val Ile
1610                1615                1620

Asp Ile Gly Val Leu Phe Phe Cys Met Gly Leu Ser Cys Cys Ser
1625                1630                1635

Gly Pro Leu Leu Gly Met Cys Cys Lys Lys Thr Gly Ser Val Met
1640                1645                1650

Ala Gly Ile Ala His Gly Ile Ala Val Val Val His Ile Val Phe
1655                1660                1665

Phe Ile Val Met Trp Val Leu Glu Gly Phe Ser Phe Val Arg Met
1670                1675                1680

Leu Ile Gly Val Val Thr Cys Ile Gln Cys Gln Arg Leu Ile Phe
1685                1690                1695

His Cys Met Thr Val Leu Leu Leu Thr Arg Glu Phe Lys Asn Asp
1700                1705                1710

His Ala Asn Thr Ala Phe Trp Thr Gly Lys Trp Tyr Ser Thr Gly
1715                1720                1725

Leu Gly Tyr Met Ala Trp Thr Gln Pro Thr Arg Glu Leu Thr Ala
1730                1735                1740

Lys Val Ile Glu Leu Ser Glu Phe Ala Ala Asp Phe Val Leu Gly
1745                1750                1755

His Val Ile Leu Ile Phe Gln Leu Pro Val Ile Cys Ile Pro Lys
1760                1765                1770

Ile Asp Lys Phe His Ser Ile Met Leu Phe Trp Leu Lys Pro Ser
1775                1780                1785

Arg Gln Ile Arg Pro Pro Ile Tyr Ser Leu Lys Gln Ala Arg Leu
1790                1795                1800

Arg Lys Arg Met Val Arg Arg Tyr Cys Ser Leu Tyr Phe Leu Val
1805                1810                1815

Leu Ile Ile Phe Ala Gly Cys Ile Val Gly Pro Ala Val Ala Ser
1820                1825                1830

Ala His Val Pro Lys Asp Leu Gly Ser Gly Leu Thr Gly Thr Phe
1835                1840                1845

His Asn Leu Val Gln Pro Arg Asn Val Ser Asn Asn Asp Thr Gly
1850                1855                1860

Ser Gln Met Ser Thr Tyr Lys Ser His Tyr Tyr Thr His Thr Pro
1865                1870                1875

Ser Leu Lys Thr Trp Ser Thr Ile Lys
1880                1885
```

<210> SEQ ID NO 9
<211> LENGTH: 5679
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(5679)
<223> OTHER INFORMATION: Candida albicans FKS1 (codon optimized)

<400> SEQUENCE: 9

| | | | | | | | | | | | | | | | | |
|---|---|---|---|---|---|---|---|---|---|---|---|---|---|---|---|---|
| atg | agc | tac | aac | gac | aac | aat | cac | tat | tac | gac | ccg | aat | cag | caa | | 48 |
| Met | Ser | Tyr | Asn | Asp | Asn | Asn | His | Tyr | Tyr | Asp | Pro | Asn | Gln | Gln | | |
| 1 | | | 5 | | | | 10 | | | | | 15 | | | | |
| ggc | gga | atg | ccc | cct | cat | caa | ggc | gga | gag | ggg | tat | tac | cag | cag | cag | 96 |
| Gly | Gly | Met | Pro | Pro | His | Gln | Gly | Gly | Glu | Gly | Tyr | Tyr | Gln | Gln | Gln | |
| | | | 20 | | | | | 25 | | | | | 30 | | | |
| tat | gat | gac | atg | ggc | caa | caa | ccg | cac | caa | cag | gac | tac | tac | gat | ccg | 144 |
| Tyr | Asp | Asp | Met | Gly | Gln | Gln | Pro | His | Gln | Gln | Asp | Tyr | Tyr | Asp | Pro | |
| | | 35 | | | | | 40 | | | | | 45 | | | | |
| aat | gct | cag | tat | cag | cag | cag | ccg | tat | gac | atg | gac | ggt | tat | cag | gac | 192 |
| Asn | Ala | Gln | Tyr | Gln | Gln | Gln | Pro | Tyr | Asp | Met | Asp | Gly | Tyr | Gln | Asp | |
| 50 | | | | | 55 | | | | | 60 | | | | | | |
| caa | gcg | aac | tac | ggc | ggt | cag | ccg | atg | aat | gcg | caa | ggc | tac | aac | gcc | 240 |
| Gln | Ala | Asn | Tyr | Gly | Gly | Gln | Pro | Met | Asn | Ala | Gln | Gly | Tyr | Asn | Ala | |
| 65 | | | | 70 | | | | | 75 | | | | | 80 | | |
| gat | ccc | gag | gcc | ttt | tcc | gac | ttc | agc | tac | ggt | ggc | cag | acc | ccg | ggt | 288 |
| Asp | Pro | Glu | Ala | Phe | Ser | Asp | Phe | Ser | Tyr | Gly | Gly | Gln | Thr | Pro | Gly | |
| | | | | 85 | | | | | 90 | | | | | 95 | | |
| acc | cca | ggc | tac | gac | cag | tac | ggt | acc | cag | tac | acc | ccg | agc | cag | atg | 336 |
| Thr | Pro | Gly | Tyr | Asp | Gln | Tyr | Gly | Thr | Gln | Tyr | Thr | Pro | Ser | Gln | Met | |
| | | | 100 | | | | | 105 | | | | | 110 | | | |
| tcc | tat | ggc | ggc | gac | ccc | cgg | tcc | tcg | ggt | gca | agc | act | ccc | att | tat | 384 |
| Ser | Tyr | Gly | Gly | Asp | Pro | Arg | Ser | Ser | Gly | Ala | Ser | Thr | Pro | Ile | Tyr | |
| | | 115 | | | | | 120 | | | | | 125 | | | | |
| ggc | ggc | cag | ggc | cag | ggt | tac | gac | cct | acc | cag | ttc | aac | atg | tcc | tcc | 432 |
| Gly | Gly | Gln | Gly | Gln | Gly | Tyr | Asp | Pro | Thr | Gln | Phe | Asn | Met | Ser | Ser | |
| | 130 | | | | | 135 | | | | | 140 | | | | | |
| aac | ctc | ccc | tac | ccc | gcc | tgg | agc | gcg | gac | ccc | cag | gcc | ccg | atc | aag | 480 |
| Asn | Leu | Pro | Tyr | Pro | Ala | Trp | Ser | Ala | Asp | Pro | Gln | Ala | Pro | Ile | Lys | |
| 145 | | | | | 150 | | | | | 155 | | | | | 160 | |
| ata | gag | cat | atc | gaa | gat | atc | ttc | atc | gac | ctc | acc | aac | aag | ttc | ggg | 528 |
| Ile | Glu | His | Ile | Glu | Asp | Ile | Phe | Ile | Asp | Leu | Thr | Asn | Lys | Phe | Gly | |
| | | | | 165 | | | | | 170 | | | | | 175 | | |
| ttc | cag | cgg | gac | tcg | atg | cgc | aat | atg | ttc | gac | tac | ttc | atg | acg | ctg | 576 |
| Phe | Gln | Arg | Asp | Ser | Met | Arg | Asn | Met | Phe | Asp | Tyr | Phe | Met | Thr | Leu | |
| | | | 180 | | | | | 185 | | | | | 190 | | | |
| ttg | gat | tcc | cgc | agc | tcg | cgc | atg | agc | ccg | gct | cag | gcc | ctc | ctc | agc | 624 |
| Leu | Asp | Ser | Arg | Ser | Ser | Arg | Met | Ser | Pro | Ala | Gln | Ala | Leu | Leu | Ser | |
| | | | 195 | | | | | 200 | | | | | 205 | | | |
| ctg | cat | gcg | gac | tat | att | ggc | ggg | gat | aac | gcg | aac | tac | cgg | aaa | tgg | 672 |
| Leu | His | Ala | Asp | Tyr | Ile | Gly | Gly | Asp | Asn | Ala | Asn | Tyr | Arg | Lys | Trp | |
| | 210 | | | | | 215 | | | | | 220 | | | | | |
| tac | ttc | agt | tcg | cag | caa | gat | ctc | gac | gac | tcg | ctg | ggc | ttc | gcg | aac | 720 |
| Tyr | Phe | Ser | Ser | Gln | Gln | Asp | Leu | Asp | Asp | Ser | Leu | Gly | Phe | Ala | Asn | |
| 225 | | | | | 230 | | | | | 235 | | | | | 240 | |
| atg | acc | ctg | ggg | aag | atc | gga | cgc | aag | gcc | cgg | aag | gcc | agc | aag | aaa | 768 |
| Met | Thr | Leu | Gly | Lys | Ile | Gly | Arg | Lys | Ala | Arg | Lys | Ala | Ser | Lys | Lys | |
| | | | | 245 | | | | | 250 | | | | | 255 | | |
| tcc | aag | aag | gcc | cgc | aaa | gcg | gcc | gag | gag | cac | ggc | cag | gac | gtg | gac | 816 |

```
                Ser Lys Lys Ala Arg Lys Ala Ala Glu Glu His Gly Gln Asp Val Asp
                                260                 265                 270 gcg aac gag ctg gaa ggc gac tat tcg ctt gag gcc gca gag atc cgc             864
Ala Asn Glu Leu Glu Gly Asp Tyr Ser Leu Glu Ala Ala Glu Ile Arg
            275                 280                 285 tgg aag gcc aag atg aat tcg ctg acc ccg gaa gaa cgc gtg cgg gac             912
Trp Lys Ala Lys Met Asn Ser Leu Thr Pro Glu Glu Arg Val Arg Asp
290                 295                 300 ctg gcg ctg tat ctc ctg atc tgg ggc gaa gcg aat cag gtc agg ttt             960
Leu Ala Leu Tyr Leu Leu Ile Trp Gly Glu Ala Asn Gln Val Arg Phe
305                 310                 315                 320 acg ccc gag tgt ctc tgc tac atc tac aaa tcg gcc acc gat tat ctg            1008
Thr Pro Glu Cys Leu Cys Tyr Ile Tyr Lys Ser Ala Thr Asp Tyr Leu
                325                 330                 335 aat tcg ccc ctt tgc cag cag cgc cag gaa ccc gtc ccg gaa ggc gac            1056
Asn Ser Pro Leu Cys Gln Gln Arg Gln Glu Pro Val Pro Glu Gly Asp
            340                 345                 350 tat ctg aac cgc gtg att acc ccc ctt tac cgc ttc atc cgg tcc caa            1104
Tyr Leu Asn Arg Val Ile Thr Pro Leu Tyr Arg Phe Ile Arg Ser Gln
        355                 360                 365 gtc tat gag atc tac gac ggc cgg ttc gtc aag cgc gag aag gac cac            1152
Val Tyr Glu Ile Tyr Asp Gly Arg Phe Val Lys Arg Glu Lys Asp His
370                 375                 380 aat aag gtc att gga tac gac gac gtg aac caa ttg ttc tgg tat ccc            1200
Asn Lys Val Ile Gly Tyr Asp Asp Val Asn Gln Leu Phe Trp Tyr Pro
385                 390                 395                 400 gag ggc atc agc cgc atc atc ttc gag gat ggc acg cgc ctg gtg gac            1248
Glu Gly Ile Ser Arg Ile Ile Phe Glu Asp Gly Thr Arg Leu Val Asp
                405                 410                 415 atc ccg cag gag gag cgg ttc ttg aag ctc gga gag gtc gag tgg aaa            1296
Ile Pro Gln Glu Glu Arg Phe Leu Lys Leu Gly Glu Val Glu Trp Lys
            420                 425                 430 aat gtg ttc ttc aag acc tat aaa gaa atc cgc acc tgg ctg cac ttc            1344
Asn Val Phe Phe Lys Thr Tyr Lys Glu Ile Arg Thr Trp Leu His Phe
        435                 440                 445 gtg acc aat ttc aac cgg atc tgg atc atc cat ggc acg atc tat tgg            1392
Val Thr Asn Phe Asn Arg Ile Trp Ile Ile His Gly Thr Ile Tyr Trp
450                 455                 460 atg tat acg gcc tac aac tcg ccg acc ctg tat acc aag cat tat gtg            1440
Met Tyr Thr Ala Tyr Asn Ser Pro Thr Leu Tyr Thr Lys His Tyr Val
465                 470                 475                 480 cag acg atc aat cag cag ccg ctg gcc tcc agc cgc tgg gcc gcc tgc            1488
Gln Thr Ile Asn Gln Gln Pro Leu Ala Ser Ser Arg Trp Ala Ala Cys
                485                 490                 495 gcc att ggc ggc gtg ctc gcc tcc ttc atc caa att ctg gcc acc ctc            1536
Ala Ile Gly Gly Val Leu Ala Ser Phe Ile Gln Ile Leu Ala Thr Leu
            500                 505                 510 ttc gag tgg att ttc gtt ccg cgg gag tgg gcg ggt gcg cag cat ctg            1584
Phe Glu Trp Ile Phe Val Pro Arg Glu Trp Ala Gly Ala Gln His Leu
        515                 520                 525 tcg agg cgc atg ctg ttc ctg gtc ctc atc ttt ctg ctt aac ctg gtc            1632
Ser Arg Arg Met Leu Phe Leu Val Leu Ile Phe Leu Leu Asn Leu Val
530                 535                 540 cct ccg gtc tat acc ttc cag ata acc aag ctc gtc atc tac tcg aag            1680
Pro Pro Val Tyr Thr Phe Gln Ile Thr Lys Leu Val Ile Tyr Ser Lys
545                 550                 555                 560 agt gcg tac gct gtg tcc atc gtg ggc ttc ttc att gcc gtg gct acc            1728
Ser Ala Tyr Ala Val Ser Ile Val Gly Phe Phe Ile Ala Val Ala Thr
                565                 570                 575
```

-continued

| | | |
|---|---|---|
| ctg gtc ttt ttc gcg gtc atg ccg ctc ggg ggc ctc ttc acg tcc tat<br>Leu Val Phe Phe Ala Val Met Pro Leu Gly Gly Leu Phe Thr Ser Tyr<br>              580              585              590 | | 1776 |
| atg aac aag cgg agt cgc cgg tat atc gcg agt cag acg ttc act gcg<br>Met Asn Lys Arg Ser Arg Arg Tyr Ile Ala Ser Gln Thr Phe Thr Ala<br>    595                    600              605 | | 1824 |
| aac tat atc aag ctc aag ggc ctc gac atg tgg atg agt tac ctc ctg<br>Asn Tyr Ile Lys Leu Lys Gly Leu Asp Met Trp Met Ser Tyr Leu Leu<br>610                  615              620 | | 1872 |
| tgg ttc ctg gtt ttc ctc gcc aag ctc gtt gag tcc tac ttc ttc agc<br>Trp Phe Leu Val Phe Leu Ala Lys Leu Val Glu Ser Tyr Phe Phe Ser<br>625                  630              635              640 | | 1920 |
| acc ctg tcg ctg cgc gac ccc atc cgc aac ctg tcc acg atg acg atg<br>Thr Leu Ser Leu Arg Asp Pro Ile Arg Asn Leu Ser Thr Met Thr Met<br>                    645              650              655 | | 1968 |
| cgc tgc gtc ggc gag gtc tgg tac aag gac atc gtg tgc cgc aac caa<br>Arg Cys Val Gly Glu Val Trp Tyr Lys Asp Ile Val Cys Arg Asn Gln<br>660                  665              670 | | 2016 |
| gcc aag atc gtc ctc ggc ctc atg tat ctg gtc gat ctg ctc ctc ttc<br>Ala Lys Ile Val Leu Gly Leu Met Tyr Leu Val Asp Leu Leu Leu Phe<br>            675              680              685 | | 2064 |
| ttc ctc gat acc tac atg tgg tac atc atc tgc aac tgc atc ttc tcc<br>Phe Leu Asp Thr Tyr Met Trp Tyr Ile Ile Cys Asn Cys Ile Phe Ser<br>690                  695              700 | | 2112 |
| ata ggc cgc agc ttc tat ctg gga att agt atc ctc acc ccg tgg cgg<br>Ile Gly Arg Ser Phe Tyr Leu Gly Ile Ser Ile Leu Thr Pro Trp Arg<br>705                  710              715              720 | | 2160 |
| aac atc ttc acg cgc ctg ccg aag cgg att tac agc aag atc ttg gcg<br>Asn Ile Phe Thr Arg Leu Pro Lys Arg Ile Tyr Ser Lys Ile Leu Ala<br>                    725              730              735 | | 2208 |
| acc acc gag atg gag atc aaa tac aaa ccc aag gtc ctt atc agc cag<br>Thr Thr Glu Met Glu Ile Lys Tyr Lys Pro Lys Val Leu Ile Ser Gln<br>            740              745              750 | | 2256 |
| atc tgg aat gcg att gtt atc tcc atg tat cgc gag cat ctc ctg gcc<br>Ile Trp Asn Ala Ile Val Ile Ser Met Tyr Arg Glu His Leu Leu Ala<br>755                  760              765 | | 2304 |
| atc gac cac gtc cag aaa ctg ctg tat cat caa gtg cca agc gag atc<br>Ile Asp His Val Gln Lys Leu Leu Tyr His Gln Val Pro Ser Glu Ile<br>    770                    775              780 | | 2352 |
| gaa ggc aag cgc acg ctg cgg gcg ccg acg ttc ttc gtg tcg caa gac<br>Glu Gly Lys Arg Thr Leu Arg Ala Pro Thr Phe Phe Val Ser Gln Asp<br>785                  790              795              800 | | 2400 |
| gac aat aat ttc gag act gag ttc ttc ccg cgc aac tcc gag gcc gag<br>Asp Asn Asn Phe Glu Thr Glu Phe Phe Pro Arg Asn Ser Glu Ala Glu<br>                    805              810              815 | | 2448 |
| cgg cgc att agt ttc ttc gcc caa tcc ctt gcg acc ccg atg ccg gag<br>Arg Arg Ile Ser Phe Phe Ala Gln Ser Leu Ala Thr Pro Met Pro Glu<br>            820              825              830 | | 2496 |
| ccc ctc ccg gtc gat aac atg ccc acg ttt acc gtg ttc acc cct cat<br>Pro Leu Pro Val Asp Asn Met Pro Thr Phe Thr Val Phe Thr Pro His<br>835                  840              845 | | 2544 |
| tac agc gag aag atc ctg ctc agc ctg cgc gag att cgc gag gac<br>Tyr Ser Glu Lys Ile Leu Leu Ser Leu Arg Glu Ile Arg Glu Asp<br>    850                    855              860 | | 2592 |
| gac caa ttc tcg cgc gtc acg ctg ctg gag tat ctc aag cag ctg cat<br>Asp Gln Phe Ser Arg Val Thr Leu Leu Glu Tyr Leu Lys Gln Leu His<br>865                  870              875              880 | | 2640 |
| ccg gtc gag tgg gac tgc ttc gtt aag gac acg aag atc ctc gcc gaa<br>Pro Val Glu Trp Asp Cys Phe Val Lys Asp Thr Lys Ile Leu Ala Glu<br>                    885              890              895 | | 2688 |

-continued

| | |
|---|---|
| gaa acc gct gcc tac gag aac ggc gac gac tcg gag aaa ttg tcc gag<br>Glu Thr Ala Ala Tyr Glu Asn Gly Asp Asp Ser Glu Lys Leu Ser Glu<br>          900                   905                910 | 2736 |
| gac ggc ctc aag tcg aag atc gat gac ctc cca ttc tac tgc atc ggc<br>Asp Gly Leu Lys Ser Lys Ile Asp Asp Leu Pro Phe Tyr Cys Ile Gly<br>          915                   920                925 | 2784 |
| ttc aaa tcc gca gca ccc gag tat acg ctc cgg acg cgc atc tgg gcg<br>Phe Lys Ser Ala Ala Pro Glu Tyr Thr Leu Arg Thr Arg Ile Trp Ala<br>   930                   935                940 | 2832 |
| agc ctg cgc agc caa acc ttg tac cgg acg gtc agc ggc ttc atg aat<br>Ser Leu Arg Ser Gln Thr Leu Tyr Arg Thr Val Ser Gly Phe Met Asn<br>945                 950                955                960 | 2880 |
| tac gcc cgc gcg ata aaa ctg ctc tat agg gtc gag aac ccg gag ctc<br>Tyr Ala Arg Ala Ile Lys Leu Leu Tyr Arg Val Glu Asn Pro Glu Leu<br>          965                   970                975 | 2928 |
| gtc cag tat ttt ggc ggc gac ccc gag ggc ctg gag ctg gcg ctg gag<br>Val Gln Tyr Phe Gly Gly Asp Pro Glu Gly Leu Glu Leu Ala Leu Glu<br>                980                985                990 | 2976 |
| cgc atg gcg cgc cgc aaa ttc cgc ttc ctc gtg agc atg cag cgc ctg<br>Arg Met Ala Arg Arg Lys Phe Arg Phe Leu Val Ser Met Gln Arg Leu<br>         995                   1000             1005 | 3024 |
| tcg aag ttc aaa gac gat gag atg gag aat gct gaa ttc ctc ctg<br>Ser Lys Phe Lys Asp Asp Glu Met Glu Asn Ala Glu Phe Leu Leu<br>1010                  1015                 1020 | 3069 |
| cgg gcc tac ccg gac ctc cag atc gcg tat ctc gac gaa gaa ccg<br>Arg Ala Tyr Pro Asp Leu Gln Ile Ala Tyr Leu Asp Glu Glu Pro<br>     1025                1030               1035 | 3114 |
| gcg ctg aat gag gac gag gaa ccg cgc gtg tac agc gca ctg atc<br>Ala Leu Asn Glu Asp Glu Glu Pro Arg Val Tyr Ser Ala Leu Ile<br>         1040                1045               1050 | 3159 |
| gac gga cac tgc gag atg ctc gag aac ggc agg cgc agg ccg aag<br>Asp Gly His Cys Glu Met Leu Glu Asn Gly Arg Arg Arg Pro Lys<br>1055                  1060                 1065 | 3204 |
| ttt cgc gtc cag ttg tcg ggc aac ccg atc ctc ggc gat ggt aag<br>Phe Arg Val Gln Leu Ser Gly Asn Pro Ile Leu Gly Asp Gly Lys<br>     1070                1075               1080 | 3249 |
| tcc gac aac cag aat cac gcc gtc atc ttc cat cgc ggc gag tat<br>Ser Asp Asn Gln Asn His Ala Val Ile Phe His Arg Gly Glu Tyr<br>         1085                1090               1095 | 3294 |
| atc cag ctg atc gac gcg aac cag gac aac tat ctg gaa gag tgc<br>Ile Gln Leu Ile Asp Ala Asn Gln Asp Asn Tyr Leu Glu Glu Cys<br>1100                  1105                 1110 | 3339 |
| ctg aag atc cgc tcg gtc ctg gct gaa ttc gaa gag atg aac gtc<br>Leu Lys Ile Arg Ser Val Leu Ala Glu Phe Glu Glu Met Asn Val<br>     1115                1120               1125 | 3384 |
| gag cat gtt aat ccg tac gcc ccg aat ttg aaa tcc gag gac aac<br>Glu His Val Asn Pro Tyr Ala Pro Asn Leu Lys Ser Glu Asp Asn<br>         1130                1135               1140 | 3429 |
| aac acg aag aaa gac ccg gtc gcc ttc ctg ggc gca cgc gag tac<br>Asn Thr Lys Lys Asp Pro Val Ala Phe Leu Gly Ala Arg Glu Tyr<br>1145                  1150                 1155 | 3474 |
| atc ttc agt gag aac tcg ggc gtg ctg ggc gac gtg gct gcg ggc<br>Ile Phe Ser Glu Asn Ser Gly Val Leu Gly Asp Val Ala Ala Gly<br>     1160                1165               1170 | 3519 |
| aaa gag cag acg ttt ggc acc ctg ttc gcc cgg acc ctc gcg cag<br>Lys Glu Gln Thr Phe Gly Thr Leu Phe Ala Arg Thr Leu Ala Gln<br>         1175                1180               1185 | 3564 |
| atc ggc ggg aag ctc cac tat ggc cat ccc gac ttc ctg aat gcg<br>Ile Gly Gly Lys Leu His Tyr Gly His Pro Asp Phe Leu Asn Ala | 3609 |

-continued

```
            1190                1195                1200
acg ttc atg ctc acg cgc ggg ggc gtg tcc aaa gcc cag aag ggc       3654
Thr Phe Met Leu Thr Arg Gly Gly Val Ser Lys Ala Gln Lys Gly
    1205                1210                1215 ctg cac ctc aac gaa gat atc tat gcg ggt atg aat gcg atg atg       3699
Leu His Leu Asn Glu Asp Ile Tyr Ala Gly Met Asn Ala Met Met
    1220                1225                1230 cgg ggt ggc aag atc aag cac tgc gag tac tac cag tgc ggt aag       3744
Arg Gly Gly Lys Ile Lys His Cys Glu Tyr Tyr Gln Cys Gly Lys
    1235                1240                1245 ggc agg gat ctt ggc ttc ggc tcc atc ctc aac ttc acc acc aag       3789
Gly Arg Asp Leu Gly Phe Gly Ser Ile Leu Asn Phe Thr Thr Lys
    1250                1255                1260 atc ggg gcc ggc atg ggc gag caa atg ctc tcg cgg gag tac ttt       3834
Ile Gly Ala Gly Met Gly Glu Gln Met Leu Ser Arg Glu Tyr Phe
    1265                1270                1275 tat ctg ggt acc cag ctt ccc ctt gac cgc ttc ctc tcg ttc tac       3879
Tyr Leu Gly Thr Gln Leu Pro Leu Asp Arg Phe Leu Ser Phe Tyr
    1280                1285                1290 tac ggg cat ccg gga ttc cac atc aac aac ctc ttc atc caa ctg       3924
Tyr Gly His Pro Gly Phe His Ile Asn Asn Leu Phe Ile Gln Leu
    1295                1300                1305 agc ctc caa gtg ttc atc ctt gtg ctt ggc aat ctg aat tcg ctg       3969
Ser Leu Gln Val Phe Ile Leu Val Leu Gly Asn Leu Asn Ser Leu
    1310                1315                1320 gcc cac gag gcc atc atg tgt tcg tac aac aaa gac gtg ccc gtc       4014
Ala His Glu Ala Ile Met Cys Ser Tyr Asn Lys Asp Val Pro Val
    1325                1330                1335 act gac gtg ctc tac ccc ttc ggc tgt tac aat atc gct ccc gcg       4059
Thr Asp Val Leu Tyr Pro Phe Gly Cys Tyr Asn Ile Ala Pro Ala
    1340                1345                1350 gtg gat tgg atc cgc cgg tat acc ctc tcg atc ttc att gtc ttt       4104
Val Asp Trp Ile Arg Arg Tyr Thr Leu Ser Ile Phe Ile Val Phe
    1355                1360                1365 ttc atc tcg ttc atc ccg ctg gtc gtc cag gag ctc ata gag cgg       4149
Phe Ile Ser Phe Ile Pro Leu Val Val Gln Glu Leu Ile Glu Arg
    1370                1375                1380 gga gtg tgg aag gct ttc cag cgg ttc gtc cgg cat ttc atc tcg       4194
Gly Val Trp Lys Ala Phe Gln Arg Phe Val Arg His Phe Ile Ser
    1385                1390                1395 atg tcc ccg ttc ttc gag gtg ttc gtg gcg cag ata tat tcg agc       4239
Met Ser Pro Phe Phe Glu Val Phe Val Ala Gln Ile Tyr Ser Ser
    1400                1405                1410 tcc gtg ttc acg gac ctc acc gtg ggt ggg gcg agg tat atc agc       4284
Ser Val Phe Thr Asp Leu Thr Val Gly Gly Ala Arg Tyr Ile Ser
    1415                1420                1425 acc ggg cgc ggg ttc gcc acc tcg cgc atc ccg ttt tcg atc aag       4329
Thr Gly Arg Gly Phe Ala Thr Ser Arg Ile Pro Phe Ser Ile Lys
    1430                1435                1440 cgc ttt gcg gat tcg agt atc tat atg ggc gct cgg ctc atg ctc       4374
Arg Phe Ala Asp Ser Ser Ile Tyr Met Gly Ala Arg Leu Met Leu
    1445                1450                1455 atc ctg ctt ttc ggt acc gtg agc cac tgg caa gcg ccg ctt ctc       4419
Ile Leu Leu Phe Gly Thr Val Ser His Trp Gln Ala Pro Leu Leu
    1460                1465                1470 tgg ttc tgg gcc tcg ctc tcc gcg ttg atg ttc tcc ccg ttc atc       4464
Trp Phe Trp Ala Ser Leu Ser Ala Leu Met Phe Ser Pro Phe Ile
    1475                1480                1485 ttt aac ccg cat cag ttc gcg tgg gaa gat ttc ttt ctc gac tat       4509
```

```
            Phe Asn Pro His Gln Phe Ala Trp Glu Asp Phe Phe Leu Asp Tyr
                1490                1495                1500 cgc gat ttc atc cgc tgg ctg tcc cgc gga aac acc aag tgg cat             4554
Arg Asp Phe Ile Arg Trp Leu Ser Arg Gly Asn Thr Lys Trp His
    1505                1510                1515 cgg aac agc tgg atc ggc tac gtt cgc ctc tcg cgg tcg cgc ata             4599
Arg Asn Ser Trp Ile Gly Tyr Val Arg Leu Ser Arg Ser Arg Ile
    1520                1525                1530 acg ggc ttc aag cgg aaa ctc acc ggc gac gtg agc gag aaa gcc             4644
Thr Gly Phe Lys Arg Lys Leu Thr Gly Asp Val Ser Glu Lys Ala
    1535                1540                1545 gct ggc gat gcc tcc agg gct cat cgc tcg aat gtg ctg ttc gcg             4689
Ala Gly Asp Ala Ser Arg Ala His Arg Ser Asn Val Leu Phe Ala
    1550                1555                1560 gac ttc ctg ccg acc ctg ata tac act gcg ggc ctc tac gtc gcc             4734
Asp Phe Leu Pro Thr Leu Ile Tyr Thr Ala Gly Leu Tyr Val Ala
    1565                1570                1575 tat acc ttc atc aac gcc cag acg ggc gtc acc agc tat ccc tac             4779
Tyr Thr Phe Ile Asn Ala Gln Thr Gly Val Thr Ser Tyr Pro Tyr
    1580                1585                1590 gag atc aat ggc tcg acg gac ccg caa cca gtt aac tcc acg ctg             4824
Glu Ile Asn Gly Ser Thr Asp Pro Gln Pro Val Asn Ser Thr Leu
    1595                1600                1605 agg ctc atc atc tgc gcc ctg gca cct gtc gtc atc gac atg ggc             4869
Arg Leu Ile Ile Cys Ala Leu Ala Pro Val Val Ile Asp Met Gly
    1610                1615                1620 tgc ctg ggt gtg tgc ctc gcc atg gcg tgc tgc gcc ggc ccg atg             4914
Cys Leu Gly Val Cys Leu Ala Met Ala Cys Cys Ala Gly Pro Met
    1625                1630                1635 ctg ggc ctg tgc tgc aag aaa acc ggc gca gtc atc gcc ggt gtc             4959
Leu Gly Leu Cys Cys Lys Lys Thr Gly Ala Val Ile Ala Gly Val
    1640                1645                1650 gcg cac ggc gtc gcc gtc atc gtc cat atc atc ttc ttc atc gtg             5004
Ala His Gly Val Ala Val Ile Val His Ile Ile Phe Phe Ile Val
    1655                1660                1665 atg tgg gtg act gag ggt ttc aat ttc gca cgc ctg atg ctt ggc             5049
Met Trp Val Thr Glu Gly Phe Asn Phe Ala Arg Leu Met Leu Gly
    1670                1675                1680 atc gcg acc atg atc tat gtg cag agg ctg ctt ttc aag ttc ctg             5094
Ile Ala Thr Met Ile Tyr Val Gln Arg Leu Leu Phe Lys Phe Leu
    1685                1690                1695 acg ctg tgc ttc ctc acc cgg gag ttc aag aac gac aaa gcc aac             5139
Thr Leu Cys Phe Leu Thr Arg Glu Phe Lys Asn Asp Lys Ala Asn
    1700                1705                1710 acc gcg ttt tgg acg ggt aag tgg tat aac acc ggc atg ggc tgg             5184
Thr Ala Phe Trp Thr Gly Lys Trp Tyr Asn Thr Gly Met Gly Trp
    1715                1720                1725 atg gcc ttc acg cag ccg agc cgc gag ttc gtg gcc aag atc atc             5229
Met Ala Phe Thr Gln Pro Ser Arg Glu Phe Val Ala Lys Ile Ile
    1730                1735                1740 gag atg agc gag ttc gcg ggt gat ttc gtc ctt gcc cac ata atc             5274
Glu Met Ser Glu Phe Ala Gly Asp Phe Val Leu Ala His Ile Ile
    1745                1750                1755 ctg ttc tgc cag ctg ccg ctc ctg ttc att ccg ttg gtc gac cgc             5319
Leu Phe Cys Gln Leu Pro Leu Leu Phe Ile Pro Leu Val Asp Arg
    1760                1765                1770 tgg cat agc atg atg ctg ttc tgg ctg aag ccg tcc cgc ctc att             5364
Trp His Ser Met Met Leu Phe Trp Leu Lys Pro Ser Arg Leu Ile
    1775                1780                1785
```

| | | | | | | | | | | | | |
|---|---|---|---|---|---|---|---|---|---|---|---|---|
| cgg | cca | cct | atc | tac | tcg | ctc | aaa | caa | gcg | cgc | ctg | |
| Arg | Pro | Pro | Ile | Tyr | Ser | Leu | Lys | Gln | Ala | Arg | Leu | |
| 1790 | | | | | 1795 | | | | | 1800 | | |
| cgc | aag | cgg | | | | | | | | | | 5409 |
| Arg | Lys | Arg | | | | | | | | | | |

| | | | | | | | | | | | | |
|---|---|---|---|---|---|---|---|---|---|---|---|---|
| atg | gtc | cgc | aaa | tac | tgt | gtc | ctg | tat | ttc | gca | gtg | |
| Met | Val | Arg | Lys | Tyr | Cys | Val | Leu | Tyr | Phe | Ala | Val | |
| | 1805 | | | | 1810 | | | | | 1815 | | |
| ctt | atc | ctg | | | | | | | | | | 5454 |
| Leu | Ile | Leu | | | | | | | | | | |

| | | | | | | | | | | | | |
|---|---|---|---|---|---|---|---|---|---|---|---|---|
| ttc | atc | gtt | atc | atc | gtc | gcg | cct | gcg | gtc | gca | tcg | |
| Phe | Ile | Val | Ile | Ile | Val | Ala | Pro | Ala | Val | Ala | Ser | |
| | 1820 | | | | 1825 | | | | | 1830 | | |
| ggg | cag | atc | | | | | | | | | | 5499 |
| Gly | Gln | Ile | | | | | | | | | | |

| | | | | | | | | | | | | |
|---|---|---|---|---|---|---|---|---|---|---|---|---|
| gcg | gtg | gac | cag | ttc | gcc | aac | att | ggc | ggc | agc | ggc | |
| Ala | Val | Asp | Gln | Phe | Ala | Asn | Ile | Gly | Gly | Ser | Gly | |
| 1835 | | | | | 1840 | | | | | 1845 | | |
| tcc | ata | gca | | | | | | | | | | 5544 |
| Ser | Ile | Ala | | | | | | | | | | |

| | | | | | | | | | | | | |
|---|---|---|---|---|---|---|---|---|---|---|---|---|
| gac | ggc | ttg | ttc | caa | ccc | cgg | aat | gtg | agc | aac | aac | |
| Asp | Gly | Leu | Phe | Gln | Pro | Arg | Asn | Val | Ser | Asn | Asn | |
| 1850 | | | | | 1855 | | | | | 1860 | | |
| gac | acc | ggg | | | | | | | | | | 5589 |
| Asp | Thr | Gly | | | | | | | | | | |

| | | | | | | | | | | | | |
|---|---|---|---|---|---|---|---|---|---|---|---|---|
| aat | cat | cgc | cca | aag | acc | tac | acc | tgg | tcc | tac | ctc | |
| Asn | His | Arg | Pro | Lys | Thr | Tyr | Thr | Trp | Ser | Tyr | Leu | |
| 1865 | | | | | 1870 | | | | | 1875 | | |
| tcg | acc | cgc | | | | | | | | | | 5634 |
| Ser | Thr | Arg | | | | | | | | | | |

| | | | | | | | | | | | | |
|---|---|---|---|---|---|---|---|---|---|---|---|---|
| ttc | acc | ggc | tcg | acc | acc | ccc | tac | tcc | acc | aat | ccc | |
| Phe | Thr | Gly | Ser | Thr | Thr | Pro | Tyr | Ser | Thr | Asn | Pro | |
| 1880 | | | | | 1885 | | | | | 1890 | | |
| ttc | agg | gtg | | | | | | | | | | 5679 |
| Phe | Arg | Val | | | | | | | | | | |

<210> SEQ ID NO 10
<211> LENGTH: 1893
<212> TYPE: PRT
<213> ORGANISM: Artificial sequence
<220> FEATURE:
<223> OTHER INFORMATION: Synthetic Construct

<400> SEQUENCE: 10

Met Ser Tyr Asn Asp Asn Asn His Tyr Tyr Asp Pro Asn Gln Gln
1               5                   10                  15

Gly Gly Met Pro Pro His Gln Gly Gly Glu Gly Tyr Tyr Gln Gln
            20                  25                  30

Tyr Asp Asp Met Gly Gln Gln Pro His Gln Gln Asp Tyr Tyr Asp Pro
                35                  40                  45

Asn Ala Gln Tyr Gln Gln Gln Pro Tyr Asp Met Asp Gly Tyr Gln Asp
50                  55                  60

Gln Ala Asn Tyr Gly Gly Gln Pro Met Asn Ala Gln Gly Tyr Asn Ala
65                  70                  75                  80

Asp Pro Glu Ala Phe Ser Asp Phe Ser Tyr Gly Gly Gln Thr Pro Gly
                85                  90                  95

Thr Pro Gly Tyr Asp Gln Tyr Gly Thr Gln Tyr Thr Pro Ser Gln Met
                100                 105                 110

Ser Tyr Gly Gly Asp Pro Arg Ser Ser Gly Ala Ser Thr Pro Ile Tyr
            115                 120                 125

Gly Gly Gln Gly Gln Gly Tyr Asp Pro Thr Gln Phe Asn Met Ser Ser
        130                 135                 140

Asn Leu Pro Tyr Pro Ala Trp Ser Ala Asp Pro Gln Ala Pro Ile Lys
145                 150                 155                 160

Ile Glu His Ile Glu Asp Ile Phe Ile Asp Leu Thr Asn Lys Phe Gly
                165                 170                 175

Phe Gln Arg Asp Ser Met Arg Asn Met Phe Asp Tyr Phe Met Thr Leu
            180                 185                 190

Leu Asp Ser Arg Ser Ser Arg Met Ser Pro Ala Gln Ala Leu Leu Ser
        195                 200                 205

Leu His Ala Asp Tyr Ile Gly Gly Asp Asn Ala Asn Tyr Arg Lys Trp
    210                 215                 220

```
Tyr Phe Ser Ser Gln Gln Asp Leu Asp Asp Ser Leu Gly Phe Ala Asn
225                 230                 235                 240

Met Thr Leu Gly Lys Ile Gly Arg Lys Ala Arg Lys Ala Ser Lys Lys
            245                 250                 255

Ser Lys Lys Ala Arg Lys Ala Glu Glu His Gly Gln Asp Val Asp
        260                 265                 270

Ala Asn Glu Leu Glu Gly Asp Tyr Ser Leu Glu Ala Ala Glu Ile Arg
    275                 280                 285

Trp Lys Ala Lys Met Asn Ser Leu Thr Pro Glu Glu Arg Val Arg Asp
290                 295                 300

Leu Ala Leu Tyr Leu Leu Ile Trp Gly Ala Asn Gln Val Arg Phe
305                 310                 315                 320

Thr Pro Glu Cys Leu Cys Tyr Ile Tyr Lys Ser Ala Thr Asp Tyr Leu
            325                 330                 335

Asn Ser Pro Leu Cys Gln Gln Arg Gln Glu Pro Val Pro Glu Gly Asp
        340                 345                 350

Tyr Leu Asn Arg Val Ile Thr Pro Leu Tyr Arg Phe Ile Arg Ser Gln
    355                 360                 365

Val Tyr Glu Ile Tyr Asp Gly Arg Phe Val Lys Arg Glu Lys Asp His
370                 375                 380

Asn Lys Val Ile Gly Tyr Asp Asp Val Asn Gln Leu Phe Trp Tyr Pro
385                 390                 395                 400

Glu Gly Ile Ser Arg Ile Ile Phe Glu Asp Gly Thr Arg Leu Val Asp
            405                 410                 415

Ile Pro Gln Glu Glu Arg Phe Leu Lys Leu Gly Glu Val Glu Trp Lys
        420                 425                 430

Asn Val Phe Phe Lys Thr Tyr Lys Glu Ile Arg Thr Trp Leu His Phe
    435                 440                 445

Val Thr Asn Phe Asn Arg Ile Trp Ile Ile His Gly Thr Ile Tyr Trp
450                 455                 460

Met Tyr Thr Ala Tyr Asn Ser Pro Thr Leu Tyr Thr Lys His Tyr Val
465                 470                 475                 480

Gln Thr Ile Asn Gln Gln Pro Leu Ala Ser Ser Arg Trp Ala Ala Cys
            485                 490                 495

Ala Ile Gly Gly Val Leu Ala Ser Phe Ile Gln Ile Leu Ala Thr Leu
        500                 505                 510

Phe Glu Trp Ile Phe Val Pro Arg Glu Trp Ala Gly Ala Gln His Leu
    515                 520                 525

Ser Arg Arg Met Leu Phe Leu Val Leu Ile Phe Leu Leu Asn Leu Val
530                 535                 540

Pro Pro Val Tyr Thr Phe Gln Ile Thr Lys Leu Val Ile Tyr Ser Lys
545                 550                 555                 560

Ser Ala Tyr Ala Val Ser Ile Val Gly Phe Phe Ile Ala Val Ala Thr
            565                 570                 575

Leu Val Phe Phe Ala Val Met Pro Leu Gly Gly Leu Phe Thr Ser Tyr
        580                 585                 590

Met Asn Lys Arg Ser Arg Arg Tyr Ile Ala Ser Gln Thr Phe Thr Ala
    595                 600                 605

Asn Tyr Ile Lys Leu Lys Gly Leu Asp Met Trp Met Ser Tyr Leu Leu
    610                 615                 620

Trp Phe Leu Val Phe Leu Ala Lys Leu Val Glu Ser Tyr Phe Phe Ser
625                 630                 635                 640
```

```
Thr Leu Ser Leu Arg Asp Pro Ile Arg Asn Leu Ser Thr Met Thr Met
            645                 650                 655

Arg Cys Val Gly Glu Val Trp Tyr Lys Asp Ile Val Cys Arg Asn Gln
        660                 665                 670

Ala Lys Ile Val Leu Gly Leu Met Tyr Leu Val Asp Leu Leu Leu Phe
    675                 680                 685

Phe Leu Asp Thr Tyr Met Trp Tyr Ile Ile Cys Asn Cys Ile Phe Ser
690                 695                 700

Ile Gly Arg Ser Phe Tyr Leu Gly Ile Ser Ile Leu Thr Pro Trp Arg
705                 710                 715                 720

Asn Ile Phe Thr Arg Leu Pro Lys Arg Ile Tyr Ser Lys Ile Leu Ala
                725                 730                 735

Thr Thr Glu Met Glu Ile Lys Tyr Lys Pro Lys Val Leu Ile Ser Gln
            740                 745                 750

Ile Trp Asn Ala Ile Val Ile Ser Met Tyr Arg Glu His Leu Leu Ala
        755                 760                 765

Ile Asp His Val Gln Lys Leu Leu Tyr His Gln Val Pro Ser Glu Ile
    770                 775                 780

Glu Gly Lys Arg Thr Leu Arg Ala Pro Thr Phe Phe Val Ser Gln Asp
785                 790                 795                 800

Asp Asn Asn Phe Glu Thr Glu Phe Phe Pro Arg Asn Ser Glu Ala Glu
                805                 810                 815

Arg Arg Ile Ser Phe Phe Ala Gln Ser Leu Ala Thr Pro Met Pro Glu
            820                 825                 830

Pro Leu Pro Val Asp Asn Met Pro Thr Phe Thr Val Phe Thr Pro His
        835                 840                 845

Tyr Ser Glu Lys Ile Leu Leu Ser Leu Arg Glu Ile Ile Arg Glu Asp
    850                 855                 860

Asp Gln Phe Ser Arg Val Thr Leu Leu Glu Tyr Leu Lys Gln Leu His
865                 870                 875                 880

Pro Val Glu Trp Asp Cys Phe Val Lys Asp Thr Lys Ile Leu Ala Glu
                885                 890                 895

Glu Thr Ala Ala Tyr Glu Asn Gly Asp Asp Ser Glu Lys Leu Ser Glu
            900                 905                 910

Asp Gly Leu Lys Ser Lys Ile Asp Asp Leu Pro Phe Tyr Cys Ile Gly
        915                 920                 925

Phe Lys Ser Ala Ala Pro Glu Tyr Thr Leu Arg Thr Arg Ile Trp Ala
    930                 935                 940

Ser Leu Arg Ser Gln Thr Leu Tyr Arg Thr Val Ser Gly Phe Met Asn
945                 950                 955                 960

Tyr Ala Arg Ala Ile Lys Leu Leu Tyr Arg Val Glu Asn Pro Glu Leu
                965                 970                 975

Val Gln Tyr Phe Gly Gly Asp Pro Glu Gly Leu Glu Leu Ala Leu Glu
            980                 985                 990

Arg Met Ala Arg Arg Lys Phe Phe Leu Val Ser Met Gln Arg Leu
            995                 1000                1005

Ser Lys Phe Lys Asp Asp Glu Met Glu Asn Ala Glu Phe Leu Leu
        1010                1015                1020

Arg Ala Tyr Pro Asp Leu Gln Ile Ala Tyr Leu Asp Glu Glu Pro
        1025                1030                1035

Ala Leu Asn Glu Asp Glu Pro Arg Val Tyr Ser Ala Leu Ile
        1040                1045                1050

Asp Gly His Cys Glu Met Leu Glu Asn Gly Arg Arg Arg Pro Lys
```

```
                1055                1060                1065
Phe Arg Val Gln Leu Ser Gly Asn Pro Ile Leu Gly Asp Gly Lys
        1070                1075                1080
Ser Asp Asn Gln Asn His Ala Val Ile Phe His Arg Gly Glu Tyr
        1085                1090                1095
Ile Gln Leu Ile Asp Ala Asn Gln Asp Asn Tyr Leu Glu Glu Cys
        1100                1105                1110
Leu Lys Ile Arg Ser Val Leu Ala Glu Phe Glu Glu Met Asn Val
        1115                1120                1125
Glu His Val Asn Pro Tyr Ala Pro Asn Leu Lys Ser Glu Asp Asn
        1130                1135                1140
Asn Thr Lys Lys Asp Pro Val Ala Phe Leu Gly Ala Arg Glu Tyr
        1145                1150                1155
Ile Phe Ser Glu Asn Ser Gly Val Leu Gly Asp Val Ala Ala Gly
        1160                1165                1170
Lys Glu Gln Thr Phe Gly Thr Leu Phe Ala Arg Thr Leu Ala Gln
        1175                1180                1185
Ile Gly Gly Lys Leu His Tyr Gly His Pro Asp Phe Leu Asn Ala
        1190                1195                1200
Thr Phe Met Leu Thr Arg Gly Gly Val Ser Lys Ala Gln Lys Gly
        1205                1210                1215
Leu His Leu Asn Glu Asp Ile Tyr Ala Gly Met Asn Ala Met Met
        1220                1225                1230
Arg Gly Gly Lys Ile Lys His Cys Glu Tyr Tyr Gln Cys Gly Lys
        1235                1240                1245
Gly Arg Asp Leu Gly Phe Gly Ser Ile Leu Asn Phe Thr Thr Lys
        1250                1255                1260
Ile Gly Ala Gly Met Gly Glu Gln Met Leu Ser Arg Glu Tyr Phe
        1265                1270                1275
Tyr Leu Gly Thr Gln Leu Pro Leu Asp Arg Phe Leu Ser Phe Tyr
        1280                1285                1290
Tyr Gly His Pro Gly Phe His Ile Asn Asn Leu Phe Ile Gln Leu
        1295                1300                1305
Ser Leu Gln Val Phe Ile Leu Val Leu Gly Asn Leu Asn Ser Leu
        1310                1315                1320
Ala His Glu Ala Ile Met Cys Ser Tyr Asn Lys Asp Val Pro Val
        1325                1330                1335
Thr Asp Val Leu Tyr Pro Phe Gly Cys Tyr Asn Ile Ala Pro Ala
        1340                1345                1350
Val Asp Trp Ile Arg Arg Tyr Thr Leu Ser Ile Phe Ile Val Phe
        1355                1360                1365
Phe Ile Ser Phe Ile Pro Leu Val Val Gln Glu Leu Ile Glu Arg
        1370                1375                1380
Gly Val Trp Lys Ala Phe Gln Arg Phe Val Arg His Phe Ile Ser
        1385                1390                1395
Met Ser Pro Phe Phe Glu Val Phe Val Ala Gln Ile Tyr Ser Ser
        1400                1405                1410
Ser Val Phe Thr Asp Leu Thr Val Gly Gly Ala Arg Tyr Ile Ser
        1415                1420                1425
Thr Gly Arg Gly Phe Ala Thr Ser Arg Ile Pro Phe Ser Ile Lys
        1430                1435                1440
Arg Phe Ala Asp Ser Ser Ile Tyr Met Gly Ala Arg Leu Met Leu
        1445                1450                1455
```

```
Ile Leu Leu Phe Gly Thr Val Ser His Trp Gln Ala Pro Leu Leu
    1460            1465            1470

Trp Phe Trp Ala Ser Leu Ser Ala Leu Met Phe Ser Pro Phe Ile
    1475            1480            1485

Phe Asn Pro His Gln Phe Ala Trp Glu Asp Phe Leu Asp Tyr
    1490            1495            1500

Arg Asp Phe Ile Arg Trp Leu Ser Arg Gly Asn Thr Lys Trp His
    1505            1510            1515

Arg Asn Ser Trp Ile Gly Tyr Val Arg Leu Ser Arg Ser Arg Ile
    1520            1525            1530

Thr Gly Phe Lys Arg Lys Leu Thr Gly Asp Val Ser Glu Lys Ala
    1535            1540            1545

Ala Gly Asp Ala Ser Arg Ala His Arg Ser Asn Val Leu Phe Ala
    1550            1555            1560

Asp Phe Leu Pro Thr Leu Ile Tyr Thr Ala Gly Leu Tyr Val Ala
    1565            1570            1575

Tyr Thr Phe Ile Asn Ala Gln Thr Gly Val Thr Ser Tyr Pro Tyr
    1580            1585            1590

Glu Ile Asn Gly Ser Thr Asp Pro Gln Pro Val Asn Ser Thr Leu
    1595            1600            1605

Arg Leu Ile Ile Cys Ala Leu Ala Pro Val Val Ile Asp Met Gly
    1610            1615            1620

Cys Leu Gly Val Cys Leu Ala Met Ala Cys Cys Ala Gly Pro Met
    1625            1630            1635

Leu Gly Leu Cys Cys Lys Lys Thr Gly Ala Val Ile Ala Gly Val
    1640            1645            1650

Ala His Gly Val Ala Val Ile Val His Ile Ile Phe Phe Ile Val
    1655            1660            1665

Met Trp Val Thr Glu Gly Phe Asn Phe Ala Arg Leu Met Leu Gly
    1670            1675            1680

Ile Ala Thr Met Ile Tyr Val Gln Arg Leu Leu Phe Lys Phe Leu
    1685            1690            1695

Thr Leu Cys Phe Leu Thr Arg Glu Phe Lys Asn Asp Lys Ala Asn
    1700            1705            1710

Thr Ala Phe Trp Thr Gly Lys Trp Tyr Asn Thr Gly Met Gly Trp
    1715            1720            1725

Met Ala Phe Thr Gln Pro Ser Arg Glu Phe Val Ala Lys Ile Ile
    1730            1735            1740

Glu Met Ser Glu Phe Ala Gly Asp Phe Val Leu Ala His Ile Ile
    1745            1750            1755

Leu Phe Cys Gln Leu Pro Leu Leu Phe Ile Pro Leu Val Asp Arg
    1760            1765            1770

Trp His Ser Met Met Leu Phe Trp Leu Lys Pro Ser Arg Leu Ile
    1775            1780            1785

Arg Pro Pro Ile Tyr Ser Leu Lys Gln Ala Arg Leu Arg Lys Arg
    1790            1795            1800

Met Val Arg Lys Tyr Cys Val Leu Tyr Phe Ala Val Leu Ile Leu
    1805            1810            1815

Phe Ile Val Ile Ile Val Ala Pro Ala Val Ala Ser Gly Gln Ile
    1820            1825            1830

Ala Val Asp Gln Phe Ala Asn Ile Gly Gly Ser Gly Ser Ile Ala
    1835            1840            1845
```

```
Asp Gly Leu Phe Gln Pro Arg Asn Val Ser Asn Asn Asp Thr Gly
    1850                1855                1860

Asn His Arg Pro Lys Thr Tyr Thr Trp Ser Tyr Leu Ser Thr Arg
    1865                1870                1875

Phe Thr Gly Ser Thr Thr Pro Tyr Ser Thr Asn Pro Phe Arg Val
    1880                1885                1890

<210> SEQ ID NO 11
<211> LENGTH: 171
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(171)
<223> OTHER INFORMATION: Zea mays (corn)  portion of 1,3-D-glucan
      synthase (codon optimized)

<400> SEQUENCE: 11 ttc aac tgt acc ctc cgc ggc ggc aat gtt acc cat cac gaa tat atc      48
Phe Asn Cys Thr Leu Arg Gly Gly Asn Val Thr His His Glu Tyr Ile
1               5                   10                  15 caa gtc ggc aaa gga cgc gac gtc ggc ctg aat caa gtg tcg atg ttc      96
Gln Val Gly Lys Gly Arg Asp Val Gly Leu Asn Gln Val Ser Met Phe
            20                  25                  30 gag gcg aaa gtc gcc tcc ggt aac ggc gag cag acg ctg agc cgc gac     144
Glu Ala Lys Val Ala Ser Gly Asn Gly Glu Gln Thr Leu Ser Arg Asp
        35                  40                  45 gtg tac cgg ctc ggg cat cgg ctg gat                                  171
Val Tyr Arg Leu Gly His Arg Leu Asp
    50                  55

<210> SEQ ID NO 12
<211> LENGTH: 57
<212> TYPE: PRT
<213> ORGANISM: Artificial sequence
<220> FEATURE:
<223> OTHER INFORMATION: Synthetic Construct

<400> SEQUENCE: 12

Phe Asn Cys Thr Leu Arg Gly Gly Asn Val Thr His His Glu Tyr Ile
1               5                   10                  15

Gln Val Gly Lys Gly Arg Asp Val Gly Leu Asn Gln Val Ser Met Phe
            20                  25                  30

Glu Ala Lys Val Ala Ser Gly Asn Gly Glu Gln Thr Leu Ser Arg Asp
        35                  40                  45

Val Tyr Arg Leu Gly His Arg Leu Asp
    50                  55

<210> SEQ ID NO 13
<211> LENGTH: 450
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(450)
<223> OTHER INFORMATION: Zea mays (corn): portion of 1,3-D-glucan
      synthase (codon optimized)

<400> SEQUENCE: 13 cag ctg aag cgc ctg cat ctc ctc ctc acc gtc aaa gac agc gcc acc      48
Gln Leu Lys Arg Leu His Leu Leu Leu Thr Val Lys Asp Ser Ala Thr
```

```
1               5                   10                  15
aac atc ccg aag aat ctt gag gcc cgg cgg cgc ctg cag ttc ttc acg      96
Asn Ile Pro Lys Asn Leu Glu Ala Arg Arg Arg Leu Gln Phe Phe Thr
             20                  25                  30 aac agc ctg ttc atg gat atc ccg caa gcg aag ccc gtg tcc gag atg     144
Asn Ser Leu Phe Met Asp Ile Pro Gln Ala Lys Pro Val Ser Glu Met
         35                  40                  45 atc ccg ttt tcg gtg ttc acc ccg tac tac tcg gag act gtt ctc tat     192
Ile Pro Phe Ser Val Phe Thr Pro Tyr Tyr Ser Glu Thr Val Leu Tyr
 50                  55                  60 tcc atg tcc gag ctg tgc gtc gag aat gag gac ggc atc agt att ctg     240
Ser Met Ser Glu Leu Cys Val Glu Asn Glu Asp Gly Ile Ser Ile Leu
 65                  70                  75                  80 ttc tac ctc caa aag atc tat ccc gac gag tgg gca aac ttc ctg gag     288
Phe Tyr Leu Gln Lys Ile Tyr Pro Asp Glu Trp Ala Asn Phe Leu Glu
                 85                  90                  95 cgc atc ggg tgc ggc gag tcg agc gaa gat gac ttc aaa gaa tcg ccg     336
Arg Ile Gly Cys Gly Glu Ser Ser Glu Asp Asp Phe Lys Glu Ser Pro
             100                 105                 110 tcc gac acg atg gaa ttg cgg ttc tgg gtg agc tac cgc ggt cag acc     384
Ser Asp Thr Met Glu Leu Arg Phe Trp Val Ser Tyr Arg Gly Gln Thr
         115                 120                 125 ctc ggc cgc acc gtc cgg ggc atg atg tat tac cgc agg gcg ctg atg     432
Leu Gly Arg Thr Val Arg Gly Met Met Tyr Tyr Arg Arg Ala Leu Met
 130                 135                 140 ctc cag tcg tat ctg gag                                             450
Leu Gln Ser Tyr Leu Glu
145             150

<210> SEQ ID NO 14
<211> LENGTH: 150
<212> TYPE: PRT
<213> ORGANISM: Artificial sequence
<220> FEATURE:
<223> OTHER INFORMATION: Synthetic Construct

<400> SEQUENCE: 14

Gln Leu Lys Arg Leu His Leu Leu Thr Val Lys Asp Ser Ala Thr
1               5                   10                  15

Asn Ile Pro Lys Asn Leu Glu Ala Arg Arg Arg Leu Gln Phe Phe Thr
             20                  25                  30

Asn Ser Leu Phe Met Asp Ile Pro Gln Ala Lys Pro Val Ser Glu Met
         35                  40                  45

Ile Pro Phe Ser Val Phe Thr Pro Tyr Tyr Ser Glu Thr Val Leu Tyr
 50                  55                  60

Ser Met Ser Glu Leu Cys Val Glu Asn Glu Asp Gly Ile Ser Ile Leu
 65                  70                  75                  80

Phe Tyr Leu Gln Lys Ile Tyr Pro Asp Glu Trp Ala Asn Phe Leu Glu
                 85                  90                  95

Arg Ile Gly Cys Gly Glu Ser Ser Glu Asp Asp Phe Lys Glu Ser Pro
             100                 105                 110

Ser Asp Thr Met Glu Leu Arg Phe Trp Val Ser Tyr Arg Gly Gln Thr
         115                 120                 125

Leu Gly Arg Thr Val Arg Gly Met Met Tyr Tyr Arg Arg Ala Leu Met
 130                 135                 140

Leu Gln Ser Tyr Leu Glu
145             150
```

```
<210> SEQ ID NO 15
<211> LENGTH: 405
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(405)
<223> OTHER INFORMATION: Oryza sativa (rice) portion of
      1,3-beta-D-glucan synthase (codon optimized)

<400> SEQUENCE: 15 gag aac tat cgc ctc tac tcg cgc tcc cat ttc gtc aaa gca ctc gaa      48
Glu Asn Tyr Arg Leu Tyr Ser Arg Ser His Phe Val Lys Ala Leu Glu
1               5                   10                  15 gtt gcc ctg ctg ctc atc atc tat att gcg tac ggc tat acc cgg ggg      96
Val Ala Leu Leu Leu Ile Ile Tyr Ile Ala Tyr Gly Tyr Thr Arg Gly
            20                  25                  30 ggc tcc tcc agc ttc atc ctg ttg acc att agt tcg tgg ttc ctc gtc     144
Gly Ser Ser Ser Phe Ile Leu Leu Thr Ile Ser Ser Trp Phe Leu Val
        35                  40                  45 gtg tcg tgg ctg ttc gct ccc tac ata ttc aac ccg agc ggc ttt gag     192
Val Ser Trp Leu Phe Ala Pro Tyr Ile Phe Asn Pro Ser Gly Phe Glu
    50                  55                  60 tgg cag aaa acc gtc gag gac ttc gac gat tgg acg aat tgg ctc ctg     240
Trp Gln Lys Thr Val Glu Asp Phe Asp Asp Trp Thr Asn Trp Leu Leu
65                  70                  75                  80 tac aag ggc gga gtg ggc gtg aag ggt gag aat agc tgg gag tcc tgg     288
Tyr Lys Gly Gly Val Gly Val Lys Gly Glu Asn Ser Trp Glu Ser Trp
                85                  90                  95 tgg gac gag gaa cag gcg cat atc caa acg ctg agg ggt cgg atc ctt     336
Trp Asp Glu Glu Gln Ala His Ile Gln Thr Leu Arg Gly Arg Ile Leu
            100                 105                 110 gag act atc ctg tcg ctg cgc ttc ctc atc ttc cag tac ggc atc gtc     384
Glu Thr Ile Leu Ser Leu Arg Phe Leu Ile Phe Gln Tyr Gly Ile Val
        115                 120                 125 tat aag ctc aag atc gcc cac                                         405
Tyr Lys Leu Lys Ile Ala His
    130                 135

<210> SEQ ID NO 16
<211> LENGTH: 135
<212> TYPE: PRT
<213> ORGANISM: Artificial sequence
<220> FEATURE:
<223> OTHER INFORMATION: Synthetic Construct

<400> SEQUENCE: 16

Glu Asn Tyr Arg Leu Tyr Ser Arg Ser His Phe Val Lys Ala Leu Glu
1               5                   10                  15

Val Ala Leu Leu Leu Ile Ile Tyr Ile Ala Tyr Gly Tyr Thr Arg Gly
            20                  25                  30

Gly Ser Ser Ser Phe Ile Leu Leu Thr Ile Ser Ser Trp Phe Leu Val
        35                  40                  45

Val Ser Trp Leu Phe Ala Pro Tyr Ile Phe Asn Pro Ser Gly Phe Glu
    50                  55                  60

Trp Gln Lys Thr Val Glu Asp Phe Asp Asp Trp Thr Asn Trp Leu Leu
65                  70                  75                  80

Tyr Lys Gly Gly Val Gly Val Lys Gly Glu Asn Ser Trp Glu Ser Trp
                85                  90                  95

Trp Asp Glu Glu Gln Ala His Ile Gln Thr Leu Arg Gly Arg Ile Leu
```

```
                     100                 105                 110
Glu Thr Ile Leu Ser Leu Arg Phe Leu Ile Phe Gln Tyr Gly Ile Val
             115                 120                 125

Tyr Lys Leu Lys Ile Ala His
         130                 135

<210> SEQ ID NO 17
<211> LENGTH: 306
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(306)
<223> OTHER INFORMATION: Oryza sativa (rice) portion of
      1,3-beta-D-glucan synthase (codon optimized)

<400> SEQUENCE: 17 tgg gtc gtt gct ttc gcc atc ctg tac aaa gaa gcc tgg aac aac cgc         48
Trp Val Val Ala Phe Ala Ile Leu Tyr Lys Glu Ala Trp Asn Asn Arg
1               5                   10                  15 aat tcg aat agc caa atc atg cgc ttt ttg tat gca gcc gcg gtg ttc         96
Asn Ser Asn Ser Gln Ile Met Arg Phe Leu Tyr Ala Ala Ala Val Phe
                20                  25                  30 atg atc ccc gag gtc ctg gcg atc gtg ctg ttc atc gtc ccg tgg gtc         144
Met Ile Pro Glu Val Leu Ala Ile Val Leu Phe Ile Val Pro Trp Val
            35                  40                  45 cgg aac gcc ctg gag aaa acc aat tgg aag att tgc tat gcg ctc acc         192
Arg Asn Ala Leu Glu Lys Thr Asn Trp Lys Ile Cys Tyr Ala Leu Thr
        50                  55                  60 tgg tgg ttc cag agc cgc tcg ttc gtg ggt cgg ggc ctc cgc gag ggc         240
Trp Trp Phe Gln Ser Arg Ser Phe Val Gly Arg Gly Leu Arg Glu Gly
65              70                  75                  80 acg ttc gac aac gtg aag tac tcc gtg ttc tgg gtc ctt ctc ctc gcg         288
Thr Phe Asp Asn Val Lys Tyr Ser Val Phe Trp Val Leu Leu Leu Ala
                85                  90                  95 gtc aag ttc gcg ttc tcc                                                 306
Val Lys Phe Ala Phe Ser
            100

<210> SEQ ID NO 18
<211> LENGTH: 102
<212> TYPE: PRT
<213> ORGANISM: Artificial sequence
<220> FEATURE:
<223> OTHER INFORMATION: Synthetic Construct

<400> SEQUENCE: 18

Trp Val Val Ala Phe Ala Ile Leu Tyr Lys Glu Ala Trp Asn Asn Arg
1               5                   10                  15

Asn Ser Asn Ser Gln Ile Met Arg Phe Leu Tyr Ala Ala Ala Val Phe
                20                  25                  30

Met Ile Pro Glu Val Leu Ala Ile Val Leu Phe Ile Val Pro Trp Val
            35                  40                  45

Arg Asn Ala Leu Glu Lys Thr Asn Trp Lys Ile Cys Tyr Ala Leu Thr
        50                  55                  60

Trp Trp Phe Gln Ser Arg Ser Phe Val Gly Arg Gly Leu Arg Glu Gly
65              70                  75                  80

Thr Phe Asp Asn Val Lys Tyr Ser Val Phe Trp Val Leu Leu Leu Ala
                85                  90                  95
```

```
Val Lys Phe Ala Phe Ser
            100
```

<210> SEQ ID NO 19
<211> LENGTH: 435
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(435)
<223> OTHER INFORMATION: Gycine max (soy) portion of 1,3-beta-D-glucan
      synthase (codon optimized)

<400> SEQUENCE: 19

```
ttg agg tcc tcg gaa atg cgg aaa att ata gcc acg ctg cgc gct ctt      48
Leu Arg Ser Ser Glu Met Arg Lys Ile Ile Ala Thr Leu Arg Ala Leu
1               5                   10                  15 gtt gaa gtc ttg gaa tcc ctg tcg aag gac gcg gat ccg ggt ggc gtc      96
Val Glu Val Leu Glu Ser Leu Ser Lys Asp Ala Asp Pro Gly Gly Val
                20                  25                  30 ggt ggc ctg atc atg gaa gaa ctc cgg aag atc aag aaa tcg agt gtg     144
Gly Gly Leu Ile Met Glu Glu Leu Arg Lys Ile Lys Lys Ser Ser Val
            35                  40                  45 acc ctg tcg ggc gag ctc acc ccc tat aac atc att ccg ctt gag gcg     192
Thr Leu Ser Gly Glu Leu Thr Pro Tyr Asn Ile Ile Pro Leu Glu Ala
        50                  55                  60 ccg tcc ctc acc aat ccc atc cgg atc ttc ccc gag gtg aag gcc gcg     240
Pro Ser Leu Thr Asn Pro Ile Arg Ile Phe Pro Glu Val Lys Ala Ala
65                  70                  75                  80 atc agc gcg atc cgc tac acg gac cag ttc cca cgc ctc cct gcc ggc     288
Ile Ser Ala Ile Arg Tyr Thr Asp Gln Phe Pro Arg Leu Pro Ala Gly
                85                  90                  95 ttc aag atc agc ggg cag cgc gac gcg gat atg ttc gac ctc ctg gag     336
Phe Lys Ile Ser Gly Gln Arg Asp Ala Asp Met Phe Asp Leu Leu Glu
            100                 105                 110 ttc gtc ttt gga ttc cag aaa gac aac gtg cgc aac cag cgg gag aat     384
Phe Val Phe Gly Phe Gln Lys Asp Asn Val Arg Asn Gln Arg Glu Asn
        115                 120                 125 gtc gtg ctg atg atc gcc aac aag caa agc cgc ctc ggc atc ccg gca     432
Val Val Leu Met Ile Ala Asn Lys Gln Ser Arg Leu Gly Ile Pro Ala
    130                 135                 140 gag                                                                  435
Glu
145
```

<210> SEQ ID NO 20
<211> LENGTH: 145
<212> TYPE: PRT
<213> ORGANISM: Artificial sequence
<220> FEATURE:
<223> OTHER INFORMATION: Synthetic Construct

<400> SEQUENCE: 20

```
Leu Arg Ser Ser Glu Met Arg Lys Ile Ile Ala Thr Leu Arg Ala Leu
1               5                   10                  15

Val Glu Val Leu Glu Ser Leu Ser Lys Asp Ala Asp Pro Gly Gly Val
                20                  25                  30

Gly Gly Leu Ile Met Glu Glu Leu Arg Lys Ile Lys Lys Ser Ser Val
            35                  40                  45

Thr Leu Ser Gly Glu Leu Thr Pro Tyr Asn Ile Ile Pro Leu Glu Ala
        50                  55                  60
```

```
Pro Ser Leu Thr Asn Pro Ile Arg Ile Phe Pro Glu Val Lys Ala Ala
 65                  70                  75                  80

Ile Ser Ala Ile Arg Tyr Thr Asp Gln Phe Pro Arg Leu Pro Ala Gly
                 85                  90                  95

Phe Lys Ile Ser Gly Gln Arg Asp Ala Asp Met Phe Asp Leu Leu Glu
            100                 105                 110

Phe Val Phe Gly Phe Gln Lys Asp Asn Val Arg Asn Gln Arg Glu Asn
                115                 120                 125

Val Val Leu Met Ile Ala Asn Lys Gln Ser Arg Leu Gly Ile Pro Ala
        130                 135                 140

Glu
145

<210> SEQ ID NO 21
<211> LENGTH: 489
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(489)
<223> OTHER INFORMATION: Veronia mespilifolia 1,3-beta-D-glucan synthase
      (codon optimized)

<400> SEQUENCE: 21 tat ggc cat cca gat gtc ttt gac cgc gtt ttt cat att acc agg gga        48
Tyr Gly His Pro Asp Val Phe Asp Arg Val Phe His Ile Thr Arg Gly
  1               5                  10                  15 gga atc agt aaa gct agc cgc gtg atc aat atc tcc gaa gat atc tat        96
Gly Ile Ser Lys Ala Ser Arg Val Ile Asn Ile Ser Glu Asp Ile Tyr
                 20                  25                  30 gcc ggc ttc aat tcc acc ctg cgg caa ggc aat atc acc cac cac gag       144
Ala Gly Phe Asn Ser Thr Leu Arg Gln Gly Asn Ile Thr His His Glu
             35                  40                  45 tat atc cag gtc ggt aag ggc cgc gac gtc ggc ctg aac cag att gcc       192
Tyr Ile Gln Val Gly Lys Gly Arg Asp Val Gly Leu Asn Gln Ile Ala
     50                  55                  60 ctc ttc gag ggc aag gtc gcg ggc ggg aac ggc gag caa gtc ctc tcg       240
Leu Phe Glu Gly Lys Val Ala Gly Gly Asn Gly Glu Gln Val Leu Ser
 65                  70                  75                  80 cgc gac atc tac cgc ctc ggc cag ctg ttc gac ttc ttc cgg atg ctg       288
Arg Asp Ile Tyr Arg Leu Gly Gln Leu Phe Asp Phe Phe Arg Met Leu
                 85                  90                  95 tcg ttc tac ttc acg acc gtg ggg tac tat ttc tgc acc atg ctg acc       336
Ser Phe Tyr Phe Thr Thr Val Gly Tyr Tyr Phe Cys Thr Met Leu Thr
            100                 105                 110 gtg acg act gtg tac ata ttc ctc tat ggt aag acc tac ttg gcc ctg       384
Val Thr Thr Val Tyr Ile Phe Leu Tyr Gly Lys Thr Tyr Leu Ala Leu
        115                 120                 125 tcg ggt gtc ggc gag gac atc cag aac cgg agc gaa gtc ctc gac aac       432
Ser Gly Val Gly Glu Asp Ile Gln Asn Arg Ser Glu Val Leu Asp Asn
    130                 135                 140 aaa gcg ctt acc gca gcg ctg aac acg cag ttc ctc ttc cag atc ggc       480
Lys Ala Leu Thr Ala Ala Leu Asn Thr Gln Phe Leu Phe Gln Ile Gly
145                 150                 155                 160 gtg ttc acg                                                           489
Val Phe Thr

<210> SEQ ID NO 22
```

-continued

```
<211> LENGTH: 163
<212> TYPE: PRT
<213> ORGANISM: Artificial sequence
<220> FEATURE:
<223> OTHER INFORMATION: Synthetic Construct

<400> SEQUENCE: 22

Tyr Gly His Pro Asp Val Phe Asp Arg Val Phe His Ile Thr Arg Gly
1               5                   10                  15

Gly Ile Ser Lys Ala Ser Arg Val Ile Asn Ile Ser Glu Asp Ile Tyr
                20                  25                  30

Ala Gly Phe Asn Ser Thr Leu Arg Gln Gly Asn Ile Thr His His Glu
            35                  40                  45

Tyr Ile Gln Val Gly Lys Gly Arg Asp Val Gly Leu Asn Gln Ile Ala
        50                  55                  60

Leu Phe Glu Gly Lys Val Ala Gly Gly Asn Gly Glu Gln Val Leu Ser
65                  70                  75                  80

Arg Asp Ile Tyr Arg Leu Gly Gln Leu Phe Asp Phe Arg Met Leu
                85                  90                  95

Ser Phe Tyr Phe Thr Thr Val Gly Tyr Tyr Phe Cys Thr Met Leu Thr
                100                 105                 110

Val Thr Thr Val Tyr Ile Phe Leu Tyr Gly Lys Thr Tyr Leu Ala Leu
            115                 120                 125

Ser Gly Val Gly Glu Asp Ile Gln Asn Arg Ser Glu Val Leu Asp Asn
        130                 135                 140

Lys Ala Leu Thr Ala Ala Leu Asn Thr Gln Phe Leu Phe Gln Ile Gly
145                 150                 155                 160

Val Phe Thr

<210> SEQ ID NO 23
<211> LENGTH: 1467
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(1467)
<223> OTHER INFORMATION: Triticum aestivum (wheat) 1,3-beta-D-glucan
      synthase (codon optimized)

<400> SEQUENCE: 23 cgc gtg ggg aag ggt agg gat gtc ggc ttg aat caa atc agt atg ttc        48
Arg Val Gly Lys Gly Arg Asp Val Gly Leu Asn Gln Ile Ser Met Phe
1               5                   10                  15 gaa gca aaa gtg gct ggg gga aat ggt gag cag act ctg tcc cgc gac        96
Glu Ala Lys Val Ala Gly Gly Asn Gly Glu Gln Thr Leu Ser Arg Asp
                20                  25                  30 gtc tac cgc ctt ggc cat ggc ctg gac ttc ttc cgg atg ctg agc ttc        144
Val Tyr Arg Leu Gly His Gly Leu Asp Phe Phe Arg Met Leu Ser Phe
            35                  40                  45 ttc tac acg acc atc ggc ttt tac ctc aat acc atg atg gtc gtc ctc        192
Phe Tyr Thr Thr Ile Gly Phe Tyr Leu Asn Thr Met Met Val Val Leu
        50                  55                  60 acg gtg tac gcc ttc gtg tgg ggt cgg ttc tac ctc gcg ctg tcg ggc        240
Thr Val Tyr Ala Phe Val Trp Gly Arg Phe Tyr Leu Ala Leu Ser Gly
65                  70                  75                  80 ctt gag gcc gac tat atc acc aat aac acc tcc tcg acc gat aat gcc        288
Leu Glu Ala Asp Tyr Ile Thr Asn Asn Thr Ser Ser Thr Asp Asn Ala
                85                  90                  95
```

```
gcg ctg tgg gca gtc ctc aac caa cag ttc ttc atc caa ttc ggc ctc     336
Ala Leu Trp Ala Val Leu Asn Gln Gln Phe Phe Ile Gln Phe Gly Leu
            100                 105                 110 ttc acg gcc ctc ccc atg atc atc gag aac tcc ctt gag cat ggc ttc     384
Phe Thr Ala Leu Pro Met Ile Ile Glu Asn Ser Leu Glu His Gly Phe
            115                 120                 125 ctc ata gcc gtc tgg gac ttc atc gtc atg cag ctg cag tgc gcg tcg     432
Leu Ile Ala Val Trp Asp Phe Ile Val Met Gln Leu Gln Cys Ala Ser
            130                 135                 140 gtg ttc tat acc ttc tgc atg ggc acc aag act cac tat tat ggc cgc     480
Val Phe Tyr Thr Phe Cys Met Gly Thr Lys Thr His Tyr Tyr Gly Arg
145                 150                 155                 160 acg ctg ctg cat ggt ggg gcc aag tac cgc cca acc ggt cgg ggc ttc     528
Thr Leu Leu His Gly Gly Ala Lys Tyr Arg Pro Thr Gly Arg Gly Phe
            165                 170                 175 gtg gtc gag cac aag aaa ttc gcc gag aac tac cgg ctg tat gcg cgc     576
Val Val Glu His Lys Lys Phe Ala Glu Asn Tyr Arg Leu Tyr Ala Arg
            180                 185                 190 agc cat ttc acc aag gct atc gag ctg ggc gtg atc ttg tgt ttg tat     624
Ser His Phe Thr Lys Ala Ile Glu Leu Gly Val Ile Leu Cys Leu Tyr
            195                 200                 205 tcc tcg tac agc aac atc gct ggc gac acc ctg gtg tat att ctg ctg     672
Ser Ser Tyr Ser Asn Ile Ala Gly Asp Thr Leu Val Tyr Ile Leu Leu
210                 215                 220 acc ctc tcg tcg tgg ttt ctc gtc tgc tcc tgg atc ctc gcg ccg ttc     720
Thr Leu Ser Ser Trp Phe Leu Val Cys Ser Trp Ile Leu Ala Pro Phe
225                 230                 235                 240 atc ttc aac ccg agc gga ctc gat tgg cag aag aat tcc aac gac ttc     768
Ile Phe Asn Pro Ser Gly Leu Asp Trp Gln Lys Asn Ser Asn Asp Phe
            245                 250                 255 gag gat ttc ttc tcg tgg atc tgg ttt cag ggc ggc ggc atc agt gtc     816
Glu Asp Phe Phe Ser Trp Ile Trp Phe Gln Gly Gly Gly Ile Ser Val
            260                 265                 270 aag tcc gac cag agc tgg gag aag tgg tgg gag gaa gaa acc gac cat     864
Lys Ser Asp Gln Ser Trp Glu Lys Trp Trp Glu Glu Glu Thr Asp His
            275                 280                 285 ctg gcg cgg acg acg acc ggc ctg tgg ggc agc atc atc gag ata att     912
Leu Ala Arg Thr Thr Thr Gly Leu Trp Gly Ser Ile Ile Glu Ile Ile
            290                 295                 300 ctg gac ctg gcg cgc acc tac ttt ttc ttc cag tat gcg atc gtt tat     960
Leu Asp Leu Ala Arg Thr Tyr Phe Phe Phe Gln Tyr Ala Ile Val Tyr
305                 310                 315                 320 cgc ctc cac atg gcc ggt ggc agc cgc tcc atc ctg gtc tat gtg ctc    1008
Arg Leu His Met Ala Gly Gly Ser Arg Ser Ile Leu Val Tyr Val Leu
            325                 330                 335 tcg tgg gcg tgc atc ccg ctc ccg ttc ctg gcg ctg gtc acc gtg acg    1056
Ser Trp Ala Cys Ile Pro Leu Pro Phe Leu Ala Leu Val Thr Val Thr
            340                 345                 350 tac ttc cgc gac aag tac tcg gcc aag aaa cat atc cgg tac cgc ctt    1104
Tyr Phe Arg Asp Lys Tyr Ser Ala Lys Lys His Ile Arg Tyr Arg Leu
            355                 360                 365 gtt caa tcg gtg att gtc tgc gca agc ctg gcg gcg att atc gtg ctc    1152
Val Gln Ser Val Ile Val Cys Ala Ser Leu Ala Ala Ile Ile Val Leu
            370                 375                 380 ctc acc ctc acc aag ttc cag ttc atc gac acc ttc acc agc ctc ctg    1200
Leu Thr Leu Thr Lys Phe Gln Phe Ile Asp Thr Phe Thr Ser Leu Leu
385                 390                 395                 400 gcc ttt ctg ccc acc ggc tgg ggc atc atc tcc atc gcc ctg gtg ttc    1248
Ala Phe Leu Pro Thr Gly Trp Gly Ile Ile Ser Ile Ala Leu Val Phe
            405                 410                 415
```

```
cgc caa tat ctg aag aaa agc gac acg gtg tgg aaa acc gtc gtc gtg      1296
Arg Gln Tyr Leu Lys Lys Ser Asp Thr Val Trp Lys Thr Val Val Val
            420                 425                 430 gtc gcg cgg ttc tac gac atc acc ctc ggc ctg att gtt atg gcg ccg      1344
Val Ala Arg Phe Tyr Asp Ile Thr Leu Gly Leu Ile Val Met Ala Pro
        435                 440                 445 atc gtc gtc ctg tcg tgg ctc cct ggc ctc cgc gag ctg cag acg cgg      1392
Ile Val Val Leu Ser Trp Leu Pro Gly Leu Arg Glu Leu Gln Thr Arg
450                 455                 460 atc ttg ttc aac gaa gcc ttc tcc aag ggc ctc cac atc tcg cag atg      1440
Ile Leu Phe Asn Glu Ala Phe Ser Lys Gly Leu His Ile Ser Gln Met
465                 470                 475                 480 atc acg cgc agg aaa acg cat cgc gcc                                  1467
Ile Thr Arg Arg Lys Thr His Arg Ala
                485
```

<210> SEQ ID NO 24
<211> LENGTH: 489
<212> TYPE: PRT
<213> ORGANISM: Artificial sequence
<220> FEATURE:
<223> OTHER INFORMATION: Synthetic Construct

<400> SEQUENCE: 24

```
Arg Val Gly Lys Gly Arg Asp Val Gly Leu Asn Gln Ile Ser Met Phe
1               5                   10                  15

Glu Ala Lys Val Ala Gly Gly Asn Gly Glu Gln Thr Leu Ser Arg Asp
            20                  25                  30

Val Tyr Arg Leu Gly His Gly Leu Asp Phe Phe Arg Met Leu Ser Phe
        35                  40                  45

Phe Tyr Thr Thr Ile Gly Phe Tyr Leu Asn Thr Met Met Val Val Leu
    50                  55                  60

Thr Val Tyr Ala Phe Val Trp Gly Arg Phe Tyr Leu Ala Leu Ser Gly
65                  70                  75                  80

Leu Glu Ala Asp Tyr Ile Thr Asn Asn Thr Ser Ser Thr Asp Asn Ala
                85                  90                  95

Ala Leu Trp Ala Val Leu Asn Gln Gln Phe Phe Ile Gln Phe Gly Leu
            100                 105                 110

Phe Thr Ala Leu Pro Met Ile Ile Glu Asn Ser Leu Glu His Gly Phe
        115                 120                 125

Leu Ile Ala Val Trp Asp Phe Ile Val Met Gln Leu Gln Cys Ala Ser
    130                 135                 140

Val Phe Tyr Thr Phe Cys Met Gly Thr Lys Thr His Tyr Tyr Gly Arg
145                 150                 155                 160

Thr Leu Leu His Gly Gly Ala Lys Tyr Arg Pro Thr Gly Arg Gly Phe
                165                 170                 175

Val Val Glu His Lys Lys Phe Ala Glu Asn Tyr Arg Leu Tyr Ala Arg
            180                 185                 190

Ser His Phe Thr Lys Ala Ile Glu Leu Gly Val Ile Leu Cys Leu Tyr
        195                 200                 205

Ser Ser Tyr Ser Asn Ile Ala Gly Asp Thr Leu Val Tyr Ile Leu Leu
    210                 215                 220

Thr Leu Ser Ser Trp Phe Leu Val Cys Ser Trp Ile Leu Ala Pro Phe
225                 230                 235                 240

Ile Phe Asn Pro Ser Gly Leu Asp Trp Gln Lys Asn Ser Asn Asp Phe
                245                 250                 255
```

```
Glu Asp Phe Phe Ser Trp Ile Trp Phe Gln Gly Gly Gly Ile Ser Val
                260                 265                 270

Lys Ser Asp Gln Ser Trp Glu Lys Trp Trp Glu Glu Thr Asp His
    275                 280                 285

Leu Ala Arg Thr Thr Thr Gly Leu Trp Gly Ser Ile Ile Glu Ile Ile
    290                 295                 300

Leu Asp Leu Ala Arg Thr Tyr Phe Phe Phe Gln Tyr Ala Ile Val Tyr
305                 310                 315                 320

Arg Leu His Met Ala Gly Gly Ser Arg Ser Ile Leu Val Tyr Val Leu
                325                 330                 335

Ser Trp Ala Cys Ile Pro Leu Pro Phe Leu Ala Leu Val Thr Val Thr
                340                 345                 350

Tyr Phe Arg Asp Lys Tyr Ser Ala Lys Lys His Ile Arg Tyr Arg Leu
                355                 360                 365

Val Gln Ser Val Ile Val Cys Ala Ser Leu Ala Ala Ile Ile Val Leu
                370                 375                 380

Leu Thr Leu Thr Lys Phe Gln Phe Ile Asp Thr Phe Thr Ser Leu Leu
385                 390                 395                 400

Ala Phe Leu Pro Thr Gly Trp Gly Ile Ile Ser Ile Ala Leu Val Phe
                405                 410                 415

Arg Gln Tyr Leu Lys Lys Ser Asp Thr Val Trp Lys Thr Val Val Val
                420                 425                 430

Val Ala Arg Phe Tyr Asp Ile Thr Leu Gly Leu Ile Val Met Ala Pro
                435                 440                 445

Ile Val Val Leu Ser Trp Leu Pro Gly Leu Arg Glu Leu Gln Thr Arg
450                 455                 460

Ile Leu Phe Asn Glu Ala Phe Ser Lys Gly Leu His Ile Ser Gln Met
465                 470                 475                 480

Ile Thr Arg Arg Lys Thr His Arg Ala
                485

<210> SEQ ID NO 25
<211> LENGTH: 336
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(336)
<223> OTHER INFORMATION: Horderum vulgars (barley) 1,3-beta-D-glucan
      synthase (codon optimized)

<400> SEQUENCE: 25 att gcc gga gca gcc gct gga atc gct gga acc ctc atg tgt cac ccc     48
Ile Ala Gly Ala Ala Ala Gly Ile Ala Gly Thr Leu Met Cys His Pro
1               5                   10                  15 ctc gaa gtc ata aaa gat cgc ttg acc gtc gac agg gtg acg tat ccg     96
Leu Glu Val Ile Lys Asp Arg Leu Thr Val Asp Arg Val Thr Tyr Pro
            20                  25                  30 tcg atc agc atc gcg ttc tcg aag atc tac cgg acc gag ggc atc cgc    144
Ser Ile Ser Ile Ala Phe Ser Lys Ile Tyr Arg Thr Glu Gly Ile Arg
        35                  40                  45 ggc ctg tat agc ggc ctg tgc ccc acc ctc att ggc atg ctg ccg tac    192
Gly Leu Tyr Ser Gly Leu Cys Pro Thr Leu Ile Gly Met Leu Pro Tyr
    50                  55                  60 tcg act tgc tac tat ttc atg tat gac acg atc aag acc tcc tac tgc    240
Ser Thr Cys Tyr Tyr Phe Met Tyr Asp Thr Ile Lys Thr Ser Tyr Cys
65                  70                  75                  80
```

```
cgg ctc cat aag aaa aag tcg ctg agt cgc cct gag ctg ctg atc atc    288
Arg Leu His Lys Lys Lys Ser Leu Ser Arg Pro Glu Leu Leu Ile Ile
                85                  90                  95 ggt gcg ctt acc agc ctc acc gcg tcc acg atc tcc ttc ccg ctg gag    336
Gly Ala Leu Thr Ser Leu Thr Ala Ser Thr Ile Ser Phe Pro Leu Glu
            100                 105                 110
```

<210> SEQ ID NO 26
<211> LENGTH: 112
<212> TYPE: PRT
<213> ORGANISM: Artificial sequence
<220> FEATURE:
<223> OTHER INFORMATION: Synthetic Construct

<400> SEQUENCE: 26

```
Ile Ala Gly Ala Ala Ala Gly Ile Ala Gly Thr Leu Met Cys His Pro
1               5                   10                  15

Leu Glu Val Ile Lys Asp Arg Leu Thr Val Asp Arg Val Thr Tyr Pro
                20                  25                  30

Ser Ile Ser Ile Ala Phe Ser Lys Ile Tyr Arg Thr Glu Gly Ile Arg
            35                  40                  45

Gly Leu Tyr Ser Gly Leu Cys Pro Thr Leu Ile Gly Met Leu Pro Tyr
50                  55                  60

Ser Thr Cys Tyr Tyr Phe Met Tyr Asp Thr Ile Lys Thr Ser Tyr Cys
65                  70                  75                  80

Arg Leu His Lys Lys Lys Ser Leu Ser Arg Pro Glu Leu Leu Ile Ile
                85                  90                  95

Gly Ala Leu Thr Ser Leu Thr Ala Ser Thr Ile Ser Phe Pro Leu Glu
            100                 105                 110
```

<210> SEQ ID NO 27
<211> LENGTH: 1293
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(1293)
<223> OTHER INFORMATION: E.coli Glucose-1-phosphate adenyltransfersase
      (Acc. No. YP 49003.1) (codon optimized)

<400> SEQUENCE: 27

```
atg gtt tcc ctg gag aaa aat gac cac ctg atg ctc gca cgc caa ctc    48
Met Val Ser Leu Glu Lys Asn Asp His Leu Met Leu Ala Arg Gln Leu
1               5                   10                  15 ccg ctt aag tcc gtc gcc ctg atc ctc gcc ggc gga cgc ggc acg cgg    96
Pro Leu Lys Ser Val Ala Leu Ile Leu Ala Gly Gly Arg Gly Thr Arg
                20                  25                  30 ctc aaa gac ctc acc aac aag cgc gcg aaa ccg gct gtc cat ttc ggt   144
Leu Lys Asp Leu Thr Asn Lys Arg Ala Lys Pro Ala Val His Phe Gly
            35                  40                  45 ggc aag ttc agg atc ata gac ttc gcg ctg tcg aac tgc atc aat tcc   192
Gly Lys Phe Arg Ile Ile Asp Phe Ala Leu Ser Asn Cys Ile Asn Ser
50                  55                  60 ggc att agg cgc atg gga gtc att acc cag tac caa tcg cat acg ctc   240
Gly Ile Arg Arg Met Gly Val Ile Thr Gln Tyr Gln Ser His Thr Leu
65                  70                  75                  80 gtc cag cat atc cag cgg ggc tgg tcg ttc ttc aac gaa gag atg aac   288
Val Gln His Ile Gln Arg Gly Trp Ser Phe Phe Asn Glu Glu Met Asn
                85                  90                  95
```

| | | |
|---|---|---|
| gag ttc gtc gac ctc ctc ccg gcg cag cag cgg atg aaa ggc gag aac<br>Glu Phe Val Asp Leu Leu Pro Ala Gln Gln Arg Met Lys Gly Glu Asn<br>100 105 110 | | 336 |
| tgg tac cgc ggc acg gct gat gcc gtt acc cag aac ctg gac att att<br>Trp Tyr Arg Gly Thr Ala Asp Ala Val Thr Gln Asn Leu Asp Ile Ile<br>115 120 125 | | 384 |
| cgc cgc tat aaa gcc gag tat gtt gtg atc ctg gcc ggt gac cac atc<br>Arg Arg Tyr Lys Ala Glu Tyr Val Val Ile Leu Ala Gly Asp His Ile<br>130 135 140 | | 432 |
| tac aaa caa gac tat agt cgg atg ctc atc gac cat gtg gaa aag ggc<br>Tyr Lys Gln Asp Tyr Ser Arg Met Leu Ile Asp His Val Glu Lys Gly<br>145 150 155 160 | | 480 |
| gct cgc tgc acc gtg gcg tgc atg cca gtg ccg atc gaa gag gcc tcc<br>Ala Arg Cys Thr Val Ala Cys Met Pro Val Pro Ile Glu Glu Ala Ser<br>165 170 175 | | 528 |
| gcg ttc ggc gtg atg gcc gtg gat gag aac gac aag atc atc gag ttc<br>Ala Phe Gly Val Met Ala Val Asp Glu Asn Asp Lys Ile Ile Glu Phe<br>180 185 190 | | 576 |
| gtg gag aag ccc gcg aac ccg ccg tcg atg ccc aac gac ccg agc aag<br>Val Glu Lys Pro Ala Asn Pro Pro Ser Met Pro Asn Asp Pro Ser Lys<br>195 200 205 | | 624 |
| agc ctg gcg tcc atg ggc atc tac gtc ttt gac gcg gat tat ctg tac<br>Ser Leu Ala Ser Met Gly Ile Tyr Val Phe Asp Ala Asp Tyr Leu Tyr<br>210 215 220 | | 672 |
| gag ctt ttg gaa gag gat gat cgg gac gag aat agc tcg cac gac ttc<br>Glu Leu Leu Glu Glu Asp Asp Arg Asp Glu Asn Ser Ser His Asp Phe<br>225 230 235 240 | | 720 |
| ggc aaa gac ctg atc ccg aag atc acc gaa gcc ggg ctg gcg tat gcc<br>Gly Lys Asp Leu Ile Pro Lys Ile Thr Glu Ala Gly Leu Ala Tyr Ala<br>245 250 255 | | 768 |
| cat cct ttt ccg ctc agc tgc gtg cag tcg gac ccc gat gcg gag ccg<br>His Pro Phe Pro Leu Ser Cys Val Gln Ser Asp Pro Asp Ala Glu Pro<br>260 265 270 | | 816 |
| tat tgg cgc gac gtg ggt acc ctg gaa gcg tac tgg aag gcc aat ctc<br>Tyr Trp Arg Asp Val Gly Thr Leu Glu Ala Tyr Trp Lys Ala Asn Leu<br>275 280 285 | | 864 |
| gac ctc gcc agc gtg gtg ccg gaa ctg gac atg tac gac cgc aat tgg<br>Asp Leu Ala Ser Val Val Pro Glu Leu Asp Met Tyr Asp Arg Asn Trp<br>290 295 300 | | 912 |
| ccg atc cgc act tac aac gag agc ctg ccc ccg gcg aag ttc gtc cag<br>Pro Ile Arg Thr Tyr Asn Glu Ser Leu Pro Pro Ala Lys Phe Val Gln<br>305 310 315 320 | | 960 |
| gac cgg agt ggc agc cac ggc atg acg ctc aat tcc ctt gtg tcg ggg<br>Asp Arg Ser Gly Ser His Gly Met Thr Leu Asn Ser Leu Val Ser Gly<br>325 330 335 | | 1008 |
| ggc tgc gtc atc tcg ggt tcg gtc gtc gtc cag tcc gtc ctc ttc agc<br>Gly Cys Val Ile Ser Gly Ser Val Val Val Gln Ser Val Leu Phe Ser<br>340 345 350 | | 1056 |
| cgg gtc agg gtc aat tcc ttc tgc aac atc gat agc gca gtg ctg ttg<br>Arg Val Arg Val Asn Ser Phe Cys Asn Ile Asp Ser Ala Val Leu Leu<br>355 360 365 | | 1104 |
| ccc gag gtc tgg gtg ggc cgc tcg tgt cgg ctg cgc cgc tgc gtg atc<br>Pro Glu Val Trp Val Gly Arg Ser Cys Arg Leu Arg Arg Cys Val Ile<br>370 375 380 | | 1152 |
| gac cgc gcc tgc gtc atc ccc gag ggc atg gtc ata ggc gag aat gcc<br>Asp Arg Ala Cys Val Ile Pro Glu Gly Met Val Ile Gly Glu Asn Ala<br>385 390 395 400 | | 1200 |
| gaa gag gac gcg cgg cgc ttc tat cgg tcc gag gag ggc atc gtg ctg<br>Glu Glu Asp Ala Arg Arg Phe Tyr Arg Ser Glu Glu Gly Ile Val Leu<br>405 410 415 | | 1248 |

```
gtc acc cgc gag atg ctg cgc aag ctc ggg cat aag caa gag cgc    1293
Val Thr Arg Glu Met Leu Arg Lys Leu Gly His Lys Gln Glu Arg
            420                 425                 430
```

<210> SEQ ID NO 28
<211> LENGTH: 431
<212> TYPE: PRT
<213> ORGANISM: Artificial sequence
<220> FEATURE:
<223> OTHER INFORMATION: Synthetic Construct

<400> SEQUENCE: 28

```
Met Val Ser Leu Glu Lys Asn Asp His Leu Met Leu Ala Arg Gln Leu
1               5                   10                  15

Pro Leu Lys Ser Val Ala Leu Ile Leu Ala Gly Gly Arg Gly Thr Arg
            20                  25                  30

Leu Lys Asp Leu Thr Asn Lys Arg Ala Lys Pro Ala Val His Phe Gly
        35                  40                  45

Gly Lys Phe Arg Ile Ile Asp Phe Ala Leu Ser Asn Cys Ile Asn Ser
    50                  55                  60

Gly Ile Arg Arg Met Gly Val Ile Thr Gln Tyr Gln Ser His Thr Leu
65                  70                  75                  80

Val Gln His Ile Gln Arg Gly Trp Ser Phe Phe Asn Glu Glu Met Asn
                85                  90                  95

Glu Phe Val Asp Leu Leu Pro Ala Gln Gln Arg Met Lys Gly Glu Asn
            100                 105                 110

Trp Tyr Arg Gly Thr Ala Asp Ala Val Thr Gln Asn Leu Asp Ile Ile
        115                 120                 125

Arg Arg Tyr Lys Ala Glu Tyr Val Val Ile Leu Ala Gly Asp His Ile
    130                 135                 140

Tyr Lys Gln Asp Tyr Ser Arg Met Leu Ile Asp His Val Glu Lys Gly
145                 150                 155                 160

Ala Arg Cys Thr Val Ala Cys Met Pro Val Pro Ile Glu Glu Ala Ser
                165                 170                 175

Ala Phe Gly Val Met Ala Val Asp Glu Asn Asp Lys Ile Ile Glu Phe
            180                 185                 190

Val Glu Lys Pro Ala Asn Pro Pro Ser Met Pro Asn Asp Pro Ser Lys
        195                 200                 205

Ser Leu Ala Ser Met Gly Ile Tyr Val Phe Asp Ala Asp Tyr Leu Tyr
    210                 215                 220

Glu Leu Leu Glu Glu Asp Asp Arg Asp Glu Asn Ser Ser His Asp Phe
225                 230                 235                 240

Gly Lys Asp Leu Ile Pro Lys Ile Thr Glu Ala Gly Leu Ala Tyr Ala
                245                 250                 255

His Pro Phe Pro Leu Ser Cys Val Gln Ser Asp Pro Asp Ala Glu Pro
            260                 265                 270

Tyr Trp Arg Asp Val Gly Thr Leu Glu Ala Tyr Trp Lys Ala Asn Leu
        275                 280                 285

Asp Leu Ala Ser Val Val Pro Glu Leu Asp Met Tyr Asp Arg Asn Trp
    290                 295                 300

Pro Ile Arg Thr Tyr Asn Glu Ser Leu Pro Pro Ala Lys Phe Val Gln
305                 310                 315                 320

Asp Arg Ser Gly Ser His Gly Met Thr Leu Asn Ser Leu Val Ser Gly
                325                 330                 335

Gly Cys Val Ile Ser Gly Ser Val Val Val Gln Ser Val Leu Phe Ser
```

```
                    340                 345                 350
Arg Val Arg Val Asn Ser Phe Cys Asn Ile Asp Ser Ala Val Leu Leu
            355                 360                 365

Pro Glu Val Trp Val Gly Arg Ser Cys Arg Leu Arg Arg Cys Val Ile
370                 375                 380

Asp Arg Ala Cys Val Ile Pro Glu Gly Met Val Ile Gly Glu Asn Ala
385                 390                 395                 400

Glu Glu Asp Ala Arg Arg Phe Tyr Arg Ser Glu Glu Gly Ile Val Leu
            405                 410                 415

Val Thr Arg Glu Met Leu Arg Lys Leu Gly His Lys Gln Glu Arg
            420                 425                 430

<210> SEQ ID NO 29
<211> LENGTH: 1227
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(1227)
<223> OTHER INFORMATION: Cornebacterium glutamicum (ATCC 13032)
      Glucose-1-phosphate adenylyltransferase (codon optimized)

<400> SEQUENCE: 29
```

| | | | | | | | | | | | | | | | | |
|---|---|---|---|---|---|---|---|---|---|---|---|---|---|---|---|---|
| atg | gtg | aag | gga | gtt | aag | gga | agg | cct | aat | gtt | ttg | gca | ata | gtt | ctg | 48 |
| Met | Val | Lys | Gly | Val | Lys | Gly | Arg | Pro | Asn | Val | Leu | Ala | Ile | Val | Leu | |
| 1 | | | | 5 | | | | | 10 | | | | | 15 | | |
| gcg | ggt | gga | gag | ggg | aaa | cgg | ttg | ttc | ccg | ctc | acc | gag | gac | cgc | gcc | 96 |
| Ala | Gly | Gly | Glu | Gly | Lys | Arg | Leu | Phe | Pro | Leu | Thr | Glu | Asp | Arg | Ala | |
| | | | 20 | | | | | 25 | | | | | 30 | | | |
| aag | ccc | gcg | gtg | ccg | ttc | ggc | ggc | acc | tac | cgc | ctg | atc | gat | ttc | gtg | 144 |
| Lys | Pro | Ala | Val | Pro | Phe | Gly | Gly | Thr | Tyr | Arg | Leu | Ile | Asp | Phe | Val | |
| | | 35 | | | | | 40 | | | | | 45 | | | | |
| ctg | tcc | aat | ctg | gtc | aat | tcg | ggt | ttc | ctc | aag | atc | gcg | gtc | ctc | acg | 192 |
| Leu | Ser | Asn | Leu | Val | Asn | Ser | Gly | Phe | Leu | Lys | Ile | Ala | Val | Leu | Thr | |
| 50 | | | | | 55 | | | | | 60 | | | | | | |
| cag | tac | aag | agc | cat | agc | ctt | gac | cgg | cat | atc | tcc | ctg | tcc | tgg | aac | 240 |
| Gln | Tyr | Lys | Ser | His | Ser | Leu | Asp | Arg | His | Ile | Ser | Leu | Ser | Trp | Asn | |
| 65 | | | | | 70 | | | | | 75 | | | | | 80 | |
| gtg | tcc | ggg | ccg | acg | ggc | cag | tac | atc | gcc | tcc | gtc | cca | gct | cag | cag | 288 |
| Val | Ser | Gly | Pro | Thr | Gly | Gln | Tyr | Ile | Ala | Ser | Val | Pro | Ala | Gln | Gln | |
| | | | | 85 | | | | | 90 | | | | | 95 | | |
| cgg | ctc | ggc | aag | cgc | tgg | ttc | acc | ggc | tcg | gcc | gac | gcc | atc | ctg | cag | 336 |
| Arg | Leu | Gly | Lys | Arg | Trp | Phe | Thr | Gly | Ser | Ala | Asp | Ala | Ile | Leu | Gln | |
| | | | 100 | | | | | 105 | | | | | 110 | | | |
| agc | ctc | aac | ctg | atc | tcc | gac | gag | aag | ccc | gac | tat | gtc | atc | gtg | ttt | 384 |
| Ser | Leu | Asn | Leu | Ile | Ser | Asp | Glu | Lys | Pro | Asp | Tyr | Val | Ile | Val | Phe | |
| | | 115 | | | | | 120 | | | | | 125 | | | | |
| ggc | gcg | gac | cac | gtg | tac | cgg | atg | gat | ccc | tcc | cag | atg | ctg | gat | gag | 432 |
| Gly | Ala | Asp | His | Val | Tyr | Arg | Met | Asp | Pro | Ser | Gln | Met | Leu | Asp | Glu | |
| | 130 | | | | | 135 | | | | | 140 | | | | | |
| cat | atc | gcg | agt | ggt | cgc | gct | gtg | tcg | gtc | gcc | ggc | atc | cgc | gtc | ccg | 480 |
| His | Ile | Ala | Ser | Gly | Arg | Ala | Val | Ser | Val | Ala | Gly | Ile | Arg | Val | Pro | |
| 145 | | | | | 150 | | | | | 155 | | | | | 160 | |
| cgc | gaa | gag | gcg | acg | gcg | ttc | ggc | tgc | atc | cag | tcc | gat | gtg | gac | ggg | 528 |
| Arg | Glu | Glu | Ala | Thr | Ala | Phe | Gly | Cys | Ile | Gln | Ser | Asp | Val | Asp | Gly | |
| | | | | 165 | | | | | 170 | | | | | 175 | | |
| aac | atc | acc | gag | ttc | ctc | gaa | aaa | ccc | gcc | gac | ccc | ccg | ggg | acc | ccg | 576 |
| Asn | Ile | Thr | Glu | Phe | Leu | Glu | Lys | Pro | Ala | Asp | Pro | Pro | Gly | Thr | Pro | |
| | | | 180 | | | | | 185 | | | | | 190 | | | |

| | | |
|---|---|---|
| gac gac ccc gac atg acc tat gcc agc atg ggc aac tac atc ttc acg<br>Asp Asp Pro Asp Met Thr Tyr Ala Ser Met Gly Asn Tyr Ile Phe Thr<br>           195                    200                    205 | 624 |
| acc gaa gca ctg atc caa gcg ctt aaa gat gat gag aat aac gaa aat<br>Thr Glu Ala Leu Ile Gln Ala Leu Lys Asp Asp Glu Asn Asn Glu Asn<br>210                    215                    220 | 672 |
| tcg gac cat gac atg ggc ggc gac atc att ccg tat ttc gtg tcg cgc<br>Ser Asp His Asp Met Gly Gly Asp Ile Ile Pro Tyr Phe Val Ser Arg<br>225                    230                    235                    240 | 720 |
| aac gac gcg cat gtc tac gac ttt tcc ggt aac atc gtg ccg ggt gcg<br>Asn Asp Ala His Val Tyr Asp Phe Ser Gly Asn Ile Val Pro Gly Ala<br>                    245                    250                    255 | 768 |
| act gag cgc gac aag ggc tat tgg cgc gac gtc ggt acc att gat gcg<br>Thr Glu Arg Asp Lys Gly Tyr Trp Arg Asp Val Gly Thr Ile Asp Ala<br>                    260                    265                    270 | 816 |
| ttc tac gag tgc cac atg gac ctg atc tcg gtc cac ccg atc ttc aat<br>Phe Tyr Glu Cys His Met Asp Leu Ile Ser Val His Pro Ile Phe Asn<br>                  275                    280                    285 | 864 |
| ctg tat aac agc gag tgg ccg atc cac acc acg tcc gag ggc aac ctc<br>Leu Tyr Asn Ser Glu Trp Pro Ile His Thr Thr Ser Glu Gly Asn Leu<br>                    290                    295                    300 | 912 |
| ccg ccg gcc aag ttc gtc cgc ggc ggc ata gcc caa tcg tcg atg gtg<br>Pro Pro Ala Lys Phe Val Arg Gly Gly Ile Ala Gln Ser Ser Met Val<br>305                    310                    315                    320 | 960 |
| agc tcc ggc agc atc atc tcg gct ggc acc gtg agg aat agc gtg ctc<br>Ser Ser Gly Ser Ile Ile Ser Ala Gly Thr Val Arg Asn Ser Val Leu<br>                    325                    330                    335 | 1008 |
| tcg aat aat gtc gtc gtc gag gag ggc gcc acg gtc gag ggc gcg gtg<br>Ser Asn Asn Val Val Val Glu Glu Gly Ala Thr Val Glu Gly Ala Val<br>                    340                    345                    350 | 1056 |
| ctc atg ccc ggt gtc cgg att ggc aag ggt gcc gtc gtg cgc cat gca<br>Leu Met Pro Gly Val Arg Ile Gly Lys Gly Ala Val Val Arg His Ala<br>                    355                    360                    365 | 1104 |
| att ctc gac aaa aac gtc gtc gtg cgc gac ggc gag ctc atc ggc gtg<br>Ile Leu Asp Lys Asn Val Val Val Arg Asp Gly Glu Leu Ile Gly Val<br>370                    375                    380 | 1152 |
| gat cag gtc cgg gac gcc cag cgc ttc aag gtc agt gcg ggc gga gtg<br>Asp Gln Val Arg Asp Ala Gln Arg Phe Lys Val Ser Ala Gly Gly Val<br>385                    390                    395                    400 | 1200 |
| gtc gtg gtc ggc aag aac caa gtc gtg<br>Val Val Val Gly Lys Asn Gln Val Val<br>                    405 | 1227 |

<210> SEQ ID NO 30
<211> LENGTH: 409
<212> TYPE: PRT
<213> ORGANISM: Artificial sequence
<220> FEATURE:
<223> OTHER INFORMATION: Synthetic Construct

<400> SEQUENCE: 30

Met Val Lys Gly Val Lys Gly Arg Pro Asn Val Leu Ala Ile Val Leu
1                 5                    10                  15

Ala Gly Gly Glu Gly Lys Arg Leu Phe Pro Leu Thr Glu Asp Arg Ala
                20                    25                    30

Lys Pro Ala Val Pro Phe Gly Gly Thr Tyr Arg Leu Ile Asp Phe Val
          35                    40                    45

Leu Ser Asn Leu Val Asn Ser Gly Phe Leu Lys Ile Ala Val Leu Thr
      50                    55                    60

```
Gln Tyr Lys Ser His Ser Leu Asp Arg His Ile Ser Leu Ser Trp Asn
 65                  70                  75                  80

Val Ser Gly Pro Thr Gly Gln Tyr Ile Ala Ser Val Pro Ala Gln Gln
                 85                  90                  95

Arg Leu Gly Lys Arg Trp Phe Thr Gly Ser Ala Asp Ala Ile Leu Gln
            100                 105                 110

Ser Leu Asn Leu Ile Ser Asp Glu Lys Pro Asp Tyr Val Ile Val Phe
        115                 120                 125

Gly Ala Asp His Val Tyr Arg Met Asp Pro Ser Gln Met Leu Asp Glu
    130                 135                 140

His Ile Ala Ser Gly Arg Ala Val Ser Val Ala Gly Ile Arg Val Pro
145                 150                 155                 160

Arg Glu Glu Ala Thr Ala Phe Gly Cys Ile Gln Ser Asp Val Asp Gly
                165                 170                 175

Asn Ile Thr Glu Phe Leu Glu Lys Pro Ala Asp Pro Pro Gly Thr Pro
            180                 185                 190

Asp Asp Pro Asp Met Thr Tyr Ala Ser Met Gly Asn Tyr Ile Phe Thr
        195                 200                 205

Thr Glu Ala Leu Ile Gln Ala Leu Lys Asp Asp Glu Asn Asn Glu Asn
    210                 215                 220

Ser His Asp Met Gly Gly Asp Ile Ile Pro Tyr Phe Val Ser Arg
225                 230                 235                 240

Asn Asp Ala His Val Tyr Asp Phe Ser Gly Asn Ile Val Pro Gly Ala
                245                 250                 255

Thr Glu Arg Asp Lys Gly Tyr Trp Arg Asp Val Gly Thr Ile Asp Ala
            260                 265                 270

Phe Tyr Glu Cys His Met Asp Leu Ile Ser Val His Pro Ile Phe Asn
        275                 280                 285

Leu Tyr Asn Ser Glu Trp Pro Ile His Thr Thr Ser Glu Gly Asn Leu
    290                 295                 300

Pro Pro Ala Lys Phe Val Arg Gly Gly Ile Ala Gln Ser Ser Met Val
305                 310                 315                 320

Ser Ser Gly Ser Ile Ile Ser Ala Gly Thr Val Arg Asn Ser Val Leu
                325                 330                 335

Ser Asn Asn Val Val Val Glu Glu Gly Ala Thr Val Glu Gly Ala Val
            340                 345                 350

Leu Met Pro Gly Val Arg Ile Gly Lys Gly Ala Val Val Arg His Ala
        355                 360                 365

Ile Leu Asp Lys Asn Val Val Arg Asp Gly Glu Leu Ile Gly Val
    370                 375                 380

Asp Gln Val Arg Asp Ala Gln Arg Phe Lys Val Ser Ala Gly Gly Val
385                 390                 395                 400

Val Val Val Gly Lys Asn Gln Val Val
                405
```

<210> SEQ ID NO 31
<211> LENGTH: 1431
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(1431)
<223> OTHER INFORMATION: Escherichia coli str. K-12 substr. W3110
      Glycogen Synthase (codon optimized)

<400> SEQUENCE: 31

```
atg caa gtt ctt cat gtg tgt tcc gaa atg ttc ccc ctc ctc aaa acc    48
Met Gln Val Leu His Val Cys Ser Glu Met Phe Pro Leu Leu Lys Thr
1               5                   10                  15 ggt ggc ctg gct gat gtc ata ggt gcc ctg ccg gct gcg cag att gcg    96
Gly Gly Leu Ala Asp Val Ile Gly Ala Leu Pro Ala Ala Gln Ile Ala
            20                  25                  30 gac ggc gtg gac gca cgg gtc ctg ctg ccg gcg ttc ccg gat atc cgc   144
Asp Gly Val Asp Ala Arg Val Leu Leu Pro Ala Phe Pro Asp Ile Arg
        35                  40                  45 cgg ggc gtg acc gac gca caa gtc gtg tcg cgc agg gac acc ttt gcc   192
Arg Gly Val Thr Asp Ala Gln Val Val Ser Arg Arg Asp Thr Phe Ala
50                  55                  60 ggc cac atc acg ctc ttg ttc ggc cac tat aac ggc gtg ggc atc tac   240
Gly His Ile Thr Leu Leu Phe Gly His Tyr Asn Gly Val Gly Ile Tyr
65                  70                  75                  80 ctg atc gat gcg ccg cat ctc tat gac agg ccg ggt tcg ccc tat cat   288
Leu Ile Asp Ala Pro His Leu Tyr Asp Arg Pro Gly Ser Pro Tyr His
                85                  90                  95 gac acg aac ctc ttc gcc tac acg gac aat gtg ctg cgg ttc gca ctt   336
Asp Thr Asn Leu Phe Ala Tyr Thr Asp Asn Val Leu Arg Phe Ala Leu
            100                 105                 110 ctg ggc tgg gtc gga gcc gag atg gca tcc ggc ctc gac ccg ttc tgg   384
Leu Gly Trp Val Gly Ala Glu Met Ala Ser Gly Leu Asp Pro Phe Trp
        115                 120                 125 cgc cct gac gtc gtc cat gcg cat gac tgg cat gcc ggc ctc gca ccc   432
Arg Pro Asp Val Val His Ala His Asp Trp His Ala Gly Leu Ala Pro
    130                 135                 140 gcg tat ttg gcc gcc cgg gga cgg ccg gct aag agc gtg ttt acc gtt   480
Ala Tyr Leu Ala Ala Arg Gly Arg Pro Ala Lys Ser Val Phe Thr Val
145                 150                 155                 160 cat aac ctc gcg tat cag ggc atg ttc tac gcc cat cac atg aat gat   528
His Asn Leu Ala Tyr Gln Gly Met Phe Tyr Ala His His Met Asn Asp
                165                 170                 175 atc cag ctg ccc tgg tcc ttc ttc aac atc cac ggt ctt gag ttc aat   576
Ile Gln Leu Pro Trp Ser Phe Phe Asn Ile His Gly Leu Glu Phe Asn
            180                 185                 190 ggc caa atc tcg ttc ctg aag gcc ggg ctg tac tac gcg gac cac atc   624
Gly Gln Ile Ser Phe Leu Lys Ala Gly Leu Tyr Tyr Ala Asp His Ile
        195                 200                 205 acc gcg gtg tcg cca acc tac gcc cgc gag atc acc gag ccg cag ttc   672
Thr Ala Val Ser Pro Thr Tyr Ala Arg Glu Ile Thr Glu Pro Gln Phe
    210                 215                 220 gcg tac ggc atg gag ggc ctg ctg caa cag cgc cac cgc gag ggc cgg   720
Ala Tyr Gly Met Glu Gly Leu Leu Gln Gln Arg His Arg Glu Gly Arg
225                 230                 235                 240 ctc agc ggc gtt ctg aac ggc gtc gac gag aaa atc tgg tcg ccc gag   768
Leu Ser Gly Val Leu Asn Gly Val Asp Glu Lys Ile Trp Ser Pro Glu
                245                 250                 255 act gac ttg ctc ctt gcc agc cgc tat acc cgc gac acg ctc gaa gat   816
Thr Asp Leu Leu Leu Ala Ser Arg Tyr Thr Arg Asp Thr Leu Glu Asp
            260                 265                 270 aaa gcc gag aat aag cgc cag ctg cag atc gcc atg ggc ctg aaa gtc   864
Lys Ala Glu Asn Lys Arg Gln Leu Gln Ile Ala Met Gly Leu Lys Val
        275                 280                 285 gac gac aag gtc ccc ctc ttc gcc gtg gtc agc cgc ctg acc tcg caa   912
Asp Asp Lys Val Pro Leu Phe Ala Val Val Ser Arg Leu Thr Ser Gln
    290                 295                 300 aag ggc ctg gac ctg gtg ctc gaa gcc ctc cct ggc ctg ctt gaa cag   960
Lys Gly Leu Asp Leu Val Leu Glu Ala Leu Pro Gly Leu Leu Glu Gln
```

```
                Lys Gly Leu Asp Leu Val Leu Glu Ala Leu Pro Gly Leu Leu Glu Gln
                305                 310                 315                 320 ggt ggc cag ttg gcg ctc ctc ggc gcc ggg gat ccg gtg ttg cag gag         1008
Gly Gly Gln Leu Ala Leu Leu Gly Ala Gly Asp Pro Val Leu Gln Glu
                325                 330                 335 gga ttc ctg gcg gct gcg gcc gag tat ccg ggc cag gtc ggc gtc cag         1056
Gly Phe Leu Ala Ala Ala Ala Glu Tyr Pro Gly Gln Val Gly Val Gln
                340                 345                 350 att ggc tac cat gaa gcg ttc agt cat cgg atc atg ggt ggg gcc gac         1104
Ile Gly Tyr His Glu Ala Phe Ser His Arg Ile Met Gly Gly Ala Asp
                355                 360                 365 gtc atc ctc gtg ccg tcc cgc ttc gag ccg tgc ggc ctc acc cag ctg         1152
Val Ile Leu Val Pro Ser Arg Phe Glu Pro Cys Gly Leu Thr Gln Leu
                370                 375                 380 tac ggc ctc aag tac gga acg ctc ccc ctg gtg cgg cgg acc ggt ggg         1200
Tyr Gly Leu Lys Tyr Gly Thr Leu Pro Leu Val Arg Arg Thr Gly Gly
385                 390                 395                 400 ctc gcc gac acc gtc agc gac tgc tcc ctg gag aac ctg gcg gat ggc         1248
Leu Ala Asp Thr Val Ser Asp Cys Ser Leu Glu Asn Leu Ala Asp Gly
                405                 410                 415 gtc gcg agc ggt ttt gtg ttc gag gac agc aac gcc tgg tcg ctg ctc         1296
Val Ala Ser Gly Phe Val Phe Glu Asp Ser Asn Ala Trp Ser Leu Leu
                420                 425                 430 cgc gcg atc cgc agg gcc ttc gtc ctg tgg agt cgc ccg tcc ctc tgg         1344
Arg Ala Ile Arg Arg Ala Phe Val Leu Trp Ser Arg Pro Ser Leu Trp
                435                 440                 445 cgc ttc gtg cag cgg cag gca atg gcc atg gac ttc tcg tgg caa gtc         1392
Arg Phe Val Gln Arg Gln Ala Met Ala Met Asp Phe Ser Trp Gln Val
450                 455                 460 gcg gcc aag tcc tat cgc gag ctc tac tat cgc ctg aag                     1431
Ala Ala Lys Ser Tyr Arg Glu Leu Tyr Tyr Arg Leu Lys
465                 470                 475

<210> SEQ ID NO 32
<211> LENGTH: 477
<212> TYPE: PRT
<213> ORGANISM: Artificial sequence
<220> FEATURE:
<223> OTHER INFORMATION: Synthetic Construct

<400> SEQUENCE: 32

Met Gln Val Leu His Val Cys Ser Glu Met Phe Pro Leu Leu Lys Thr
1               5                   10                  15

Gly Gly Leu Ala Asp Val Ile Gly Ala Leu Pro Ala Ala Gln Ile Ala
                20                  25                  30

Asp Gly Val Asp Ala Arg Val Leu Leu Pro Ala Phe Pro Asp Ile Arg
            35                  40                  45

Arg Gly Val Thr Asp Ala Gln Val Val Ser Arg Arg Asp Thr Phe Ala
        50                  55                  60

Gly His Ile Thr Leu Leu Phe Gly His Tyr Asn Gly Val Gly Ile Tyr
65                  70                  75                  80

Leu Ile Asp Ala Pro His Leu Tyr Asp Arg Pro Gly Ser Pro Tyr His
                85                  90                  95

Asp Thr Asn Leu Phe Ala Tyr Thr Asp Asn Val Leu Arg Phe Ala Leu
            100                 105                 110

Leu Gly Trp Val Gly Ala Glu Met Ala Ser Gly Leu Asp Pro Phe Trp
        115                 120                 125

Arg Pro Asp Val Val His Ala His Asp Trp His Ala Gly Leu Ala Pro
    130                 135                 140
```

Ala Tyr Leu Ala Ala Arg Gly Arg Pro Ala Lys Ser Val Phe Thr Val
145                 150                 155                 160

His Asn Leu Ala Tyr Gln Gly Met Phe Tyr Ala His His Met Asn Asp
                165                 170                 175

Ile Gln Leu Pro Trp Ser Phe Phe Asn Ile His Gly Leu Glu Phe Asn
            180                 185                 190

Gly Gln Ile Ser Phe Leu Lys Ala Gly Leu Tyr Tyr Ala Asp His Ile
        195                 200                 205

Thr Ala Val Ser Pro Thr Tyr Ala Arg Glu Ile Thr Glu Pro Gln Phe
    210                 215                 220

Ala Tyr Gly Met Glu Gly Leu Leu Gln Gln Arg His Arg Glu Gly Arg
225                 230                 235                 240

Leu Ser Gly Val Leu Asn Gly Val Asp Glu Lys Ile Trp Ser Pro Glu
                245                 250                 255

Thr Asp Leu Leu Leu Ala Ser Arg Tyr Thr Arg Asp Thr Leu Glu Asp
            260                 265                 270

Lys Ala Glu Asn Lys Arg Gln Leu Gln Ile Ala Met Gly Leu Lys Val
        275                 280                 285

Asp Asp Lys Val Pro Leu Phe Ala Val Val Ser Arg Leu Thr Ser Gln
    290                 295                 300

Lys Gly Leu Asp Leu Val Leu Glu Ala Leu Pro Gly Leu Leu Glu Gln
305                 310                 315                 320

Gly Gly Gln Leu Ala Leu Leu Gly Ala Gly Asp Pro Val Leu Gln Glu
                325                 330                 335

Gly Phe Leu Ala Ala Ala Glu Tyr Pro Gly Gln Val Gly Val Gln
            340                 345                 350

Ile Gly Tyr His Glu Ala Phe Ser His Arg Ile Met Gly Gly Ala Asp
        355                 360                 365

Val Ile Leu Val Pro Ser Arg Phe Glu Pro Cys Gly Leu Thr Gln Leu
    370                 375                 380

Tyr Gly Leu Lys Tyr Gly Thr Leu Pro Leu Val Arg Arg Thr Gly Gly
385                 390                 395                 400

Leu Ala Asp Thr Val Ser Asp Cys Ser Leu Glu Asn Leu Ala Asp Gly
                405                 410                 415

Val Ala Ser Gly Phe Val Phe Glu Asp Ser Asn Ala Trp Ser Leu Leu
            420                 425                 430

Arg Ala Ile Arg Arg Ala Phe Val Leu Trp Ser Arg Pro Ser Leu Trp
        435                 440                 445

Arg Phe Val Gln Arg Gln Ala Met Ala Met Asp Phe Ser Trp Gln Val
    450                 455                 460

Ala Ala Lys Ser Tyr Arg Glu Leu Tyr Tyr Arg Leu Lys
465                 470                 475

<210> SEQ ID NO 33
<211> LENGTH: 1227
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(1227)
<223> OTHER INFORMATION: Cornebacterium glutamicum (ATCC 13032)
      Glycosyltransferase (codon optimized)

<400> SEQUENCE: 33

```
atg cca cct ttc cgc tat cgc tgt gct act gtt ttc cgc tgg ttg att    48
Met Pro Pro Phe Arg Tyr Arg Cys Ala Thr Val Phe Arg Trp Leu Ile
1               5                   10                  15 ttt gaa ata atg cgc gtc ggg atg atg acc cgc gag tac ccg cct gaa    96
Phe Glu Ile Met Arg Val Gly Met Met Thr Arg Glu Tyr Pro Pro Glu
            20                  25                  30 gtg tac ggt gga gcc ggg gtc cat gtg acc gag ctt acc cgg ttc atg   144
Val Tyr Gly Gly Ala Gly Val His Val Thr Glu Leu Thr Arg Phe Met
        35                  40                  45 cgc gag atc gca gag gtc gac gtg cac tgc atg ggc gca ccg cgc gac   192
Arg Glu Ile Ala Glu Val Asp Val His Cys Met Gly Ala Pro Arg Asp
    50                  55                  60 atg gag ggt gtt ttc gtg cac ggc gtc gac ccg gca ctc gaa tcg gcg   240
Met Glu Gly Val Phe Val His Gly Val Asp Pro Ala Leu Glu Ser Ala
65                  70                  75                  80 aac ccc gcc atc aag acg ctc tcg acg ggc ctg cgg atg gcc gag gcc   288
Asn Pro Ala Ile Lys Thr Leu Ser Thr Gly Leu Arg Met Ala Glu Ala
            85                  90                  95 gcg aat aat gtt gac gtc gtg cat tcg cat acc tgg tat gcg ggc ctg   336
Ala Asn Asn Val Asp Val Val His Ser His Thr Trp Tyr Ala Gly Leu
        100                 105                 110 ggt ggc cat ctc gcg gcc agg ctg cac ggc atc ccg cat gtg gcg acg   384
Gly Gly His Leu Ala Ala Arg Leu His Gly Ile Pro His Val Ala Thr
    115                 120                 125 gcg cat agc ctg gag ccg gac cgg ccc tgg aag cgc gag caa ctc ggc   432
Ala His Ser Leu Glu Pro Asp Arg Pro Trp Lys Arg Glu Gln Leu Gly
130                 135                 140 ggc ggc tac gac gtg agc tcc tgg tcg gag aaa aac gcg atg gag tac   480
Gly Gly Tyr Asp Val Ser Ser Trp Ser Glu Lys Asn Ala Met Glu Tyr
145                 150                 155                 160 gcg gac gcc gtg atc gcc gtc agt gcc cgg atg aaa gac tcc atc ctg   528
Ala Asp Ala Val Ile Ala Val Ser Ala Arg Met Lys Asp Ser Ile Leu
            165                 170                 175 gcg gct tat ccg cgc atc gag ccc gat aat gtg cgc gtg gtg ctg aac   576
Ala Ala Tyr Pro Arg Ile Glu Pro Asp Asn Val Arg Val Val Leu Asn
        180                 185                 190 ggc atc gac acc gag ctc tgg cag ccg agg ccg acc ttc gac gac gcc   624
Gly Ile Asp Thr Glu Leu Trp Gln Pro Arg Pro Thr Phe Asp Asp Ala
    195                 200                 205 gag gat tcc gtg ctg cgc agc ctg ggc gtc gac ccg caa cgg ccc atc   672
Glu Asp Ser Val Leu Arg Ser Leu Gly Val Asp Pro Gln Arg Pro Ile
210                 215                 220 gtc gcg ttt gtc gga cgg att acg cgg cag aaa ggc gtg gag cac ctc   720
Val Ala Phe Val Gly Arg Ile Thr Arg Gln Lys Gly Val Glu His Leu
225                 230                 235                 240 atc aaa gcc gcc gcc ctg ttc gac gag tcc gtc cag ctc gtc ctc tgc   768
Ile Lys Ala Ala Ala Leu Phe Asp Glu Ser Val Gln Leu Val Leu Cys
            245                 250                 255 gcg ggt gcc ccc gac acc ccg gag atc gcg gct cgg acc acg gcg ctg   816
Ala Gly Ala Pro Asp Thr Pro Glu Ile Ala Ala Arg Thr Thr Ala Leu
        260                 265                 270 gtc gag gaa ctc caa gcg aag cgc gag ggc atc ttc tgg gtc cag gat   864
Val Glu Glu Leu Gln Ala Lys Arg Glu Gly Ile Phe Trp Val Gln Asp
    275                 280                 285 atg ctg ggg aag gat aag atc cag gag atc ctc acc gcc gct gac acc   912
Met Leu Gly Lys Asp Lys Ile Gln Glu Ile Leu Thr Ala Ala Asp Thr
290                 295                 300 ttc gtg tgc ccg tcg atc tat gag ccc ctg ggc atc gtc aac ctc gaa   960
Phe Val Cys Pro Ser Ile Tyr Glu Pro Leu Gly Ile Val Asn Leu Glu
305                 310                 315                 320
```

```
gcc atg gcg tgc aat acc gcc gtg gtc gcg agc gac gtc ggc ggc atc      1008
Ala Met Ala Cys Asn Thr Ala Val Val Ala Ser Asp Val Gly Gly Ile
            325                 330                 335 cca gag gtc gtc gtg gac ggc acg ggc gca ctg gtg cat tac gat          1056
Pro Glu Val Val Val Asp Gly Thr Thr Gly Ala Leu Val His Tyr Asp
        340                 345                 350 gag aac gat gtg gaa acg ttc gag cgc gac att gcc gaa gcc gtg aac      1104
Glu Asn Asp Val Glu Thr Phe Glu Arg Asp Ile Ala Glu Ala Val Asn
        355                 360                 365 aag atg gtc gcg gat cgc gag act gcc gcg aag ttc ggt ctt gca ggc      1152
Lys Met Val Ala Asp Arg Glu Thr Ala Ala Lys Phe Gly Leu Ala Gly
        370                 375                 380 cgg gag cgg gcg atc aat gac ttc agc tgg gcc acc atc gcc cag cag      1200
Arg Glu Arg Ala Ile Asn Asp Phe Ser Trp Ala Thr Ile Ala Gln Gln
385                 390                 395                 400 acc atc gac gtc tat aag tcg ctg atg                                  1227
Thr Ile Asp Val Tyr Lys Ser Leu Met
                405
```

<210> SEQ ID NO 34
<211> LENGTH: 409
<212> TYPE: PRT
<213> ORGANISM: Artificial sequence
<220> FEATURE:
<223> OTHER INFORMATION: Synthetic Construct

<400> SEQUENCE: 34

```
Met Pro Pro Phe Arg Tyr Arg Cys Ala Thr Val Phe Arg Trp Leu Ile
1               5                   10                  15

Phe Glu Ile Met Arg Val Gly Met Met Thr Arg Glu Tyr Pro Pro Glu
            20                  25                  30

Val Tyr Gly Gly Ala Gly Val His Val Thr Glu Leu Thr Arg Phe Met
        35                  40                  45

Arg Glu Ile Ala Glu Val Asp Val His Cys Met Gly Ala Pro Arg Asp
    50                  55                  60

Met Glu Gly Val Phe Val His Gly Val Asp Pro Ala Leu Glu Ser Ala
65                  70                  75                  80

Asn Pro Ala Ile Lys Thr Leu Ser Thr Gly Leu Arg Met Ala Glu Ala
                85                  90                  95

Ala Asn Asn Val Asp Val Val His Ser His Thr Trp Tyr Ala Gly Leu
            100                 105                 110

Gly Gly His Leu Ala Ala Arg Leu His Gly Ile Pro His Val Ala Thr
        115                 120                 125

Ala His Ser Leu Glu Pro Asp Arg Pro Trp Lys Arg Glu Gln Leu Gly
    130                 135                 140

Gly Gly Tyr Asp Val Ser Ser Trp Ser Glu Lys Asn Ala Met Glu Tyr
145                 150                 155                 160

Ala Asp Ala Val Ile Ala Val Ser Ala Arg Met Lys Asp Ser Ile Leu
                165                 170                 175

Ala Ala Tyr Pro Arg Ile Glu Pro Asp Asn Val Arg Val Leu Asn
            180                 185                 190

Gly Ile Asp Thr Glu Leu Trp Gln Pro Arg Pro Thr Phe Asp Asp Ala
        195                 200                 205

Glu Asp Ser Val Leu Arg Ser Leu Gly Val Asp Pro Gln Arg Pro Ile
    210                 215                 220

Val Ala Phe Val Gly Arg Ile Thr Arg Gln Lys Gly Val Glu His Leu
225                 230                 235                 240
```

```
Ile Lys Ala Ala Ala Leu Phe Asp Glu Ser Val Gln Leu Val Leu Cys
                245                 250                 255

Ala Gly Ala Pro Asp Thr Pro Glu Ile Ala Ala Arg Thr Thr Ala Leu
            260                 265                 270

Val Glu Glu Leu Gln Ala Lys Arg Glu Gly Ile Phe Trp Val Gln Asp
        275                 280                 285

Met Leu Gly Lys Asp Lys Ile Gln Glu Ile Leu Thr Ala Ala Asp Thr
    290                 295                 300

Phe Val Cys Pro Ser Ile Tyr Glu Pro Leu Gly Ile Val Asn Leu Glu
305                 310                 315                 320

Ala Met Ala Cys Asn Thr Ala Val Val Ala Ser Asp Val Gly Gly Ile
                325                 330                 335

Pro Glu Val Val Val Asp Gly Thr Thr Gly Ala Leu Val His Tyr Asp
            340                 345                 350

Glu Asn Asp Val Glu Thr Phe Glu Arg Asp Ile Ala Glu Ala Val Asn
        355                 360                 365

Lys Met Val Ala Asp Arg Glu Thr Ala Ala Lys Phe Gly Leu Ala Gly
    370                 375                 380

Arg Glu Arg Ala Ile Asn Asp Phe Ser Trp Ala Thr Ile Ala Gln Gln
385                 390                 395                 400

Thr Ile Asp Val Tyr Lys Ser Leu Met
                405

<210> SEQ ID NO 35
<211> LENGTH: 2184
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(2184)
<223> OTHER INFORMATION: E. coli 1,4-alpha-glucan branching enzyme
      (Acc.No. YP 492001.1) (codon optimized)

<400> SEQUENCE: 35 atg tcc gac cgc att gat agg gac gtc ata aat gca ctg atc gct ggc       48
Met Ser Asp Arg Ile Asp Arg Asp Val Ile Asn Ala Leu Ile Ala Gly
1               5                   10                  15 cac ttt gct gac ccg ttc tcc gtt ctg ggc atg cat aag acc acc gcc       96
His Phe Ala Asp Pro Phe Ser Val Leu Gly Met His Lys Thr Thr Ala
                20                  25                  30 ggt ctg gag gtc cgc gcg ctg ctg ccc gac gcg acc gac gtc tgg gtc      144
Gly Leu Glu Val Arg Ala Leu Leu Pro Asp Ala Thr Asp Val Trp Val
            35                  40                  45 atc gag ccc aag act ggc cgc aaa ctg gcg aaa ctt gag tgc ctc gac      192
Ile Glu Pro Lys Thr Gly Arg Lys Leu Ala Lys Leu Glu Cys Leu Asp
        50                  55                  60 agc cgg gga ttc ttt agc ggc gtg atc ccg cgg cgg aag aac ttc ttt      240
Ser Arg Gly Phe Phe Ser Gly Val Ile Pro Arg Arg Lys Asn Phe Phe
65                  70                  75                  80 agg tat caa ctc gcc gtc gtg tgg cat ggg cag cag aac ctg atc gat      288
Arg Tyr Gln Leu Ala Val Val Trp His Gly Gln Gln Asn Leu Ile Asp
                85                  90                  95 gat ccc tac agg ttc ggt ccc ttg atc caa gag atg gat gcg tgg ctg      336
Asp Pro Tyr Arg Phe Gly Pro Leu Ile Gln Glu Met Asp Ala Trp Leu
                100                 105                 110 ctc tcc gag ggc acc cac ctc cgc ccg tac gag act ctc ggg gca cat      384
Leu Ser Glu Gly Thr His Leu Arg Pro Tyr Glu Thr Leu Gly Ala His
```

-continued

```
                 115                 120                   125
gcg gac acg atg gac ggc gtg acg ggc acc cgc ttc tcg gtc tgg gct       432
Ala Asp Thr Met Asp Gly Val Thr Gly Thr Arg Phe Ser Val Trp Ala
    130                 135                 140 ccg aat gca cgc cgg gtg tcc gtg gtc gga cag ttc aat tac tgg gat       480
Pro Asn Ala Arg Arg Val Ser Val Val Gly Gln Phe Asn Tyr Trp Asp
145                 150                 155                 160 ggt cgg cgc cac ccc atg cgg ctg cgg aag gaa tcg ggt atc tgg gag       528
Gly Arg Arg His Pro Met Arg Leu Arg Lys Glu Ser Gly Ile Trp Glu
                165                 170                 175 ttg ttc atc cca ggc gcc cat aac ggg cag ctc tac aaa tac gaa atg       576
Leu Phe Ile Pro Gly Ala His Asn Gly Gln Leu Tyr Lys Tyr Glu Met
            180                 185                 190 atc gat gcg aat ggc aac ctc cgg ctg aaa agt gac ccg tat gcc ttc       624
Ile Asp Ala Asn Gly Asn Leu Arg Leu Lys Ser Asp Pro Tyr Ala Phe
        195                 200                 205 gaa gcg cag atg cgc ccc gaa acg gcg tcc ctg atc tgc ggc ctc cct       672
Glu Ala Gln Met Arg Pro Glu Thr Ala Ser Leu Ile Cys Gly Leu Pro
    210                 215                 220 gaa aaa gtc gtc cag acc gag gaa cgc aag aag gcc aac caa ttc gac       720
Glu Lys Val Val Gln Thr Glu Glu Arg Lys Lys Ala Asn Gln Phe Asp
225                 230                 235                 240 gcg ccg atc tcg atc tat gag gtc cac ctg ggc tcg tgg cgc agg cac       768
Ala Pro Ile Ser Ile Tyr Glu Val His Leu Gly Ser Trp Arg Arg His
                245                 250                 255 acc gac aac aat ttc tgg ctc tcg tac cgc gag ctg gcg gac caa ctc       816
Thr Asp Asn Asn Phe Trp Leu Ser Tyr Arg Glu Leu Ala Asp Gln Leu
            260                 265                 270 gtg ccg tat gct aag tgg atg gga ttc acg cat ttg gaa ctg ctg ccg       864
Val Pro Tyr Ala Lys Trp Met Gly Phe Thr His Leu Glu Leu Leu Pro
        275                 280                 285 atc aac gaa cat ccc ttc gac ggc agc tgg ggc tat cag ccg acc ggc       912
Ile Asn Glu His Pro Phe Asp Gly Ser Trp Gly Tyr Gln Pro Thr Gly
    290                 295                 300 ctc tac gcc ccg act cgc cgg ttc ggc acg cgg gat gac ttc cgg tac       960
Leu Tyr Ala Pro Thr Arg Arg Phe Gly Thr Arg Asp Asp Phe Arg Tyr
305                 310                 315                 320 ttc atc gat gcc gcg cat gcc gcc ggc ctc aac gtc atc ctg gac tgg       1008
Phe Ile Asp Ala Ala His Ala Ala Gly Leu Asn Val Ile Leu Asp Trp
                325                 330                 335 gtg ccc ggt cac ttt ccc acc gac gac ttc gcg ctg gcc gag ttc gac       1056
Val Pro Gly His Phe Pro Thr Asp Asp Phe Ala Leu Ala Glu Phe Asp
            340                 345                 350 ggc acc aac ctc tac gag cat agt gat ccg cgc gag ggc tac cat cag       1104
Gly Thr Asn Leu Tyr Glu His Ser Asp Pro Arg Glu Gly Tyr His Gln
        355                 360                 365 gac tgg aac acg ctc atc tac aat tac ggt cgc cgc gag gtc agc aac       1152
Asp Trp Asn Thr Leu Ile Tyr Asn Tyr Gly Arg Arg Glu Val Ser Asn
    370                 375                 380 ttc ctg gtt ggg aat gcg ctg tat tgg att gag cgc ttc ggc ata gac       1200
Phe Leu Val Gly Asn Ala Leu Tyr Trp Ile Glu Arg Phe Gly Ile Asp
385                 390                 395                 400 gcc ctg cgc gtc gac gcc gtg gca tcc atg atc tac cgc gat tat tcc       1248
Ala Leu Arg Val Asp Ala Val Ala Ser Met Ile Tyr Arg Asp Tyr Ser
                405                 410                 415 cgc aaa gag ggc gag tgg atc ccc aat gag ttc ggt ggc cgc gag aac       1296
Arg Lys Glu Gly Glu Trp Ile Pro Asn Glu Phe Gly Gly Arg Glu Asn
            420                 425                 430 ctt gag gcc att gag ttc ctt agg aat acg aac cgg atc ctg ggg gaa       1344
```

|     |     |     |     |     |     |     |     |     |     |     |     |     |     |      |
|-----|-----|-----|-----|-----|-----|-----|-----|-----|-----|-----|-----|-----|-----|------|
| Leu | Glu | Ala | Ile | Glu | Phe | Leu | Arg | Asn | Thr | Asn | Arg | Ile | Leu | Gly Glu |
|     |     |     | 435 |     |     |     | 440 |     |     |     | 445 |     |     |      |

```
caa gtg tcc ggg gct gtc acc atg gca gag gag agc acc gat ttt ccc      1392
Gln Val Ser Gly Ala Val Thr Met Ala Glu Glu Ser Thr Asp Phe Pro
        450                 455                 460 ggc gtg tcg cgc ccg caa gac atg ggt ggc ctg ggc ttc tgg tac aag      1440
Gly Val Ser Arg Pro Gln Asp Met Gly Gly Leu Gly Phe Trp Tyr Lys
465                 470                 475                 480 tgg aat ctg ggc tgg atg cac gac acc ctc gac tac atg aag ctt gat      1488
Trp Asn Leu Gly Trp Met His Asp Thr Leu Asp Tyr Met Lys Leu Asp
                485                 490                 495 ccg gtc tat cgc cag tat cac cat gac aag ctc acg ttc ggc atc ctg      1536
Pro Val Tyr Arg Gln Tyr His His Asp Lys Leu Thr Phe Gly Ile Leu
            500                 505                 510 tat aac tat acc gag aat ttc gtg ctc ccg ttg agc cat gac gaa gtt      1584
Tyr Asn Tyr Thr Glu Asn Phe Val Leu Pro Leu Ser His Asp Glu Val
        515                 520                 525 gtc cat ggc aag aag agt att ctg gac cgg atg cca ggc gac gcg tgg      1632
Val His Gly Lys Lys Ser Ile Leu Asp Arg Met Pro Gly Asp Ala Trp
530                 535                 540 cag aaa ttc gcg aat ctc cgc gcc tat tat ggc tgg atg tgg gcg ttc      1680
Gln Lys Phe Ala Asn Leu Arg Ala Tyr Tyr Gly Trp Met Trp Ala Phe
545                 550                 555                 560 ccg ggc aaa aag ctc ctg ttc atg gga aat gag ttc gcc cag ggc cgg      1728
Pro Gly Lys Lys Leu Leu Phe Met Gly Asn Glu Phe Ala Gln Gly Arg
                565                 570                 575 gag tgg aac cat gac gcg agc ctc gac tgg cat ctc ctt gag ggc gga      1776
Glu Trp Asn His Asp Ala Ser Leu Asp Trp His Leu Leu Glu Gly Gly
            580                 585                 590 gac aac tgg cac cac ggc gtg cag cgc ctc gtg cgg gac ctc aac ctg      1824
Asp Asn Trp His His Gly Val Gln Arg Leu Val Arg Asp Leu Asn Leu
        595                 600                 605 acc tac cgc cat cat aaa gcc atg cac gag ctg gat ttc gac ccg tac      1872
Thr Tyr Arg His His Lys Ala Met His Glu Leu Asp Phe Asp Pro Tyr
610                 615                 620 ggc ttc gag tgg ctc gtc gtc gac gat aag gag cgc tcg gtc ctc att      1920
Gly Phe Glu Trp Leu Val Val Asp Asp Lys Glu Arg Ser Val Leu Ile
625                 630                 635                 640 ttc gtg cgc agg gac aag gaa ggc aac gag atc atc gtg gcg agc aac      1968
Phe Val Arg Arg Asp Lys Glu Gly Asn Glu Ile Ile Val Ala Ser Asn
                645                 650                 655 ttc acc ccg gtc ccg cgg cac gac tac cgc ttc ggc atc aat cag ccg      2016
Phe Thr Pro Val Pro Arg His Asp Tyr Arg Phe Gly Ile Asn Gln Pro
            660                 665                 670 ggc aag tgg cgc gag atc ctg aac acg gac tcg atg cat tat cat ggt      2064
Gly Lys Trp Arg Glu Ile Leu Asn Thr Asp Ser Met His Tyr His Gly
        675                 680                 685 tcg aac gcc ggg aat ggc ggc acc gtg cac tcg gac gag atc gcc tcc      2112
Ser Asn Ala Gly Asn Gly Gly Thr Val His Ser Asp Glu Ile Ala Ser
690                 695                 700 cat ggc cgc cag cat agc ttg tcc ctg acc ctg ccc cct ctc gcg acc      2160
His Gly Arg Gln His Ser Leu Ser Leu Thr Leu Pro Pro Leu Ala Thr
705                 710                 715                 720 atc tgg ctg gtg cgc gag gcc gag                                      2184
Ile Trp Leu Val Arg Glu Ala Glu
                725
```

```
<210> SEQ ID NO 36
<211> LENGTH: 728
<212> TYPE: PRT
```

<213> ORGANISM: Artificial sequence
<220> FEATURE:
<223> OTHER INFORMATION: Synthetic Construct

<400> SEQUENCE: 36

```
Met Ser Asp Arg Ile Asp Arg Asp Val Ile Asn Ala Leu Ile Ala Gly
1               5                   10                  15

His Phe Ala Asp Pro Phe Ser Val Leu Gly Met His Lys Thr Thr Ala
            20                  25                  30

Gly Leu Glu Val Arg Ala Leu Leu Pro Asp Ala Thr Asp Val Trp Val
        35                  40                  45

Ile Glu Pro Lys Thr Gly Arg Lys Leu Ala Lys Leu Glu Cys Leu Asp
50                  55                  60

Ser Arg Gly Phe Phe Ser Gly Val Ile Pro Arg Arg Lys Asn Phe Phe
65                  70                  75                  80

Arg Tyr Gln Leu Ala Val Val Trp His Gly Gln Gln Asn Leu Ile Asp
                85                  90                  95

Asp Pro Tyr Arg Phe Gly Pro Leu Ile Gln Glu Met Asp Ala Trp Leu
            100                 105                 110

Leu Ser Glu Gly Thr His Leu Arg Pro Tyr Glu Thr Leu Gly Ala His
        115                 120                 125

Ala Asp Thr Met Asp Gly Val Thr Gly Thr Arg Phe Ser Val Trp Ala
130                 135                 140

Pro Asn Ala Arg Arg Val Ser Val Val Gly Gln Phe Asn Tyr Trp Asp
145                 150                 155                 160

Gly Arg Arg His Pro Met Arg Leu Arg Lys Glu Ser Gly Ile Trp Glu
                165                 170                 175

Leu Phe Ile Pro Gly Ala His Asn Gly Gln Leu Tyr Lys Tyr Glu Met
            180                 185                 190

Ile Asp Ala Asn Gly Asn Leu Arg Leu Lys Ser Asp Pro Tyr Ala Phe
        195                 200                 205

Glu Ala Gln Met Arg Pro Glu Thr Ala Ser Leu Ile Cys Gly Leu Pro
210                 215                 220

Glu Lys Val Val Gln Thr Glu Arg Lys Lys Ala Asn Gln Phe Asp
225                 230                 235                 240

Ala Pro Ile Ser Ile Tyr Glu Val His Leu Gly Ser Trp Arg Arg His
                245                 250                 255

Thr Asp Asn Asn Phe Trp Leu Ser Tyr Arg Glu Leu Ala Asp Gln Leu
            260                 265                 270

Val Pro Tyr Ala Lys Trp Met Gly Phe Thr His Leu Glu Leu Leu Pro
        275                 280                 285

Ile Asn Glu His Pro Phe Asp Gly Ser Trp Gly Tyr Gln Pro Thr Gly
290                 295                 300

Leu Tyr Ala Pro Thr Arg Arg Phe Gly Thr Arg Asp Asp Phe Arg Tyr
305                 310                 315                 320

Phe Ile Asp Ala Ala His Ala Ala Gly Leu Asn Val Ile Leu Asp Trp
                325                 330                 335

Val Pro Gly His Phe Pro Thr Asp Asp Phe Ala Leu Ala Glu Phe Asp
            340                 345                 350

Gly Thr Asn Leu Tyr Glu His Ser Asp Pro Arg Glu Gly Tyr His Gln
        355                 360                 365

Asp Trp Asn Thr Leu Ile Tyr Asn Tyr Gly Arg Arg Glu Val Ser Asn
370                 375                 380

Phe Leu Val Gly Asn Ala Leu Tyr Trp Ile Glu Arg Phe Gly Ile Asp
```

```
                385                 390                 395                 400
        Ala Leu Arg Val Asp Ala Val Ala Ser Met Ile Tyr Arg Asp Tyr Ser
                        405                 410                 415

Arg Lys Glu Gly Glu Trp Ile Pro Asn Glu Phe Gly Gly Arg Glu Asn
                        420                 425                 430

Leu Glu Ala Ile Glu Phe Leu Arg Asn Thr Asn Arg Ile Leu Gly Glu
                        435                 440                 445

Gln Val Ser Gly Ala Val Thr Met Ala Glu Glu Ser Thr Asp Phe Pro
                        450                 455                 460

Gly Val Ser Arg Pro Gln Asp Met Gly Gly Leu Gly Phe Trp Tyr Lys
        465                 470                 475                 480

Trp Asn Leu Gly Trp Met His Asp Thr Leu Asp Tyr Met Lys Leu Asp
                        485                 490                 495

Pro Val Tyr Arg Gln Tyr His His Asp Lys Leu Thr Phe Gly Ile Leu
                        500                 505                 510

Tyr Asn Tyr Thr Glu Asn Phe Val Leu Pro Leu Ser His Asp Glu Val
                        515                 520                 525

Val His Gly Lys Lys Ser Ile Leu Asp Arg Met Pro Gly Asp Ala Trp
                        530                 535                 540

Gln Lys Phe Ala Asn Leu Arg Ala Tyr Tyr Gly Trp Met Trp Ala Phe
        545                 550                 555                 560

Pro Gly Lys Lys Leu Leu Phe Met Gly Asn Glu Phe Ala Gln Gly Arg
                        565                 570                 575

Glu Trp Asn His Asp Ala Ser Leu Asp Trp His Leu Leu Glu Gly Gly
                        580                 585                 590

Asp Asn Trp His His Gly Val Gln Arg Leu Val Arg Asp Leu Asn Leu
                        595                 600                 605

Thr Tyr Arg His His Lys Ala Met His Glu Leu Asp Phe Asp Pro Tyr
                        610                 615                 620

Gly Phe Glu Trp Leu Val Val Asp Asp Lys Glu Arg Ser Val Leu Ile
        625                 630                 635                 640

Phe Val Arg Arg Asp Lys Glu Gly Asn Glu Ile Ile Val Ala Ser Asn
                        645                 650                 655

Phe Thr Pro Val Pro Arg His Asp Tyr Arg Phe Gly Ile Asn Gln Pro
                        660                 665                 670

Gly Lys Trp Arg Glu Ile Leu Asn Thr Asp Ser Met His Tyr His Gly
                        675                 680                 685

Ser Asn Ala Gly Asn Gly Gly Thr Val His Ser Asp Glu Ile Ala Ser
                        690                 695                 700

His Gly Arg Gln His Ser Leu Ser Leu Thr Leu Pro Pro Leu Ala Thr
        705                 710                 715                 720

Ile Trp Leu Val Arg Glu Ala Glu
                        725

<210> SEQ ID NO 37
<211> LENGTH: 2193
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(2193)
<223> OTHER INFORMATION: Corynebacterium glutamicum (ATCC 13032)
      Glycogen branching enzyme (codon optimized)

<400> SEQUENCE: 37
```

```
atg acc gtc gac ccc gcg tcc cat atc acg atc ccc gaa gcc gac ctc     48
Met Thr Val Asp Pro Ala Ser His Ile Thr Ile Pro Glu Ala Asp Leu
1               5                   10                  15 gca cgc ctc cgc cac tgc aac cat cac gac ccc cat gga ttc tac ggg     96
Ala Arg Leu Arg His Cys Asn His His Asp Pro His Gly Phe Tyr Gly
                20                  25                  30 tgg cat gaa act gag gcc ggg tcc gtc att cgc acc cgc cag gtc ggc    144
Trp His Glu Thr Glu Ala Gly Ser Val Ile Arg Thr Arg Gln Val Gly
            35                  40                  45 gcg acc cag gtg aat ctg ctc att gat gac acg agc cat gtc atg acg    192
Ala Thr Gln Val Asn Leu Leu Ile Asp Asp Thr Ser His Val Met Thr
        50                  55                  60 ccc atc ggc gac gac atc ttc gcg atc gac ctc ggg cat cgg gag cgc    240
Pro Ile Gly Asp Asp Ile Phe Ala Ile Asp Leu Gly His Arg Glu Arg
65                  70                  75                  80 gct gat tac cgc ctt gag gtc acg tgg ccg gac caa gag cca cag gtg    288
Ala Asp Tyr Arg Leu Glu Val Thr Trp Pro Asp Gln Glu Pro Gln Val
                85                  90                  95 aaa gct gac ccg tac tat ttc ctc ccc acg gtc ggt gag atg gac atc    336
Lys Ala Asp Pro Tyr Tyr Phe Leu Pro Thr Val Gly Glu Met Asp Ile
            100                 105                 110 tat ctg ttc tcc gag ggt cgg cac gaa cgg ctc tgg gag atc ctc ggc    384
Tyr Leu Phe Ser Glu Gly Arg His Glu Arg Leu Trp Glu Ile Leu Gly
        115                 120                 125 gcc aat atc aag acc tat cag acc gcg ctg ggc acc gtc cgc ggc acg    432
Ala Asn Ile Lys Thr Tyr Gln Thr Ala Leu Gly Thr Val Arg Gly Thr
    130                 135                 140 gcg ttc acc gtc tgg gca ccc aac gcg atc ggc tgc gcg gtc gtg ggg    480
Ala Phe Thr Val Trp Ala Pro Asn Ala Ile Gly Cys Ala Val Val Gly
145                 150                 155                 160 ggc ttc aac ggt tgg aac gcc agt caa cac ccg atg cgg agc atg ggc    528
Gly Phe Asn Gly Trp Asn Ala Ser Gln His Pro Met Arg Ser Met Gly
                165                 170                 175 gga tcc ggc ctt tgg gag ctg ttc atc ccg ggc atc gag gag ggc gag    576
Gly Ser Gly Leu Trp Glu Leu Phe Ile Pro Gly Ile Glu Glu Gly Glu
            180                 185                 190 gtg tac aag ttt gcg gtg cag acc cgc gaa ggc cag cgc agg gat aag    624
Val Tyr Lys Phe Ala Val Gln Thr Arg Glu Gly Gln Arg Arg Asp Lys
        195                 200                 205 gcc gac ccc atg gcg cgg cgc gcc gag ctg gca cca gcc acc ggc agc    672
Ala Asp Pro Met Ala Arg Arg Ala Glu Leu Ala Pro Ala Thr Gly Ser
    210                 215                 220 ata gtt gcc tcg tcc gag tac cag tgg cag gac tcc gag tgg ctg cgc    720
Ile Val Ala Ser Ser Glu Tyr Gln Trp Gln Asp Ser Glu Trp Leu Arg
225                 230                 235                 240 gag cgg agc cag act gac ctc gcc agc aag cct atg tcc gtg tat gag    768
Glu Arg Ser Gln Thr Asp Leu Ala Ser Lys Pro Met Ser Val Tyr Glu
                245                 250                 255 gtg cat ctg ggt tcg tgg cgc tgg ggc aag aac tac gaa gat ctg gcg    816
Val His Leu Gly Ser Trp Arg Trp Gly Lys Asn Tyr Glu Asp Leu Ala
            260                 265                 270 acc gag ctc gtc gat tat gtt gcg gac ctg ggt tat acg cat gtc gag    864
Thr Glu Leu Val Asp Tyr Val Ala Asp Leu Gly Tyr Thr His Val Glu
        275                 280                 285 ttc ctg ccg gtg gcg gag cac ccg ttc ggc ggc tcg tgg ggc tac caa    912
Phe Leu Pro Val Ala Glu His Pro Phe Gly Gly Ser Trp Gly Tyr Gln
    290                 295                 300 gtc acg ggt tat tac gcg ccg acc agc cgc tgg ggc acc ccg gac cag    960
Val Thr Gly Tyr Tyr Ala Pro Thr Ser Arg Trp Gly Thr Pro Asp Gln
```

-continued

| | | | | |
|---|---|---|---|---|
| | 305 | 310 | 315 | 320 |

| | |
|---|---|
| ttc cgc gcg ttg gtc gac gcg ttc cac gcc agg gga atc ggc gtc atc<br>Phe Arg Ala Leu Val Asp Ala Phe His Ala Arg Gly Ile Gly Val Ile<br>  325       330       335 | 1008 |
| atg gac tgg gtt ccc gca cat ttc ccg aaa gat gat tgg gcg ctg gcg<br>Met Asp Trp Val Pro Ala His Phe Pro Lys Asp Asp Trp Ala Leu Ala<br>340       345       350 | 1056 |
| cgg ttc gac ggc gag gcc ctc tat gag cac ccg gac tgg cgg cgg ggt<br>Arg Phe Asp Gly Glu Ala Leu Tyr Glu His Pro Asp Trp Arg Arg Gly<br>  355       360       365 | 1104 |
| gag cag aaa gat tgg ggg acc ctc gtg ttc gat ttt ggc cgg aac gaa<br>Glu Gln Lys Asp Trp Gly Thr Leu Val Phe Asp Phe Gly Arg Asn Glu<br>370       375       380 | 1152 |
| gtc cgc aac ttc ttg gtc gcg aac gcg ctc tat tgg att gaa gag ttc<br>Val Arg Asn Phe Leu Val Ala Asn Ala Leu Tyr Trp Ile Glu Glu Phe<br>385       390       395       400 | 1200 |
| cat att gac ggc ctc cgg gtc gac gcc gtc gcc tcg atg ctc tac ctg<br>His Ile Asp Gly Leu Arg Val Asp Ala Val Ala Ser Met Leu Tyr Leu<br>  405       410       415 | 1248 |
| gac tac tcg cgc gag cac ggc gag tgg gag ccg aac atc tat ggc gga<br>Asp Tyr Ser Arg Glu His Gly Glu Trp Glu Pro Asn Ile Tyr Gly Gly<br>  420       425       430 | 1296 |
| cgg gag aat ctc gaa gcc gtc cag ttc ctg caa gag atg aac gca acc<br>Arg Glu Asn Leu Glu Ala Val Gln Phe Leu Gln Glu Met Asn Ala Thr<br>  435       440       445 | 1344 |
| gtg ctc cgc ctg cat cct ggt gcg ctg acc atc gca gag gaa tcg acc<br>Val Leu Arg Leu His Pro Gly Ala Leu Thr Ile Ala Glu Glu Ser Thr<br>450       455       460 | 1392 |
| tcg tgg ccg ggt gtg acc gct ccg acc tgg gac ggt ggc ctt ggt ttc<br>Ser Trp Pro Gly Val Thr Ala Pro Thr Trp Asp Gly Gly Leu Gly Phe<br>465       470       475       480 | 1440 |
| agc ctg aag tgg aat atg ggc tgg atg cat gac acc ctt gag tat ttc<br>Ser Leu Lys Trp Asn Met Gly Trp Met His Asp Thr Leu Glu Tyr Phe<br>  485       490       495 | 1488 |
| tcg aag aat ccg gtg cac agg gcc ttc cac cat tcc gag ctg acg ttc<br>Ser Lys Asn Pro Val His Arg Ala Phe His His Ser Glu Leu Thr Phe<br>  500       505       510 | 1536 |
| tcg ctt gtc tac gcc ttc agt gag cgc ttc gtg ctg ccg atc tcc cat<br>Ser Leu Val Tyr Ala Phe Ser Glu Arg Phe Val Leu Pro Ile Ser His<br>  515       520       525 | 1584 |
| gac gaa gtc gtc cac ggc aag ggc tcc ctg tgg gac cgg atg ccg ggt<br>Asp Glu Val Val His Gly Lys Gly Ser Leu Trp Asp Arg Met Pro Gly<br>  530       535       540 | 1632 |
| gac acc tgg aat aaa gcc gca ggc ctc cgc acg ttc ctg gcg tac atg<br>Asp Thr Trp Asn Lys Ala Ala Gly Leu Arg Thr Phe Leu Ala Tyr Met<br>545       550       555       560 | 1680 |
| tgg agc cac ccg ggc aag aaa ctg ctg ttc atg ggc caa gag ttc ggc<br>Trp Ser His Pro Gly Lys Lys Leu Leu Phe Met Gly Gln Glu Phe Gly<br>  565       570       575 | 1728 |
| cag cgc gag gag tgg gcc gag ggc cag ggc ctg ccc tgg gac atc gtg<br>Gln Arg Glu Glu Trp Ala Glu Gly Gln Gly Leu Pro Trp Asp Ile Val<br>  580       585       590 | 1776 |
| gac ggg tgg cag ggc gag tat cat gaa gcg atc cgc acc ctc acg cgc<br>Asp Gly Trp Gln Gly Glu Tyr His Glu Ala Ile Arg Thr Leu Thr Arg<br>  595       600       605 | 1824 |
| agc ctg aac ggc gtg tac agc gat agt ccg gcg ctc cat acc caa gat<br>Ser Leu Asn Gly Val Tyr Ser Asp Ser Pro Ala Leu His Thr Gln Asp<br>  610       615       620 | 1872 |
| ttc acc ggc gag ggc ttc acg tgg aac aaa ggt gac gac gcc acc aat<br> Phe Thr Gly Glu Gly Phe Thr Trp Asn Lys Gly Asp Asp Ala Thr Asn | 1920 |

```
Phe Thr Gly Glu Gly Phe Thr Trp Asn Lys Gly Asp Asp Ala Thr Asn
625                 630                 635                 640 aac atc ctc gcc ttc acc cgc ttt ggc tcc gac ggc tcg cag atg ctc    1968
Asn Ile Leu Ala Phe Thr Arg Phe Gly Ser Asp Gly Ser Gln Met Leu
                    645                 650                 655 tgc gtg ttc aac ctc tcg ggc acc tcg cag ccg gag tac cag ctc ggg    2016
Cys Val Phe Asn Leu Ser Gly Thr Ser Gln Pro Glu Tyr Gln Leu Gly
            660                 665                 670 gtg gcc gct ggg ggc gag tgg aag ctt gtg ctg aat acc gac gac gcc    2064
Val Ala Ala Gly Gly Glu Trp Lys Leu Val Leu Asn Thr Asp Asp Ala
        675                 680                 685 gag ttt ttg gga gcc gaa aac gat atc gcg acg agc gtg caa gct gct    2112
Glu Phe Leu Gly Ala Glu Asn Asp Ile Ala Thr Ser Val Gln Ala Ala
    690                 695                 700 gcc act ccc agg gac aat ttc gcc tat tcc ctg agc ctg cat gtc ccc    2160
Ala Thr Pro Arg Asp Asn Phe Ala Tyr Ser Leu Ser Leu His Val Pro
705                 710                 715                 720 gcc atg tcg gcg cag ttc tac tcg ctc cag aag                        2193
Ala Met Ser Ala Gln Phe Tyr Ser Leu Gln Lys
                725                 730

<210> SEQ ID NO 38
<211> LENGTH: 731
<212> TYPE: PRT
<213> ORGANISM: Artificial sequence
<220> FEATURE:
<223> OTHER INFORMATION: Synthetic Construct

<400> SEQUENCE: 38

Met Thr Val Asp Pro Ala Ser His Ile Thr Ile Pro Glu Ala Asp Leu
1               5                   10                  15

Ala Arg Leu Arg His Cys Asn His His Asp Pro His Gly Phe Tyr Gly
            20                  25                  30

Trp His Glu Thr Glu Ala Gly Ser Val Ile Arg Thr Arg Gln Val Gly
        35                  40                  45

Ala Thr Gln Val Asn Leu Leu Ile Asp Asp Thr Ser His Val Met Thr
    50                  55                  60

Pro Ile Gly Asp Asp Ile Phe Ala Ile Asp Leu Gly His Arg Glu Arg
65                  70                  75                  80

Ala Asp Tyr Arg Leu Glu Val Thr Trp Pro Asp Gln Glu Pro Gln Val
                85                  90                  95

Lys Ala Asp Pro Tyr Tyr Phe Leu Pro Thr Val Gly Glu Met Asp Ile
            100                 105                 110

Tyr Leu Phe Ser Glu Gly Arg His Glu Arg Leu Trp Glu Ile Leu Gly
        115                 120                 125

Ala Asn Ile Lys Thr Tyr Gln Thr Ala Leu Gly Thr Val Arg Gly Thr
    130                 135                 140

Ala Phe Thr Val Trp Ala Pro Asn Ala Ile Gly Cys Ala Val Val Gly
145                 150                 155                 160

Gly Phe Asn Gly Trp Asn Ala Ser Gln His Pro Met Arg Ser Met Gly
                165                 170                 175

Gly Ser Gly Leu Trp Glu Leu Phe Ile Pro Gly Ile Glu Glu Gly Glu
            180                 185                 190

Val Tyr Lys Phe Ala Val Gln Thr Arg Glu Gly Gln Arg Arg Asp Lys
        195                 200                 205

Ala Asp Pro Met Ala Arg Arg Ala Glu Leu Ala Pro Ala Thr Gly Ser
    210                 215                 220
```

```
Ile Val Ala Ser Ser Glu Tyr Gln Trp Gln Asp Ser Glu Trp Leu Arg
225                 230                 235                 240

Glu Arg Ser Gln Thr Asp Leu Ala Ser Lys Pro Met Ser Val Tyr Glu
            245                 250                 255

Val His Leu Gly Ser Trp Arg Trp Gly Lys Asn Tyr Glu Asp Leu Ala
        260                 265                 270

Thr Glu Leu Val Asp Tyr Val Ala Asp Leu Gly Tyr Thr His Val Glu
    275                 280                 285

Phe Leu Pro Val Ala Glu His Pro Phe Gly Gly Ser Trp Gly Tyr Gln
290                 295                 300

Val Thr Gly Tyr Tyr Ala Pro Thr Ser Arg Trp Gly Thr Pro Asp Gln
305                 310                 315                 320

Phe Arg Ala Leu Val Asp Ala Phe His Ala Arg Gly Ile Gly Val Ile
            325                 330                 335

Met Asp Trp Val Pro Ala His Phe Pro Lys Asp Asp Trp Ala Leu Ala
        340                 345                 350

Arg Phe Asp Gly Glu Ala Leu Tyr Glu His Pro Asp Trp Arg Arg Gly
    355                 360                 365

Glu Gln Lys Asp Trp Gly Thr Leu Val Phe Asp Phe Gly Arg Asn Glu
370                 375                 380

Val Arg Asn Phe Leu Val Ala Asn Ala Leu Tyr Trp Ile Glu Glu Phe
385                 390                 395                 400

His Ile Asp Gly Leu Arg Val Asp Ala Val Ala Ser Met Leu Tyr Leu
            405                 410                 415

Asp Tyr Ser Arg Glu His Gly Glu Trp Glu Pro Asn Ile Tyr Gly Gly
        420                 425                 430

Arg Glu Asn Leu Glu Ala Val Gln Phe Leu Gln Glu Met Asn Ala Thr
    435                 440                 445

Val Leu Arg Leu His Pro Gly Ala Leu Thr Ile Ala Glu Glu Ser Thr
450                 455                 460

Ser Trp Pro Gly Val Thr Ala Pro Thr Trp Asp Gly Gly Leu Gly Phe
465                 470                 475                 480

Ser Leu Lys Trp Asn Met Gly Trp Met His Asp Thr Leu Glu Tyr Phe
            485                 490                 495

Ser Lys Asn Pro Val His Arg Ala Phe His His Ser Glu Leu Thr Phe
        500                 505                 510

Ser Leu Val Tyr Ala Phe Ser Glu Arg Phe Val Leu Pro Ile Ser His
    515                 520                 525

Asp Glu Val Val His Gly Lys Gly Ser Leu Trp Asp Arg Met Pro Gly
530                 535                 540

Asp Thr Trp Asn Lys Ala Ala Gly Leu Arg Thr Phe Leu Ala Tyr Met
545                 550                 555                 560

Trp Ser His Pro Gly Lys Lys Leu Leu Phe Met Gly Gln Glu Phe Gly
            565                 570                 575

Gln Arg Glu Glu Trp Ala Glu Gly Gln Gly Leu Pro Trp Asp Ile Val
        580                 585                 590

Asp Gly Trp Gln Gly Glu Tyr His Glu Ala Ile Arg Thr Leu Thr Arg
    595                 600                 605

Ser Leu Asn Gly Val Tyr Ser Asp Ser Pro Ala Leu His Thr Gln Asp
610                 615                 620

Phe Thr Gly Glu Gly Phe Thr Trp Asn Lys Gly Asp Asp Ala Thr Asn
625                 630                 635                 640
```

-continued

```
Asn Ile Leu Ala Phe Thr Arg Phe Gly Ser Asp Gly Ser Gln Met Leu
            645                 650                 655

Cys Val Phe Asn Leu Ser Gly Thr Ser Gln Pro Glu Tyr Gln Leu Gly
            660                 665                 670

Val Ala Ala Gly Gly Glu Trp Lys Leu Val Leu Asn Thr Asp Asp Ala
            675                 680                 685

Glu Phe Leu Gly Ala Glu Asn Asp Ile Ala Thr Ser Val Gln Ala Ala
            690                 695                 700

Ala Thr Pro Arg Asp Asn Phe Ala Tyr Ser Leu Ser Leu His Val Pro
705                 710                 715                 720

Ala Met Ser Ala Gln Phe Tyr Ser Leu Gln Lys
                725                 730
```